US012165372B2

(12) United States Patent
Deliwala

(10) Patent No.: US 12,165,372 B2
(45) Date of Patent: Dec. 10, 2024

(54) CODED LED OR OTHER LIGHT FOR TARGET IMAGING OR ANALYSIS

(71) Applicant: Emcode Photonics LLC, Andover, MA (US)

(72) Inventor: Shrenik Deliwala, Andover, MA (US)

(73) Assignee: Emcode Photonics LLC, Andover, MA (US)

( * ) Notice: Subject to any disclaimer, the term of this patent is extended or adjusted under 35 U.S.C. 154(b) by 0 days.

(21) Appl. No.: 18/045,701

(22) Filed: Oct. 11, 2022

(65) Prior Publication Data

US 2023/0108409 A1 Apr. 6, 2023

Related U.S. Application Data

(63) Continuation of application No. PCT/US2022/017503, filed on Feb. 23, 2022.
(Continued)

(51) Int. Cl.
*G06V 10/143* (2022.01)
*A61B 5/00* (2006.01)
(Continued)

(52) U.S. Cl.
CPC .......... *G06V 10/143* (2022.01); *A61B 5/0075* (2013.01); *G01J 3/2823* (2013.01);
(Continued)

(58) Field of Classification Search
CPC ............... G01D 5/35316; G01N 15/06; G01N 2015/0693; G01N 2015/0046;
(Continued)

(56) References Cited

U.S. PATENT DOCUMENTS 7,265,830 B2 9/2007 Wang
7,339,170 B2 3/2008 Deliwala
(Continued)

FOREIGN PATENT DOCUMENTS

DE 102010053978 A1 6/2012
WO WO-2022182747 A2 9/2022
WO WO-2022182747 A3 9/2022

OTHER PUBLICATIONS

"International Application Serial No. PCT/US2022/017503, International Search Report mailed Sep. 9, 2022", 8 pgs.
(Continued)

*Primary Examiner* — Michael J Vanchy, Jr.
(74) *Attorney, Agent, or Firm* — Schwegman Lundberg & Woessner, P.A.

(57) ABSTRACT

Modulation-encoded light, using different spectral bin coded light components, can illuminate a stationary or moving (relative) target object or scene. Response signal processing can use information about the respective different time-varying modulation functions, to decode to recover information about a respective response parameter affected by the target object or scene. Electrical or optical modulation encoding can be used. LED-based spectroscopic analysis of a composition of a target (e.g., SpO2, glucose, etc.) can be performed; such can optionally include decoding of encoded optical modulation functions. Baffles or apertures or optics can be used, such as to constrain light provided by particular LEDs. Coded light illumination can be used with a focal plane array light imager receiving response light for inspecting a moving semiconductor or other target. Encoding can use orthogonal functions, such as an RGB illumination sequence, or a sequence of combinations of spectrally contiguous or non-contiguous colors.

34 Claims, 58 Drawing Sheets

Related U.S. Application Data

(60) Provisional application No. 63/262,370, filed on Oct. 11, 2021, provisional application No. 63/202,325, filed on Jun. 7, 2021, provisional application No. 63/200,241, filed on Feb. 24, 2021.

(51) Int. Cl.
| | |
|---|---|
| *G01J 3/28* | (2006.01) |
| *G01J 3/433* | (2006.01) |
| *G01N 21/25* | (2006.01) |
| *G06V 10/141* | (2022.01) |
| *A61B 5/1455* | (2006.01) |
| *G01N 21/3504* | (2014.01) |
| *G01N 21/95* | (2006.01) |

(52) U.S. Cl.
CPC ............ *G01J 3/433* (2013.01); *G01N 21/255* (2013.01); *G06V 10/141* (2022.01); *A61B 5/14551* (2013.01); *A61B 5/742* (2013.01); *G01J 2003/4334* (2013.01); *G01N 21/3504* (2013.01); *G01N 21/9501* (2013.01)

(58) Field of Classification Search
CPC ......... G01N 2021/3144; G01N 21/255; G01N 21/31; G01N 21/3504; G01N 21/4795; G01N 21/61; G01N 21/8806; G01N 21/8851; G01N 21/9501; G02B 6/0208; G02B 6/02138; G02B 6/29319; G02B 6/4215; G02B 6/4231; G08B 17/107; G08B 17/113; G08B 17/103; H01L 31/167; A61B 2560/0209; A61B 2562/0238; A61B 2562/043; A61B 5/0205; A61B 5/02422; A61B 5/14551; A61B 5/14552; A61B 5/6826; A61B 5/6843; A61B 5/0075; A61B 5/742; G01B 11/2509; G01B 9/02091; G01J 2003/104; G01J 2003/4332; G01J 2003/4334; G01J 3/2803; G01J 3/2823; G01J 3/42; G01J 3/427; G01J 3/433; G06V 10/141; G06V 10/143
See application file for complete search history.

(56) References Cited

U.S. PATENT DOCUMENTS

| | | |
|---|---|---|
| 10,066,977 B2 | 9/2018 | Hasson et al. |
| 2002/0001080 A1* | 1/2002 | Miller .................. G01J 3/0218 356/326 |
| 2005/0270528 A1 | 12/2005 | Geshwind et al. |
| 2005/0286049 A1 | 12/2005 | Hagler |
| 2007/0093717 A1 | 4/2007 | Nagar et al. |
| 2007/0296969 A1 | 12/2007 | Goldstein et al. |
| 2010/0008588 A1* | 1/2010 | Feldkhun ................ G01S 7/484 382/206 |
| 2010/0056928 A1* | 3/2010 | Zuzak ........................ G01J 3/10 356/302 |
| 2012/0080611 A1* | 4/2012 | Jones .................... G01J 3/0291 356/342 |
| 2012/0248985 A1 | 10/2012 | Lin et al. |
| 2012/0307081 A1* | 12/2012 | Dewald ..................... G01J 3/10 348/E5.029 |
| 2014/0233028 A1 | 8/2014 | Englund |
| 2015/0241003 A1* | 8/2015 | Ikami ................ G01N 21/6456 362/231 |
| 2017/0059408 A1 | 3/2017 | Körner et al. |
| 2017/0164848 A1 | 6/2017 | Nadeau et al. |
| 2018/0136042 A1 | 5/2018 | Goldring et al. |
| 2019/0150839 A1 | 5/2019 | Kurfiss et al. |
| 2020/0011734 A1* | 1/2020 | Lee ............................ G01J 3/18 |
| 2022/0163634 A1* | 5/2022 | Gorman ................ G01S 7/4816 |

OTHER PUBLICATIONS

"International Application Serial No. PCT/US2022/017503, Invitation to Pay Additional Fees mailed May 24, 2022", 21 pgs.

"International Application Serial No. PCT/US2022/017503, Written Opinion mailed Sep. 9, 2022", 26 pgs.

"U.S. Appl. No. 18/045,695, Notice of Allowance mailed Feb. 16, 2023", 10 pgs.

Caramazza, Piergiorgio, et al., "Transmission of natural scene images through a multimode fibre", Nature Communications / https://doi.org/10.1038/s41467-019-10057-8, (2029), 1-6.

Sugimoto, Nobuo, "Hadamard transform active long-path absorption spectrometer system for measurements of atmospheric trace species", Applied Optics, vol. 25, No. 6, (Mar. 15, 1986), 863-865.

U.S. Appl. No. 18/751,080, Non Final Office Action mailed Sep. 13, 2024, 41 pgs.

\* cited by examiner

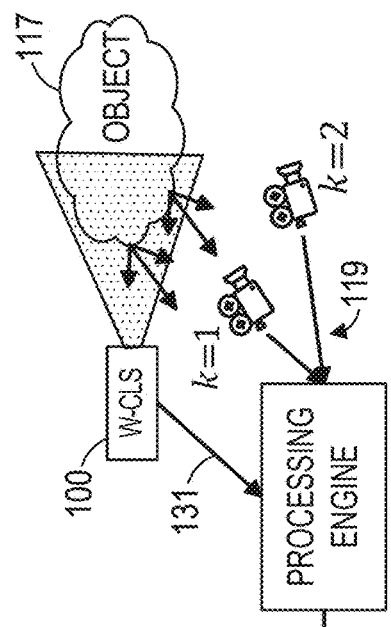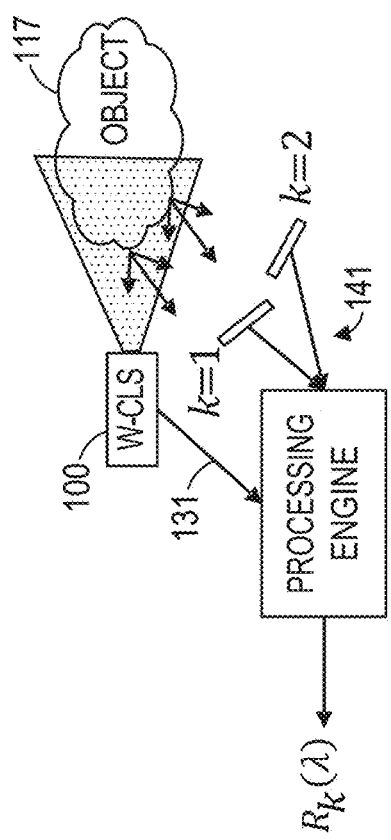
FIG. 2B

LOCAL ENVIRONMENTAL CHANGES CAUSE THE RESONANCE WAVELENGTH OF THE CONCATENATED FIBER BRAGG GRATINGS (FBGS), EACH WITH DIFFERENT RESONANT WAVELENGTH, TO SHIFT.

ENVIRONMENTAL CHANGES CAUSE THE RESONANCE WAVELENGTH OF THE FABRY PEROT (FP) CAVITY TO SHIFT.

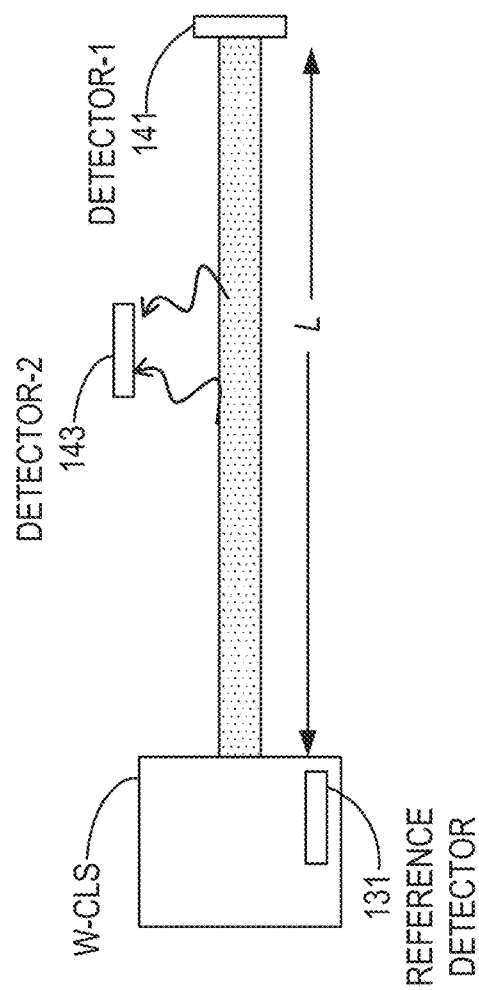
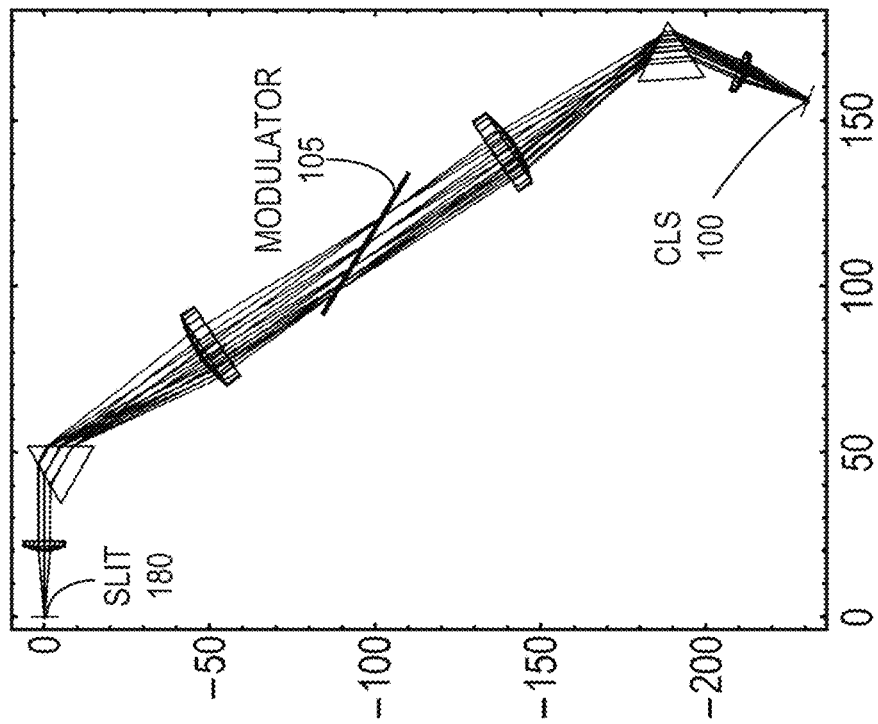
FIG. 14B
FIG. 14A

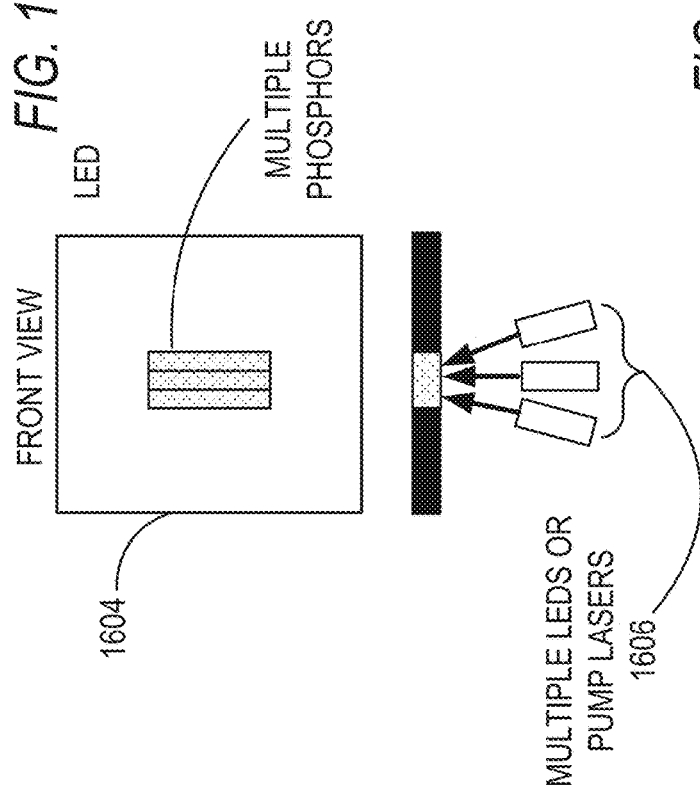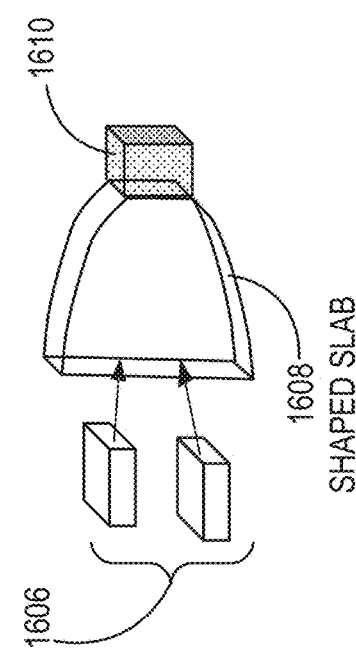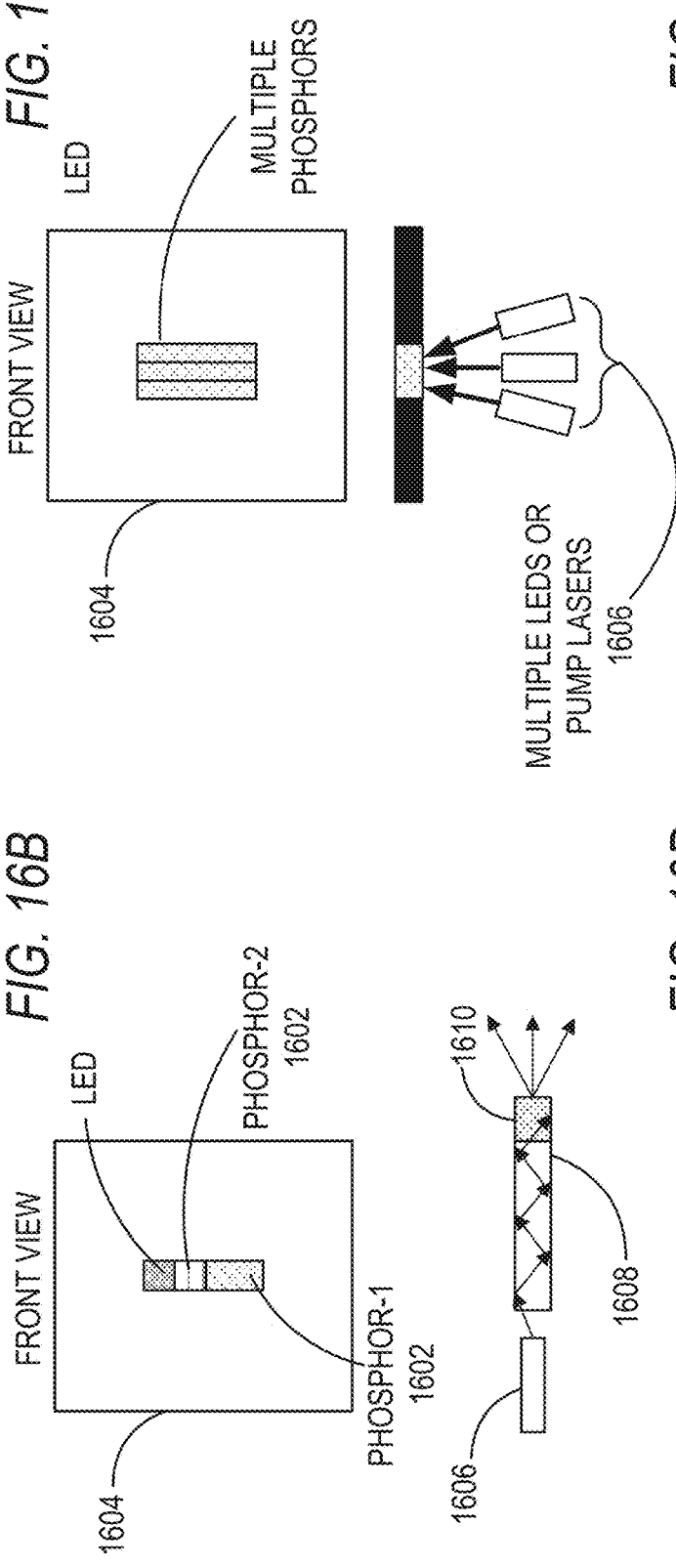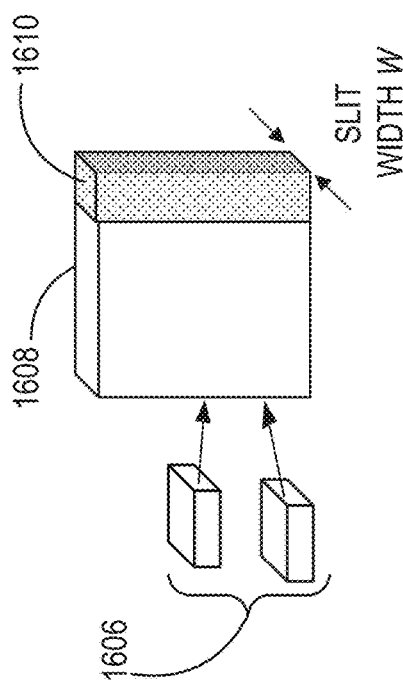

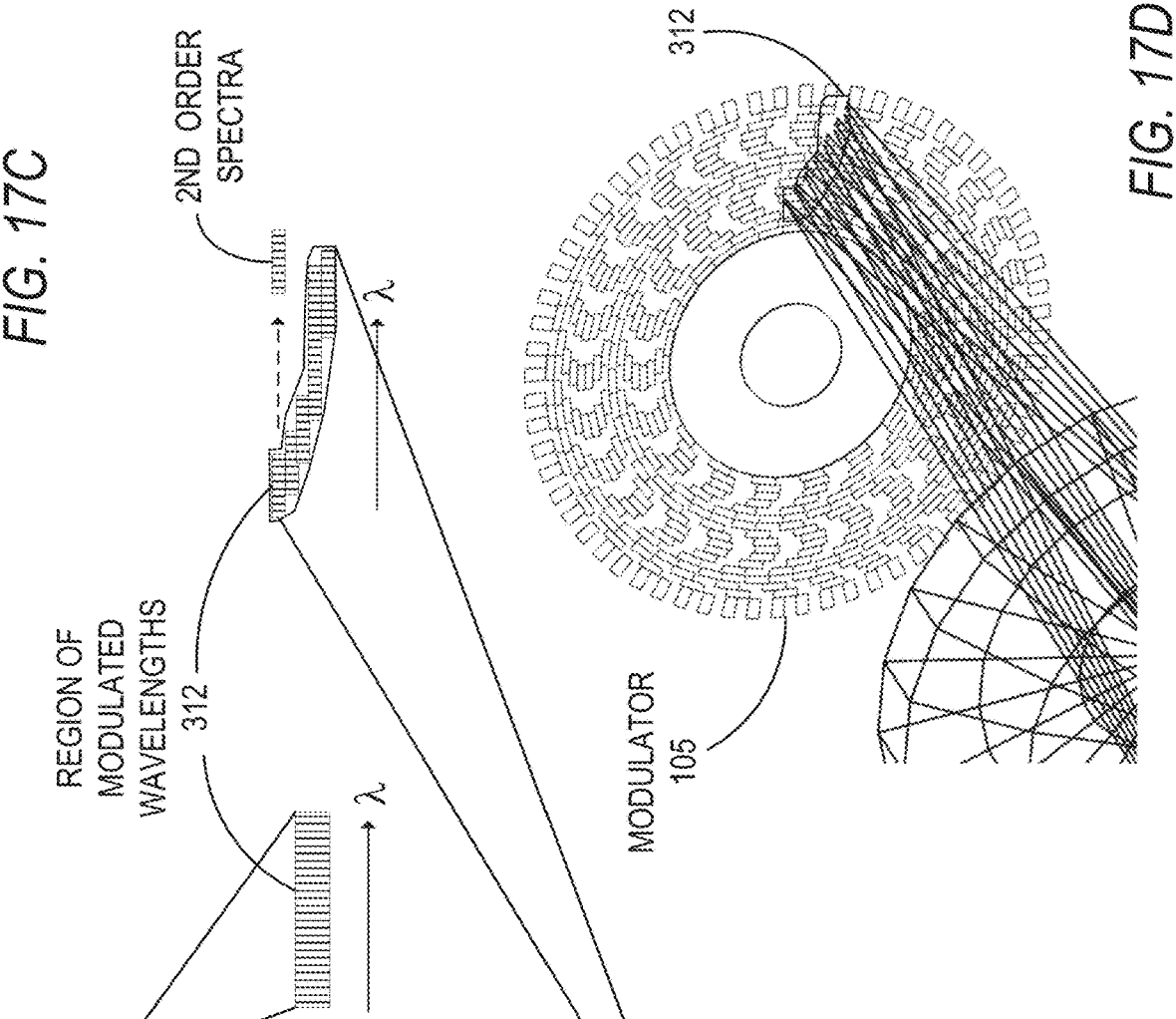
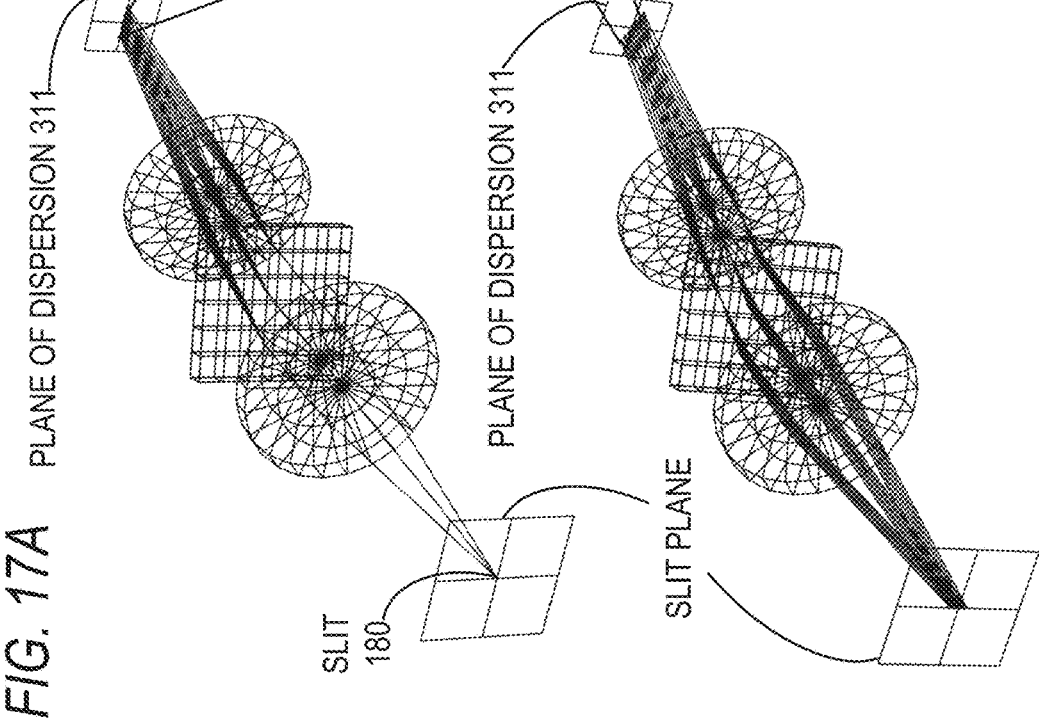

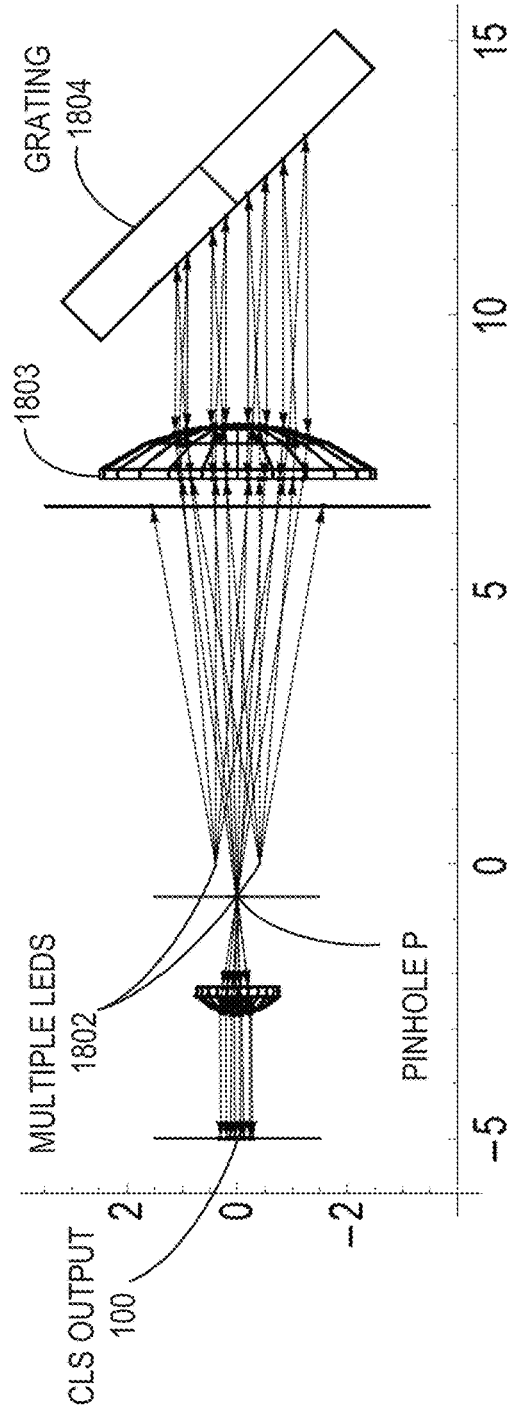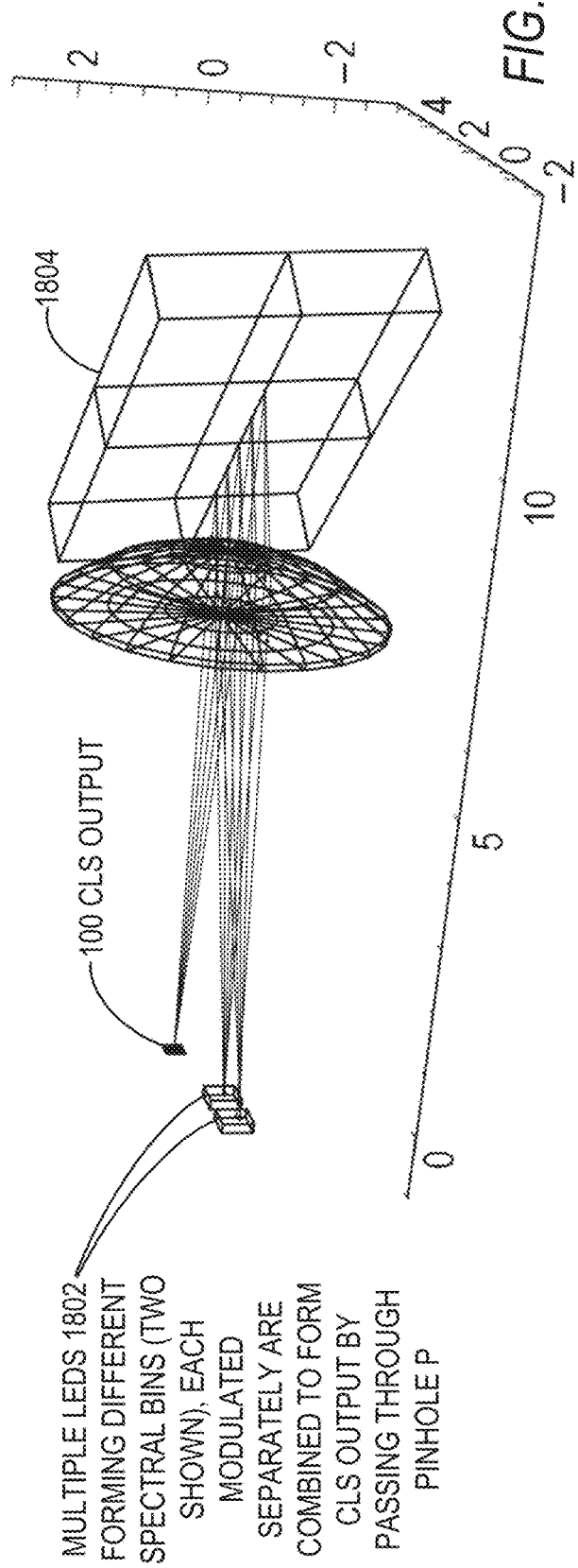

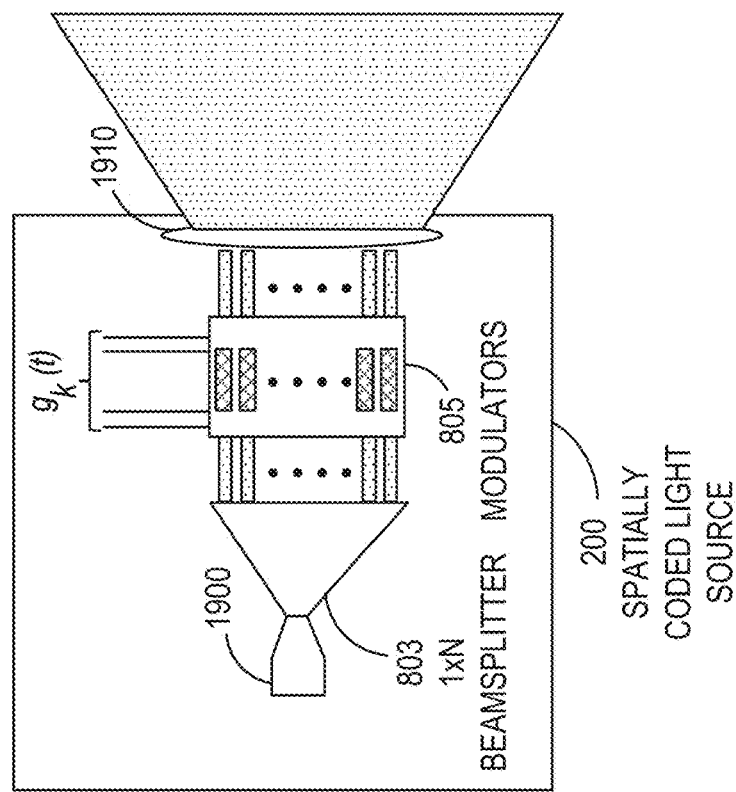
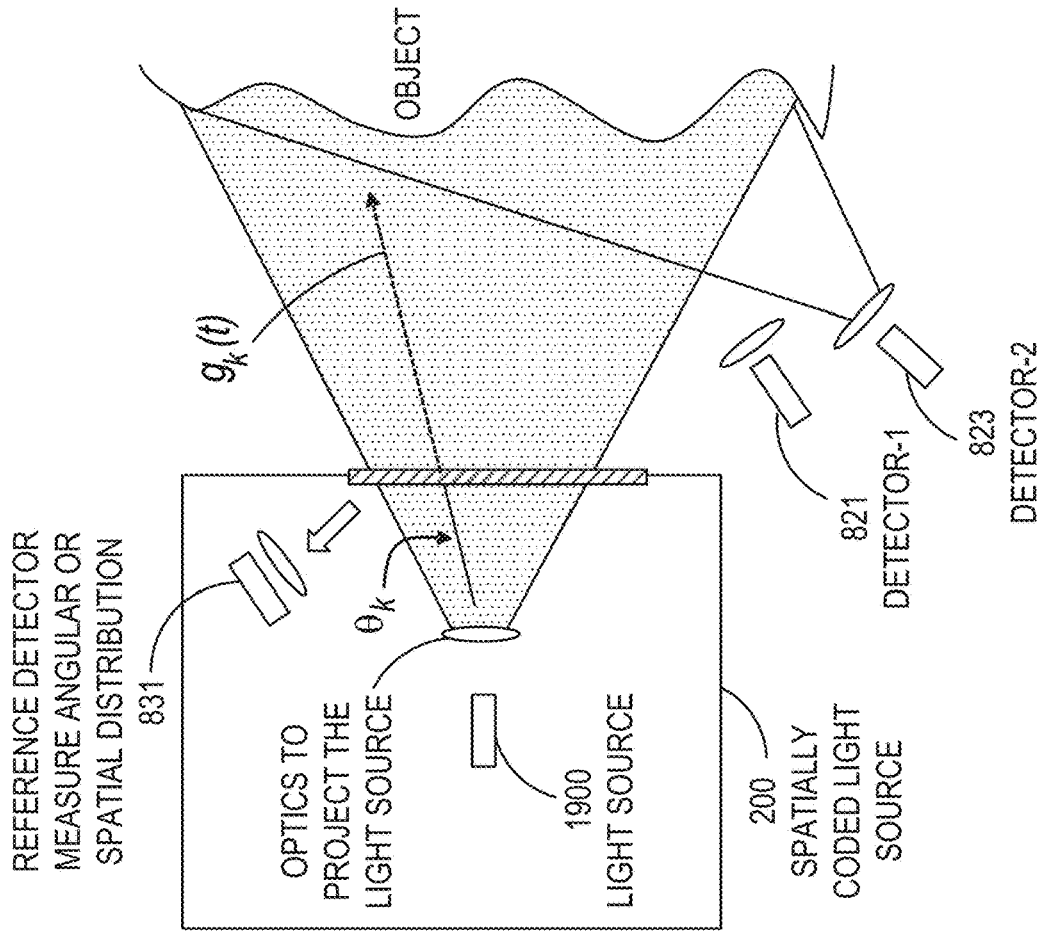
FIG. 21B
FIG. 21A

POLARIZATION CODING
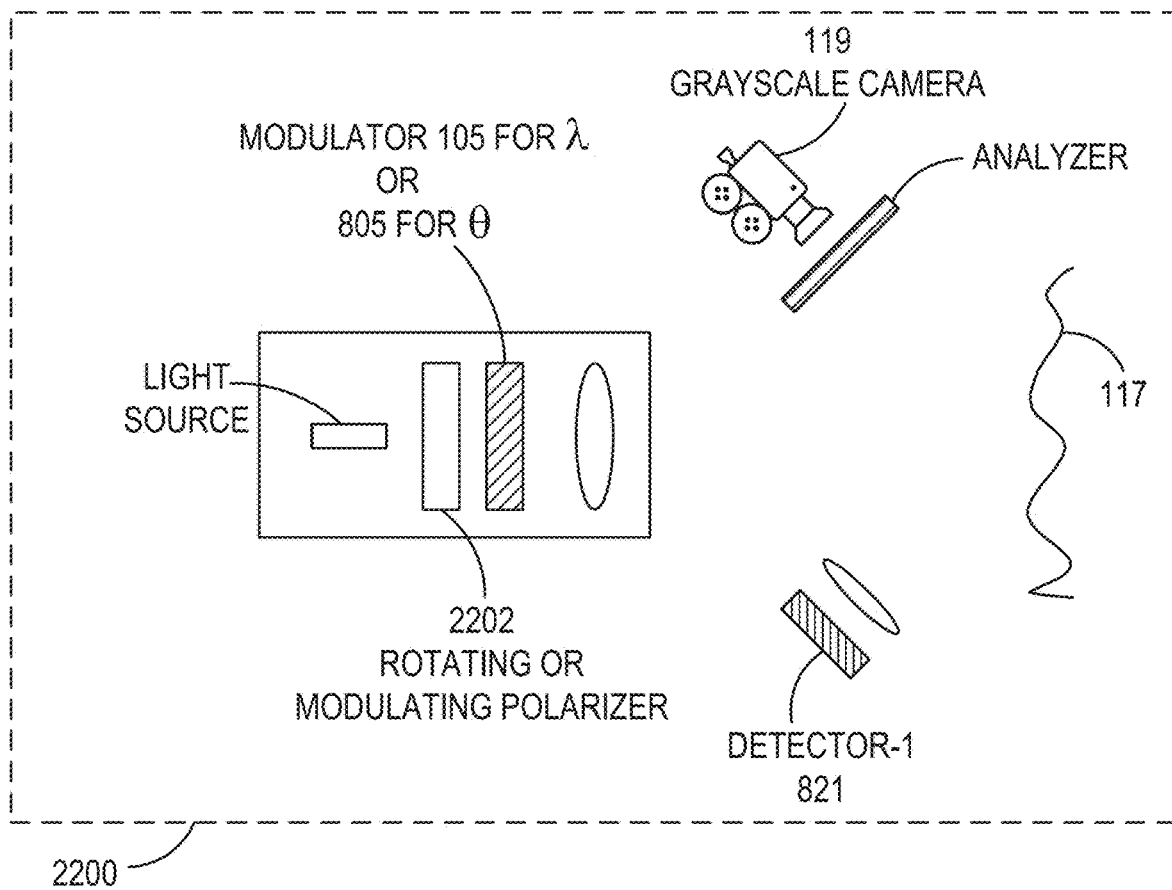
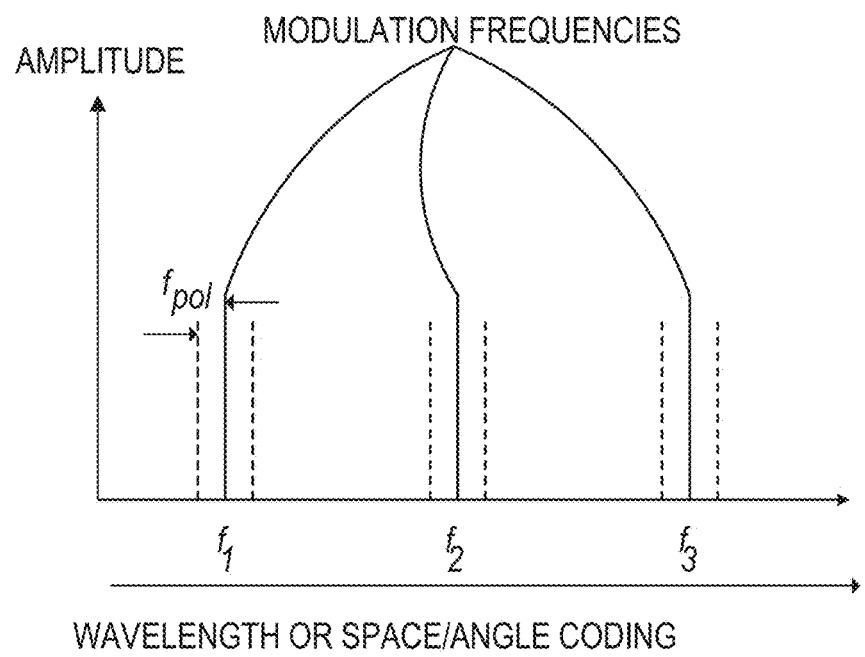
FIG. 24

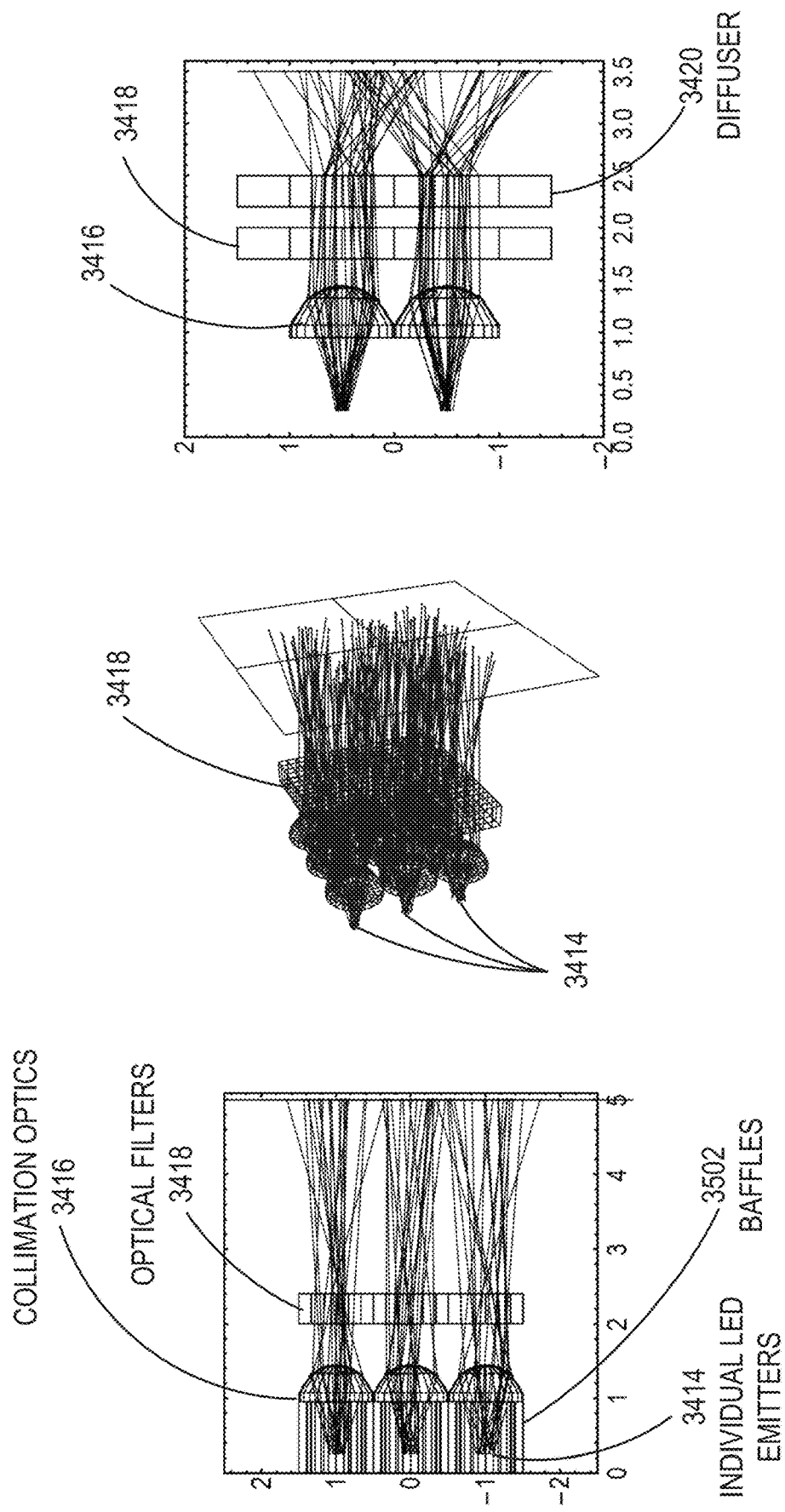

OPTICAL FILTERS SUPPRESS VARIABILITY IN LED SPECTRA

OPTICAL FILTER FWHM = 15 NM

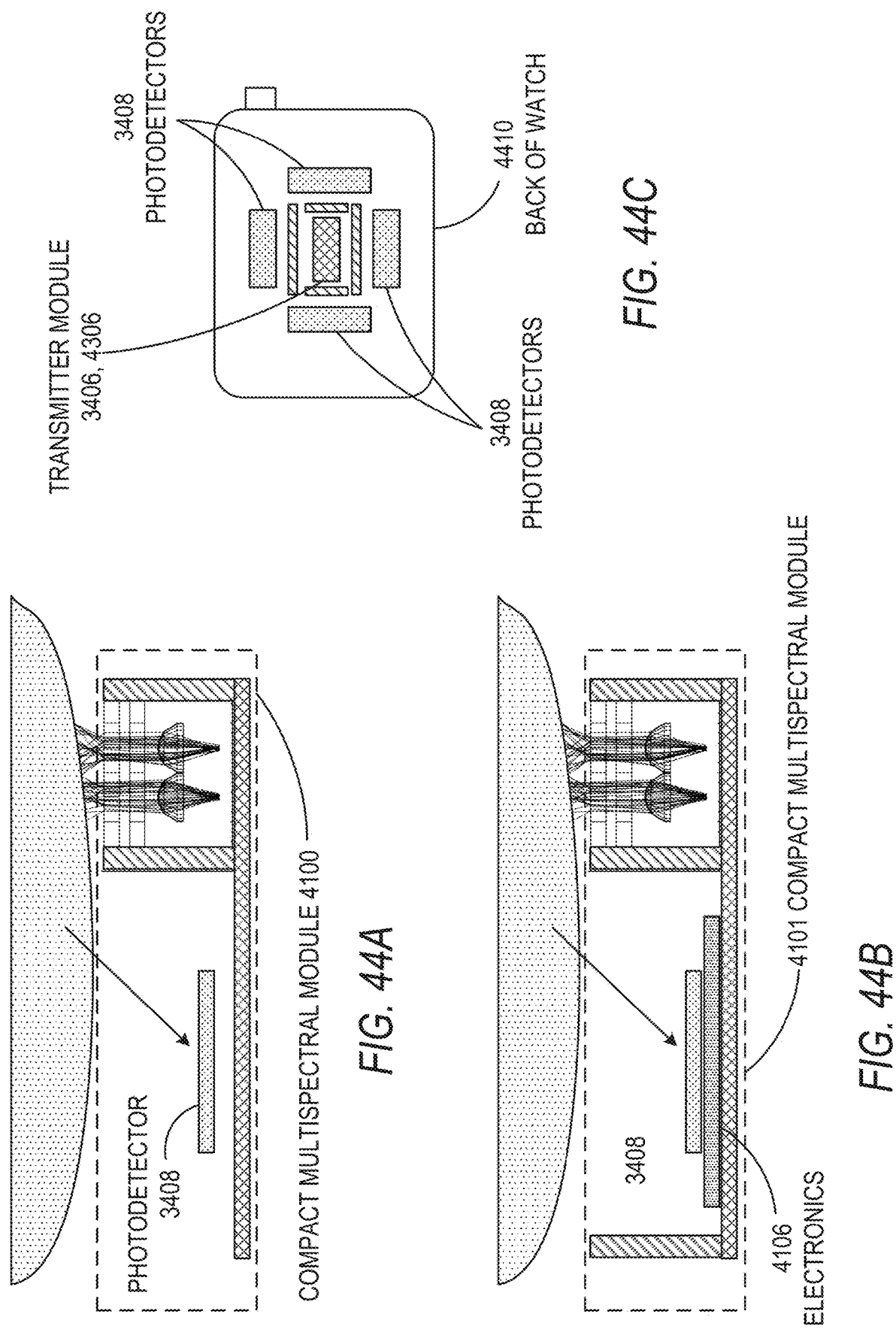

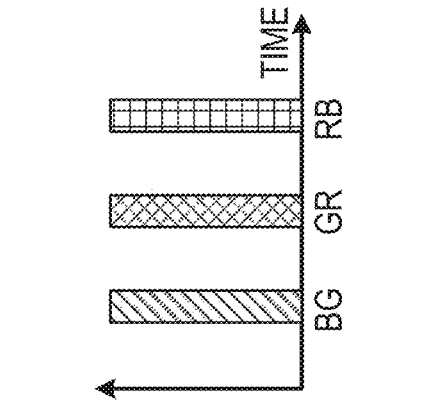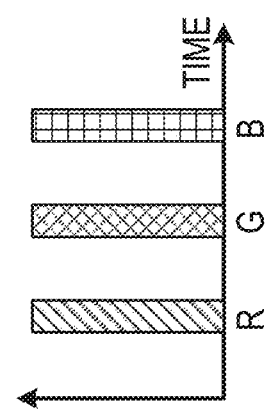
FIG. 50

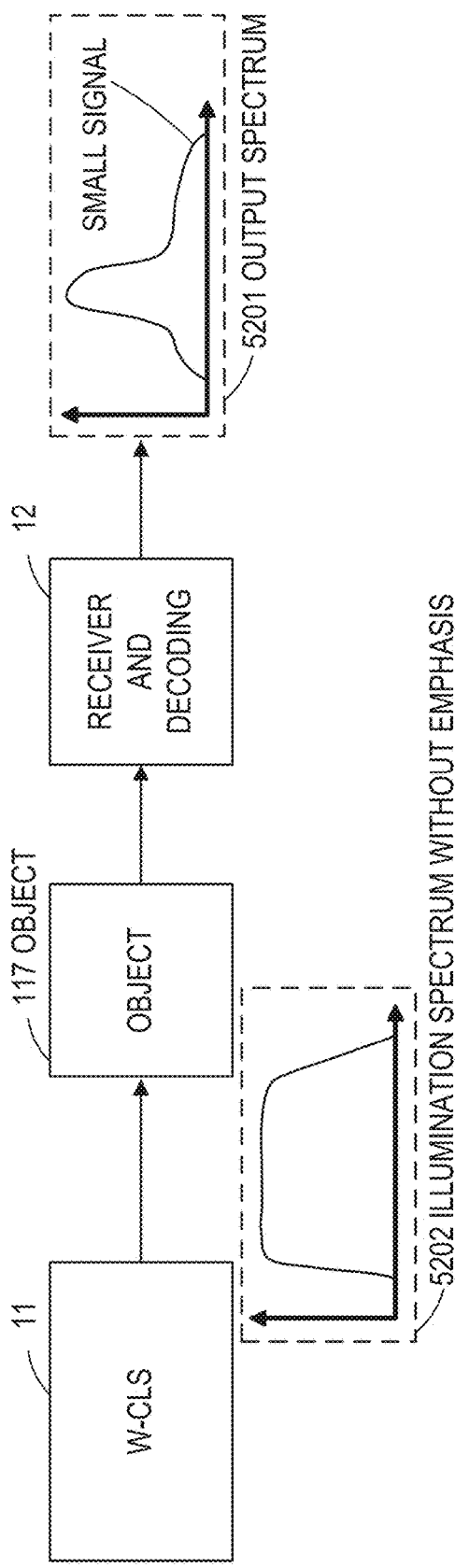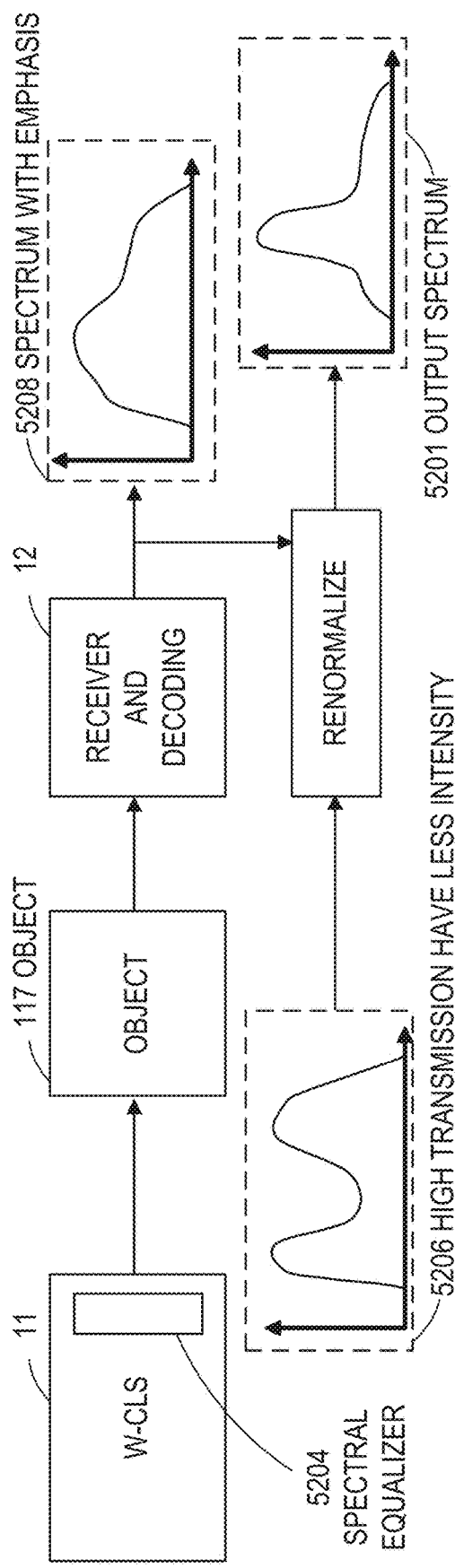

CODED LED OR OTHER LIGHT FOR TARGET IMAGING OR ANALYSIS

CLAIM OF PRIORITY

This application is a continuation of International Patent Application Serial No. PCT/US2022/017503, filed Feb. 23, 2022, which claims the benefit of priority to U.S. Provisional Application Ser. No. 63/262,370, filed Oct. 11, 2021; and 63/202,325, filed Jun. 7, 2021; and 63/200,241, filed Feb. 24, 2021, each of which are incorporated by reference herein in their entirety.

TECHNICAL FIELD

This document pertains generally, but not by way of limitation, to systems, devices, and methods for using coded light such as for target imaging or analysis, such as spectroscopy, such as for wrist-wearable pulse oximetry, e.g., using LEDs, and a number of other applications, or such as of a moving target, for example, such as for semiconductor or other inspection.

BACKGROUND

A general problem of optical characterization or measurement is to measure a change in a characteristic of illuminating light or electromagnetic ("EM") radiation (these terms will be used interchangeably) after it has interacted with a target object. The target object can be characterized by a variation in its spatial or temporal characteristics, which are themselves a function of the wavelength or frequency of the electromagnetic radiation. The response of the target object to external radiation can be denoted by the intensity ("I") of the scattered, transmitted, or reflected electromagnetic radiation. The object will have a different spectral response to different radiation wavelengths $\lambda_1, \lambda_2, \ldots$ etc. at different locations $\vec{r} = \{x, y, z\}$ on the object, and these responses may vary with time t. Thus, an object can be characterized in general by the response:

$$\text{Obj} = I[\vec{r}, t, \lambda_1, \lambda_2, \ldots, p] \qquad \text{Eq. 1}$$

A photodetector can be used, such as in a camera or spectrometer, to detect the intensity response I[ . . . ] from the target object.

A fingertip-worn pulse oximeter to measure blood oxygen saturation is an example of an application of spectroscopy. Different wavelengths of light from light emitting diodes (LEDs) are delivered to one side of a fingertip of a patient or other subject. A light detector on the other side of the subject's fingertip can be used to detect these different wavelengths of light that have passed through the subject's fingertip. The resulting information can be used to determine an indication of the subject's blood oxygen saturation level. But reproducing such spectroscopic blood oxygenation saturation results at another location of the patient's body (e.g., other than on the fingertip, which presents unique physiological advantages) can be difficult. Techniques that work at the fingertip can be complicated by other physiologic considerations when applied at other body locations. There is also a need for multi-spectral measurement in compact and power efficient fashion for many other molecules and materials as well as many other applications including multispectral imaging.

An illustrative application of machine vision is for inspection, such as semiconductor wafer inspection. The semiconductor wafers to be inspected are placed on a moving stage or belt. Providing accurate color images of the moving target integrated circuit die on the semiconductor wafer can be challenging, for a variety of reasons.

Summary/Overview

In one approach to spectroscopy or imaging analysis of a target object or scene, the illuminating light is shined upon the target object to be analyzed, and the task of performing the spectroscopy or imaging or other analysis is performed largely on the receive side, that is, relying on the response signal from the target object or scene after the illumination light has interacted with the object. After such interaction with the target object or scene, the amount of response light available for processing and analysis, e.g., from scattering, reflection, absorption, fluorescence, polarization, or transmission, is generally quite limited—and sometimes extremely limited, making such receive-side spectroscopic optical signal conditioning and corresponding transduced electrical signal analysis challenging.

In contrast to approaches the are overly reliant on receive-side dispersive optics and demanding receive-side signal-processing of the very limited amount of response light from a target object, the present inventor has recognized, among other things, that using a coded light source (CLS) to provide illuminating light onto the target object can help reduce the demanding nature of receive-side optics, transducing, signal-processing of the response light signal from the target object. The CLS illumination can modulation-encode multiple different modulation functions (such as corresponding to different wavelengths or different spectral bins of groups or sub-groups of wavelengths) that can be combined into the illuminating beam upon the target object or scene—such that these multiple different modulation functions can be concurrently delivered to the target object or scene and, similarly, can be concurrently decoded from the target object or scene on the receive side, such as by providing the encoding information and/or corresponding timing information from the transmit side of the system to the receive side of the system for performing the decoding. The use of the term "spectral bin" herein to refer to different groups or sub-groups of one or more wavelengths, which spectral bins may be contiguous or non-contiguous (e.g., with a zone of intervening wavelengths between spectral bins) with each other is intended to allow the term "wavelength" to be referred to interchangeably with spectral bins of such groups of wavelengths.

Thus, the present approach can provide spectroscopic or imaging techniques that can concurrently obtain spectroscopic or spectral imaging information corresponding to multiple encoded and decoded spectral bins. Such a concurrent spectroscopic or spectral imaging approach can be contrasted with a scanning wavelength system approach in which each wavelength (or spectral bin) is presented in sequence such as by a tunable laser or a scanning monochromator, and the resulting output is similarly sequentially obtained and analyzed. Among other things, such a scanning approach takes longer to perform spectroscopic analysis or spectral imaging. Other benefits can also be obtained using the present approach.

For example, in a typical spectrometer each spectral bin is assigned its own photodetector or imager. Thus, very few photons are received by the photodetector or the imager. In such cases, the ability to detect the optical response signal from the target object or scene is limited by the noise of the read-out electronics. The scarcity of response photons might be mitigated by increasing the integration time of the signal processing of the output signal from the photodetector or imager, which would to allow more photons to be collected, actively cooling and decreasing the temperature of the photodetector or imaging sensor to reduce thermal noise, and increasing the intensity of the illumination light to the maximum extent possible without allowing the illumination light intensity to cause changes in the target object sample or scene due to intense illumination light.

By contrast, the present technique, all the response light from the target object or scene arrives at the photodetector or other imaging sensor at the same time (concurrently) for all the spectral bins. This means that the total number of photons received by the photodetector or imaging sensor can be many times larger than in the typical approach described above. This can be enough to overcome the receiver noise of the photodetector or imaging sensor, such that the response signal detection is limited merely by unavoidable Shot-noise. Furthermore, because the optical illumination signal can be concurrently modulated for the different spectral bins, and concurrently demodulated and measured continuously for the different spectral bins, some of the practical problems of dark currents, 1/f noise and drifts in that may otherwise occur due to long integration time can be avoided. This, in turn, can allow reducing illumination light intensity or integration time, or can permit using lower-cost photodetectors or imaging sensors that need not be actively cooled. Thus the CLS illumination coding of different spectral bins and corresponding decoding of the different spectral bins can help provide enormous practical advantages, and can make practical acquisition and analysis of weak signals.

The present inventors have recognized, among other things, that existing approaches of optical characterization or measurement of a target object may have limitations, including requiring calibration, which may be cumbersome or difficult. For example, in an approach, the response I[ ... ] of Eq. 1 can represent one or more of reflectance, transmittance, or scattering properties of the object such as for different polarization states p. A photodetector or other response light transducer or response light detector, such as in a camera or other imaging device, a spectrometer, or other device can be used to measure one or more aspects of the same object, such as from the same or different viewpoints. In an approach, the imaging device can map location on the object onto a pixel or similar location of the light sensor, and thus just measures the two-dimensional projection from the target object onto the light sensor. Therefore, the camera or other imaging device measures the subtended angles on the target object with the imaging system located at an origin of a coordinate system:

$$\mathrm{Obj} = I[\theta_x, \theta_y, t, \lambda_1, \lambda_2, \ldots, p] \qquad \text{Eq. 2}$$

In an approach using a camera, the absolute distance of the target object is likely unknown, and only its apparent angular size is projected onto the focal plane of a lens of the camera. Depending on the context, the term $\vec{r}$ is used interchangeably with $\{\theta_x, \theta_y\}$, with the intensity/being the transmitted, reflected, or scattered light from the target object. In an example, the distance to the object can be measured, such as using time-of-flight (ToF) or by triangulation.

Some illustrative examples of different types of optical devices that can be used to measure I or a close representation of/are listed in Table 1.

TABLE 1

Various approaches in which object's properties can be measured.

| | | |
|---|---|---|
| Grayscale Camera: | $I[0_x, 0_y, t_0, \text{"All visible"}]$ | A whole group of visible wavelengths can be combined into one bin and taken at a specific time $t_0$ |
| RGB Camera: | $I[0_x, 0_y, t_0, \text{"R G B"}]$ | Each location can be divided into three spectral bins |
| RGB movie: | $I[0_x, 0_y, t_k, \text{"R G B"}]$ | Generates a series of RGB pictures generated at times $t_k$ |
| Spectrometer | $I[X, t_k, \lambda_1, \lambda_2, \ldots]$ | Response at many wavelengths can be measured from a specific object location. |
| Hyperspectral Camera | $I[0_x, 0_y, t_k, \lambda_1, \lambda_2, \ldots]$ | Extension of a color camera with more than 3 wavelength groups per location on the object. |
| LIDAR system | $I[0_x, 0_y, z, t_k, \lambda_1, \lambda_2, \ldots]$ | 3D information can be measured by using ToF for EM radiation to travel to the object and back to the detector, along with the angular position of the object |

The above illustrative exemplary list of Table 1 is quite general. In some cases, it can be advantageous to measure the response of the target object to different states of polarization of the illuminating light. In another approach, a thermal imaging camera can capture a grayscale picture of blackbody radiation emanating from a warm object, with such emanating radiation being in the wavelength range of between 7 micrometers and 12 micrometers, similar to the way in which a Black and White camera operates with visible light. In another approach, a two-color thermal camera can be implemented, such as by having some pixels of the camera's light detector respond to one group of light wavelengths and the other group of pixels responsive to different light wavelengths. These different group of pixels may be interspersed amongst each other similar to interspersing pixels in a RGB camera for ordinary visible light.

In general, a camera can provide one-dimensional or two-dimensional information by having an array of pixels that is sensitive to a group of wavelengths of light. A one-dimensional camera can be converted into two-dimensional imager by "scanning" the other dimension.

A spectrometer can provide a spectrum of the incident light, i.e., the spectrometer can decompose the incident light into different wavelength components or "bins" and can provide a light signal proportional to the energy of the light in each of the wavelength bins. The incident light may be used to illuminate a target object under test, and interaction of the illuminating light with the target object can produce scattered, reflected, or transmitted light from a region of the target object under test.

In an approach in which only the object's true reflectance or transmittance is of interest, the spectral variation of the illuminating light can be "divided out". This can be accomplished by calibrating the spectrometer with illumination alone, such as by using a "white card" and a "black card" in place of the target object, to calibrate dark response and white response of the source-sensor combination without the target object being present. Such a calibration procedure can be quite cumbersome and repeating the calibration may be needed, such as before every measurement, or after a few measurements, or every few days, or the like.

In an approach to using a sensor, such as those sensors mentioned above, a source of illuminating electromagnetic radiation first impinges on the object and then the scattered, reflected, or transmitted light is collected. For each of the parameters in the argument of the intensity function of Equation (1), a pixel or other light detector can be assigned. For example, in a grayscale camera having a two-dimensional array of pixels, each pixel represents light gathered over a group of light wavelengths at angles ($\theta_x$, $\theta_y$) as projected onto the target object. In a RGB camera, each pixel can additionally be provided with an optical filter that can function to respond to a specific group of light wavelengths. Thus, the task of determining a target object's characteristics falls on the light receiver—be that a camera or a spectrometer.

In such an approach, the illuminating light is shined upon the target object to be analyzed, and the task of performing the spectroscopy or other analysis is performed after the illumination light has interacted with the object. After such interaction with the target object, the amount of response light available for processing and analysis, e.g., from scattering, reflection, absorption, fluorescence, polarization, or transmission, is generally limited, making such receive-side spectroscopic optical signal conditioning and corresponding transduced electrical signal analysis challenging.

For example, in order to ascertain the true response of the target object (e.g., in reflection, transmission, or scattering mode), multiple steps may be needed. The user may be required to carry out "dark" calibration, such as to measure internal leakages in the signal processing electronics. Then, the user may be required to carry out a "white card" calibration. The white card calibration presumably reflects all colors equally. Therefore, the white card calibration allows measurement of the product of the light source spectrum and a transfer function of a receive-side dispersive optics system (e.g., using the white card in place of the target object). After the dark calibration and the white card calibration, a response characteristic of the target object can be measured. The first two steps (e.g., dark calibration and white card calibration) will need to be carried out recurrently, such as periodically, such as to ensure accuracy—and possibly before every measurement of the response characteristic of the target object. This can be quite cumbersome.

Furthermore, there may be no easy way to provide wavelength-specific calibration. In such an approach, the light source may need to carry wavelength-specific calibrating sources. Such wavelength-specific calibration sources can be expensive and mostly feeble, such as relative to the actual illumination light power that is used. Thus, it may be practically difficult to provide "on-line" wavelength-specific calibration. A spectrometer may have internal wavelength-specific calibration, but such calibration may require that the measurement of the response of the target object be stopped, and the wavelength-specific calibrating source be placed at the input of the system-such as in a required manner such that during such calibration, light must arrive at the receive optics and photodetector in a manner similar to that in which the actual response light would have arrived from the target object.

In contrast to approaches the are overly reliant on dispersive optics and demanding signal-processing of response light from a target object, the present inventor has recognized, among other things, that using a coded light source (CLS) to provide illuminating light onto the target object can help reduce the demanding nature of receive-side optics, transducing, signal-processing of the response light signal from the target object.

For example, the present techniques can include an approach that can include a particular form of active illumination and sensing, such as in which direct measurement of one or more properties of the target object can be carried out using coded active illumination light upon the target object. On the receive side, the encoded information can then be decoded from response light received from the target object. This approach can thereby help ease demands on other receive side componentry, such as receive-side optics, transducing, or signal processing circuitry constraints operating using the more limited response light available from the interaction with the target object.

In an example, the present CLS approach can be accomplished using an ordinary light source, such as a light bulb, a LED, or a laser for generating light for use in illuminating the target object. The light generated by the light source can be divided into several or many light components, such as corresponding to several or many spatial or spectral bins (e.g., not limited to using just 3 spectral bins, such as RGB, but also permitting use of more spectral bins, such as 10s, 100s, 1000s of bins, or the like). The various divided light components can be modulated or otherwise encoded, such as using different specified time-varying mathematical encoding functions corresponding to the individual bins of the divided light components of the light generated by the light source. After encoding, the subdivided encoded divided light components can then be re-combined, such as to re-synthesize the light source as a coded light source (CLS). The CLS can be used to illuminate the target object or scene, such as to concurrently deliver various modulation-encoded spectral bin light components via an illumination beam to a target object or scene. A resulting reflection, transmission, or scattering (response light) from the coded re-combined illumination light directed upon the target object or scene can be detected and measured, such as can include using one or more photodetectors, which can be arranged or otherwise configured based on a particular wavelength region or other characteristic of interest. Using a photodetector and associated signal processing componentry having a temporal bandwidth matching or exceeding any requirements resulting from the temporal encoding that was carried out for providing the CLS, a reconstruction algorithm or technique can be applied to the response light, such as to recover information about properties of the target object or scene that are particularly associated with one or more attributes or characteristics (e.g., wavelength) associated with the corresponding coding functions of the CLS. For example, for a spectrally-encoded CLS, spectra of the target object or scene can be measured using a single photodetector (or multiple photodetectors) without requiring using any dispersive optics acting upon the response light provided resulting from the illumination light interacting with the target object or scene. Such reconstruction can be applied concurrently or simultaneously such as can include using multiple photodetectors that can be located, positioned, or oriented differently from each other, such as relative to the target object or scene. Also, the approach of coding illumination light via a CLS and decoding the response light can be fully compatible with further higher frequency modulation of the light source, such as for using the system to recover the frequency response of response light in the MHz to GHz range. This can allow concurrently obtaining a complex response (e.g., amplitude vs. high frequency) from the target object or scene, and this can be obtained by detecting and measuring light from a single photodetector, if desired, or from multiple detectors. Thus, the present approach can provide spectroscopic techniques that can concurrently provide spectroscopic information corresponding to multiple encoded and decoded spectral bins. Such a concurrent spectroscopy approach can be contrasted with a scanning wavelength system in which each wavelength (or spectral bin) is presented in sequence such as by a tunable laser or a scanning monochromator, and the resulting spectroscopic output is similarly sequentially obtained and analyzed. Among other things, such a scanning approach takes longer to perform spectroscopic analysis. Other benefits can also be obtained using the present approach.

This document also describes, among other things, techniques such as can include one or more of systems, devices, methods, or articles of manufacture, such as which can allow combining light of different wavelengths or colors from respective individual ones of multiple LEDs. The present techniques can help provide a more stable spectral measurement or spectral analysis of a biological or other target-such as even while the underlying illumination spectra corresponding to the LEDs can vary. For example, the underlying LED spectra can vary due to temperature, bias current, manufacturing variations, or aging effects.

The present techniques can be applied to spectral measurements in many application areas. While this document focuses on applying the present techniques to spectroscopic measurement and analysis in a blood oxygen saturation application that can be advantageous at locations other than at a subject's fingertip (for example, in a wrist-worn "smartwatch" type wearable device), such techniques can be applied to other commercial and research applications. Some illustrative examples of such other applications can include, for example, quality measurements in agricultural products, process control in industrial manufacturing, and many other examples of multicolor spectroscopy or hyperspectral imaging.

LED-based spectroscopic analysis of a composition of a target (e.g., SpO2, glucose, etc.) can include individual LEDs having corresponding downstream collimation or focusing optics (such as lenses or reflectors), and one or more further downstream optical filters, such as can accommodate variability in LED light emission characteristics by optical filtering. Response light from the target can be detected and analyzed for the spectroscopic analysis. Analysis of the response light can optionally include decoding of encoded optical modulation functions that can optionally be imposed onto the illumination light. Baffles or apertures can be used to constrain light provided by particular LEDs. A light diffuser can be included to homogenize light wavelengths for illumination of the target. A beam combiner can be used to co-locate illumination light at a common exit illumination location from a device to illuminate a common entry location of the sample providing the target being analyzed. Diffractive or sub-diffractive optical elements, geometrical phase optical elements, or metamaterial elements can be used in the individual optical pathways, such as to help collimate, filter, or direct light toward a shared target incidence location.

The present techniques (e.g., such as including optical wavelength filtering, such as with pre-filtering collimation) can help provide spectrally well-defined illumination light from each of the potentially broadband light sources, such as can include individual LEDs or SLEDs. The present techniques can also help provide a well-defined projection beam into a sample, which can significantly reduce unwanted scatter, which, in turn, can help to ensure that the illumination photons reach the nearby photodetectors such as to be detectable as response light. The present techniques can include coding or modulation of illumination light, such as using orthogonal encoding functions, such as described or incorporated herein, which can help allow concurrent illumination. Concurrent coded illumination can help improve the SNR, which may otherwise suffer as the number of different wavelengths is increased and a sequential illumination scheme is used.

In case of $SpO_2$, the response signal can be measured at sufficiently high measurement repetition rate, such as at 50 Hz, so as to recognize and compensate for any pulsatile component in the response signal, such as superimposed by the cardiac stroke of a beating heart. The Ratio of Ratio (RoR) described herein can be calculated, from which an oxygen level determination can be made. When there are many more different illumination light wavelengths, then a more sophisticated fitting can be used to fit the spectrum of the analyte concentration. This can be performed for the AC/DC ratio at each wavelength, for the "DC" spectrum, or both. The changes in the "DC" spectrum across different photodetectors at different locations can provide a direct measure of absorption and scattering coefficients from the tissue sample or other target object, and can be used to monitor chemical and structural changes over time. The AC/DC spectrum (or the ratio spectrum) can be useful in that it can allow measuring changes in the arterial blood (or anything that pulses with the heart) and can allow tracking of one or more analytes in the blood.

The above-described measurements can be applied to one or more other analytes, such as glucose or alcohol. Because the spectra of these molecules can be affected by small changes in the amount of the target analyte present, such molecules can benefit from a detection technique having providing high SNR. But good measurements can also benefit from high spectral certainty. Thus, the present techniques can be used to provide an appropriate illumination spectral width (corresponding to illumination at a particular illumination wavelength) to retain the spectral features of the analyte, such as to help produce high contrast to help reduce measurement error of measurements that can be made at multiple illumination wavelengths. Such an approach can be helpful to measure changes in the analyte in the presence of background spectral influences and shifts. The present techniques can help enable in-vivo measurement in humans as well as measurement of other molecules in other samples or target objects, such as plant or other media.

This document also describes how coded light illumination can be used with a focal plane array (FPA) light imager receiving response light from a moving target object, such as for machine vision inspection of integrated circuit (ICs) or semiconductor wafers or other parts to be inspected on a moving stage or belt. The illumination light can be encoded with orthogonal functions, such as an RGB illumination sequence, or a sequence of combinations of spectrally contiguous or non-contiguous colors. This approach can provide advantages over certain other approaches, such as a dichroic combiner or a 3 CCD imaging system using dichroic splitting at a camera as opposed to at the illumination side. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file may contain at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2B shows a diagrammatic example of a Coded Light Source (CLS) approach to spectroscopy.

FIGS. 14A, 14B show an example of how coding can be provided at the various important wavelengths of interest for a particular gas, aerosol, or particulate measurement.

FIGS. 16A, 16B, 16C, 16D, and 16E show examples of an active slit or active strip, such as can be used in a CLS system.

FIG. 17A shows an example of a detailed ray trace associated with a vertical active slit, such as can be made up of an arbitrary combination of the light emitters.

FIG. 17B shows an example of a detailed ray trace associated with a horizontal active slit 1702, such as can be made up of an arbitrary combination of the light emitters, such as in the arrangement shown in FIG. 17C.

FIG. 17C shows an active slit with an aperture at a plane of dispersion shaped to reject higher order spectra.

FIG. 17D shows the aperture of FIG. 17C, at which the plane of dispersion is located at a rotating permanent mask modulator, as an illustrative example.

FIGS. 18A, 18B show an example of a CLS arrangement that can include multiple light sources and a reflective (or transmissive) grating and a pinhole in a screen that can be used to pass desired wavelengths from the grating, with the screen being used to reject undesired wavelengths from the grating, detecting response light elicited in response to the incident CLS.

FIG. 21A shows an example of an S-CLS.

FIG. 21B shows an example of a waveguide-based implementation of a multifunction modulator for S-CLS.

FIG. 24 shows an example of a CLS system such as can include a linear polarized light source in a S-CLS or W-CLS system configuration.

FIGS. 35A, 35B, and 35C show illustrative examples of an arrangement of components and accompanying illustrative ray traces of an optical transmitter of a practical system for multi-wavelength spectroscopic analysis of a biological or other target or object. FIG. 35C shows an example in which the optional optical diffuser can be included, and the resulting ray traces.

FIGS. 44A, 444B, and 44C show various views of an example of a configuration in which an optical transmitter module can be included on the back of a smartwatch or similar wrist-worn or other wearable device.

FIG. 49B) and arbitrary wavelength components (FIG. 49C) that can be spectrally contiguous or non-contiguous.

FIG. 50 is a diagram comparing various versions of the techniques described with respect to FIGS. 49A, 49B, and 49C to help explain some potential benefits of substituting combined spectral channels (e.g., such as shown in FIGS. 49B and 49C) in place of the simple RGB channels shown in FIG. 49A.

FIGS. 52A-52B are conceptualized schematic block diagrams illustrating an example of equalization and using feedback for dynamic spectral intensity control of the spectrum of the modulation-encoded CLS optical illumination light beam.

DETAILED DESCRIPTION

Section A: Coded Light Examples for Target Imaging or Analysis

This Section A explains, among other things, how light can be modulation encoded, such as for imaging or analyzing a target object or scene, using different spectral bin light components. Individual ones of the different spectral bin light components can include an individual wavelength or wavelength distribution. The target object or scene can be illuminated using different spectral bin light components that are modulation encoded, using respective different time-varying modulation functions. These modulation encoded different spectral bin light components can be combined into an illumination light beam for illuminating the target object or scene to be imaged or analyzed. For example, the illumination light beam can concurrently provide the modulation encoded at least two individually modulated different spectral bin light components to the target object or scene. In response to the illumination light beam illuminating the target object or scene, the resulting response light can be used to produce an electrical response signal. From this electrical response signal, using information about the respective different time-varying modulation functions, the electrical response signal can be decoded, such as to recover information about a respective response parameter of the modulation encoded different spectral bin light components to provide a spectral bin response output affected by the target object or scene.

1. Introduction to CLS Vs. Non-CLS Approaches, and Examples of CLS

Figure 2A:
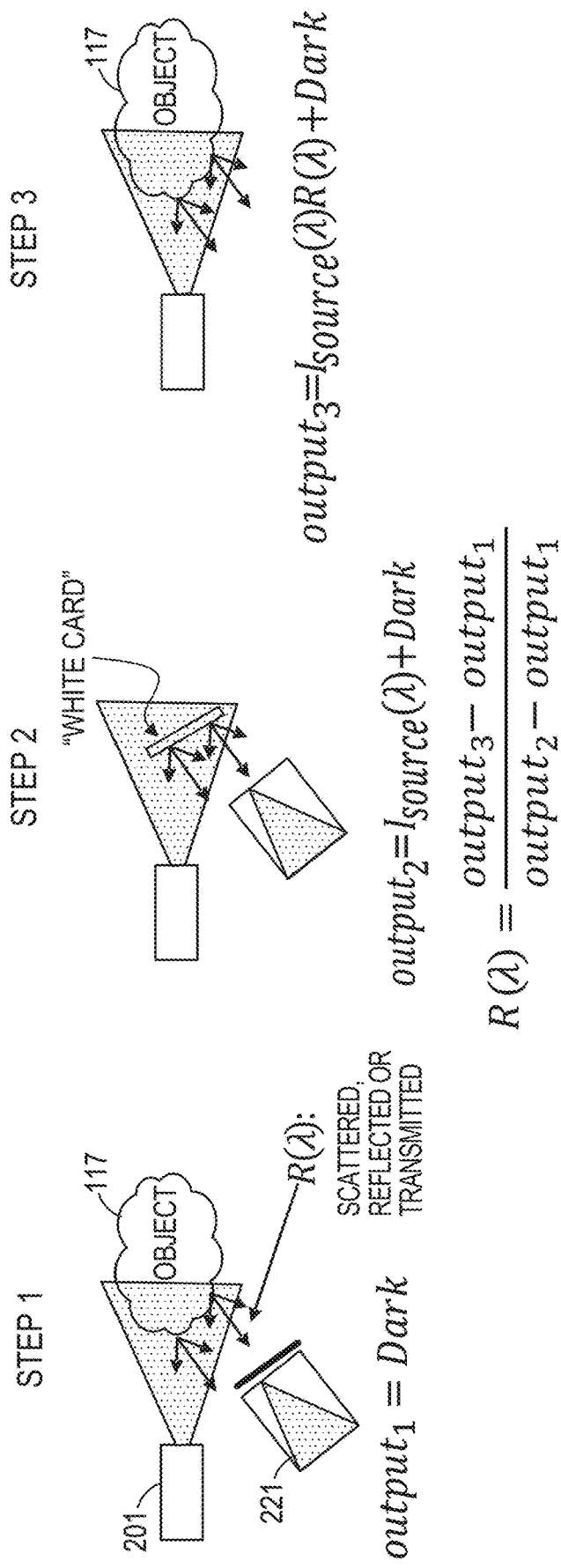
FIG. 2A shows a diagrammatic example of a non-Coded Light Source (non-CLS) approach, for comparison.

Using spectroscopy as an illustrative use-case example, FIG. 2A shows a non-Coded Light Source (non-CLS) approach, which can be compared to a CLS approach to spectroscopy, such as shown in FIG. 2B.

In FIG. 2A, on the light-transmit side of the system shown, a non-CLS light source 201 can be used to illuminate a target object or scene 117. The non-CLS illumination light can interact with the target object or scene 117, which results in response light $R(\lambda)$, such as from scattering, reflectance, or transmission. Some of the response light $R(\lambda)$ is directed toward a light receiver 221, such as can include dispersive system optics for performing spectral separation on the response light $R(\lambda)$ before detection at a light detector and processing by signal processing circuitry or componentry. Thus, in the example of FIG. 2A, the light source 201 illuminates the object and then the task of spectral separation and measurement is carried out on the limited response light $R(\lambda)$ after the light has interacted with the target object or scene 117. Cumbersome or inefficient calibration may be required, such as described previously above, and such as shown at Step 2 of FIG. 2A, before the output can be used to determine spectral characteristics of the response light $R(\lambda)$, such as for determining one or more spectroscopic properties of the target object or scene 117, such as shown at Step 3 of FIG. 2A.

FIG. 2B shows an illustrative example of an approach for using CLS such as to perform spectroscopic analysis of the spectroscopic properties of the target object or scene 117. A multispectral coded light source, such as described further in detail below, can include a CLS 100, such as to provide coded light, such as for illuminating the target object or scene 117. In this illustrative example, the CLS 100 can be wavelength-encoded such that each wavelength group of interest has been differently encoded, such as to provide a wavelength-encoded CLS (or W-CLS) 100. For example, each contiguous or non-contiguous wavelength group of interest (also referred to as a "spectral bin") can be encoded with a unique temporal modulation pattern or function in time or can be provided with an identifiable modulation code, and the modulation-encoded light from the various different wavelength groups (spectral bins) of interest can be re-combined to provide illumination light output from the W-CLS 100, such as for illuminating the target object or scene 117. The encoded light from the CLS 100 can be received by one or more light detectors, and beam-splitting or another technique can be used to direct the encoded light as desired. For example, a reference portion of the encoded light from the CLS 100 may be directed to a reference detector 131, rather than at the target object or scene, to which an illumination component of the encoded light from the CLS 100 can be directed toward the target object or scene, from which response light $R(\lambda)$ can be scattered, reflected, or transmitted, and detected by one or more light detectors 141. In such an approach, the reference portion of the encoded light can be transduced into an electrical signal and used for normalization or calibration of the detected response light $R(\lambda)$, such as to reduce one or more effects of system variability on the detecting and signal processing of the response light $R(\lambda)$ that has interacted with the target object or scene 117. Thus, the reference detector 131 can include a light source measurement transducer, which can be optically coupled to receive a portion of light provided to form the light beam, prior to or without illuminating the target object or scene 117. The reference detector 131 can be used to produce an electrical illumination variability indication signal that is independent of the target object or scene 117. The signal processing circuitry 13 can be configured to use information from the illumination variability indication signal and information about the respective different modulation functions, to recover information about the parameter of the modulation-coded different wavelength components to provide the color response output affected by the target object or scene 117. The term "color response" output is intended to refer to a response having components that occur across different wavelengths or spectral bins.

In the example of FIG. 2B, each of the light detectors can produce a complex time-varying detected response light signal. This can be analyzed by signal processing componentry, such as to retrieve individual wavelength group components of the response light signal spectrum, since the CLS illumination light was encoded with unique modulation functions corresponding to the individual ones of the different wavelength groups. A group or array of light detectors can be used to form a gray scale camera 119, which can be used to produce a hyperspectral or multi-spectral image. Each response light detector can effectively act as a spectrometer, such that there is no need for requiring a traditional spectrometer with its complex and inefficient dispersive optics. Thus, the present CLS approach can help enormously boost light gathering power, which can help enable new applications. The present CLS techniques can also be used to provide unique modulation functions corresponding to different directions of light emerging from the CLS. In such a directional-encoding CLS approach, each light detector can be used to generate a direction-dependent map of the target object or scene 117. The direction-dependent map can be one-dimensional or multi-dimensional. For example, if the direction-dependent map forms a one-dimensional map, then it would form a line image at the light detector 141.

To recap and further explain, the present CLS approach can relate to generation of a coded light source in which different optical wavelengths (or one or more other degrees of freedom, such as directions or polarization) can be temporally modulated for encoding. Such encoding can include unique temporal signatures or codes or functions. The resulting response light signal detected by the one or more response light detectors 141 can be processed by signal processing componentry, such as to decipher or digitally reconstruct one or more characteristics of the response of the target object or scene 117 to the illumination light encoded with the one or more degrees of freedom. The response light from the target object or scene 117 may include one or more of scattered, transmitted, or reflected EM radiation. Thus, for example, every coded degree of freedom can be received, detected, and recovered at each of the one or more response light detectors 141. For example, such a system using a CLS, when used as a spectrometer, can provide separate reading of individual ones of the encoded spectral bins at each of the response light detectors 141. No specialized dispersive optics are required on the receive side, such as at or corresponding to the response light detector 141. This can help provide an enormous advantage over an approach requiring such dispersive optics, since it makes it possible to concurrently measure the optical response of the target object or scene 117 from multiple locations, at which one or more light detectors 141 can be placed, without incurring the significant added cost and bulk of requiring dispersive or imaging optics placed in the optical path before each response light detector. Detailed examples and preferred embodiments on practical implementations are described further in this document. Since individual ones of the coded degrees of freedom can be encoded using different time-varying functions, DC offsets such as dark current or low frequency noise sources can be automatically removed from the response light signal. The present approach allows judiciously placing or locating one or more light detectors before and after interaction of the coded illumination light with the target object or scene 117, which can help attenuate or even eliminate many sources of drift or offset in the signal.

The present CLS approach can extend beyond techniques such as chopping, strobing, or phase-modulating or amplitude-modulating. For example, (A) chopping can include chopping a light beam at a fixed rate, and then using a lock-in detection to reduce noise in measurement; (B) strobing the light can "freeze" motion of one or more fast-moving objects; or (C) phase modulating or amplitude modulating light at high frequency can be used to measure time-of-flight (ToF) of the light to and from a target object. In all such cases (A), (B), or (C) only one or two "chopping" frequencies are used. By contrast, in the present CLS approach, many different degrees of freedom can be concurrently encoded-more than three, generally, 10s, 100s, or even 1000s of degrees of freedom are concurrently encoded onto the CLS, which can then be used to illuminate the target object or scene 117. This difference in degrees of freedom can provide vastly and disproportionately different capabilities as compared to mere chopping, strobing, or phase-modulating or amplitude-modulating illumination light. In an example of the present approach, after the illumination light interacts with the target object or scene 117, a light detector 141 is used to collect the response light from the target object or scene 117, and such response light contains the coded degrees of freedom. Thus, the tagged degrees of freedom can then be computationally separated by signal processing componentry, such as to recover a property or characteristic of the target object or scene 117 corresponding to the individual ones of the various coded degrees of freedom.

TABLE 2

Illustrative Examples of Coding of the CLS with various coded degrees of freedom.

| Coded degree of freedom | Name/ Abbreviation | Example of Capabilities | Examples of uses/advantages |
|---|---|---|---|
| CLS codes for different light wavelengths | W-CLS | Single detector (or multiple detectors) can retrieve the entire spectrum | Calibration free spectrometer with high SNR; wide band measurement; |
| CLS with high frequency modulation and codes for different wavelengths | W-CLS w HFM | Can measure phase or temporal delay as a function of modulation frequency at all wavelengths | Direct measurement of absorption and scattering parameters in diffuse media; string of fiber Bragg sensors. |

TABLE 2-continued

Illustrative Examples of Coding of the CLS with various coded degrees of freedom.

| Coded degree of freedom | Name/ Abbreviation | Example of Capabilities | Examples of uses/advantages |
|---|---|---|---|
| CLS codes for different angles or projected locations in space | S-CLS | Single detector (or multiple detectors) can retrieve line image or image formed according to illumination pattern | High SNR and particularly useful in IR and regions of EM spectrum where light detector arrays are difficult to make and light sources are weak |
| CLS with high frequency modulation and codes for different angles or projected locations in space | S-CLS w HFM | Can measure distance to the object at all coded space locations | Scanner-less system; extensible to IR and THz regions. |

The examples in Table 2 can also be encoded by polarization as an additional degree of freedom. Such polarization encoding of illumination light can help provide even more details about the target object or scene 117 at each light detector 141.

2. Spectral/Wavelength Coded Light Source (W-CLS)

Figure 1:
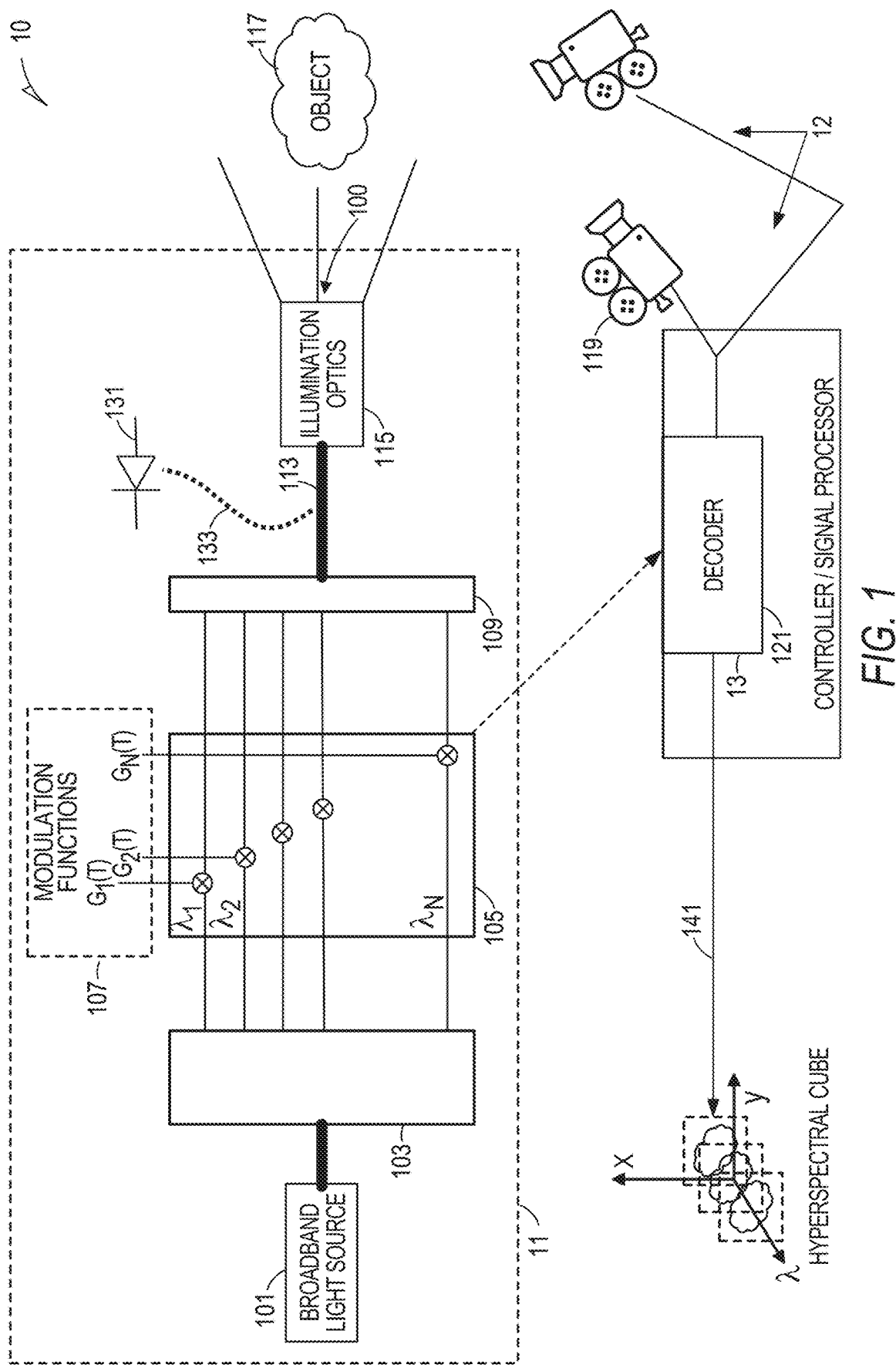
FIG. 1 is a block schematic diagram showing an illustrative example of portions of an optoelectronic system configured for using coded light for imaging or analysis of a target object or scene, such as for hyperspectral imaging or other spectroscopic analysis or imaging.

FIG. 1 is a block schematic diagram showing an illustrative example of portions of an optoelectronic system 10. The system 10 can be configured for using coded light for imaging or analysis of a target object or scene 117, such as for hyperspectral imaging or other spectroscopic analysis or imaging, such as described herein. In the example of FIG. 1, an optical illuminator or transmit portion 11 of the system 10 can include or be coupled to a light source 101, such as a broadband light source, generating input light from which an output coded light source (CLS) 100 can be generated or provided, such as for illuminating the target object or scene 117.

More particularly, light from the light source 101 can be received by a spectral separator 103. The spectral separator 103 can be configured to separate (e.g., spatially or interferometrically) the light output or otherwise provided from the light source 101 into different spectral components, such as into 4 or more (e.g., 10s, 100s, 1000s) of spectrally contiguous (joint) or spectrally disjoint wavelength component groups or bins ($\lambda_1, \lambda_2, \lambda_3, \ldots, \lambda_n$). The separated spectral light wavelength components ($\lambda_1, \lambda_2, \lambda_3, \ldots, \lambda_n$) can be output or otherwise provided from the spectral separator 103, such as via corresponding output channels, and can be input or otherwise received by an encoder such as a multi-function optical modulator 105, such as via corresponding input channels of the multi-function modulator 105. The modulation provided by the optical modulator 105 can include receiving and modulating input light to provide modulated output light or, alternatively or additionally, can include modulating an electrical input signal powering or controlling a light source to provide modulated output light, both of which are described herein. The multi-functional modulator 105 can be configured to respectively individually optically modulate the separated spectrally contiguous or spectrally disjoint spectral light wavelength components ($\lambda_1, \lambda_2, \lambda_3, \ldots, \lambda_n$). Such individualized modulation can include using corresponding stored or otherwise specified different optical modulation functions 107, e.g., $g_1(t)$, $g_2(t), g_3(t) \ldots, g_n(t)$. The individually differently modulated separated spectral light wavelength components ($\lambda_1$ ($g_1$), $\lambda_2$ ($g_2$), $\lambda_3$ ($g_3$) ..., $\lambda_n$ ($g_n$)) can be spectrally contiguous or can be spectrally disjoint, and some or all of these modulated wavelength components can be output or otherwise provided by the multi-function modulator 105 to an optical spectral combiner 109 such as to create a combined multi-band wavelength modulation encoded ("coded") light signal (W-CLS). such as can be wavelength homogeneous, and such as which can optionally communicated for output via an optical fiber or bundle or other optical waveguide of the optical illuminator or transmit portion 11 of the system 10. In an example, the wavelength-homogenous light beam illuminating the target object or scene is wavelength-homogeneous such that the different wavelength light components cannot be separated by spatial or angular division of the wavelength-homogenous light beam. In an example, the wavelength-homogeneous light beam illuminating the target object or scene is wavelength-homogeneous such that the light beam, when normalized for intensity across different emanating angles of illumination toward the target object or scene, has a wavelength-homogeneous distribution of modulation-coded different wavelength light components across the different emanating angles of illumination toward the target object or scene. In an example, the illuminating light beam emanates toward the target object or scene over a Field Of View (FOV) defining the plurality of different emanating angles of illumination having the intensity-normalized wavelength-homogeneous distribution of modulation-coded different wavelength light components at all of the different emanating angles of illumination across the FOV. In an example, wherein the wavelength-homogeneous distribution of modulation-coded different wavelength light components includes spectral variation of less than 50% across the FOV.

A beamsplitter or other optical signal separator can be used to provide a reference portion of the combined W-CLS for output to a reference photodetector 131 and associated circuitry. Another portion of the combined W-CLS light signal can provide a multi-band modulation-coded illumination light signal that can be output, such as via an optical fiber or other waveguide 113, to local or remote illumination optics 115, which can provide projection or other direction of the CLS 100 by the optical illuminator or transmit portion 11 to illuminate the target object or scene 117.

A receive portion 12 of the system 10 can include or be coupled to a response light transducer, such as one or more cameras or other photodetectors 119. The photodetectors 119 can be arranged at one or more specified locations such as to receive response light generated in response to an interaction between the illumination light from the CLS 100 and the target object or scene 117. The detected response light can be transduced into corresponding transduced electrical response signals, which can be coupled to and received by signal processing circuitry, such as a controller or signal processor circuitry 13. The signal processor circuitry 13 can include decoder circuitry 121 to recover information about a parameter of the modulation-coded different wavelength components to provide a color response output affected by the target object or scene. In an example, the color response output affected by the target object or scene can be in response to a wavelength-homogeneous or other illuminating light beam interacting with a material of the target object or scene, such as to produce at least one of an absorption color response, a reflectance color response, a scattering color response, a fluorescence color response, or a polarization color response, such as explained elsewhere herein. In an example, the signal processing circuitry is configured to recover information about the parameter, wherein the parameter includes at least one of a complex amplitude parameter, a real amplitude parameter, or a phase parameter of the modulation-coded different wavelength components to provide the color response output affected by the target object or scene.

The decoder circuitry 121 can be configured to decode multi-frame data. Such decoding can include using information about the original specified modulation functions 107, e.g., $g_1(t), g_2(t), g_3(t), \ldots, g_n(t)$ and a timing reference signal such as a frame synchronization signal received from the transmit portion 11 of the system 10 at a frame synchronization signal input 141 of the signal processor 13 on the receive side 12 of the system 10. In a hyperspectral imaging use-case example, the decoding of the multi-frame data of electrical response signals and/or the reading of the pixel array can be synchronized in this manner (e.g., in hardware or in software) and used to generate a hyperspectral cube, e.g., of wavelength-group specific characteristics of the target object or scene 117, such as a hyperspectral cube having (x, y, $\lambda$) dimensions such as for each frame of data from a particular photodetector 119, which can include an (x, y) array of pixels.

Thus, FIG. 1 illustrates an example of performing spectrometry or hyperspectral imaging using techniques according to the present approach. There are many specific implementations, examples of which are shown in and further described herein with respect to other figures as well as FIG. 1. In an illustrative example of a hyperspectral imaging use case, each photodetector 119 in a camera can act like a spectrometer. Thus, the present approach can enable expanding spectroscopic techniques using a single or few detectors, such as with particularly important applications, such as to industrial process control, medical devices, environmental monitoring, or other applications.

Figure 3:
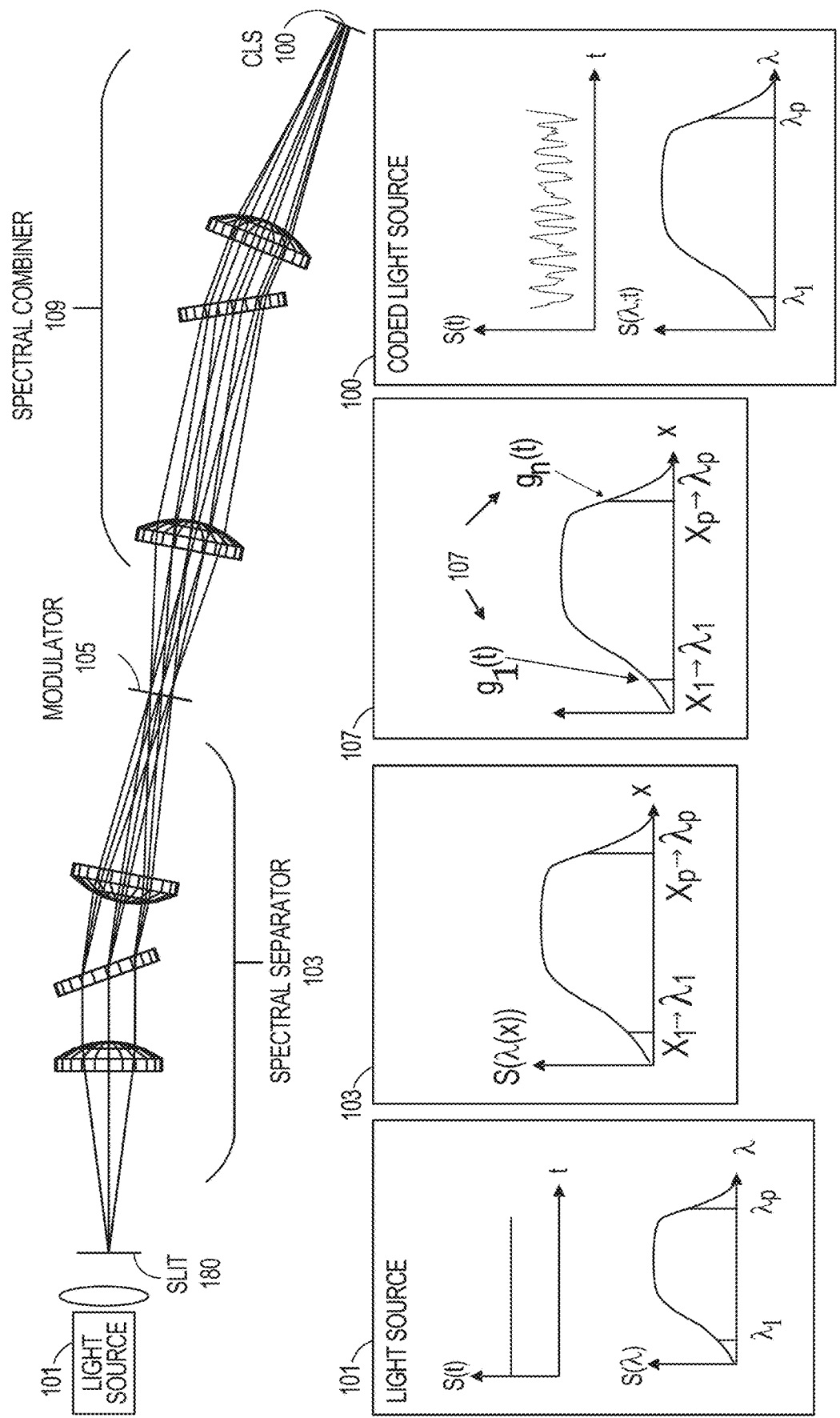
FIG. 3 shows an illustrative example of portions of the transmit portion of the system of FIG. 1, together with ray traces and corresponding conceptualized illustrations of spatial, temporal, and wavelength characteristics of the light signal at various locations of interest.

FIG. 3 shows an illustrative example of portions of the optical illuminator or transmit portion 11 of the system 10 of FIG. 1, including the light source 101, the spectral separator 103, the modulator 105, and the spectral combiner 109. FIG. 3 also shows ray traces and corresponding conceptualized illustrations of spatial, temporal, and wavelength characteristics of the light signal at various locations of interest of the transmit portion 11 of the system 10.

In the illustrative example of FIG. 3, light from the light source 101 can be directed, such as via a slit, toward the spectral separator 103. The spectral separator 103 can receive light via the slit, such as can be incident upon a light refractor of the spectral separator 103, such as a lens L1. Light exiting from the lens L1 can be directed toward a light dispersive element of the spectral separator 103, such as a prism or a diffractive grating G2. Light exiting from the dispersive element such as the prism or grating G2 can include differently-angled wavelengths of exiting light, which can be directed toward a light refractor of the spectral separator 103, such as a lens L2. Light exiting from the lens L2 can be directed toward the modulator 105, with different wavelengths of light ($\lambda_1, \lambda_2, \lambda_3, \ldots, \lambda_n$) being directed toward different spatial locations of the modulator 105. This can permit the modulator 105 to be used for providing different encoding modulation functions 107 e.g., $g_1(t), g_2(t), g_3(t) \ldots g_n(t)$ to the different wavelengths of light ($\lambda_1, \lambda_2, \lambda_3, \ldots, \lambda_n$).

Thus, the modulator 105 allow multiple unique time-varying functions to be imposed on each of the wavelength bins. After this modulation, we recombine these modulated spectra, such using the spectral combiner 109. More particularly, differently modulated separated spectral light components ($\lambda_1(g_1), \lambda_2(g_2), \lambda_3(g_3) \ldots, \lambda_n(g_n)$) can be output or otherwise provided by the multi-function modulator 105 to an optical spectral combiner 109, which can "inverse" optics functionality to that of the spectral separator 103. For example, the spectral combiner 108 can include a refractive element such as the lens L3 (e.g., such as can provide "inverse" functionality to lens L2). Refracted modulated light exiting the lens L3 can be directed toward a dispersive element, such as a prism or diffractive grating G1 (e.g., such as can provide "inverse" optics functionality to that of the dispersive element such as the prism or grating G2). Dispersed, refracted, modulated light exiting the grating G1 can be directed toward a refractive element, such as lens L4 (e.g., such as can provide "inverse" optics functionality to that of the lens L1). Refracted, dispersed, refracted, and modulated light exiting the lens L4 can be directed toward or via an optical conduit to illumination optics 115, from which it can be projected or otherwise directed toward a target object or scene 117.

FIG. 3 shows an example of one of the many possible implementations of componentry of a dispersive system. The dispersive system may be implemented using one or more prisms or one or more gratings or one or more other dispersive systems, such as in either reflective or transmissive geometries or arrangements. One can note that the dispersive system shown in FIG. 3 separates the wavelength components of the light source 101 and then recombines them after individually (e.g., differently, independently, or uniquely) coding each of the wavelength bins. The spectral resolution in the physics sense or the optical sense can be set by the configuration of the dispersive system, but the number of independent measurements of the target object or scene 117 can be set by the number of independent codes or modulation functions 107.

The coded light spectrum emerging from the device at CLS 100 may be reflected, scattered, or transmitted through the medium of the target object or scene 117, and its spectrum will be modified or affected according to one or more properties of the target object or scene 117. The resulting response light may be detected by one or more photodetectors 119. For example, individual (same or different) detectors can be placed in different directions with respect to the target object or scene 117. The response light from the target object or scene 117 can be transduced into a corresponding electrical signal by each of the photodetectors 119. The resulting electrical response signal can be processed or analyzed such as to provide measurement of the response light signal spectrum detected by each of the photodetectors 119. A camera can include an array of pixels or other arrangement of photodetectors 119. The present approach of using CLS can be used, among other things, for converting any black and white or grayscale camera into a colorimetric or hyperspectral camera.

There is a greater degree of freedom in the spectrometry that is afforded by the present CLS technique. For example, one can use and code a light source that is wider in wavelength range than any single photodetector 119 material can measure, yet that can provide a fully calibrated spectra across multiple photodetectors 119 measuring response light from a target object or scene 117 in different wavelength bands. This can help provide an especially important commercial and practical advantage. An ordinary light bulb with a hot filament or a supercontinuum laser based light source or a plasma source, can provide broadband light such as that spans from 300 nanometers to 5000 nanometers in wavelength. This is a wider wavelength band than any particular individual photodetector technology permits for detecting or measuring EM radiation. For example, silicon photodetectors are limited approximately to wavelengths below 1000 nanometers. InGaAs based photodetectors work from 700-1700 nanometers. PbS photodetectors operate in a span from 1500-3000 nanometers. PbSe photodetectors operate in a span from 2000-5000 nanometers. Each of these types of photodetectors may need different electrical signal conditioning circuits for optimum performance. Other examples of photodetectors that can be used can include silicon, germanium, InGaAs, PbS, GaSb, PbSe, HgCdTe, or many other semiconductors and material systems that can be configured to receive and detect electromagnetic radiation.

In one approach to a multi-photodetector system, one may need to buy three or more different types of spectrometers to measure the response light signal using the different types of photodetectors for various wavelengths of interest. Such measurements can be hard to carry out concurrently, and it may even be hard to keep different spectrometer systems calibrated across the entire wavelength range of interest.

By contrast, in the present approach of using a CLS based system, the entire broadband light source spectrum can be coded, and then the scattered, reflected, or transmitted light can be received concurrently, such as by multiple photodetectors of different types having overlapping spectral sensitivity. Each photodetector's output can be processed to produce the spectrum as seen by each of the individual photodetectors, and the overlapping spectral portions can be used to keep the spectra across all of the different types of photodetectors adjusted, normalized, or calibrated. Furthermore, such a compositely continuously correctly joined spectrum across multiple photodetectors can be compared with a response provided by a reference detector 131 that can be included within the transmit portion 11 of the system 100 or elsewhere located before the interaction of the illuminating light with the target object or scene 117, such as described herein.

While this explanation shows the flexibility in using multiple photodetectors that can be sensitive to different wavelength bands to provide broadband spectrometry, this flexibility is also extended to the light source itself. For example, multiple light sources 101, such as with different light output spectra (e.g., overlapping or non-overlapping) can be combined to synthesize a broadband light source 101. Examples of this type of heterogeneous light source arrangement are further described herein. Since it is the optical modulation or coding step that associates a particular physical frequency or wavelength to the code-often itself denoted by electrical frequency, the wavelength drift of the individual light sources of the heterogenous broadband light source 101 does not matter. This can be a particularly desirable feature in a particular product or application, since the effects of changes in spectra from batch-to-batch, over time, or over different temperature and other environmental conditions can be highly suppressed by using the present CLS approach. This is particularly obtainable by including a reference detector 131 such as to detect and measure a reference spectrum, which can be continuously available, such as for calibration or normalization, if desired.

3. Hyperspectral Imaging Example

To recap and expand upon the previous section's description of a hyperspectral imaging use-case of W-CLS techniques, it can be noted that FIG. 1 shows an illustrative example of concurrent spectroscopy of coded response light from a target object or scene 117. The coded light can be received at an array of photodetectors 119, such as can be placed or located at a focal plane. The transduced response signal can be processed or analyzed, such as to provide a hyperspectral imaging function. The analysis for the hyperspectral imaging can be applied to one or multiple separate detectors such as can be placed at arbitrary positions around, or with respect to, the target object or scene 117. The approach described with respect to FIG. 1 can be used to transform a grayscale camera into a hyperspectral camera. This can be accomplished while maintaining high light collection efficiency, accurate spectral channels, excellent image registration across channels, and flexibility of software programmable hypercube resolution (e.g., multiple coded spectral bins can be selectively combined in software, such as for selecting between update rate and resolution, as desired, such as also discussed elsewhere herein).

For example, consider a coded light source (CLS) 100 in which the light intensities at different spectral bins of wavelengths are coded by amplitude modulation at different frequencies. In this example, the entire code for the entire spectrum repeats after some time T. In this case, each of the spectral bins are updated in time T. But due to properties of sinusoids or Fourier transforms, one can halve the resolution and halve the update time. Thus, it becomes possible for the present system to include (e.g., in software) settings that can permit the user or the application to select the update rate and spectral resolution, such as to be suitable for a particular desired application. In some applications, e.g., after experimentation, it may be determined that a fixed superposition of spectral colors is desired, such as to create a pseudo-color image that represents the underlying material properties. The present system can be configured to carry out such a superposition directly on the raw data to output desired pseudo-color image.

In the example of FIG. 1 and other figures, the CLS 100 can provide a modulated broadband light source, such as in which each of multiple (e.g., 4 or more, 10s, 100s, or even 1000s) of spectral components of interest can be coded or tagged, such as using a unique set of corresponding respective repeating time-dependent modulation functions 107, and then recombined to form the wavelength coded light source (CLS) or W-CLS 100. A series of frames can be captured by a camera including a photodetector 119 (which can include an array of pixels). Each frame can be captured at specified times.

These frame capture times can be synchronized with the coding modulation functions 107, such as via a frame synchronization signal 141. The frame synchronization signal 141 can be issued or received by the controller/signal processor 13, or both. The controller/signal processor circuitry 13 can be configured to control operation of the multifunction modulator 105 on the transmit portion 11 of the system 10. The controller/signal processor circuitry 13 can also receive the frame synchronization signal 141 for use on the receive portion 12 of the system 10, such as for synchronizing decoding of the modulation functions 107. Such decoding, in turn, can be used for extracting spectral information about the target object or scene 117 at the respective wavelength groups corresponding to the coding modulation functions 107. The decoding can apply one or more mathematical identities or reconstruction algorithms to the time-series of each of the "pixels" in the image frame captured by the one or more photodetectors 119, such as to reconstruct the spectral content. This is because the modulation functions 107 (e.g., $g_1(t)$, $g_2(t)$, $g_3(t)$ . . . , $g_n(t)$) corresponding to each of the spectral components (e.g., $\lambda_1$, $\lambda_2$, $\lambda_3$, . . . , $\lambda_n$) can be unique, and can be chosen such as to permit the reconstruction from the time-series data. For example, the modulation functions 107 the modulation functions 107 (e.g., $g_1(t)$, $g_2(t)$, $g_3(t)$ . . . , $g_n(t)$) can form an orthogonal (or almost orthogonal) set of modulation functions.

In the example of FIG. 1, to generate the W-CLS 100, a broadband light source (LS) 101 can be provided. Examples can include one or more of a thermal light source (e.g., hot filament, glow-bar, or the like), a superluminescent or other light emitting diode (LED), a phosphor-based light source (e.g., a white LED, or a laser-pumped or LED-pumped phosphor), or even a light source including or composed of many different colored light sources, such as to produce broadband or other multispectral output in the multiple or many wavelengths of interest.

In the example of FIG. 1, the spectral separator 103 can receive broadband or other multi-spectral light from the light source 101 and can spatially separate the received light, such as into p distinct spectral components. The spectral separator 103 can be implemented in a number of different ways, some examples of which are shown in FIG. 3, FIGS. 4A-4B, and FIG. 13A. As explained above with respect to FIG. 3, after spatial light dispersion is achieved by the spectral separator 103, the resulting light can be modulated or otherwise encoded, such as by the multi-function modulator 105. The multifunction modulator (MFM) 105 can encode different (e.g., unique) functions 107 as $g_i(t)$, where i represents individual ones of the n spatial locations that corresponds to the n spectral components of the light output by the spectral separator 103. Multiple illustrative examples of such modulators 105 are described herein.

After applying the modulation, such as using MFM 105, these differently modulated spectral components can be recombined, such as using spectral combiner 109 in FIG. 3, FIGS. 4A-4B, and FIG. 13A. In an example, the spectral combiner 109 can optionally be configured to provide the "inverse" optical functionality of the spectral separator 103, if desired, but this is not required. For example, the spectral combiner 109 can include a lens or a mirror system, such as can be configured to collect the various modulated spectral components output by the MFM 105, and to combine and homogenize them, such as using a light diffuser, such as shown in the example of FIG. 5C. Combining of the different wavelengths of the modulated components output by MFM 105 can be advantageous, such as for making a good spectral measurement of one or more characteristics of the target object or scene 117. More particularly, it can be advantageous to illuminate the target object or scene 117 using illumination light in which the different spectral components have relatively the same weight directed in different directions toward the target object or scene. Otherwise, it will be difficult to get a good spectrum incident at different locations on the target object or scene 117, which, in turn, will affect the quality of the analysis of the response light detected and analyzed in response to the illumination light interacting with the target object or scene 117. The illuminator optics 115 can optionally be included and used, such as to help produce an appropriate illumination pattern on the target object or scene 117, as well as to help homogenize and prepare the light provided at the wavelength coded light source 100 for illumination of the target object or scene 117.

Figure 4B:
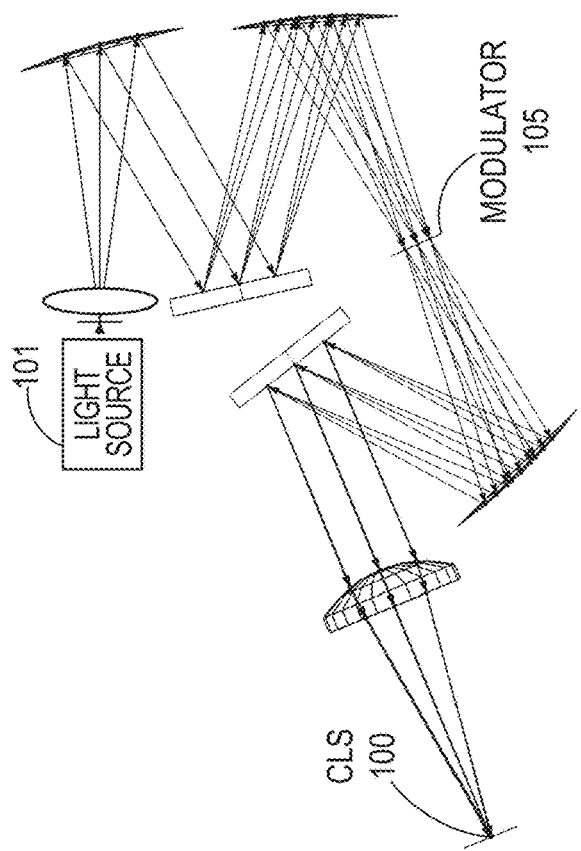
FIG. 4B shows an example of transmit portion components that can include other arrangements reflective components, with accompanying conceptual ray tracings to help illustrate its operation.
Figure 4A:
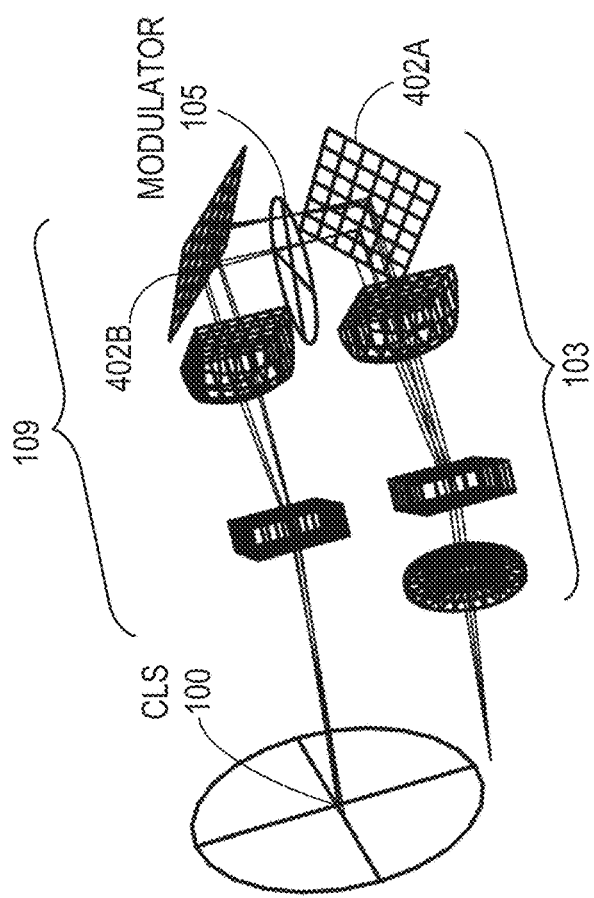
FIG. 4A shows an example of a folded compact geometry of the transmit portion components, with accompanying conceptual ray tracings to help illustrate its operation.

FIGS. 4A, 4B show different variations of portions of the transmit portion 11 of the system 10 shown in FIGS. 1 and 3. FIG. 4A shows an example of a folded compact geometry of the transmit portion components, with accompanying conceptual ray tracings to help illustrate its operation. FIG.

4B shows an example of transmit portion components that can include other arrangements reflective components, with accompanying conceptual ray tracings to help illustrate its operation. The various examples of FIGS. 1, 3, 4A, and 4B can be combined in various ways, and other examples of implementations of the transmit portion 11 of the system 11 are also possible.

In FIG. 4A, the light output by the broadband or other multi-spectral light source 101 can be directed toward a spectral separator 103, such as can include elements such as L1, G2, and L2 of FIG. 3, which can be arranged to transmit light generally in a first direction. Light output from the spectral separator 103 can be provided to a light reflector 402A, such as can be arranged at a 45 degree angle to the first direction, such as to reflect the light output from the spectral separator 103 in a direction orthogonal to the first direction, where it can be received and modulated by a modulator 105 providing modulation functions 107. Light output from the modulator 105 can be received by a light reflector 402B, such as can be oriented at a 45 degree angle to reflect light back in a second direction, e.g., opposite to the first direction. Such reflected light can be received by the spectral combiner 109, and recombined similar to as described above, to provide a coded light source 100 that can project or direct illumination light toward the target object or scene 117 in a direction that is generally opposite to that of the light output by the light source 101. The arrangement in FIG. 4A can provide a more compact transmit portion 11 of the system 10 shown in FIGS. 1 and 3. The arrangement in FIG. 4A can optionally be modified to accomplish one or more other objectives, if desired.

In FIG. 4B, light output by the light source 101 can be reflected by a mirror M3, instead of being refracted by a lens L1. A reflective dispersive element G2 can receive the light exiting from M3. The reflective dispersive element G2 can disperse the light and can direct the dispersed light toward a mirror M2. The mirror M2 can reflect the dispersed light toward the modulator 105 providing modulation functions 107. Modulated light exiting the modulator 105 can be directed to a mirror and reflected toward a reflective spectral combining element G1, such as can provide an "inverse" optical function to the dispersion provided by G2. The resulting light reflected by element G1 can be focused by a refractive element, such as L4, onto a focal plane of illumination optics 115, such as for providing a coded light source 100 for illumination of a target object or scene 117.

Figure 5A:
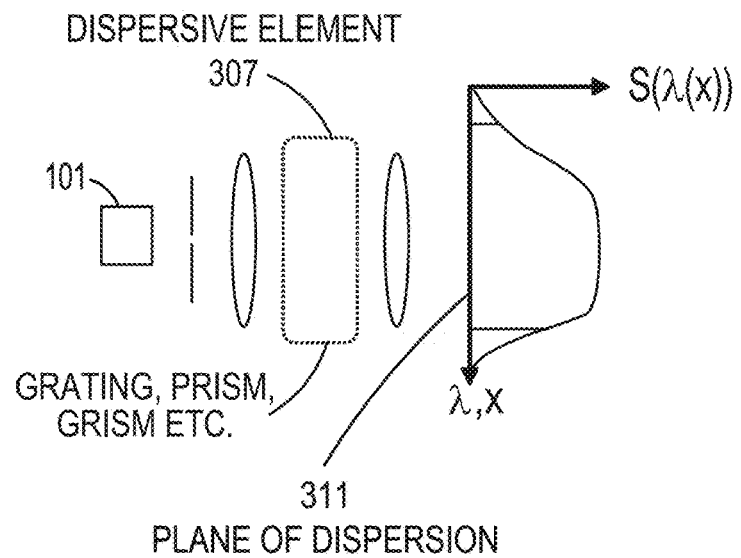
FIGS. 5A, 5B are a general representations of illustrative examples of a dispersive system, such as can be used in the spectral separator shown in and described with respect to FIGS. 3, 4A-4B, and 13A.

FIG. 5A is a general representation of an illustrative example of a dispersive system, such as can be used in the spectral separator 103 shown in and described with respect to FIGS. 3, 4A-4B, and 13A. As explained, such a dispersive system can include a dispersive element 307 (e.g., such as a grating, a prism, a grism, or other wavelength-dispersive element) such as to disperse different wavelengths to different locations along a plane of dispersion 311. These different locations along the plane of dispersion 311 can provide respective inputs to corresponding "channels" of the optical modulator 105. This can allow the optical modulator 105 to receive the respective dispersed spectral components at the different locations of the different channels, so that different (e.g., unique) modulation functions can be applied by the optical modulator 105 to the different spectral components of the different channels.

Figure 5B:
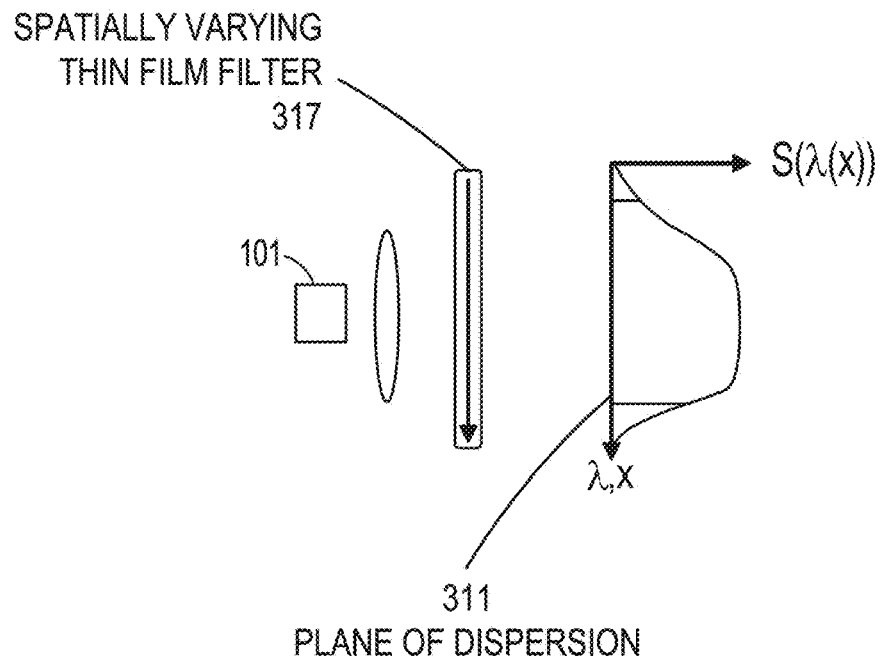
Figure 5C:
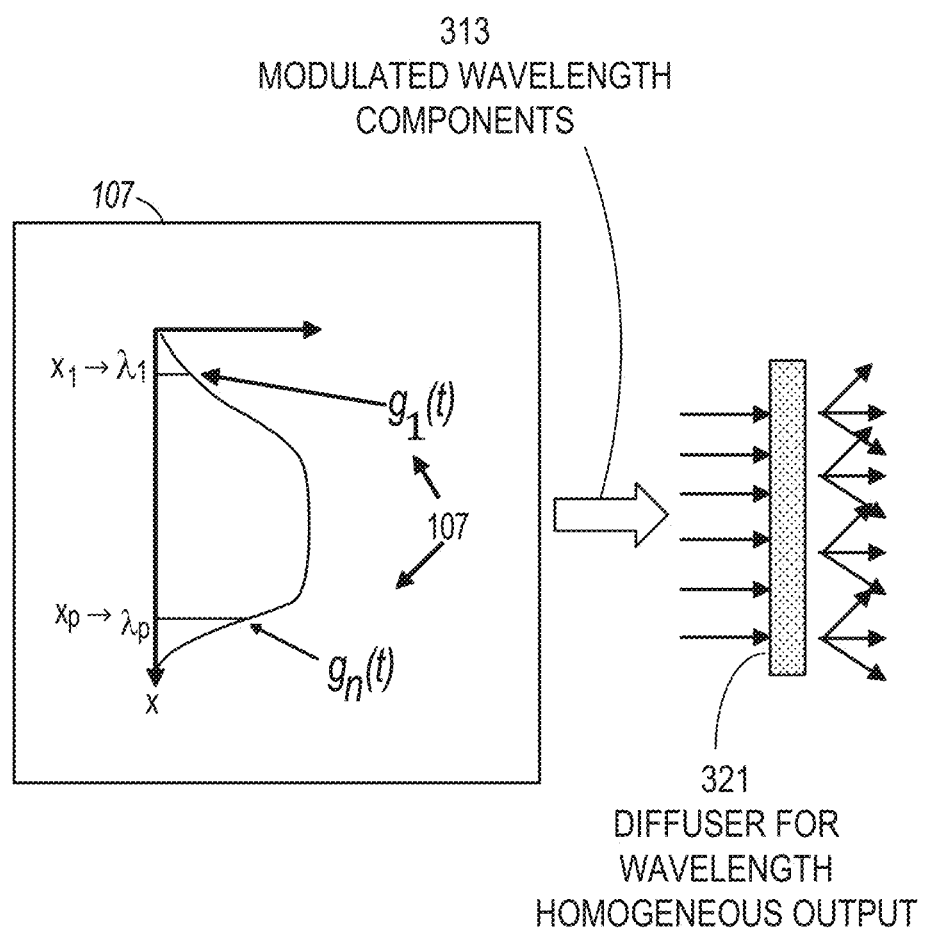
FIG. 5C is a general representation of an illustrative example of a spectral combiner 109.

FIG. 5B is another general representation of an illustrative example of a dispersive system, such as can be used in the spectral separator 103 shown in and described with respect to FIGS. 3, 4A-4B, and 13A. In the example of FIG. 5B, a spatially variable thin film filter 317 can be used as the dispersive element such as to disperse different wavelengths to different locations along a plane of dispersion 311. These different locations along the plane of dispersion 311 can provide respective inputs to corresponding "channels" of the optical modulator 105. This can allow the optical modulator 105 to receive the respective dispersed spectral components at the different locations of the different channels, so that different (e.g., unique) modulation functions can be applied by the optical modulator 105 to the different spectral components of the different channels.

FIG. 5C is a general representation of an illustrative example of a spectral combiner 109. Although the spectral combiner 109 has been described herein as implementing an "inverse" function of the spectral separator 105, this need not be so. FIG. 5C shows an example of a spectral combiner 109, in which the modulated wavelength light components 313, such as output by the modulator 105, can be collected (e.g., by a lens or mirror system) and directed toward a light diffuser 321, such as can be included in our optically coupled to the illumination optics 115. The light diffuser 321 can help spatially homogenize the different wavelength components, such as for being provided as the coded light source 100 for illuminating the target object or scene 117. The combining of the different wavelength components, e.g., by the light diffuser 321, can help to reform a wavelength-homogeneous light source with modulated wavelength components. This can be very helpful to making a good spectral measurement on the target object or scene 117. It can be advantageous to illuminate the target object or scene 117 by coded light in which the different spectral components have relatively the same weight in different directions. Otherwise, it can be difficult to get a good spectrum at different locations on the target object or scene 117. The optional illuminator optics 115 can be used to produce appropriate illumination pattern (e.g., structured or unstructured) as well as homogenize light to be provided by the wavelength CLS 100 for illuminating the target object or scene 117.

The spectral separator 105 of the various FIGS. may be mathematically represented as mapping spectral components of the source S with intensity $a(\lambda)$. which is its spectrum, to different locations in space:

$$S = \Sigma a(\lambda) \Rightarrow \Sigma a(\lambda(x)) \qquad \text{Eq. 3}$$

Once the components are spatially separated at different locations along the plane of dispersion 311, the modulator 105 can receive these spatially separated components for encoding by different "channels" of the modulator 105. Such encoding can include using different encoding functions $g_i(t)$ for each corresponding respective wavelength group centered around A ¿. Various different types of spatial light modulators 105 can be used to provide modulation. FIGS. 6A, 6B, 7A, and 7B show some illustrative examples of these different types of spatial light modulators. Once n wavelength groups or different spectral bins are modulated by the modulator 105, the modulated components may be recombined, such as described herein, such as to form a spectrally coded light source that can be mathematically represented as:

$$S_{CLS}(t; \lambda) = \sum_{i=1}^{n} a(\lambda_i) g_i(t) \qquad \text{Eq. 4}$$

Figures 6A, 6B:
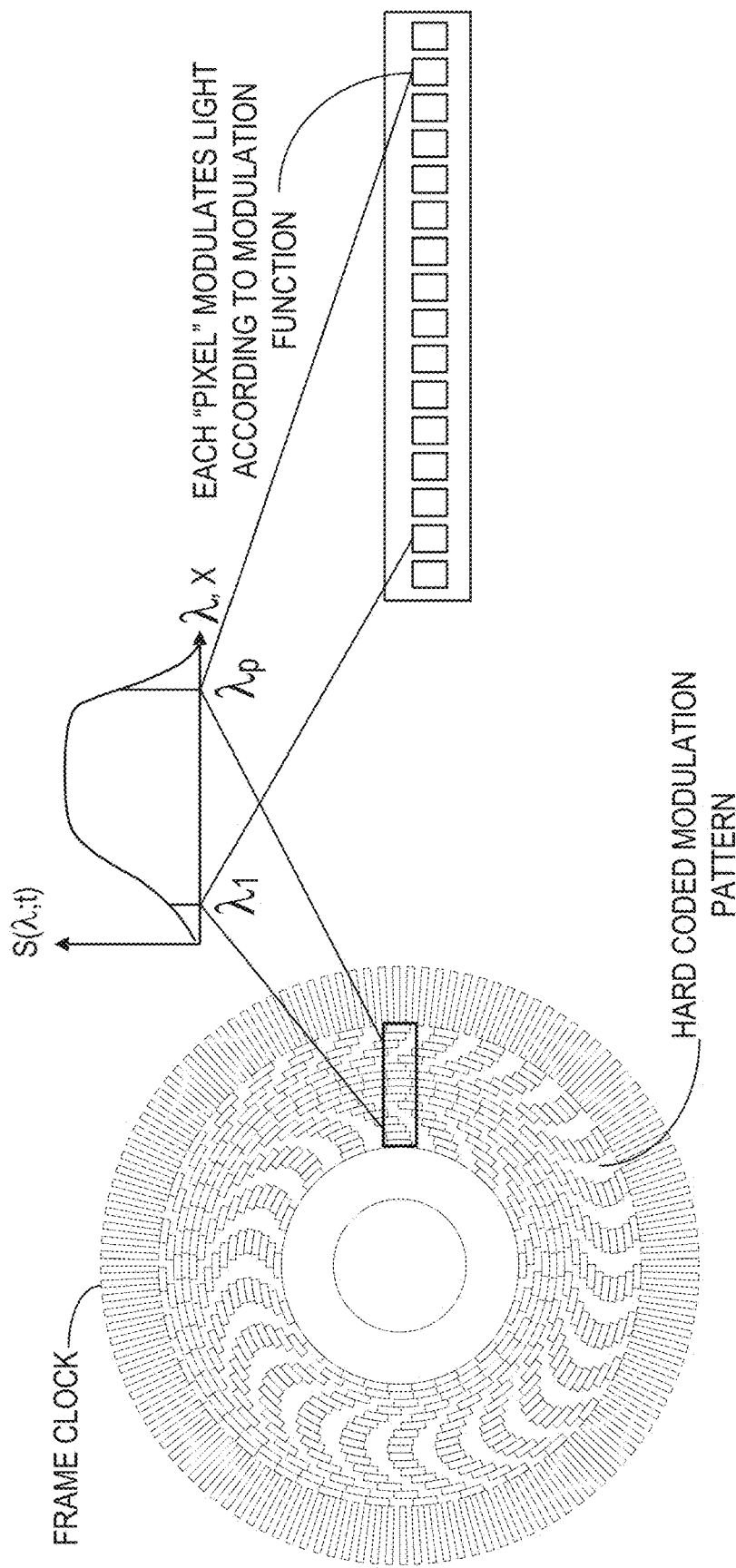
FIGS. 6A, 6B, 7A, and 7B show some illustrative examples of different types of spatial light modulators.

FIG. 6A shows an example of a modulator 105 that can use a moving pattern, such as a pattern that can include patterned transmissive and non-transmissive regions, on a rotating mechanical disk or wheel, such as described in and shown in U.S. Pat. No. 7,339,170, which is incorporated herein by reference. By dispersing the different spectral bin components of the incoming light radially across the rotating mechanical disk or wheel, and rotating the mechanical wheel, different channels of the modulator 105 can encode different modulation functions onto light corresponding to particular respective wavelength groups, which can then be spectrally recombined, such as explained herein. The example of FIG. 6A also shows inclusion of a peripheral circumferential "frame clock." This "frame clock" can include circumferentially periodic transmissive and non-transmissive regions, such as can be used to modulate light in the peripheral "frame clock" region according to a rotation period of the rotating mechanical disk or wheel. Light passing through the peripheral "frame clock" region can be detected and used to generate a frame sync signal 141 that can be provided from the transmit portion 11 of the system to the receive portion 12 of the system 10 to synchronize detection and decoding of response light from the target object or scene 117.

FIG. 6B shows an example of a modulator 105 that need not include a moving pattern Instead, a stationary pattern of electronically controllable light valve "pixels" or channels can be provided, such as the longitudinal sequence of pixels or channels shown in FIG. 6B. Incoming light can be wavelength-dispersed across the length of the arranged longitudinal sequence, to provide wavelength bins corresponding to the different channels. The channels can include electronically controlled light valves such as can temporally modulate light transmission through the light valves, such as under control from corresponding modulation electrical signals 107 from one or more electrical signal generator circuits, such as can be included in the controller/signal processor 13. Examples of electronically controlled modulator light valves can include, among other things, an array or sequence arrangement of liquid crystal (LC) elements, or digital micromirror (DMD) elements such as DLP from Texas Instruments (TI). Using the arrangements of either FIG. 6A or 6B, modulation according to Equation 4 can be provided, such as with spectral re-combining that can provide a spectrally homogeneous illumination beam to the target object or scene 117.

Returning to FIG. 6A, a modulator is shown that can include a patterned mask or wheel. Rotation of the mask causes different modulation codes $g_i(t)$ to be imposed on different wavelengths of light, where such different wavelengths of light have been dispersed across a specified region of the mask or wheel. In this example, the rotational or other motion of the mask and its patterns together determine the coding functions. For example, the mask may be controllably actuated so as to be made to rotate in one direction, or to rotatably oscillate back-and-forth. In either case, it is desirable to generate an accurate coding "clock" or synchronization signal that is directly related to the motion of the pattern on the mask-such a coding clock can be used for synchronizing the encoding on the transmit side 11 of the system 10 with the decoding to be performed on the receive side 13 of the system 10. Such a coding clock can be implemented by including a high resolution pattern to be placed on the mask, for example, such as shown in FIG. 6A by the printed pother otherwise patterned "encodings for the frame clock" that are shown as being distributed uniformly around the circumferential periphery of the mask or wheel being used for the multifunction modulator 105. Such a coding clock needs to be read with high precision, such as for accurate synchronization between transmit encoding and receive decoding.

For an illustrative example of a hyperspectral imaging application, frame rates can be in the 100s of Hz. This means that the harmonics of the ambient noise from the electrical line frequencies, e.g., 60 Hz, 120 Hz, 180 Hz, or the like, as used by electrical utilities in North America, could potentially directly interfere with the receive-side recovery of the information from some of the transmitted codes that happen to have frequencies that overlap with the utility line frequency harmonics.

But techniques can be employed to reduce such interference for any coding functions, such that the external, unsynchronized interference cancels while preserving information from the coding. As an illustrative, non-limiting example of such a noise-immunity technique, a "sign" or sense of the modulation can be inverted or "flipped" at one or more specified points in the modulation period (e.g., exactly half-way through the modulation period of a full rotation) such that opaque becomes transparent, and vice-versa, for the optical modulation for every coding function at that specified point in the cycle. If this is done on the transmit side, then while decoding on the receive side, the decoder signal processing software can "unflip" at that exact moment, such as using information about the peripheral frame synchronization coding clock, which synchronization information can be provided from the transmit side to the receive side. This technique can cause the unsynchronized ambient noise to be cancelled as the data is reconstructed over the entire modulation time period. There are other similar methods that can be employed, such as to enhance ambient noise immunity. Such noise-cancellation techniques are not limited to a modulator in the form of a mechanically-rotating wheel, but can similarly be applied to the drive of a MEMS based modulator or a PIC based modulator, or even to a directly electrical-input-signal modulated CLS, such as described elsewhere in this document.

A particular characteristic of modulation that that can be desirable for imaging applications is to avoid generation of higher frequencies in each of the modulation functions $g_i(t)$. This is because, frame rates are limited, and to provide for a maximum update rate, it can be desirable to generate codes that are operating as close to the Nyquist frequency as practical, but without incurring optical aliasing, or at least helping to reduce it to an acceptable value. There is the possibility that higher harmonics of such modulation codes $g_i(t)$ could alias back and create mixing. This aliasing can be avoided by either operating far from the Nyquist limit, or by generating codes that are as close to sinusoidal as possible, since a pure sinusoidal code will avoid generating the higher order harmonics of a square-wave or binary coding scheme. Binary masks, or on-off optical valves, will generate square or "squarish" looking time-domain signatures, which can be subject to having such higher-order harmonics. One way to generate sinusoidal time-domain profile is to make a grayscale mask with a sinusoidal transmission or reflection characteristic, e.g., of the modulation function formed into the permanent mask. Another way is to make the slit 180 in FIG. (or other slit, such as the slit 1602 shown in FIG. 20) provide a sinusoidal light transmissivity along the length of the slit. Since it is light passing via this slit that is projected onto the rotating modulator mask or wheel, and the output of the modulator in the time domain is convolution of the fixed slit pattern (e.g., sinusoidal) with a moving pattern defined by the modulator mask or wheel, the projection together with the modulation can generate, via such convolution, a predominantly sinusoidal code. Such an output from the modulator 105 can help avoid higher-order harmonics, which, in-turn, can help avoid aliasing of such higher-order harmonics.

In some cases, the modulation function of Equation 4 may not require separation of different wavelengths using a dispersive element. Instead, the modulation coding functions may be encoded otherwise, e.g., without using a dispersive element, such as can include using an integrated bank of encoders of a photonic integrated circuit or "PIC", such as explained below.

Figure 7A:
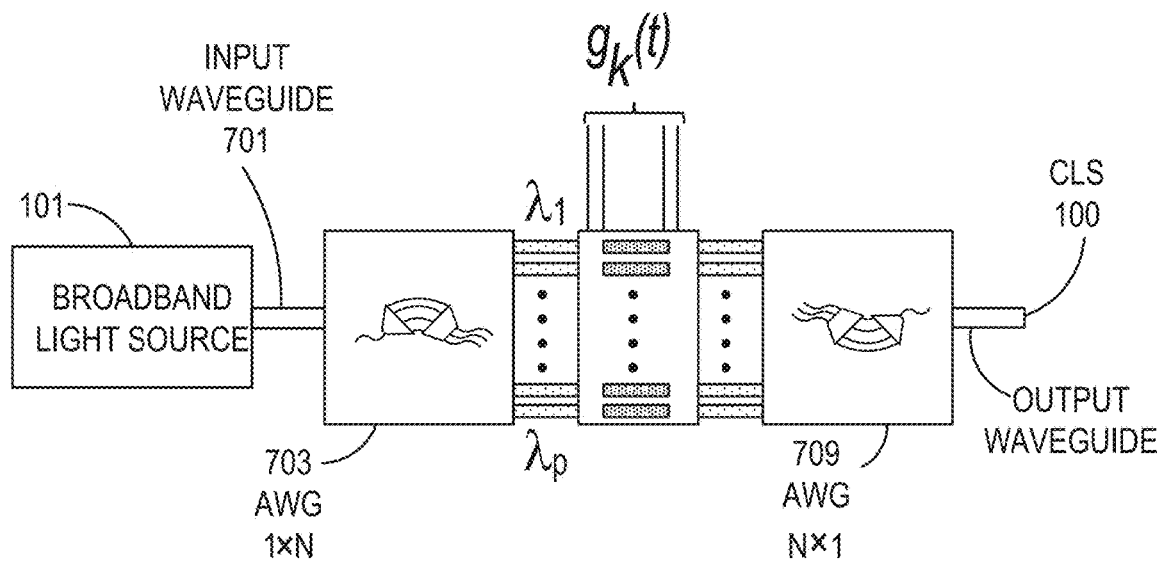
Figure 7B:
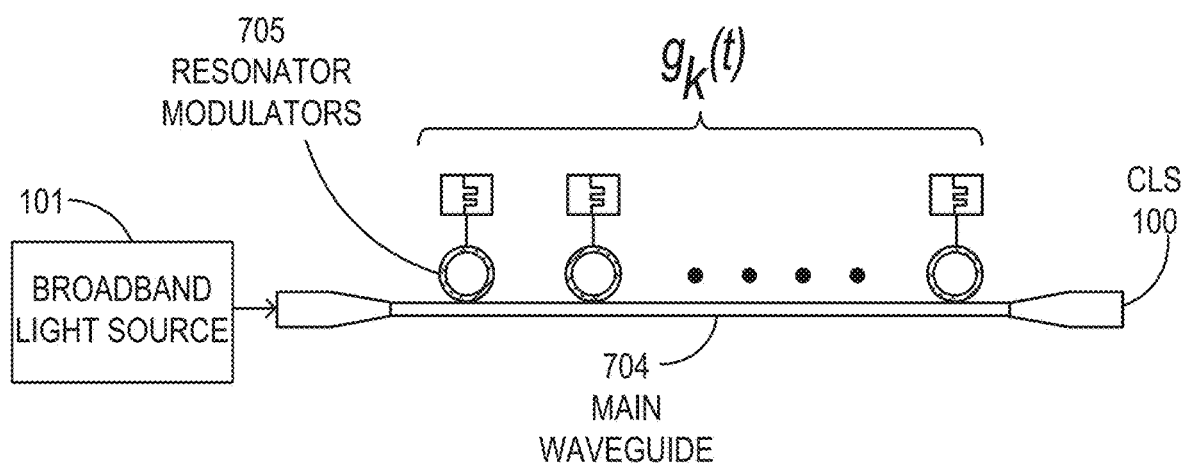

FIGS. 7A and 7B represent illustrative examples of a PIC based approach. For example, FIG. 7A shows a transmit portion 11 example in which a sufficiently broadband light source 101, such as a super luminescent LED or a continuum generating laser can be coupled efficiently to an input waveguide 701. The input waveguide 701 can optically communicate the broadband light from the light source 101 to an arrayed waveguide grating (AWG) 703. The AWG can be used to separate different spectral components of the light into different bins or groups of wavelengths (2.1 . . . \n). These different bins or groups of the spectral components of the light can then be delivered to a parallel modulator bank 704 of waveguide-based photonic modulators, such as can be respectively individually driven by corresponding electrical signals that impose corresponding different modulation functions $g_i(t)$. Then, modulated light from the modulator 704 can be recombined by an AWG 709, such as to produce a spectrally-reconstituted broadband coded light source 100.

FIG. 7B illustrates yet another example of a transmit portion 11. In the example of FIG. 7B, a PIC based approach can be used, such as which requires no wavelength separation and can still produce the output in accordance with Equation 4. In the example of FIG. 7B, the broadband light output from the light source 101 can be input into a waveguide 704. A series of resonator structures 705 can be configured to act as individual modulators 705. Each of the resonators 705 can be tuned to a different wavelength, corresponding to a particular modulation channel. Moreover, each of the resonators can be driven by a different modulation function gr (t), for providing a unique modulation function encoded onto the corresponding wavelength of the particular resonator 705. In this manner, the broadband light can have different spectral components differently modulated in the main waveguide 704 without requiring spatial dispersion of the light according to wavelength.

In general, the waveguide-based modulators 704, 705 may take one of several different forms, such as electro-optic, thermo-optic, phase-change, MEMS based, or another form. Modulators in PICs can offer the ability to use all electronic modulation and to use more complex codes, such as compared to the rotating wheel or disk mechanical modulator of FIG. 6A. Electro-optic modulators can offer modulation including in a MHz or GHz range. As discussed herein, such high frequency modulation can help allow for direct measurement of frequency response of the target object or scene to different optical frequencies. This capability can be useful in diffuse light spectroscopy of medically important parameters in human tissues, in distance or range measurements (e.g., in a ToF system), or measurement of one or more semiconductor properties. Waveguide-based modulators 704, 705 can also be applied to create a spatial map rather than a spectral map of the object, as described herein. Another advantage of PIC based approach of FIGS. 7A, 7B may be to help provide one or more reference detectors 131 on the PIC substrate, such as in an integrated or hybrid fashion, thereby making the entire solution extremely compact.

Other approaches to light modulation can also be used. To the extent that such approaches can provide good coding of the functions $g_1(t)$, they may be useful when they are capable of concurrently modulating multiple functions with adequate bandwidth and signal quality Within the W-CLS generating system 10, it may be advantageous to include a reference detector 131. For example, the reference detector 131 can sample the outgoing CLS using a light sampler 133, such as shown in FIG. 1. The light sampler 133 may include or consist of a beam splitter, such as an optical-fiber-based splitter or any other suitable means to sample a small portion of the outgoing illumination light to be communicated via the CLS 100. The reference detector 131 can be used to reconstruct the spectrum of the light source 101 after modulation coding. The reference signal acquired by the reference detector 131 includes the losses of all the preceding optical and modulating components (e.g., spectral separator 103, modulator 105, spectral combiner 109). The reference detector 131 can be used to help reduce or eliminate the effect of variation in the CLS 100, such as continuously or otherwise on an ongoing basis, such as to represent the true spectral characteristics of the target object or scene 117 by dividing the main measurement of the detected optical response signal by the reference measurement before illumination of the target object or scene 117. In certain cases, it may be advantageous to construct reference detector 131 out of a detector system closely matching or identical to that of the main detector on the receive portion 12 of the system 10 that receives response light after the illumination light interacts with the target object or scene 117. The light sampled by the reference detector 131 can be represented as:

$$S_{CLS}^{ref}(t; \lambda) = \beta \sum_{i=1}^{n} a(\lambda_i) g_i(t) \qquad \text{Eq. 5}$$

where β is some scale parameter representing the sampling by the light sampler 133.

The W-CLS response light from the target object or scene 117 can be captured in a series of frames by the photodetector 119 camera, which can include a focal plane array (FPA) with an appropriate imaging system. The camera can be operated at frame rate F, which can provide a series of images I(x, y; $t_k$) taken at times $t_k$. Electrical representations of these images can be sent to the decoder 121. The frame capture times $t_k$ are often synchronized to the coding system or the modulator 105 in the CLS 100. This is shown as Frame Sync signal 141. As described later, there are other ways to transmit frame sync signals including by coding on the CLS itself as well as using radiofrequency (RF) or other links if the camera or the detector system and the CLS are in different systems or are far away and electrical cabling is cumbersome. In most cases, this synchronization is advantageous and allows for precise reconstruction of the coding function.

The decoder 121 can receive electrical signal representations of frames taken at times $t_k$ from the camera. With the knowledge of pre-specified $g_i(t_k)$, the decoder 121 can compute a hyperspectral image H(x, y, $\lambda_p$). As explained herein, each of the $g_i(t_k)$ codes for the particular wavelength bin $\lambda_i$. The recovery of the spectral information from each pixel of the photodetector 119 can be accomplished such as by using an orthogonality or pseudo-orthogonality condition for the coding modulation functions $g_i(t)$, such that $$\sum_{k=1}^{N} g_i(t_k)\widetilde{g_r^*}(t_k) = \gamma \delta_{ir} \qquad \text{Eq. 6}$$

where $\gamma$ is again a scale factor, over N frames for p ($p \leq N$) independent modulation functions.

Eq. 6 is written for perfectly orthogonal reconstruction but can be generalized for real-world cases with pseudo-orthogonal functions, or for cases in which crosstalk can be created in the CLS 100, such as can be due to imperfections in optics or limitation of the modulator 105. For example, the modulator 105 need not be placed precisely on a plane of dispersion. If one or more portions of the modulator 105 is instead placed at a location other than the plane of dispersion, then instead of modulator codes respectively corresponding to different wavelengths or different wavelength bins, the modulator codes can respectively correspond to a unique linear combination of different wavelengths or a unique linear combination of different wavelength bins. The applicable equations can be expressed as matrix equations, and the respective unique coding linear combinations on the transmit portion of the system can still be used by the decoder on the receive portion of the system to recover individual responses corresponding to different wavelengths or corresponding to different wavelength bins. Thus, the cross-terms which can be known either from the properties of the chosen mathematical functions or from characterization of the CLS 100 can be included in the analysis. Here, the analysis is kept simple for clarity, using Equation 6, but straightforward extensions of Equation 6 can include solving a system of linear equations to recover the coded information, such techniques can be incorporated herein without loss of generality.

From the orthogonality condition, it follows that the hyperspectral reconstruction of N frames taken at times $t_k$ is:

$$H(x, y, \lambda_p) = \sum_{k=1}^{N} I_k(x, y; t_k)\widetilde{g_p^*}(t_k) \qquad \text{Eq. 7}$$

$$= \sum_{k=1}^{N}\sum_{i=1}^{p} r(x, y, \lambda_i)a_i(\lambda_i)g_i(t_k)\widetilde{g_p^*}(t_k)$$

$$= r(x, y, \lambda_p)a(\lambda_p)$$

Eq. 7 is easier to understand by focusing on any one pixel of the camera. This will also be true of the single photodetector 119 or a few photodetectors 119, as used for illustrating spectrometer functionality. The last equality in Eq. 7 follows from Eq. 6, as it is applied to each pixel. Thus, we can recover a complete hyperspectral image cube every N-frames.

Furthermore, the reconstruction to the reference channel 131 can be applied separately to recover:

$$\beta a(\lambda_p) = \sum_{k=1}^{N}\sum_{i=1}^{p} S_{CLS}^{ref}(t_k; \lambda)\widetilde{g_p^*}(t_k) \qquad \text{Eq. 8}$$

By dividing the output of Eq. 7 with Eq. 8, an accurate measure of the reflectance, transmittance, or scattering r(x, y, $\lambda$) of the target object or scene 117 can be generated. Clearly, reference channel measurement of the CLS 100 can be used to automatically remove an effect of light source drift from the response light measurement. Such reference measurement can also help remove the need to calibrate the CLS 100, such as using a "white card," as normalization using the reference detector 131 carries out such calibration on an ongoing basis. Since each spectral bin can be reconstructed using the same time-varying functions used for encoding, low frequency or "DC" dark current drifts can also be removed from the measurement. This is an advantageous property of the present approach of using coded light for measuring the response light spectrum. With this approach, using the reference detector 131 can help avoid the need for both dark and white-card calibration. These advantages can extend broadly to any spectral measurements (or spatial measurements, also described herein) carried out by such techniques-either with a few discrete photodetectors 119 or an array of photodetectors 119, as in the hyperspectral imaging example described. Practically, can help speed up real-world data taking, lower the cost of using the system 10 relative to an approach requiring calibration, and make it far more robust than such an approach requiring calibration, such as explained herein with respect to the description of and comparison between FIGS. 2A and 2B.

Another advantage of the present approach, including using the reference detector 131, can follow from the way W-CLS is constructed, which allows direct wavelength or spectral calibration or ongoing normalization of the coded spectral light system 10. For example, the system 10 can include either the dispersive approach shown in FIGS. 3, 4A, and 4B or the modulators of FIGS. 7A, 7B that do not require wavelength dispersion but can still provide a mapping between the wavelength and modulation code or the modulation frequency to which it is assigned. If there is drift over time due to drift in various opto-mechanical components, such as from temperature, humidity, age, or other condition, a W-CLS based spectrometer or hyperspectral imager can be out of calibration with regards to the wavelength. While current spectrometers or spectral imaging devices can require periodic calibration, such as by updating the internal calibration parameters, the present approach can eliminate the painstaking job of calibrating spectral intensity variations of the light source and CLS, as explained herein. The present approach can also help provide a technique for continuous or quasi-continuous wavelength calibration or rather a map of wavelength to modulation codes. This can help allow ongoing measurement use, such as permitting calibration without stopping the measurement. For example, a narrow-wavelength line source, such as a neon calibration lamp, can be mixed or otherwise combined with the input light source 101. The calibration lamp can be turned on recurrently or periodically, or can be left on continuously such as to produce one or more extra features in the light spectrum, which can be picked up by the reference detector 131 for calibration purposes, and normalized out of the response signal measurement, if desired. The specific modulation frequencies or codes at which the calibration lamp's spectral lines show up can be used to calibrate the map from modulation codes to wavelength. An active slit source, such as described herein, can directly incorporate one or more specific materials having known emission spectra, such as to help provide continuous or ongoing calibration.

Figure 8:
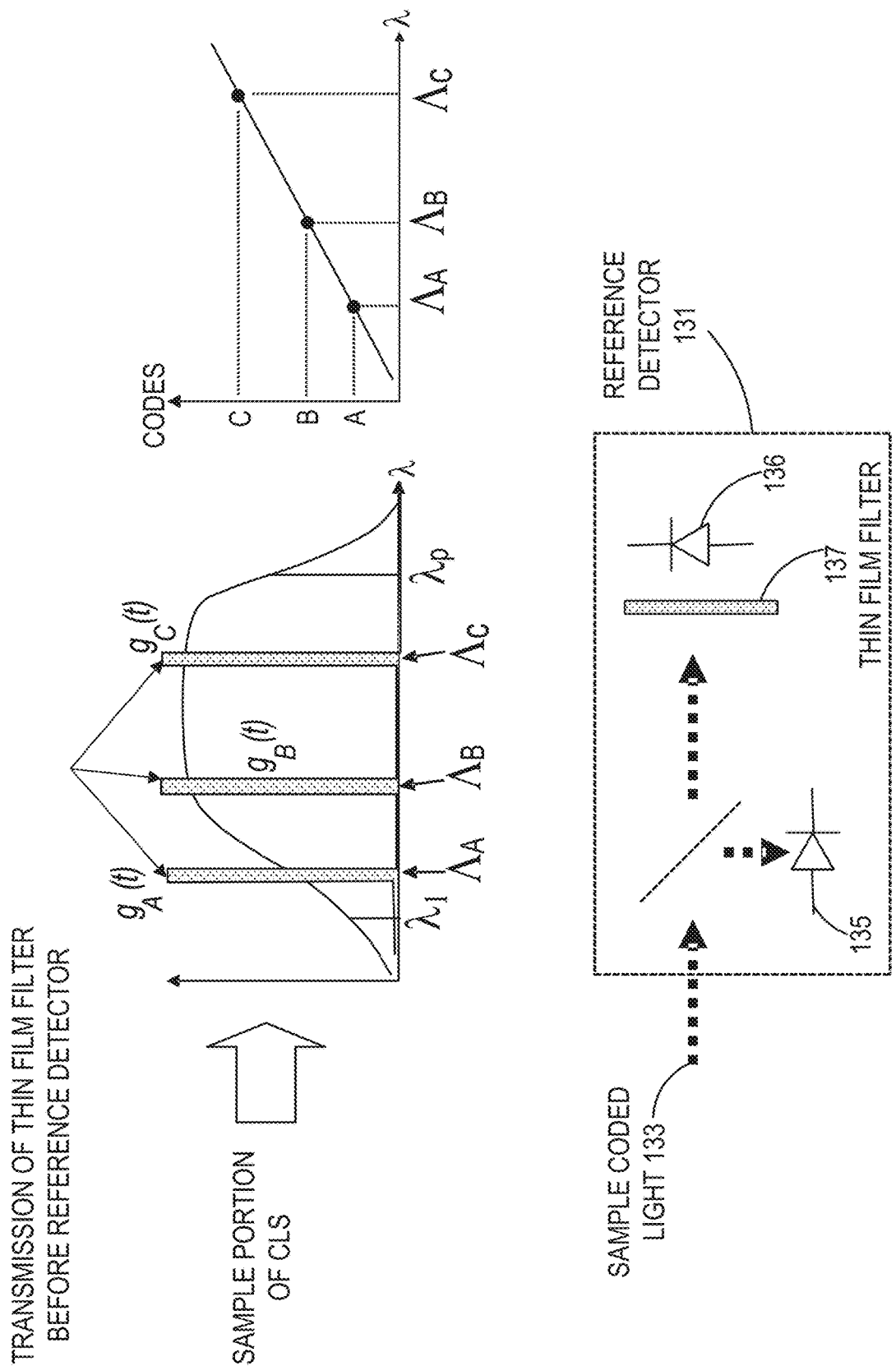
FIG. 8 shows an example of an approach in which a light filter can be placed in front of the reference detector shown in FIG. 1, such as can be used to make a map between wavelengths and modulation codes.

FIG. 8 shows an example of a cost-effective, robust, and stable approach in which a thin film light filter 137 (e.g., with a calibrated light transmission spectrum) can be placed in front of the reference detector 131 shown in FIG. 1, such as to make a map between wavelengths and modulation codes. For example, as shown in FIG. 8, the reference detector 131 can be located such as to receive a reference sample of the coded light 133 to be provided to the illumination optics 115 for illuminating the target object or scene 117. The reference detector 131 can be composed of multiple reference detectors 135, 136. A beamsplitter 134 can be used to direct a first portion of the reference sample of the coded light 133 to the first reference detector 135, and to direct a second portion of the reference sample of the coded light 133 to the second reference detector 135, such as through a wavelength-specific filter 137. For example, the wavelength-specific filter 137 can be configured to selectively pass one or more transmission wavelength bands $\Lambda_A$, $\Lambda_B$, $\Lambda_C$, corresponding to some or all of the coded wavelengths from the modulator 105. The light detected using the first reference detector 135 can provide a measure of the overall CLS efficiency, such as described by Equation 8. A ratio or other differential relationship between an intensity of the light detected at the second reference detector 136 and the intensity of the light detected at the first reference detector 135 can be used to provide a reference signal level that can be used by the receive portion 12 of the system 10, such as during decoding by the decoder 121 or for reconstructing the coded functions by the control/signal processor 13. In this way, the wavelength-specific light of the reference sample of coded light 133 detected by the second detector 136 and the wavelength-composite light of the reference sample of coded light 133 detected by the first detector 135 can be used to create an intensity normalization map for particular coded wavelengths, such as for use in decoding and reconstruction. Depending upon the type of shifts in the wavelength transmission bands, one or more wavelength transmission bands $\Lambda_A$, $\Lambda_B$, $\Lambda_C$, can be included, such as by configuring the thin film filter 137. In sum, this can provide a technique that can immediately and directly provide calibration of the wavelengths without a need to take the system offline from its measurement job to perform calibration.

Thus, the present approach can provide a spectral measurement system that can be free of DC drifts, and which need not require white card calibration to maintain calibration with respect to the wavelength. This is a unique and valuable advantage that can impact the ownership cost and usability. The inclusion and use of one or more reference detector(s) 131 can be useful and can be included with the present approach.

Table 3 lists some examples of the modulation functions $g_i$ and $\tilde{g}_k$.

TABLE 3

Examples of modulation functions $g_i$ and $\tilde{g}_k$.

| $g_i(t)$ | $\tilde{g}_k(t)$ |
| --- | --- |
| Sinusoidal modulation including pulse width modulation. | $\exp[i\, 2\pi f_k t]$ |
| Square wave modulation at frequencies $f_i$ represented by $\mathrm{sq}[f_i, t_k]$ | $\exp[i\, 2\pi f_k t]$ |
| Triangular wave modulation at frequencies $f_i$ represented by $\mathrm{tri}[f_k, t]$ | $\exp[i\, 2\pi f_k t]$ Or $\mathrm{tri}[f_k, t]$ |

TABLE 3-continued

Examples of modulation functions $g_i$ and $\tilde{g}_k$.

| Hadamard functions | Hadamard functions |
| --- | --- |
| Combined Golay complementary coding and triangular/square functions | Decode using orthogonality and then Golay signal recovery process. |
| Pseudorandom or random codes as well as chirped waveforms | Autocorrelation |
| Sign change ("flip/unflip") during period to avoid/cancel noise | Undo sign change before signal processing |

Since each pixel can reconstruct the full spectrum independently using the reconstruction procedure corresponding to the pre-specified coding functions, each pixel generates a spectrum of the light corresponding to a particular location on the target object or scene 117. This guarantees spatial registration of all the various wavelength bins in the hyperspectral image. Depending on the type of modulation function used for coding, multiple spectral bins (e.g., coded by different modulating functions) can be combined in software. Such combining of spectral bins can help reduce the number of spectral bins and can also help increase the update rate of the hyperspectral cube. (This was described previously and referred to as "software programmable hypercube resolution).

For example, coarse hyperspectral information can be provided at one rate while continuing to refine the spectral resolution as a number of frames used in the reconstruction is increased. This is apparent when the modulation functions are Fourier components, since the spectral resolution of reconstruction depends on the number of time points or frames used to reconstruct the image. Note, most modulation functions can be cyclic (e.g., repeating after some time T or after a certain number of frames). This means that a rolling update at the raw frame rate is indeed possible and that a sliding set of frames can be used to update the hyperspectral image.

Figure 9:
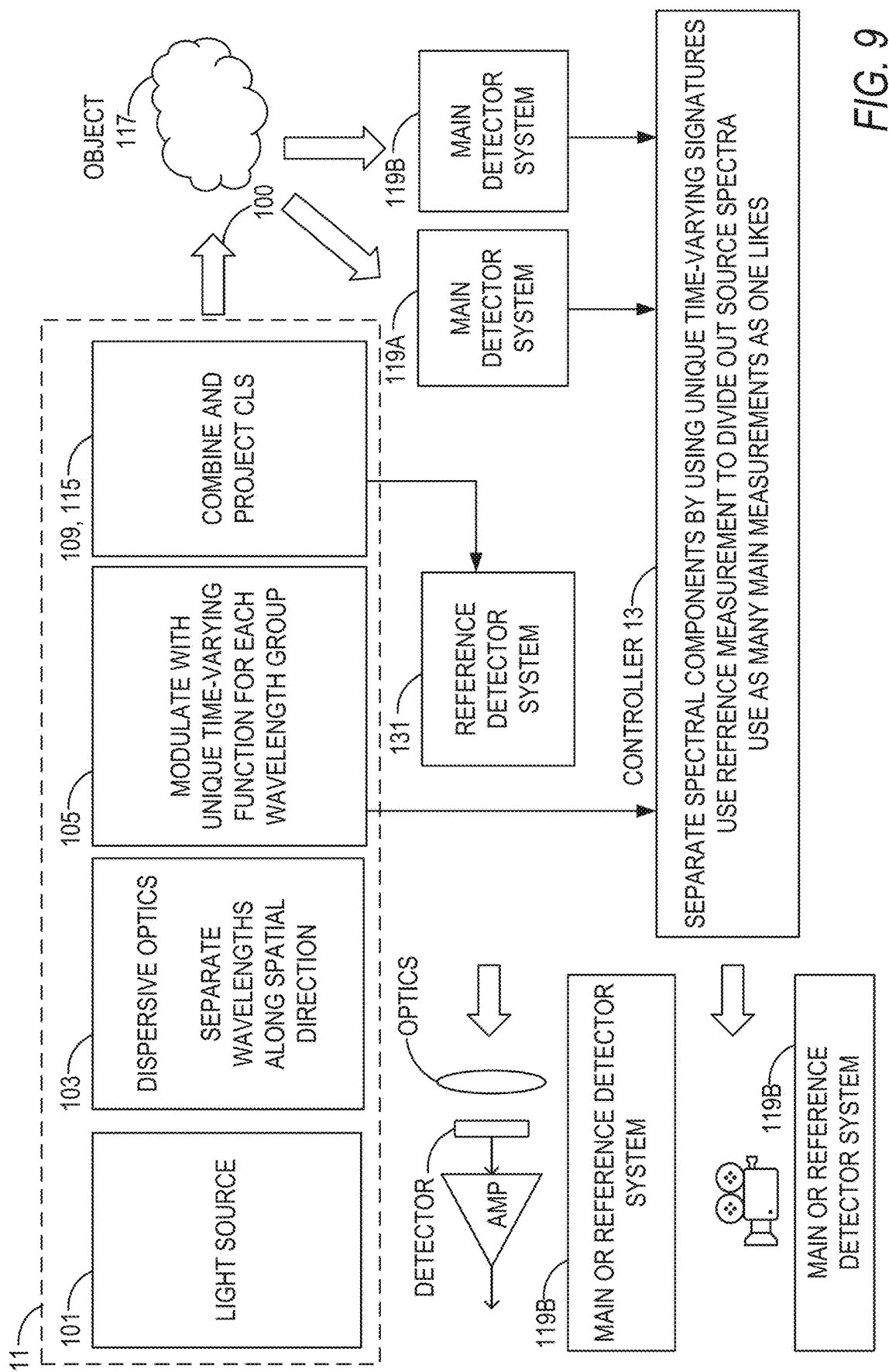
FIG. 9 shows an CLS system example, similar to that of FIG. 1, but providing concurrent detection and signal processing such as can provide concurrent hyperspectral and black-and-white images.

From the preceding explanation and the mathematical methods described herein, it also follows that a "black & white or grayscale" image without spectral binning is also concurrently available. This "black & white or grayscale" image can be provided such as using the "average value" of the frame, or an average of multiple frames, without applying any reconstruction algorithm. This is unlike other hyperspectral cameras in that both the spectral data and "grayscale" data can be concurrently available and fully registered spatially with no parallax, and with no temporal delay. The black & white data will have far higher SNR and can be used in image processing stages to great advantage. An example of the entire process is illustrated in FIG. 9, which is similar to the example shown in FIG. 1, but with FIG. 9 showing concurrent detection and signal processing using a hyperspectral detector channel 119A and a black and white detector channel 119B.

Table 4 compares various hyperspectral technologies.

TABLE 4

Examples of Hyperspectral Technologies

| Approach | Image resolution | Color fidelity | Image registration | Complex calibratoni | Usability | Comments |
|---|---|---|---|---|---|---|
| Pixel-level filters | Low Resolution per color is divided by number of filters | Low hard to achieve high quality filters | OK Needs interpolation but different colors are close to each other | Yes | High | Complex manufacturing technology; hyperspectral output at the frame rate |
| Color-filter array, FPA divided into mini-cameras | Low Same as above | High Separate color filters | Poor to OK Image parallax leads to poor image registration | Yes | Medium | Complex optical assembly and color filter array. Needs excellent alignment to micron sized pixels. Lots of "dead" region between color filter array |
| Scanned Color filters | High | High But color filters have narrow field of view | High | No | Medium | Low speed, large mechanical assembly, or complex optics and narrow field of view |
| Push-broom | High | High | High | Yes | Low | Requires image or camera motion to produce image; complex optical assembly, low throughput given by the f# of the input spectrometer |
| Multi-camera | High | High | Poor | Yes | Low | Need to manage many FPA's, complex electronics and optics |
| Present Approach | High | High | Excellent | No; continuous | High | Use any B&W camera with frame sync |

The present approach can be suitable, by way of example, for controlled environments such as for machine vision, medical devices, process control, imaging spectroscopy, or anywhere that active illumination by W-CLS is possible.

As explained herein, multiple cameras or photodetectors such as shown in FIG. 1 can be used to observe the response light from the target object or scene 117. Each camera can recover full spectral information. But using the different cameras can permit viewing the target object or scene 117 from different vantage points or can allow coverage of different parts of the target object or scene 117. In some cases, the W-CLS 100 illumination light may have a spectral range that can be broader than the wavelength range of a first camera on the receive portion 12 of the system 10. A second camera may be employed, with the second camera including a photodetector that can be made from different detector materials than that of the first camera. The first and second cameras can be used to concurrently generate a hyperspectral cube from the same target object or scene, but including different (but possibly overlapping) wavelength bands. This approach can be advantageous. Once the W-CLS illuminates the target object or scene 117, any camera can be converted to a hyperspectral camera with synchronization of frame data and reconstruction software.

Any black and white or grayscale camera—e.g., in a personal computer (PC), mobile device, or a stand-alone device can be "converted" to hyperspectral camera by adding W-CLS illumination, a frame-sync signal, and reconstruction software. An example of this is shown in FIG. 9, which shows a mobile device 241, such as a smartphone, that can be used for hyperspectral imaging. Many PCs or cell phone cameras already include high quality cameras. A black and white camera can be easily added to the multiple cameras in a PC or a mobile device or can be used with an RGB camera. An auxiliary W-CLS 111 can be used to illuminate the target object or scene 117. The W-CLS 111 can be incorporated into and integrated with the mobile device 241, but for the clarity of illustration and for complete generality, it is shown separately in FIG. 10, as described below.

Figure 10:
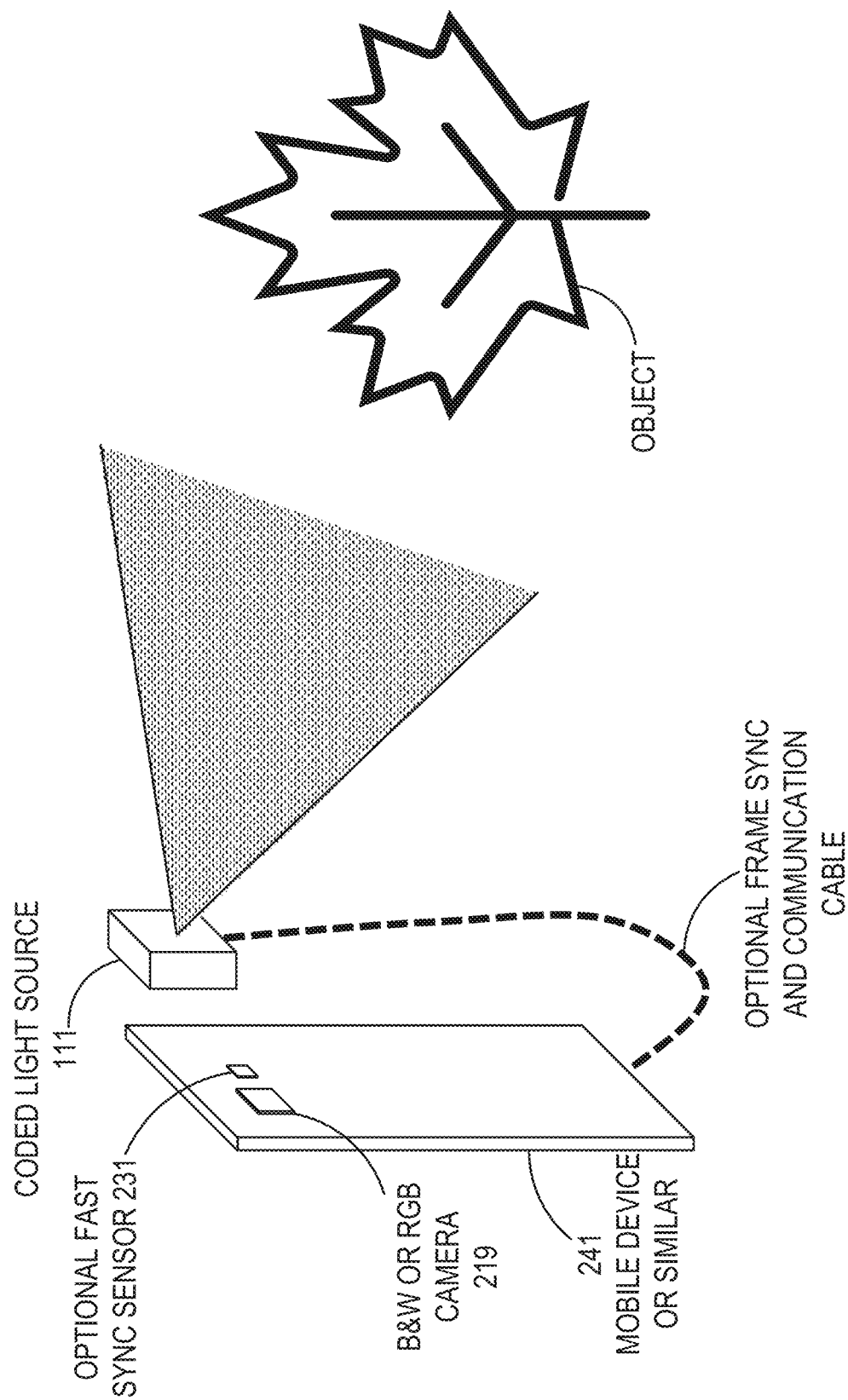
FIG. 10 shows an example of a CLS system, portions of which can be included in a handheld mobile smartphone device with a camera, and such as can include an integrated or separate accessory CLS, such as can be controlled using the mobile device.

FIG. 10 shows an example of a CLS system such as can include a mobile device, e.g., to provide a controller, signal processor, and camera, and including wired or wireless connected accessory CLS illuminate a target object or scene 117. In an example, a cable connecting W-CLS 111 and the mobile device 241 can carry frame-sync information or the W-CLS can code the frame sync clock directly on the light to be detected by a separate fast detector. For example, most ambient light sensors have adequate bandwidth to be useful for clock synchronization. Having frame capture synchronized to the W-CLS can help make the data reconstruction more robust and can help lower the computational load. Thus, hyperspectral imaging can be made ubiquitous, and this can significantly help in remote assessment of diseases, in measurement of skin conditions, or for spectral measurement of plants, paints, or many other things. For example, such techniques can help a physician to assess the color changes in the skin and layers of skin below, perhaps even do image-based blood analysis to provide high quality patient care. Some of the applications are described in detail for diffuse light spectroscopy based on the present approach may equally well apply to hyperspectral imaging.

The present approach can be equally well applied to a RGB camera and need not require a grayscale camera. Each pixel in the RGB camera is sensitive to a portion of the spectral bands with some overlap between them. During reconstruction, "R" pixel will be able to regenerate only the spectral bins that lie within the transmission curve for "R" and so on for 'G" and "B" pixels. If there is no IR-cut filter on the RGB camera then most of the pixels will be sensitive to NIR wavelength too. Thus, the present approach is not limited to a grayscale camera but can easily work with a color camera. In such a context, the present approach is not any different than having different grayscale cameras operating in different wavelength bands but receiving scattered light from a W-CLS illuminated target object or scene whose spectral width is greater than that of any one camera.

There can be yet another advantage of using modulating functions to code for spectral bins. Doing so sets up a map from wavelength to modulation function, that is, from $\lambda \rightarrow g_i(t)$. What is reconstructed are amplitude of $g_i$. If one is interested in some spectral measurement of the target object or scene 117 in which one or more of the characteristics of the target object or scene 117 can be described by linear combination of various spectral components then, from Eq. 7, it can be seen that one can directly demodulate to the desired spectral output by using a linear combination of reconstructing functions. This means one can construct an abstract hyperspectral cube in which each "color" is a linear combination of spectral components. In many applications such as measurement of chlorophyll content, or skin disease or process control for color fidelity or other use case, one can directly synthesize the appropriate metrics and reduce data transmission to higher levels of image processing, such as described elsewhere herein.

While the present approach has been described emphasizing use of a two-dimensional focal plane array in the analysis for the W-CLS based hyperspectral imager, the present approach and analysis applies equally well to one dimensional line imager. This can be useful for some applications, as the W-CLS light source can be focused to a one dimensional line, which, in turn, can substantially increase the illumination power. Compared to the areal illumination, line illumination can be tens to hundreds of times brighter and the pixel size of one dimensional line pixel array can also bigger relative to a planar or other two-dimensional pixel array. These two benefits, taken together, can allow using either a much smaller W-CLS 101 or collecting data faster, or both. The particular actual application considerations may influence the choice between a line arrays or a two-dimensional array, and it is possible to use both together, in a combined approach.

There are too many applications of hyperspectral imaging to list them all. The approach described herein can be applied to any of these potential applications, such as can include process control, precision agriculture by measuring the chemical content of leaves, stems, fruits, or other target, or in remote or clinical settings in health for diagnosis of skin diseases such as psoriasis, tissue perfusion, or in art analysis, validation, and authentication, such as to help uncover fakes or understand master artworks. As this technique becomes widely available, a consumer may use it for matching furniture and paint independent of lighting conditions, or in cooking or in shopping for more nutritious food. By making hyperspectral imaging as accessible as RGB color camera, many new applications will be enabled, or many other applications will finally become available at price point made practical.

Similar to the manner described above in which the present W-CLS techniques can be used to convert a black-and-white camera or RGB camera into a hyperspectral imager, the present W-CLS techniques can be used to convert a black-and-white camera into an RGB camera. The typical spectral response curves of a camera are different from the typical spectral response curves of a human eye. Therefore, complex color adjustments may be needed with a typical camera to produce pleasing skin tones or other colors for a human observer. The RGB color imaging in an ordinary camera depends on the physical filters that transmit different spectral components to the underlying pixels. Including the present W-CLS based system can provide great flexibility in the spectral characteristics of such physical filters, such as desired by the photographer or artist. There are multiple ways to accomplish RGB rendering using the W-CLS based technique. For example, the dispersive system and coding can be arranged to directly produce the desired map to required RGB colors. In another fashion, a much higher resolution hyperspectral data can be generated, and then different spectral bins can be combined, such as in software, such as to produce a coarse three-color RGB image. This later approach may provide better control over the exact spectral shape of each of the RGB channels, and can thus help provide a high degree of color rendering capability. Moreover, this can be accomplished with a sufficient and desired degree of brightness, such as using a high intensity light source or the active slit techniques described herein.

4. Structured Light and Hyperspectral Imaging Example

The present techniques can enable diffuse light spectroscopy, including medical device applications of diffuse light spectroscopy of tissue. In an example, hyperspectral imaging using W-CLS can be combined with structured light to illuminate a target object or scene 117 that can include a skin surface and underlying tissue. Using structured light and hyperspectral imaging can help provide unprecedented detail on spectroscopic or structural information (or both) of the skin. It may allow measuring perfusion, blood gases, hemoglobin concentration, or other useful biomedical diagnostic information, as well as information about how the photons propagate across the entire face or illuminated area, which can be useful in characterizing or diagnosing tumors.

Figure 11:
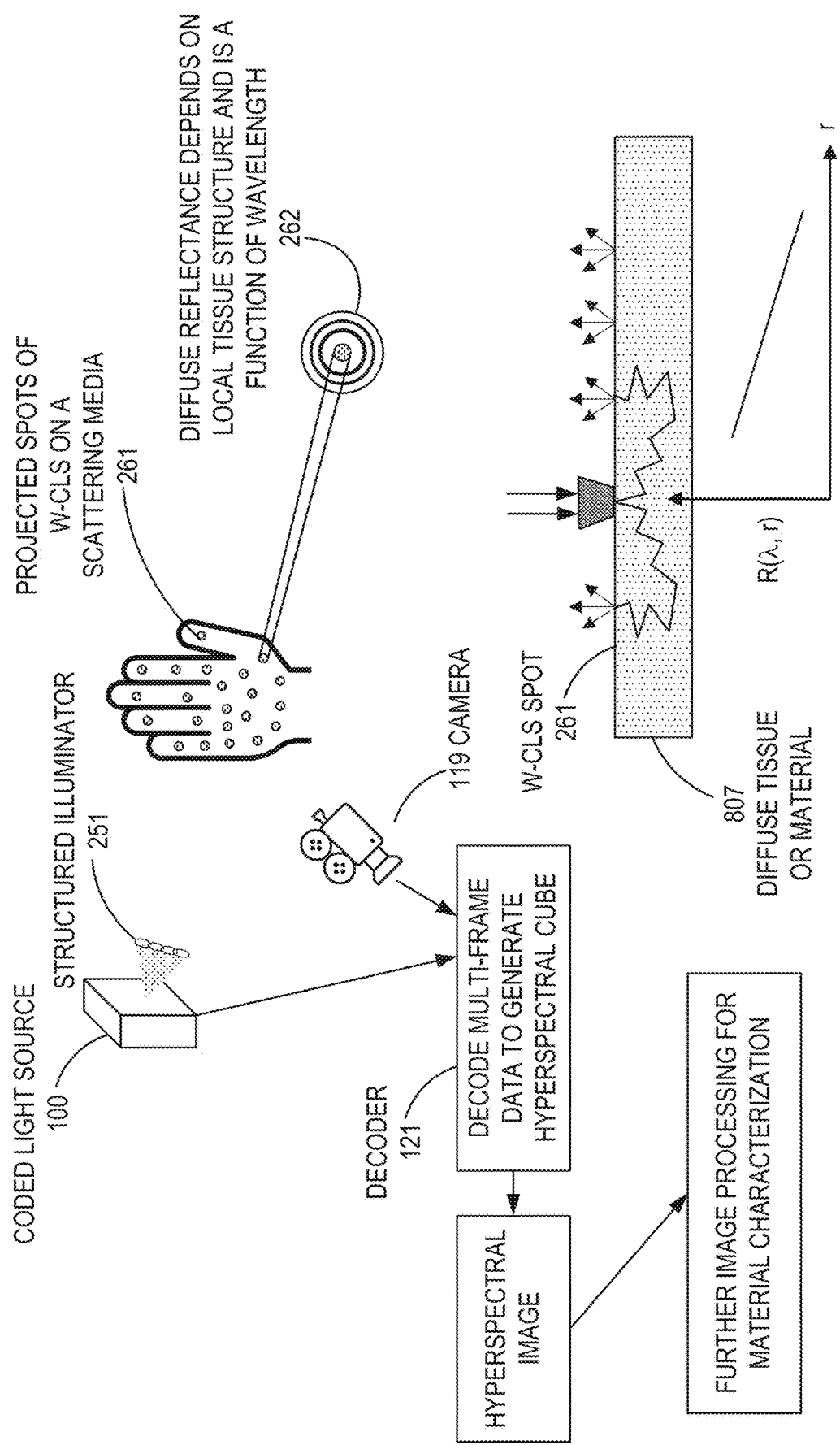
FIG. 11 shows an example of portions of a CLS system in which the illumination optics 115 can include or be used with a structured-light illuminator.

FIG. 11 shows an example of portions of the system 10 in which the illumination optics 115 can include or be used with a structured-light illuminator 251. The structured-light illuminator 251 can receive light from a W-CLS light source 100, such as explained herein, and can produce patterned or otherwise structured W-CLS light such as can be projected onto a skin surface or other target object or scene 117. The structured-light illuminator 251 can include a patterned mask or screen or scanner or other technique such as can form an incident pattern of the W-CLS light upon the target object or scene 117. Illustrative examples of such a pattern can include a pattern of dots or lines on the surface of the target object or scene 117. An illustrative example is shown in FIG. 11 in which, without loss of generality, a pattern of light dots has been projected onto a target object or scene 117 that can include a subject's hand. Line patterns of light (e.g., of like or varying pitch between the lines) can also be used as a projection pattern, in an example.

As shown in FIG. 11, the present techniques can be used to measure the structural properties of the target object or scene 117, such as can include the skin surface and underlying tissue, such as using one or more characteristics (e.g., absorption, scattering, or other characteristic) of light propagation in the tissue using a W-CLS based hyperspectral camera system 10 such as described in FIG. 1 and modified to include the structured-light illuminator 251. Each of the projected spots or dots 261 can be produced using W-CLS light. Hence, diffuse light emerging from the tissue around each dot 261 carries information about light transport in tissue at each of the coded wavelengths of the W-CLS light. This is an enormously rich data set that can be used to measure either or both of the absorption or scattering coefficients of the tissue across the spectrum of the W-CLS light. The decoded information can provide detailed measurements on the chemical and structural composition of the tissue or other sample being used as the target object or scene 117. But, by imaging using the structured-light illuminator 251, such information can be derived at multiple locations, such as corresponding to the various dots 261. The structured-light illuminator 251 can include a scanner or light deflector. By scanning or moving the spots or dots 261, information about the entire surface of the tissue or other target object or scene 117 can be reconstructed.

Spatially mapped measurement of tissue properties can help provide direct insight into tissue structure as well as tissue composition. When these insights are applied to human health, they can help effectively diagnose, predict, or characterize patient health, such as skin or tissue health. This can include diagnosing or characterizing skin cancers, psoriasis, various diseases of the epidermis and dermis, tissue perfusion, oxygenation and state of hemoglobin (e.g., using principles similar to $SpO_2$ measurement) or other properties. But the present techniques can make a spatial map of one or more such properties. Therefore, they can also be used to image or segment or otherwise identify or distinguish blood vessels or other structures. For example, arteries and veins can be imaged and distinguished, such as from their spectral properties due to differences in their oxygenation states of hemoglobin be carried in the blood vessel. In the near-infrared (NIR) region of the spectrum, where there is deep penetration of photons, such spatial mapping can enable diagnosis of malignant tissue, such as by looking for angiogenesis or increased scattering or change in local oxygenation levels. Thus the present techniques can be used in applications such as cancer screening, such as for breast cancer.

Furthermore, at high enough frame rate and SNR, one can directly measure the photoplethysmography signal from the arterial pulsation—a common technique used in $SpO_2$, heart rate measurement detectors-across the entire surface. Image processing techniques combined with rich spectral information, will allow measurement of a photoplethysmogram (PPG) along arteries and along veins, which are identifiable and distinguishable in the hyperspectral image due to the different color of the blood in the veins from that in the arteries. Such a fast, registered, spectrally-resolved image can permit measuring one or more physiological or other secondary parameters, such as of one or more of arterial, venous, or tissue targets. For example, such parameters can relate to oxygenation, hemoglobin content, pH, or one or more other blood or tissue properties.

In an example, the present techniques can be used to provide a diagnostic tool such as can allow non-invasive measurement of blood pressure or of tissue response to stress. For example, pulse wave velocity of blood in a blood vessel can represent a blood pressure wave spreading along each of the major arteries as the heart pumps blood. Such pulse wave velocity is a strong function of arterial stiffness. Pulse wave velocity in a human subject can range from 4 meters/second to 15 meters/second, e.g., depending on the subject's age, arterial compliance, etc. But for a particular human subject, pulse wave velocity also depends on the subject's blood pressure. Thus, pulse wave velocity can be used as a proxy for non-invasively measuring the subject's blood pressure. For example, W-CLS based hyperspectral imaging techniques such as described herein can be used to visualize the blood pressure wave propagating along the arteries. For example, an arterial PPG can be obtained using the present techniques for obtaining spectral information, and the arterial PPG can be used to measure pulse wave velocity. For typical human pulse wave velocities, a W-CLS based hyperspectral camera system 10 can be configured with an update rate in the 60 frames per second range, which is readily achievable.

The present techniques can be further extended to W-CLS using a polarized light source, such as explained further in the Polarization Coding Example described elsewhere herein. This can further deepen the insight into material properties. For example, a crossed analyzer can be placed in front of the receive side camera. This can be used to separate specular reflection of the projected incident light spot from the diffuse reflectance around the light spot. In some cases, such as those involving measurement of homogeneities or stress in a sheet of material (e.g., such as a plastic sheet), polarization mapping can help provide an internal map of material stress, while measurement of one or more scattering parameters can provide insight into the size distribution of inhomogeneities in the sheet of material.

While the previous description has focused on human tissue measurements and its applications to dermatology and endoscopy, the present techniques can be applied in other uses, such as can be extended to plant tissues, to paints (which are scattering particles and absorbers suspended in a matrix), such as to analysis of material characteristics of historical art and paintings, or semiconductor wafer inspection (e.g., for defects).

4. Wavelength Coded Light Source Based Spectrometer Example

This section describes a W-CLS based spectrometer, including a description of scattering, such as by a target object or scene 117, such as in tissues and other turbid media. The spectrometer can use techniques similar to those described herein for hyperspectral imaging, but the spectrometer may involve using few or fewer detectors. This section describes examples of various spectroscopic applications and ways in which W-CLS can be enhanced, such as to help provide even more rich information, which may otherwise be difficult to obtain via spectroscopy.

The hyperspectral imaging described previously can be used for spectroscopy applications. Advantageously, various components of light emerging from the target object or scene 117 sample—which can be either reflected, transmitted, or scattered—can be measured concurrently, or even at multiple locations, without requiring multiple spectrometers. Every detector can effectively act like a spectrometer. Various detectors can be placed at desired locations anywhere around the target object or scene 117 as desired for a particular application. Thus, the present techniques can provide a complete, fully calibrated spectrometer for the cost of the detector and electronics at any desired location. Since the present approach allows for the collection optics to simply gather photons from the target object or scene 117 or sample, the light detection and processing can be far more efficient than traditional spectrometric analysis of light after interaction with the sample, such as shown in the illustrative example of FIG. 2B. The high light collection efficiency afforded by the present technique can provide an incredible efficiency advantage, believed to be between 10× and 1000× more efficient, as compared to traditional spectrometric analysis of light after interaction with the sample, such as shown in the illustrative example of FIG. 2B. This increased efficiency can be used to help enable other uses or applications, or to help significantly improve the signal-to-noise ratio as compared to traditional spectrometry techniques. Without loss of generality, a detailed example below is described, in which a CLS based technique can be applied to tissue or diffuse light spectroscopy, in which the attenuation of light by the diffuse material of the target object or scene 117 is substantial. This example can help highlight how a CLS-based spectrometer according to the present techniques can not only provide a signal advantage, but the present techniques can also help enable new modalities that can be difficult to achieve using traditional spectroscopy techniques.

Figure 12B:
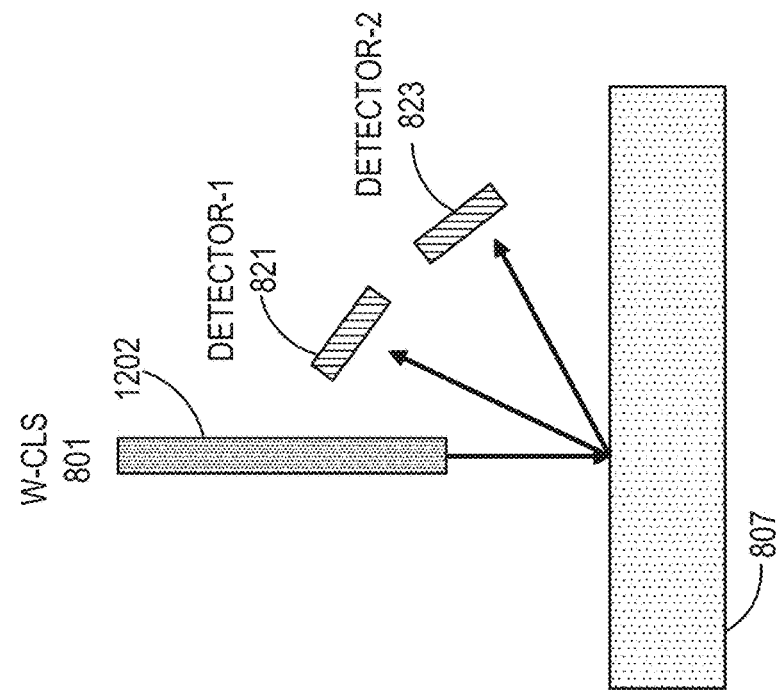
FIGS. 12A, 12B are schematic diagrams illustrating generally an example of portions of a system for performing spectrometry on scattering light passing through (FIG. 12A) or emerging from (FIG. 12B) a target object or scene, such as can include biological tissue or another material capable of diffusing light passing through (FIG. 12A) or reflectively scattering light from a surface (FIG. 12B).
Figure 12A:
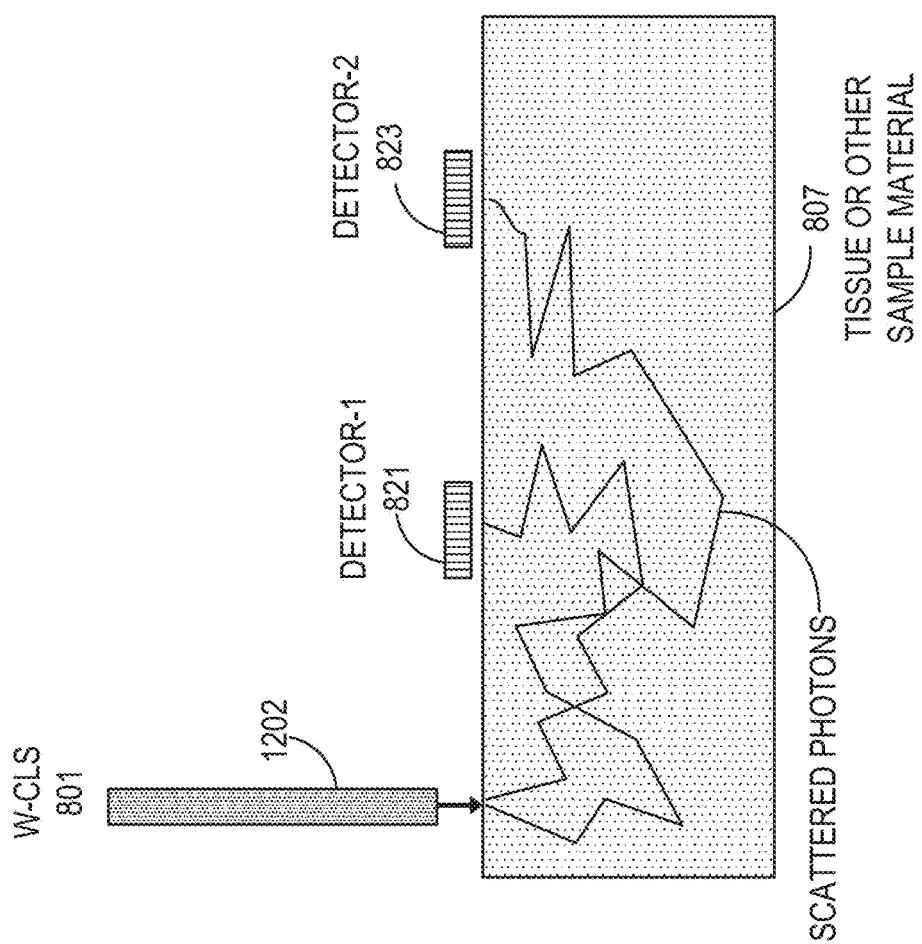

FIGS. 12A, 12B are schematic diagrams illustrating generally an example of portions of a system for performing spectrometry on scattering light passing through (FIG. 12A) or emerging from (FIG. 12B) a target object or scene 117, such as can include biological tissue or another material 807 capable of diffusing light passing through (FIG. 12A) or reflectively scattering light from a surface (FIG. 12B), such as for detecting and analyzing using the present techniques. For example, consider a light source providing broadband light, such as including wavelengths from 600 nanometers to 1000 nanometers, such as which can be separated into N=20 spectral bins. Without loss of generality, N can be any reasonable number, such as from 5 spectral bins through 500 or more spectral bins, or such as otherwise described herein. Each of the N spectral bins can be given a unique time-varying modulation, such as described herein. After imposing the time-varying signal modulation, the modulated light corresponding to the various wavelength bins can be combined to reformulate coded white or broadband light, such as to form a spatially homogeneous W-CLS light source. This W-CLS light source can be carried to the skin or tissue sample 807, providing a target object or scene 117, such as by an optical fiber bundle or optical fiber 1202, such as shown in FIG. 12A, or by placing other optics or even the entire W-CLS system in proximity with the skin or tissue sample 807 providing a target object or scene 117.

The W-CLS light incident upon and coupled into the skin or tissue sample 807 can be transported through the skin or tissue 807 and can then be measured by one or more photodetectors 821, 823. The one or more photodetectors 821, 823 can be placed upon the skin or tissue 807 or otherwise positioned at one or more various specified respective locations and distances away from the location at which the W-CLS light is coupled into the skin or tissue sample 807. This is similar to the description with respect to FIG. 10 using structured light illumination for a W-CLS based hyperspectral imager. In FIG. 12A, different spectral components of the light passing through the skin or tissue sample 807 are attenuated differently through the skin or tissue sample 807. This attenuation can depend on the distance between the photodetector 821, 823 and the location at which the W-CLS light is coupled into the skin or tissue sample 807. The attenuation can also depend upon the composition of the skin or tissue sample 807. In an example, the photodetectors 821,823 can be configured to recover the entire spectrum of the light passing through the skin or tissue 807 and reaching such photodetectors 821,823. The photodetectors 821, 823 can be large, for example, such as to provide enough surface area to collect most or all of the photons that emerge from the skin or tissue sample 807 or other scattering target object or scene 117. The resulting electrical signals from the photodetectors 821, 823 can be signal processed by signal processing circuitry to permit measurement of a spectrum of response light. This signal processing can be used to determine wavelength-dependent absorption and scattering cross-sections of the skin or tissue 807 sample, such as using spectral measurements of response light detected by detectors 821, 823 located at different distances from the location at which light is coupled into the skin or tissue 807 sample. Such spectral measurements can carry information about state of different molecular components in the blood and the tissue of the sample 807. The spectral measurement can be performed fast enough to measure changes in the light absorption due to pulsation of arteries and veins, which is due to the pumping action of the heart and in a smaller part due to breathing inhalation and exhalation of respiration. Photoplethysmography (PPG) techniques can use these pulsatile measurements to detect information about a chemical state of the blood. An example of such a technique is $SpO_2$ measurement, in which oxygen saturation in the blood can be measured with just two wavelengths of light, or at more wavelengths using more sophisticated measurements. Certain approaches can use multiple LEDs of different colors to produce light from different locations to illuminate tissue. The pulsatile component of light absorption is typically of the order of 0.1% to 3% of the total light absorption, and therefore requires high SNR to measure accurately. However, the present techniques using W-CLS can provide a higher fidelity signal (such as explained below) and can also provide a method to extend the present W-CLS techniques to a wider electromagnetic spectrum, providing frequencies at which many more of the chemicals that can be present in blood or tissue can be measured.

For many scattering-based measurements-especially related to tissue-based spectroscopy in humans, the quality of the spectral measurement depends on all wavelengths of light having started from the same spatial location of incoupling into the tissue sample 807. For example, calibration is easier when the separation between the incoupling light source and the photodetector is not wavelength dependent, and it can also help reduce motion artifacts. This is because most analysis of spectra will relate to relative changes amongst spectra. To the extent that motion of the body changes all of the light equally, it cancels. Motion of the body can include changes in the muscle fibers, skin structure, or the like, as well as motion of the light source and the light detector with respect to the body. Since the present W-CLS techniques can provide all photons for all the colors starting at the same location, the present techniques can be employed to suppress motion-induced changes, unlike a unlike an approach in which different LEDs provide different colors that illuminate the body at different locations.

The present CLS-based approach to spectroscopy can provide significant improvement in signal-to-noise ratio (SNR) over a non-CLS based approach to spectroscopy. Table 5 below provides a rough summary of light collection starting from light source to spectral measurement. The amount of light collected at each stage is proportional to the ratio of the input etendue ($A*\Omega$) to the output etendue at each stage. Here, A represents the area and $\Omega$ represents the solid angle of the light at each stage in the spectroscopic system. In the table below, we calculate the ratio of etendue for the conventional spectroscopic system and for the W-CLS-based spectroscopic system. The subscripts refer to the stage where the etendue is calculated.

TABLE 5

Signal chain for Non-CLS and CLS-based spectroscopy for diffuse measurements

| Stage | Non-CLS Spectroscopy | | CLS Spectroscopy | |
|---|---|---|---|---|
| | Comment | Loss factor | Comment | Loss factor |
| 1 Light from the source is collimated and sent to the sample: The collection efficiency is a strong function of the light source | For broad band light sources such as LED or filaments, a fraction of the light is collected by the fiber for transport to the sample | $\eta_1 = \dfrac{A_{fib}\Omega_{fib}}{A_{source}\Omega_{source}}$ | The broadband light can be directly coupled to the modulation mechanism, which can include dispersive optics | $\eta'_1 = \dfrac{A_{CLS}\Omega_{CLS}}{A_{source}\Omega_{source}} * CLS_{loss}$ <br> $CLS_{loss}$~0.1 − 0.5 |
| 2 Loss thru diffuse media 807 | | $\eta_2$ | | $\eta_2$' |
| 3 Collection of diffuse, Lambertian light spread over large area | Only the light that makes it thru the collection fiber and/or spectrometer slit is received. | $\eta_3 = \dfrac{A_{spec}\Omega_{spec}}{A_{sample}\Omega_{sample}}$ | Direct collection by detector | $\eta'_3 = \eta_3 = \dfrac{A_{det}\Omega_{det}}{A_{sample}\Omega_{sample}}$ |
| 4 Spectral measurement | Detector array receives fraction of the light entering the spectrometer. | $\eta 4 = SPEC_{loss}$~ (0.1 − 0.5) | Mathematical loss from imperfect modulation | $\eta 4$'~0.3 − 1 |

The information provided in Table 5 can be used to compare between a non-CLS and a CLS-based spectrometer, such as shown in Equation 9, such as using variables and notation as defined or explained in Table 5.

$$G = \frac{\eta'_1 \eta'_2 \eta'_3 \eta'_4}{\eta_1 \eta_2 \eta_3 \eta_4} \quad \text{Eq. 9}$$

$$= \frac{\dfrac{A_{CLS}\Omega_{CLS}}{A_{source}\Omega_{source}} CLS_{loss} \dfrac{A_{det}\Omega_{det}}{A_{sample}\Omega_{sample}}}{\dfrac{A_{fib}\Omega_{fib}}{A_{source}\Omega_{source}} SPEC_{loss} \dfrac{A_{spec}\Omega_{spec}}{A_{sample}\Omega_{sample}}}$$

$$= \left(\frac{A_{CLS}\Omega_{CLS}}{A_{fib}\Omega_{fib}}\right)\left(\frac{CLS_{loss}}{SPEC_{loss}}\right)\left(\frac{A_{det}\Omega_{det}}{A_{spec}\Omega_{spec}}\right)$$

$$\sim \frac{A_{det}\Omega_{det}}{A_{spec}\Omega_{spec}}$$

In the last line of the above Equation 9, it is assumed that the dispersive system loss (for example, one or more prisms) is roughly comparable whether the dispersive system is placed at the transmitter, as in the CLS-based approach to spectroscopy, or placed at the receiver as in non-CLS spectroscopy approach. However, a CLS-based approach to spectroscopy will have better light throughput than a non-CLS approach for the same given dispersive system. This is because, in the CLS-based approach, the light source and the CLS are in the same optical system. In a non-CLS-based approach, the etendue of the receiving spectrometer is much less than the diffuse light after it has traversed through scattering tissue or material 807.

But even with such simplifying assumptions, the last term in Equation 9 clearly shows the advantage of using a CLS-based approach to spectroscopy. For a photodetector that is capable of receiving radiation from all directions, $\Omega_{det}=\pi$. For a spectrometer with a given f/#, $$\Omega_{spec} \sim \frac{\pi}{(f\#)^2}.$$

An example of a slit area for a spectrometer is of the order of couple 100 micrometers of width and at most few millimeters in height. This example gives a slit area in the range of 0.1-0.5 millimeters$^2$. The area of the photodetector can easily exceed few millimeters$^2$. An area of the photodetector in the range of 7-20 millimeters$^2$ is easily achievable. Thus, the last term of Eq. 9 is of the order of (f #)$_2$ (40-100)>500. When all the other advantages are included, CLS-based spectroscopy can provide even higher signal. This advantage can be used to provide benefit in many ways. For example, a portable CLS-based spectrometer with a small battery-operated light source can provide the same SNR as a system with a large, fixed light source, such as a tungsten halogen lamp or a supercontinuum laser costing thousands of dollars. In some applications, the CLS-based spectrometer can include using one or more extremely sensitive photodetectors, such as one or more avalanche photodiodes (APDs), to help increase sensitivity. These kind of photodetectors are almost always extremely costly or difficult or impossible to use with an array of photodetectors, such as in a traditional spectrometers not using a CLS-based approach.

The present CLS-based approach can provide one or more other benefits over a non-CLS-based spectrometer that uses a photodetector array. With the present CLS-based approach (which need not require a photodetector array of different photodetectors to detect different wavelength ranges) there is no pixelation such as would otherwise result from using an array of photodetectors. Therefore, in the present CLS-based approach there is no concern about pixel-to-pixel inhomogeneity in the detected response, nor is there a concern about pixel saturation. Moreover, by using identical detectors for the reference channel detector 131, inside the CLS, and the one or more response measurement detectors 821, 823 after light has interacted with the sample 807, calibration or normalization, using information from the reference channel detector 131, can be employed to reduce or remove the effect of spectral variation of the W-CLS light source 100, 801. Such techniques can also be used to adjust for responsivity of the photodetectors 821, 823, such as described earlier, such that a fully calibrated spectral response signal can be obtained. Using the present CLS-based approach, issues with DC dark balance can also be avoided, since the modulation and reconstruction can operate to remove any DC drift. As discussed earlier, adding a wavelength-calibrating light source can also provide ongoing or continuous spectral calibration, without requiring a separate encoded wavelength for calibration purposes.

The present CLS-based approach can offer other advantages, such as for in-vivo tissue spectroscopy. For example, consider measurement of the light as it passes through a subject's finger or some other tissue sample 807, such as for measuring blood and tissue composition of the sample 807, such as in an oxygen saturation (SpO$_2$) measuring device use case. For illustrative comparison, a multi-wavelength SpO$_2$ device available on the market (https://www.masimo.com/technology/co-oximetry/set/) measures more than just the blood oxygen levels. In such a tissue measurement device, multiple LED light sources are used to measure light transmission through a sample of tissue. But good measurements require stability of LED wavelengths, which can depend upon temperature, injection current, and batch-to-batch variations. Thus, these multiple LED light source devices can require careful calibration and complex manufacturing. This substantially increases the cost of making and using such devices. Also, because all the different LED colors are not incident on the skin at the same light incoupling location, such devices can be susceptible to calibration errors and motion artifacts. The physics of diffuse light transport in tissue is quite sensitive to the source-detector separation. With different LEDs, the source-detector separation is a function of LED color, because the different color LEDs have different distances from the detector. Also, deducing arterial blood components from the spectral response measurements at different LED wavelengths depends on certain assumptions, for example, that the light travel paths taken by photons of different colors are same. This can be problematic when different colors are sourced by different LEDs that are at different locations. Also, the LEDs may produce slightly different colors, such as from batch-to-batch, or over different temperatures or bias currents. Thus, the available two color SpO$_2$ measurement devices can have substantial measurement errors, such as arising from wavelength uncertainty and the assumption that all wavelengths of illumination light have travelled the same paths.

Most of these difficulties can be reduced or eliminated using the present W-CLS approach, such as explained in this Section A of this document, and such as further explained in examples provided in Section B of this document, which explains applications of LED based spectroscopy, among other things. The coded light containing all the different wavelengths can be incident upon and incoupled into the tissue sample 807 at the same location, such as using an optical fiber or fiber bundle 1202, such as shown in FIG. 12A. A photodetector 821, 823 can measure the entire coded response spectrum from the tissue sample 807, such as with the benefit of a fixed and well-defined source-detector separation distance. More than one photodetector 821, 823 can be used to measure light transport at specified different source-detector separations, which, in turn, can help provide more detailed and accurate information about the composition or other properties or attributes of the tissue sample 807. As explained, a reference detector 131 can be employed to obtain calibrated spectral response, such that an accurate sample measurement can be taken in the field.

In addition to the benefits of using the present W-CLS approach for tissue measurements, such as described above, there are at least two further and enabling benefits of the present W-CLS approach to spectroscopy. The present W-CLS approach is scalable—it allows using more spectral bins as desired, while maintaining spectral accuracy. The present W-CLS approach also can provide from 100× to 1000× more light gathering ability for diffuse tissue spectrometry measurements over traditional spectrometry not using W-CLS.

For spectrometric analysis of light diffusing through a tissue sample 807, such as shown in FIG. 12A, or reflectance from a scattering surface, such as shown in in FIG. 12B, a conventional non-W-CLS spectrometry technique relies on having a spectrometer at each location in FIGS. 12A, 12B at which a detector 821, 823 is shown. A high resolution spectrometer will admit very little of the attenuated response light, as explained earlier (including with respect to Table 5 and Equation 9). Thus, a conventional approach to spectrometric measurements necessitates using an intense light source, such as a supercontinuum light source, a plasma generated light source, or a large Xenon/Xenon-tungsten bulb consuming 100s of Watts of power or costing tens of thousands of dollars. By contrast, the present approach does not require a high intensity light source, but such a high intensity light source can optionally be used with the present approach, but in a manner that obtains additional benefits, such as to illuminate a larger surface area or fainter target object, or to collect data more rapidly or with higher SNR, among other things. Further, to repeat an already-stated point, in the conventional approach to spectroscopic measurements, making two concurrent measurements using a conventional non-W-CLS approach involves using two expensive spectrometers. Thus, the detailed scientific understanding and promise of multi-spectral or hyperspectral spectrometric analysis has remained confined to a laboratory in which such expensive equipment exists to carry out such studies. By contrast, the present W-CLS approach can free such measurements from the confines of the laboratory, and can make it practical to carry out spectroscopic measurements with equal or even higher quality in the field and using small power light sources and adding spectrometric measurement capability to every photodetector. The high photon collection efficiency capability of the present W-CLS approach means that it is indeed possible to have high enough bandwidth and maintain needed SNR to measure a photoplethysmogram (PPG) and other dynamic phenomena across multiple or many spectral channels, such as to help provide accurate non-invasive measurements of a tissue sample of a subject, such as for helping diagnose human or animal health.

Thus, the present W-CLS technique can provide many practical measurement benefits, such as a compact, inexpensive, single broadband light source. More particularly, because of the higher light collection obtainable by avoiding a conventional spectrometer's need for dispersive optics in the lower-light environment of the receive side from the sample, the transmit side light source power can be reduced. Also, as explained, the present W-CLS approach can allow all wavelengths of the illumination light to be incident at the same single location on the target sample 807, thereby helping avoid inaccuracies resulting from different wavelengths taking different paths through a sample and, therefore, experiencing different interactions with the sample. The present W-CLS approach can also provide the ability to reconstruct spectra at multiple locations, with arbitrary geometry, with high SNR wherever the photodetectors are positioned or located. Using multiple photodetectors, such as can be positioned at various different locations, measurement of separate scattering and absorption coefficients at different wavelengths is obtainable. This can open applications not only for patient monitoring spectrometry devices that measure blood parameters, such as described earlier, but also for numerous other uses, such as measuring turbidity of fluids, or measuring one or more characteristics of plant physiology, or functional imaging of the brain or breast such as using near-infrared spectroscopy, which can use multiple light response signal pick-up locations for tomographic reconstruction.

Some other illustrative examples applications are described below. For example, the present W-CLS approach can be used in high SNR spectroscopy in the shortwave infra-red region, such as to measure one or more components such as fat, protein, alcohol, or glucose. Non-invasive measurement of glucose (NIG) can be enabled by the present W-CLS approach-previous attempts at NIG appear to have failed due to one or more of the following: inadequate spectral coverage, inability to get high enough SNR, inability to access multiple spectral regions such as 800-1000 nanometers as well as 1500-1800 nanometers and to obtain independent measurement of scattering and absorption. For NIG, the optical properties of the tissue need to be measured with sufficient diversity to allow signal processing to remove one or more confounding effects, e.g., the effect of skin type, tissue hydration, body temperature, etc. Previous attempts at NIG were "tricked" by changes in glucose inducing systemic changes in one or more other parameters, which also change for other reasons.

The present approach of W-CLS can permit concurrently performing multi-point (e.g., from multiple detectors, such as can be differently spatially positioned or located as desired) diverse spectral measurements such as can provide the basis for robust glucose diagnosis or prediction. For example, using the present W-CLS approach, spectral response can be measured from 700-1800 nanometers to cover a host of phenomena and materials found in the body. With high enough SNR, a PPG pulse can be tracked across the entire wavelength range, which can eliminate one or more effects of other tissues, such as using techniques analogous to those applied to $SpO_2$ measurement. The spectral response can be monitored at multiple locations using the present W-CLS techniques, such as to help ascertain changes in one or more scattering parameters that change with the glucose concentration. Slow changes not related to PPG can also be monitored across all the wavelengths. Since the present W-CLS approach allows all wavelengths of incident light to be incoupled into the sample at the same location, motion artifacts can be reduced or can be systematically related to the placement of the light source on the sample being tested. This allows an accurate optical model of the tissue to be built, so that changes in the tissue can be tracked. Furthermore, once the appropriate spectral regions are determined, the W-CLS wavelength encoding can be "tuned" to provide only the necessary wavelengths, such as described previously with reference to "programmable resolution." Other improvements can include using an active slit or a PIC-based modulator. While this explanation has emphasized a NIG use case in some detail, the approach can be applied to many other chemicals found in the body, in a plant, or in another target.

For example, the present W-CLS approach can be applied to spectrometric analysis of plant tissue, such as in the 800-2400 nm region, such as to measure one or more of flavonoids, alkaloids, polyphenols, or the like.

FIG. 12B illustrates an arrangement that can use the present W-CLS approach such as to provide a multi-angle, multi-wavelength measurement of light scattering from a surface of a sample. Uses can include characterizing surface texture, surface type, and material composition, and can be implemented in a compact module, such as described with respect to FIG. 45 in Section B and elsewhere in this document. A similar approach can be used for other scattering-based measurements, for example, such as characterizing aerosols.

Figure 13B:
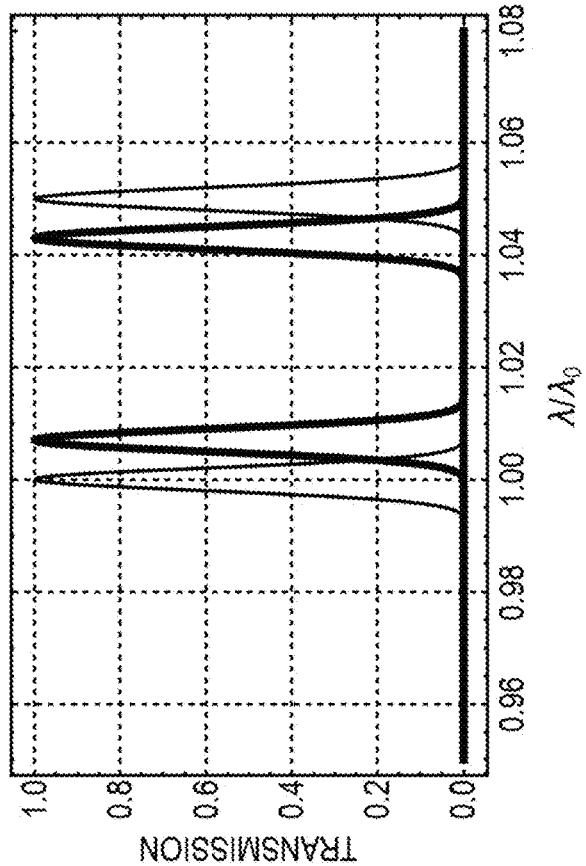
FIG. 13B shows an example of transmission wavelength spectral response shift for a structure including a Fiber Bragg Grating (FBG).
Figure 13A:
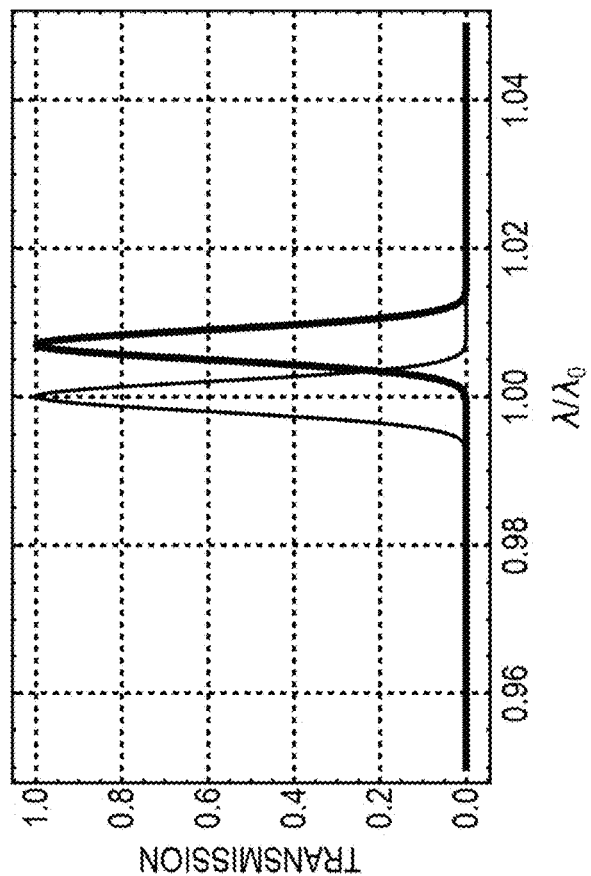
FIG. 13A shows an example of transmission wavelength spectral response shift for a Fabry-Perot resonator.

The present W-CLS techniques can also be applied to an optical sensor, such as a sensor that can measure temperature or strain or pressure or magnetic field or some other stimulus variable by a change in a spectral response in proportion to or other function of the stimulus variable. This can be advantageous in high electromagnetic interference (EMI) or other rugged environment, since the present W-CLS approach can permit measuring spectral shift independently of light intensity or of aging of various components. Examples of such sensor systems can include Fabry-Perot (FP) resonator (e.g., with a transmission wavelength spectral response shift such as shown in FIG. 13A) or Fiber Bragg Grating (FBG) (e.g., with a transmission wavelength spectral response shift such as shown in FIG. 13B) structures. A W-CLS approach can provide direct measurement of spectral shifts, such as shown in FIGS. 13A, 13B, such as when interrogating a FP resonator, a FBG resonator, or other optical sensor structure.

The present W-CLS approach can also be used in air quality measurement applications, such as to provide a compact, robust, instrument that can measure one or more gases or aerosols, for example, such as $O_2$, $CO_2$, water vapor, $CH_4$, as well as smoke or other particulate matter. Optical gas measurements can use infrared absorption spectroscopy, using a Non-Dispersive Infrared (NDIR) instrument targeted at one or more specific gases. Detection or characterization of particle scattering can be carried out using visible light wavelengths. For aerosol classification, both attenuation and scattering can be measured at multiple angles. For the present W-CLS, with encoded wavelengths spanning from 500 nm to 5000 nm, this can be accomplished using an ordinary light bulb as a light source. The light source can be encoded using broadband coding of specific wavelengths that can be obtained using a dispersive component, such as prism.

FIGS. 14A, 14B show an example of how coding can be provided at the various important wavelengths of interest for a particular gas, aerosol, or particulate measurement. FIG. 14B shows an example of how response light detection can be performed using a composite photodetector 141 (e.g., made from Silicon, InGaAs, PbS, and PbSe), which can provide various photodetector elements that can all concurrently detect respective wavelengths. In this way, the various photodetector elements of the composite photodetector can be as to measure the entire wavelength spectrum of interest after the W-CLS illumination light has travelled through the air or other medium to be tested for a fixed distance. A side photodetector 143 can be used to measure scattering from particles either in the visible/NIR or across the entire wavelength spectrum. The photodetector 141 can measure optical attenuation by different gases and can therefore be capable of directly measuring their respective concentrations. Smoke and other particulate matter (e.g., pollen, bacteria, or the like) will scatter light into the side photodetector 143 as well as cause attenuation at the photodetector 141 due to light scattering. A broadband (e.g., visible light and NIR light) can be used to provide detailed information on various types of particles and particle distribution. Further, one or more specific light absorption bands can be tracked by the photodetector 141, such as to measure various relevant atmospheric gases as well as aerosols, such as shown in FIG. 14B. As explained elsewhere herein, such as with respect to FIG. 23, a configuration can be used in which light can be reflected back, such as using one or more retroreflectors, which can help avoid the need for remote detector. Characterization of aerosols (small particles ranging from nanometer to micrometer) have specific wavelength-dependent scattering and attenuation that can depend on both particle size distribution as well as material absorption. As explained herein, the present W-CLS approach can be configured to allow for multi-angle measurements (optionally at different polarizations) such as to help accurately determine or classify the aerosol type. This can have safety applications. It can also be useful for monitoring environmental allergens in air. Spectroscopic characterization of aerosols is not readily available in the home or office or factory floor due to high cost of existing spectrometers. The present W-CLS approach can help make it commercially feasible to provide air quality information, such as can be used for intelligent control of air quality, for measurement of different types of smoke, or for other applications. For example, in a smoke-detection application, using information about multiple-angle, multiple-wavelength scattering can help significantly reduce false alarms and can allow distinguishing between different types of smoke, e.g., to alert to the presence of a property-combustion or similar fire, but not alert to the presence of burning incense.

The above example can be extended to many systems that involve measurement of absorbance of scattering at multiple angles. The system shown in FIG. 11 can be combined with that shown in FIGS. 14A, 14B in numerous ways. Important commercial markets can include turbidity measurements in water, flow cytometry, or as atmospheric measurement, such as over a long baseline.

In the above applications, the reconstruction can include using orthogonality or auto-correlation, which can be aided by the W-CLS encoding clock on the transmit side of the system being synchronized to or aligned with the reconstruction clock on the receive side of the system, such as to help facilitate high SNR reconstruction. For small footprint systems, such as enabled above, the coding clock can be transmitted over the wire from the transmit side of the CLS system to the signal measurement componentry on the receive side of the system attached to the photodetectors. But the technique shown in and described with respect to FIGS. 14A-14B can be extended over a long baseline, such as where the photodetector 141 can be located many meters or kilometers from the CLS-without having to transmit the clock over a physical wire or wirelessly using radio transmission. Instead, the clock information can be directly encoded on the CLS itself at a specified frequency, such as at a frequency that is much higher than the frequency region occupied by the coding functions. This can be accomplished similarly to what was described elsewhere herein, such as in the description of frame-synchronization information transmitted from CLS to the camera for the hyperspectral imaging application of FIG. 10. This allows the coding clock to be recovered at the remote-end for high fidelity reconstruction without requiring having a direct wired or RF communication with the transmit side of the W-CLS system. An illustrative application in which transmission of coding clock over the W-CLS channel can be used is in characterizing aerosols in the atmosphere. In this case, the path between the W-CLS source and the detector can be long. Therefore, it may be impractical to run a wire from the W-CLS source to the detector for proper reconstruction. Thus, the optical CLS signal itself may be optically encoded so as to include a timing reference output to provide a timing reference signal, and wherein the timing reference signal is optically embedded onto at least one of the modulation-coded different wavelength components on the transmit side, and optically recovered to provide a synchronization or timing reference signal on the receive side. Alternatively (or additionally), the coding clock may also be transmitted over separate RF. This will allow measurement of the atmospheric scattering parameters.

5. Example of W-CLS with High-Speed Modulation of the Light Source

As explained above, measurement of W-CLS light scattering and light absorption can be performed using spatially diverse measurements, such as using a structured light hyperspectral camera, such as explained above with respect to FIG. 11, or using multi-detector measurements, such as explained above with respect to FIGS. 12A, 12B. Alternatively or additionally, the travel time of the illumination light can be measured, e.g., the time for such light to travel through the diffuse tissue or material of a target object or sample 807, 117 to the photodetector 821, 823.

For example, this travel time of the light through the target object or sample 807 can be measured (e.g., by the signal processor circuitry 13) as phase delay vs. high frequency modulation of the illuminating light source. For example, for light travel time delay in nanosecond range, the high frequencies of modulation, e.g., for performing phase delay measurement, are in the tens of MHz to GHz range. For example, one or more techniques such as time domain diffuse light reflectance spectroscopy ("TD-DLS") or Fourier-domain diffuse light reflectance spectroscopy ("FD-DLS") can be used, such as to allow a direct measurement of scattering and absorption in the scattering media of the sample 807 as a function of light wavelength. As explained previously, such measurements are useful for characterizing the sample 807, such as for multiple endeavors. Illustrative examples can include non-invasive measurement of a medically relevant parameter of a tissue or other biological sample 807, such as one or more of tissue temperature, hydration, SpHb, glucose, among others.

The present W-CLS techniques can be used together with high frequency modulation of the LS to provide a practical approach to making such measurements, such as in a clinical or an industrial setting. For example, FD-DLS can be used together with W-CLS. The W-CLS modulation of the different light wavelength groups in the kHz to 100s of kHz range by the optical illuminator or transmit side 11 of the system 10 can additionally be modulated by the same or a different modulator of the optical illuminator or transmit side 11 of the system 10 at an even higher frequency, such as a high frequency (HF) modulation in the MHz to GHz range, such as to enable the FD-DLS techniques to be used in characterizing the sample 807. Information about such modulation on the transmit side 11 of the system 10 can be used by the controller/signal processor 13 on the receive side 12 of the system 10, such as to decode and recover amplitude or phase or other response information about the W-CLS spectral bins or using the higher frequency modulation, to synchronize reading of pixel or other information from the cameras 119 or other photodetectors, e.g., 821, 823, or both, such as by hardware or software that can also use illumination modulation timing reference information.

Figure 15:
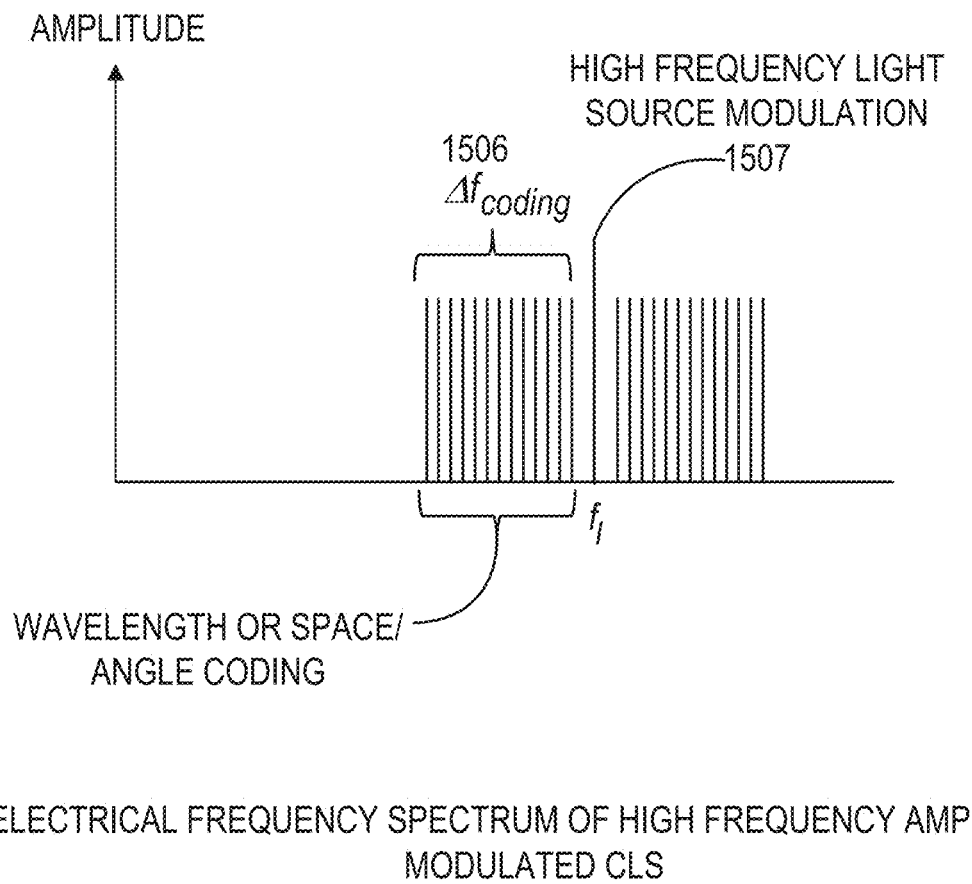
FIG. 15 shows a conceptual graph of amplitude vs. frequency using both W-CLS modulation and HF modulation.

FIG. 15 shows a conceptual graph of amplitude vs. frequency using both W-CLS modulation and HF modulation. FIG. 15 illustrates an example of the different W-CLS modulated light components 1506. These modulated light components 1506 can have modulation frequencies in the kHz to 100s of kHz range. The modulated light components 1506 can be individually encoded at various wavelengths using the corresponding modulation frequencies, such as described herein. Such encoding and modulation can involve using a mechanical modulator or other modulator, examples of which are described herein. Additionally, the light source 101 that supplies light to the modulator 105 can itself be modulated, such as at a high frequency around $f_l$, such as by using a high-frequency light modulator coupled between the light source 101 and the encoding modulator 105. In this way, the light source 101 can provide light that can then be modulated at a high frequency, such as to provide a high frequency modulated light component 1507 to the encoding modulator 105. An example of the resulting spectrum output from the encoding modulator 105 is shown in FIG. 15, for amplitude modulated CLS.

As explained below, the high modulation frequency $f_l$ can be scanned or swept, such as to produce a complex response of the system at different optical wavelengths. The scanning of the high frequency can be done by sweeping the frequency of the modulation of the LS or by using PIC based modulators, such as described with respect to FIGS. 7A, 7B. Electro-optic modulator arrays can provide sufficient bandwidth to directly generate the modulation spectrum, such as the one shown in FIG. 15 at all the optical wavelengths. It should be noted that modulation frequencies can be pushed into MHz to GHz range, such as to measure phase or frequency response of the light transport through the sample 807. Decoding of such high frequencies can use one or more RF demodulation techniques. For example, for the spectrum shown in the example of FIG. 15, the high frequency $f_l$ can be demodulated to an intermediate frequency, thereby transferring the phase information to the intermediate frequency. Then, direct digital conversion and I-Q demodulation at each of the coded light source frequencies can be used to recover both the amplitude and phase information. This is similar to the earlier-described technique for recovering spectral information for a hyperspectral camera, in which the phase term was not addressed because, in the earlier case, the frame rates may be too slow compared to the speed of light traveling through the sample 807. But the W-CLS techniques can work well even with the more advanced signal processing of high frequency system response at multiple wavelengths.

Such signal processing techniques can include using Frequency Domain Dynamic Light Scattering ("FD-DLS") with W-CLS or with S-CLS, such as with LIDAR or other applications. For example, assume that the optical spectrum of interest spans the frequencies used for the W-CLS modulation codes, having a total bandwidth (BW) that can be represented as $\Delta f_{code}$. In other words, the W-CLS modulation codes ranging from $g_1(t)$ to $g_n(t)$ span the frequency region $\Delta f_{code}$. In the initial description of W-CLS, the light source 101 itself was not modulated. Instead, the unmodulated light source 101 delivered light to a modulator 105, which performed the W-CLS modulation. For employing FD-DLS measurements of the optical signal, such as at multiple wavelengths such as used for W-CLS, the broad-spectrum light source 101 can itself be modulated, such as at a high frequency, Ω. The HF modulation frequency Ω can be in the MHz range, such as desired to be consistent with the expected phase change or time delay to be measured in association with the light passing through the sample 807. The HF modulation frequency 12 can be achieved, in an example, by directly modulating a superluminescent LED ("SLED") light source 101, or by using a phosphor-based light source 101, in which the phosphor's broadband light output can be modulated by a pump laser or using one or more waveguide modulators, such as shown in FIG. 7B. Thus, the signal spectrum of light passing through the sample 807 and received at the photodetector 821, 823 will include high frequency modulation, due to direct HF modulation at 22 of the light source 101, flanked by two sidebands corresponding to the W-CLS coding modulation (e.g., in an example in which the W-CLS coding was amplitude modulation coding). If there were no W-CLS coding modulation, then the high frequency modulation at Ω of the light source 101 will be received at the one or more photodetectors 821, 823, such as with a delay $$\tau = \frac{2z}{c}, \text{ or a corresponding phase} \phi = \Omega \tau \qquad \text{Eq. 10}$$

with respect to the phase of the incident light illuminating and incoupled into the sample 807, where z represents the distance between the incoupling location and the photodetector 821, 823, and c represents the speed of light in the medium of the sample 807. The high frequency modulation at the modulation frequency 2 can be demodulated using an I-Q demodulation technique. But, as explained below, with W-CLS the phase delay can be measured using one or more or all of the spectral components of the W-CLS light.

To understand how FD-DLS can be applied with W-CLS, it can be assumed that the high frequency modulation can be a sinusoidal modulation at frequency $\Omega_l$. It can also be assumed that each of the W-CLS codes are encoded sinusoidally, such as at corresponding frequencies $\omega_k$. The analysis would be similar using other orthogonal or quasi-orthogonal functions instead of using sinusoidal functions. For illustrative clarity, without loss of generality, the present explanation focuses on sinusoidal functions. For W-CLS coding frequencies $\omega_k$ in the range of kHz, or less than the high modulation frequency $\Omega_l$ of the light source 101, the outgoing W-CLS illumination light can be described as:

$$W_{CLS}(t; \theta_k) = \exp(i\Omega_l t) \sum_{k=1}^{N} a_k \exp(i\omega_k t) \qquad \text{Eq. 10}$$

In Eq. 11, $\omega_k$ represents the different individual modulation frequencies for each of the wavelengths $\lambda_k$ of the W-CLS encoding modulation. A conceptual illustration of the frequency domain description of the modulated light components is shown in FIG. 14. The resulting received light signal at the photodetector 821, 823, after the light has interacted with the medium 807, can be represented as:

$$D(t) = W_{CLS}(t - \tau_k; \omega_k) \qquad \text{Eq. 11}$$

$$= \sum_{k=1}^{N} r_k a_k \exp(i(\Omega_l + \omega_k)(t - \tau_k))$$

Using a signal processing demodulation technique such as I-Q demodulation in a demodulator in the controller/signal processor 13—which can be applied concurrently at multiple "carriers" at frequencies $\Omega_l + \omega_k$—the phase and amplitude at each $\lambda_k$ can be recovered. Signal processing such as I-Q demodulation techniques can be applied using more than one carrier frequency $\Omega_l$ such as to remove ambiguity due to phase wrapping whenever $\phi_k = \Omega_l \tau_k > 2\pi$. Note that the coefficients $a_k$ in Eq. 12 and the timing of the outgoing light illumination signal, can be measured using the reference detector 131, and communicated to the decoder 121 of the controller/signal processor 13. Hence, the demodulator in the controller/signal processor 13 can directly measure ($r_k$, $\tau_k$), which can be performed for each particular $\lambda_k$ and represented as ($r_{\lambda_k}$, $\tau_{\lambda_k}$). This decoded phase delay information can provide detailed information on the nature of the dispersive and scattering medium of the sample 807.

As explained above, the high modulation frequency $\Omega_l$ can be scanned or swept, such as to produce a complex response of the system at different optical wavelengths. The scanning of the high frequency can be done by sweeping the frequency of the modulation of the light source or by using PIC based modulators, such as described with respect to FIGS. 7A, 7B. Electro-optic modulator arrays can provide sufficient bandwidth to directly generate the modulation spectrum, such as the one shown in FIG. 15 at all the optical wavelengths.

Although FIG. 15 illustrates an example corresponding to Amplitude modulation with sidebands, one or more other suitable modulation techniques can be applied. For example, individual spectral components can respectively be encoded with a unique pseudo-random, random, or noise-like signal or sequence, such as can have a wide bandwidth. In such a wideband coding case, cross-correlation of the output signal at each photodetector 821, 823 with the input modulation for each of the pseudo-random, random, or noise-like signals or sequences can be used to directly produce the high frequency spectral response of the system at each of the various wavelengths.

Both a swept high frequency technique, such as illustrated in the example shown in FIG. 15, or noise-like wideband coding can be used, such as to generate an impulse response of the system from its frequency domain measurements. Some illustrative examples of applications of such wideband W-CLS are included in the following description. First, frequency response or phase delay at different wavelengths can be used to characterize human, animal, or other biological tissue. This can be useful for non-invasive medical diagnostic or therapy devices, including such as explained elsewhere herein. A second illustrative example can include measuring electrical frequency response of semiconductor sample arranged as an optical detector, such as over a wide spectral range to measure responsivity and one or more electrical characteristics of the optical detector over an optical spectrum. A third illustrative example can include obtaining concurrent measurements of 10s or 100s of concatenated Fiber Bragg Gratings (FBGs), such as in which both temporal delay and spectral shifts can be measured and characterized. The present techniques, including using W-CLS, can offer convenience and simplification in each of these three (and other) illustrative examples.

For a semiconductor measurement or characterization, such as mentioned in the second illustrative example above, the present techniques employing W-CLS can provide benefits such as rapid and convenient measurement, which, in turn, can speed up research in material properties. The mobility of photon-induced charges and the absorption depth of photons in the semiconductor can determine the intrinsic electrical bandwidth of a particular detector as well its responsivity. A detailed characterization of responsivity vs. wavelength vs. frequency can be time consuming and painstaking. In comparison, using W-CLS techniques for illuminating a semiconductor sample arranged as a photodetector can directly measure the responsivity of the semiconductor sample by simply using the semiconductor sample being tested as the photodetector such as described elsewhere herein. Further modulating the light source 101 at a high frequency, such as in the MHz to GHz range, can map out the responsivity of the sample/detector as a function of modulating frequency, thereby generating a detailed map of frequency dependent responsivity. This approach can be used in new detector research as well as characterization and design of new detectors and photosensitive materials. The examples mentioned above are illustrative, other applications can also employ the present techniques.

Illustrative examples of broadband light sources 101 that can be efficiently modulated at high frequencies and can provide basis for wideband W-CLS are now described further. First, in an example, a superluminescent LED can provide a spectral width of 20-100 nanometers, and can be directly modulated to 100s of MHz and possibly 1000 MHz modulation. Second, a laser pumped phosphor can be modulated, such as can have a modulation bandwidth defined by the emission time of the phosphor. Some phosphors are capable of modulation at 100s of MHz. These phosphors, or mixture of phosphors, can have spectral width that can range from 500-1000 nanometers or even up to 1500 nanometers, such as to form a broadband light source capable of fast modulation.

6. Active Slit Light Source Example

As explained above, W-CLS techniques can be used in a number of configurations and applications. Among other things, the present W-CLS techniques and system configurations can help shift the burden of spectrometry from the receive side 12 (with its relative scarcity of available photons after interacting with the target object or scene 117, 807) to the transmit side 11 or to the light source 101 (which have a relative abundance of available photons, compared to the photons available after interacting with the target object or scene 117, 807). Of course, there may be some additional digital signal processing performed on the receive side 12, such as for decoding light that was encoded on the transmit side 11, such as using the present W-CLS techniques. A reference detector 131 and frame synchronization can be included on the transmit side 11, such as to communicate information to the receive side, such as for efficient decoding on the receive side 12.

In the above explanation of the examples of FIGS. 3, 4A, 4B, certain light dispersion techniques employed were described as including examples in which a "slit" can be used to deliver light to a light dispersive optical element, such as for light-dispersive spectrometry, hyperspectral imaging, or various other applications such as described herein. But the slit restricts the amount of light that can be gathered from the light source LS 101. Therefore, such a slit can represent a significant loss of optical efficiency. However, such efficiency can be significantly improved in the configurations and applications described above, as well as in other configurations and applications, such as by providing an "active slit," such as described herein. The active slit such as described herein can also help enable or provide additional functionality and flexibility in constructing the system 10 using W-CLS, and can provide a tunable active slit light source that can find use in other applications even outside the context of a system 10 using W-CLS.

An active slit can be constructed using certain phosphors and LEDs. For example, using a laser-pumped phosphor, an active slit with a luminous brightness of 100-1000 microWatts/nanometer can be provided. This is comparable to the luminous brightness of a laser pumped plasma source or supercontinuum generation from a short-pulse laser or a Xenon-Tungsten lamp consuming hundreds of Watts of electrical power to achieve such luminosity. By constructing an active slit with an appropriate phosphor to provide such a high degree of luminous brightness and efficiency, the size of the system can be reduced, since there will be reduced thermal requirements (e.g., for power delivery and heat sinking) when less electrical power is consumed to produce such bright light. An output luminous power intensity of 1-100 Watts/millimeter$^2$ can be achieved using a white LED phosphor, such as can be used for automotive headlamps or general illumination. Laser and LED pumped phosphor-based light sources usable in other technologies can be used in the present systems and techniques to construct a high efficiency W-CLS.

A substantial advantage of certain such sources is that, if desired, the entire broadband spectrum can be generated using a single high temperature source (e.g., filament, gas, etc.) that is spectrally stable, when measured over time, over temperature, and from manufacturing batch-to-batch, as compared to a collection of LEDs or phosphors. Certain approaches to spectroscopy can benefit from a stable light source to illuminate the target object or scene 117 or sample 807, such as to then measure the spectral response of the target object or scene 117 or sample 807. As explained herein, in certain approaches, before every spectroscopic measurement (or every so often) a "white card" test to calibrate source-detector response and a "dark" calibration needs to be carried out. Also, to transmit light from a light source through an optical fiber (or fiber bundle) or to provide well-collimated illumination, such as for microscopy or angle sensitive spectral measurements, or to focus the light source to a small spot, the etendue $G=A_{source}\Omega_{source}$ of the source should be as small as, or smaller than, an illumination and coupling requirement. In sum, such considerations can make it difficult to use a LED or a LED/laser pumped phosphor source in certain approaches to spectroscopy.

Indeed, some spectrometric approaches can involve extensive calibration, an internal spectrometer, or an array of photodetectors to measure spectral output. Certain dispersive tunable light sources can be based on a broadband light source coupled to a monochromator or a system of narrow band filters (that require collimated light). and that can provide a user-selectable narrow band of light.

The present techniques, such as explained below, can include an active slit that can potentially surpass the performance of certain other tunable light sources. Significantly, such an active slit can provide an extremely compact and power efficient light source 101, such as for using a CLS technique, such as W-CLS. In particular, as described below, using an active slit CLS method can reduce or remove certain barriers in using heterogeneous light sources, such as a mixture of light sources that are spatially separated, such as shown in FIG. 16B and FIG. 18, as described elsewhere herein.

In an example of the present approach, the target object of scene 117 or sample 807 can be illuminated with coded wavelengths, with spectrometric spectral dispersion being provided at the light source 101 or on the transmit side 11 of the system 10, before the illumination light interacts with the target object or scene 117 or sample 807. This transmit-side approach can be used with an additional optical technique that can allow using an LED or LED/laser pumped phosphor-based active slit light source 101—and can advantageously work around and avoid the calibration problems alluded to previously. Instead, the present approach can itself provide ongoing or continuous calibration to the spectral output of the W-CLS. Using a highly-efficient active slit light source 101, e.g., including one or more phosphors pumped by one or more LED/lasers, a precise, low power spectrometry can be provided that can exceed the performance of certain other approaches to spectrometers.

Figure 16A:
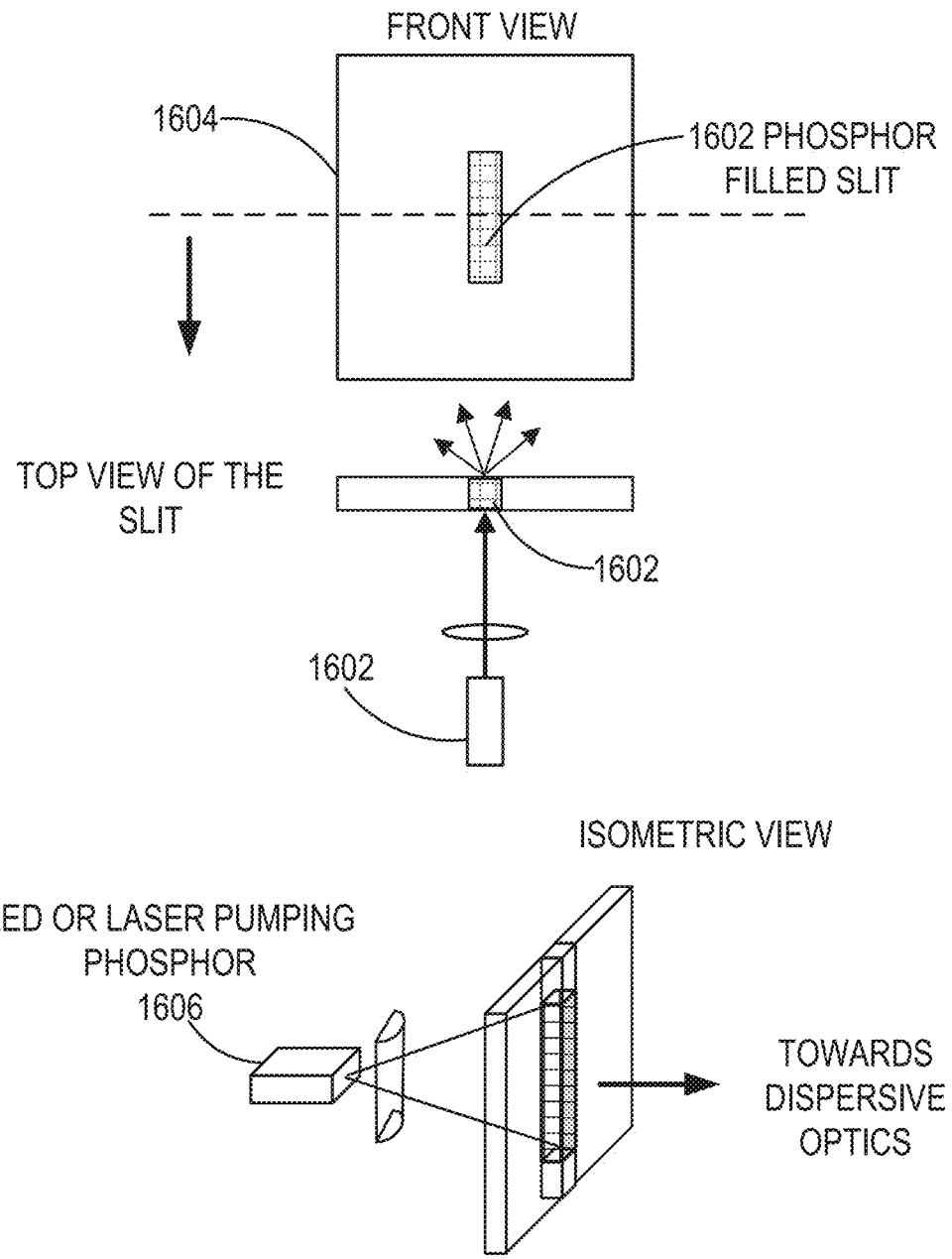

FIG. 16A shows an example of an active slit including a defined-shape non-opaque passage, such as a slit 1602, in an opaque housing or screen 1604 separating or shielding the light source 101 from downstream spectrometric or other componentry, such as dispersive optics, a modulator, etc., such as shown in FIGS. 3, 4A, 4B, 14A, 14B. In a conventional approach to a spectrometer slit, the slit 1602 is just an opening that is illuminated by the light source—for high efficiency, the light from the light source must be focused on the slit. The radiance of the slit (power per unit area per unit steradian) determines the amount of light passing through the slit that one can gather and use downstream in the rest of the dispersive system.

In the present active slit technique, an "opening" slit is replaced with an active slit 1602. The active slit 1602 constitutes more than just a mere non-opaque opening in an opaque screen. Instead, the active slit 1602 is configured to actively generate light in the region forming the active slit 1602, for example, such as by providing one or more phosphor materials in the active slit 1602 region. In this way, a light source having a desired-shape (e.g., slit) geometrical light generating area directly forms the active slit 1602 of the spectral system. The phosphor-filled active slit 1602 can be induced to actively emit light from the active slit 1602 by stimulating the phosphor materials in the active slit 1602 with incident light, such as from one or more LEDs or lasers forming a stimulating light source 1606 for stimulating the light emission from the phosphor-filled active slit 1602.

FIGS. 16B, 16C, 16D, and 16E show examples of various ways in which such an active "slit" 1602 or similar W-CLS structure can be implemented. In the example of FIG. 16A, one or more phosphors can fill the active slit 1602. In the example of FIG. 16B, a combination of multiple phosphors (which can be of the same phosphor type, or different phosphor types) can be located in different regions of the active slit 1602, such as at different locations along a length of the active slit 1602, such as shown in the example of FIG. 16B. The different types of phosphors in the active slit 1602 region can be used to provide light in different regions of the light spectrum, if desired. The phosphors in the active slit 1602 region can be pumped by incident light from any suitable direction from a laser or LED light source 1606. The active slit 1602 region can optionally include one or more LED light sources in addition or alternative to the phosphors, if desired. The active slit 1602 can form a multi-wavelength active light source, such as is defined spatially by the light emission region of the active slit 1602. As an illustrative example suitable for an example of a dispersive system, the typical width (defined as the direction in which dispersion is applied and is, in general, the narrower of the two dimensions) of the active slit 1602 can be in a range of 10-1000 micrometers, inclusive. Phosphors and LEDs are capable of being sized and shaped within such dimensions, such as to provide light output from the active slit 1602. Phosphors come in a wide variety of material types and can be selected, mixed, or both, such as to provide a desired straightforward or complex spectral light emission, as desired. In an example, a fluorescent or sharp spectral line generating material can be included or mixed in the materials in the active slit 1602 region, such as for use in providing wavelength calibration, such as described elsewhere herein for use with W-CLS.

FIG. 16C shows an example in which different portions of the active slit 1602 (e.g., different width portions in the example shown in FIG. 16C) can be illuminated by different LEDs/lasers or made from different phosphors (e.g., different phosphor types or different phosphor compositions). In such an example, different portions of the active slit 1602 can optionally be modulated separately or together, such as using incident light from one or more appropriately modulated pump lasers, LEDs, or both. Such modulation can be performed electrically on the stimulating light source. This can be useful, such as in a number of different ways. For example, it is possible to retain the resolution of a single thin slit of width w while having the light-gathering capability of n-slits of aggregated width of nw, such as by modulating each thin slit of width w in a specific sequence, such as a Golay sequence. Such an approach can help improve optical throughput. Modulation of a slit can be difficult-particularly for a conventional air-opening slit. With multiple width-zones, such as shown in the example of FIG. 16C, each zone can act like a slit, and one or more Golay sequences or other modulation sequences can be employed (such as by electronically modulating one or more light-emission stimulating light sources) to help improve the total light provided by the active slit 1602 and made available downstream for W-CLS. Each "zone" can optionally be made from different phosphor materials or compositions, respectively spanning different wavelength ranges of interest. Thus, such an active slit 1602 such as shown in FIG. 16C can be used in a W-CLS to provide light output in different spectral ranges, if desired.

FIG. 16D shows an example in which one or more lasers or LEDs 1606 can be coupled to a glass or other waveguiding slab 1608. The glass slab 1608 can guide the incoupled light to the phosphor 1610 in the active slit 1602 region formed at the end of the slab of glass 1608. Thus, in this example, the active "slit" 1602 is instead simply the glowing phosphor active strip 1610 peripherally bounded active light-emitting region at the edge of the glass slab 1608—without requiring an opaque screen or shield 1604 to define the peripheral boundaries of an active slit 1602. The glass slab 1608 may be sized, shaped, or otherwise configured to itself define such peripheral boundaries of an active strip provide for efficient pumping, gathering, and guiding of the light, such as shown in the "light funnel" example of FIG. 16E.

Thus, as explained herein, the present techniques can allow for using the light source itself as an active "slit" 1602 or similar interchangeable active "strip" of a dispersive system. While FIGS. 16A-16E were described with a particular focus on phosphor materials or LED materials as being used as the light emitters in the active slit 1602 or active strip region, the present techniques are not so limited. For example, thin hot filament or a hot wire of a thermal source or an appropriately shaped gas discharge region can additionally or alternatively form an active slit 1602 (or interchangeable active strip), such as for use with W-CLS or one or more other applications.

FIG. 17A shows an example of a detailed ray trace associated with a vertical active slit 1602. The active slit 1602 can be made up of an arbitrary combination of the light emitters, such as in the arrangement shown in FIG. 16B. FIG. 17B shows an example of a detailed ray trace associated with a vertical active slit 1602, such as can be made up of an arbitrary combination of the light emitters, such as in the arrangement shown in FIG. 16B.

In an illustrative example of a dispersive spectral separator that includes a dispersive optic (such as shown in FIGS. 17A, 17B as a grating, without loss of generality), light passing through different vertical regions of the active slit 1602 can be imaged onto a dispersion plane 311 at different locations, such as at different heights, such as illustrated in FIG. 17A. FIG. 17B shows an example in which active light sources (which can be configured to emit different light wavelengths) that form the active slit 1602 map to different vertical regions in the plane of dispersion 311. By masking out other regions, and passing light using only the wavelengths passing through the mask in a desired specified region of interest 312, unwanted orders of light (e.g., higher diffractive orders) can be avoided without requiring the use of an order-sorting filter, which might otherwise be needed. Since the light spectra in the plane of dispersion 311 will be modulated (for example, such as using the multifunction modulator 105, an example of which is shown in FIG. 17D), it can be desirable for the multifunction modulator 105 to be able to modulate at different heights along the plane of dispersion 311. FIG. 17D shows an example of such an implementation. In FIG. 17D, the multifunction modulator 105 can include a rotating patterned mask at the plane of dispersion 311, such as shown and described above with respect to FIG. 6A. Such a modulator 105 can be used to modulate different spectral components of light-along the plane of dispersion 311. By using an optical mask or a reticle (omitted from FIG. 17D, for clarity) in front of the modulator 105, only the modulation of light in the specified region of interest 312 is allowed. Unwanted higher diffractive orders from the grating can be shielded from the modulator 105 by the optical mask or reticle. In this way, any need for order sorting can be eliminated. An example of yet another approach to avoiding order sorting filters is shown in FIG. 18, such as explained below.

7. Example of Active or Other Light Source Input Modulation and Wavelength Calibration, and Higher Resolution Operation As described earlier, a reference detector 131 and transmit side 11 measurement methodology can be used. This can help enable providing wavelength calibration, or can help allow drift-free measurement (or both)—even when using multiple light sources, such as in which various individual ones of the multiple light sources can drift independently, such as over temperature, age, or from manufacturing batch-to-batch. One or more other techniques can additionally or alternatively be employed, such as to help achieve one or more such objectives.

FIGS. 18A, 18B show an example of a CLS light source 1800 arrangement that can include multiple light sources and a reflective (or transmissive) grating and a pinhole in an opaque screen that can be used to pass desired wavelengths from the grating, with the off-pinhole locations on the screen being used to reject undesired wavelengths from the grating. In the example of FIG. 18A, multiple (e.g., two) LEDs 1802 (e.g., producing light of different wavelengths) can respectively be placed at different corresponding desired locations. Each LED 1802 can provide a different wavelength of light, such as for contributing to a CLS light source 1800. Control circuitry can be used to drive or power each LED 1802 with a corresponding electrical modulation signal, and this electrical signal input modulation of the LED can be used to encode the light output by each individual LED 1802 at its designated wavelength. The ray traces from these different LEDs 1802 are respectively shown with red and blue colors for illustration. These ray traces respectively represent two different wavelength groups from these two different LEDs 1802, which can be directed through a refractive or collimator element 1803 and directed toward a grating 1804. In FIG. 18A, the grating 1804 can be arranged in a Littrow configuration, in which a blaze angle of the grating 1804 can be selected such that the diffraction angle and incidence angle of the grating 1804 are identical. In this configuration, the light rays incident upon the grating 1804 can be diffracted back toward the source LEDs 1802. The "reflection" geometry of back-diffracting is not necessary, but such a geometry can offer compactness by directing light back along a folded path. A transmission geometry can work similarly well. The back-diffracted rays from the grating 1804 can be directed toward and passed through a pinhole P in an opaque sheet. Since the LEDs 1802 are at different spatial locations, only a certain portion of the back-diffracted wavelength spectrum of each respective LED 1802 will pass through the pinhole P, depending on the placement of the individual LED 1802 and its emitted light spectrum. Variation in the LED spectrum over temperature, or from manufacturing batch-to-batch, or small variation in placement of the LED 1802, may affect the light throughput emerging from the pinhole P, but will not change the spectral group selected from each LED. Thus, the back-diffracted light from the grating 1804 and passed through the pinhole P can be relatively immune to drifts or changes or variations in an emission wavelength of the LED 1802. This variation-immunity can help reduce or avoid the need for using reference detector 131 for performing transmit-side measurements.

To recap, light from multiple LEDs 1802 or LED pumped phosphors with different emission spectra can have their wavelengths be combined after passing through the pinhole P, such as to form a W-CLS 100. Moreover, each LED 1802 or light source can be separately directly electrically input-modulated, such as by controlling the electrical power signal for a particular LED 1802 according to a specified modulation sequence for that particular LED 1802. Thus, in this example, there is no need for an external modulator 105. Instead, a multi-wavelength heterogeneous light source can be directly input-modulated using electrical signals delivered to corresponding LEDs 1802.

FIG. 18B shows an example of a three-dimensional (3D) view corresponding to the two-dimensional (2D) illustration of FIG. 18A. FIG. 18B shows only those light rays that are converging to the pinhole P. The folded light path approach shown in FIGS. 18A, 18B can be used to form an extremely compact W-CLS 100. The compactness can leverage advancing micro-LED technology. Furthermore, many LED and phosphor based light sources can be modulated at high frequencies, such as in the range of 10s of MHz. This can allow the active slit 1802 or active strip or LEDs 1802 to be directly used for FD-DLS or TD-DLS, such as described above.

Figures 18C, 18D:
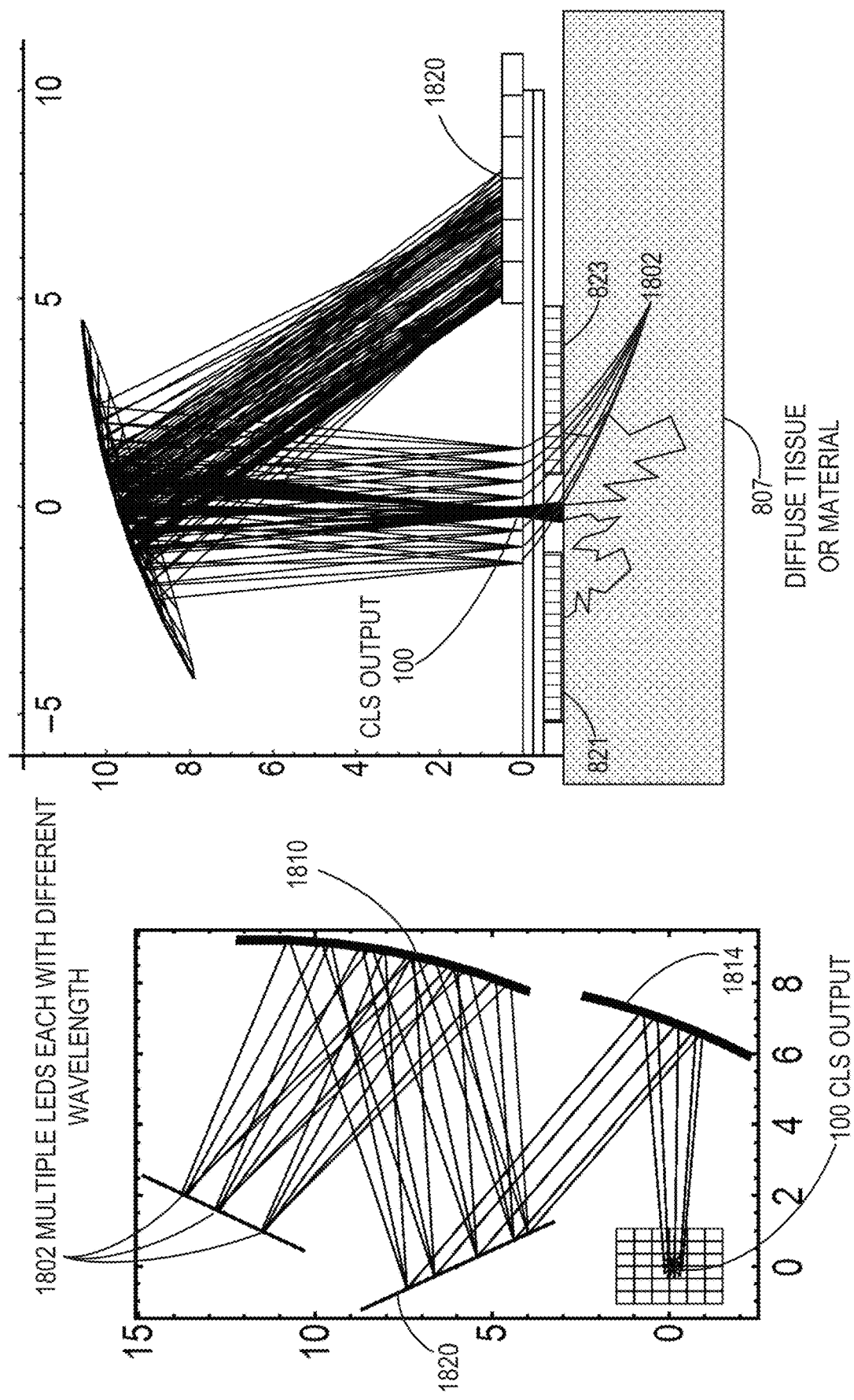
FIGS. 18C, 18D show examples of different ways to provide a CLS with a single light beam containing various wavelengths of light that can respectively be electrically input-modulated with different coding functions.

FIG. 18C shows another example that can help generalize the example of FIGS. 18A, 18B. In FIG. 18C, more than two active light sources, such as LEDs 1802, can be individually electrically-input modulated, and the resulting light can be communicated along a path to a pinhole P in a screen S to selectively provide a recombined multi-wavelength homogeneous CLS. In FIG. 18C, the folded light path between the LEDs 1802 and the pinhole P can include a concave reflective mirror (M3) 1810, which can reflect light from the LEDs 1802 toward a reflective-mode diffractive grating (G) 1812. The reflective-mode diffractive grating (G) 1812 can selectively diffract certain wavelengths of its received light toward a concave reflective mirror (M2) 1814, which can reflect and focus the light toward the pinhole P in the opaque screen S, through which a recombined multi-wavelength homogeneous CLS can be provided, such as for use in the various system configurations described herein.

FIG. 18D shows an example of such a particular system configuration in which the LEDs 1802 can include a number (e.g., 8, as shown) IC chip LEDs 1802 that can be machine "pick-and-placed" upon a printed circuit board (PCB) 1820, with a positioning accuracy that falls within a certain manufacturing tolerance. The LEDs 1802 can emit light at different wavelengths, and can be individually electrically-input modulated with different modulation waveform codes $g_i(t)$, such as explained previously. The light emitted from the LEDs 1802 can be reflected, such as by a concave mirror (M2) 1822, toward a reflective-mode grating (G) 1824. The reflective-mode diffractive grating (G) 1824 can selectively diffract certain wavelengths of its received light back toward a concave reflective mirror (M2) 1822. The mirror (M2) 1822 can reflect and focus the light toward the pinhole P in the opaque PCB 1820 screen S. Through the pinhole P, a CLS can be provided incident upon and into a target object or sample 807. The sample 807 can include human or other biological tissue or other diffuse material, for example. The underside of the PCB 1820 can have, mounted thereto, light detectors 821, 823, such as for detecting response light elicited in response to the incident CLS.

FIGS. 18C, 18D show examples of different ways to provide a CLS with a single light beam containing various wavelengths of light that can respectively be electrically input-modulated with different coding functions. Each of the LEDs 1802, emanating different wavelengths of light, can be placed at different locations, but arranged in a configuration such that the action of the dispersive system is to bring all the different wavelengths to pass through a common pinhole. The LEDs 1802 can respectively be directly electrically input-modulated with codes $g_i(t)$. The CLS output can provide, for example, between 3 and 32 discrete wavelength groups from each of the independently modulated LEDs 1802. For the various examples shown herein, including the examples of FIGS. 18A, 18B, 18C, and 18D, a reference detector 131 (such as described elsewhere herein) can be used to augment signal processing of the response signal to account for transmit-side illumination variability.

Because the emission spectra of the LEDs vary, such as due to temperature, current, and from batch-to-batch, it can be very difficult to use such LED sources in spectroscopy unless they are carefully selected and calibrated. However, in the configurations shown in FIGS. 18A, 18B, 18C, and 18D, wavelengths that pass through the pinhole P can be fixed or selected by the dispersive characteristics of the optics. Thus, the changes in the LED spectra become changes in the available light intensity at the selected wavelengths passed through the pinhole P. But, as explained previously, using a reference detector to accommodate changes in light source intensity allows the effects of variations in light source intensity to be substantially eliminated in the signal-processing of the response light. The reference detector is not shown in FIGS. 18A-18D, for clarity, but can be included in a manner similar to that shown elsewhere herein.

FIG. 18D is a compact version in which a single grating 1824, e.g., in a Littrow configuration, is shown, such as to combine light from 8 LEDs 1802, each emitting different wavelengths. The configuration of FIG. 18D can be used to measure one or more tissue or blood properties, for example, in a compact geometry. A single PCB 1820 carries appropriately placed LEDs 1802, a grating 1824, and a single focusing mirror 1822 assembly as well as photodetectors 821, 823 on its bottom surface. The LEDs 1802 generate the CLS beam via the pinhole P in the PCB 1820 that is incident upon and enters the tissue (or other media), and one or more photodetectors 821, 823 can collect scattered photons. In the case shown in FIG. 18D, tissue properties can be determined using spectral analysis at all the LED wavelengths, such as described previously. The optical geometry can be made even more compact by reflecting the LED light by a right angle. In sum, a thin, compact CLS light source can be provided, that meets all the needs for performing a good scattering measurement of material properties.

Figure 19:
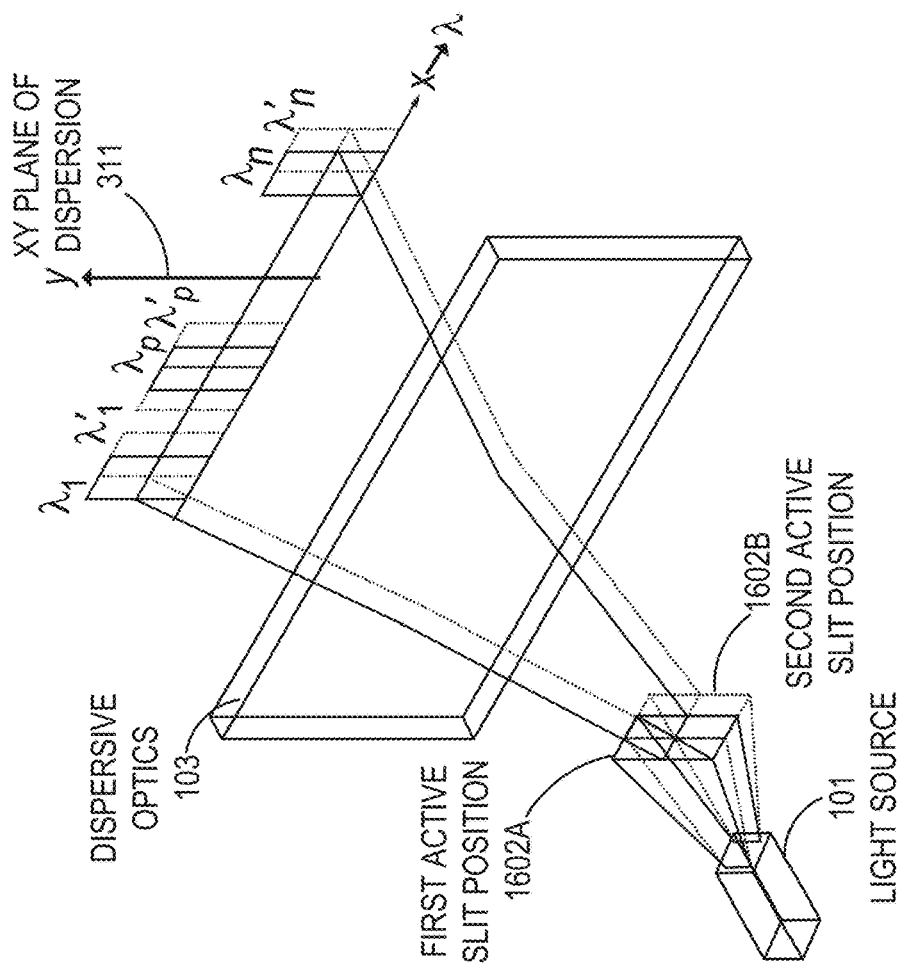
FIG. 19 shows an example of selectively directing or scanning an active slit or pumped region, then directing the resulting light through dispersive optics to perform shifting of a wavelength-to-location mapping along a dispersive plane.

FIG. 19 shows an example in which a broadband or multi-spectral light source (e.g., one or more LEDs) 101 can be selectively directed or scanned, such as to pump or otherwise provide source light to more than one pump region, e.g., different active slit regions 1602A, 1602B at different times, such as in an alternating or other temporal sequence. These different active slit regions 1602A, 1602B can be located on an opaque screen, such as described elsewhere herein. The active slit regions can provide light to dispersive optics 103, such as can perform wavelength separation into desired wavelength bins, $\lambda_1, \ldots, \lambda_n$ (from active slit 1602A) and $\lambda'_1, \ldots, \lambda'_n$ (from active slit 1602B) such as at an xy-plane of dispersion 311. A multifunction modulator 105 can be located at the plane of dispersion 311, such as described elsewhere herein.

By selectively directing or scanning to a particular one of the pumped region locations, e.g., one of active slit regions 1602A, 1602B, a map of dispersed wavelengths along an x-axis can be shifted, such as by a desired amount (e.g., half a wavelength). Thus, at an x-axis location at which $\lambda 1$ was modulated when light is pumping active slit 1602A, such location modulates a slightly different wavelength $\lambda'1$, when light is pumping active slit 1602B.

Figure 20:
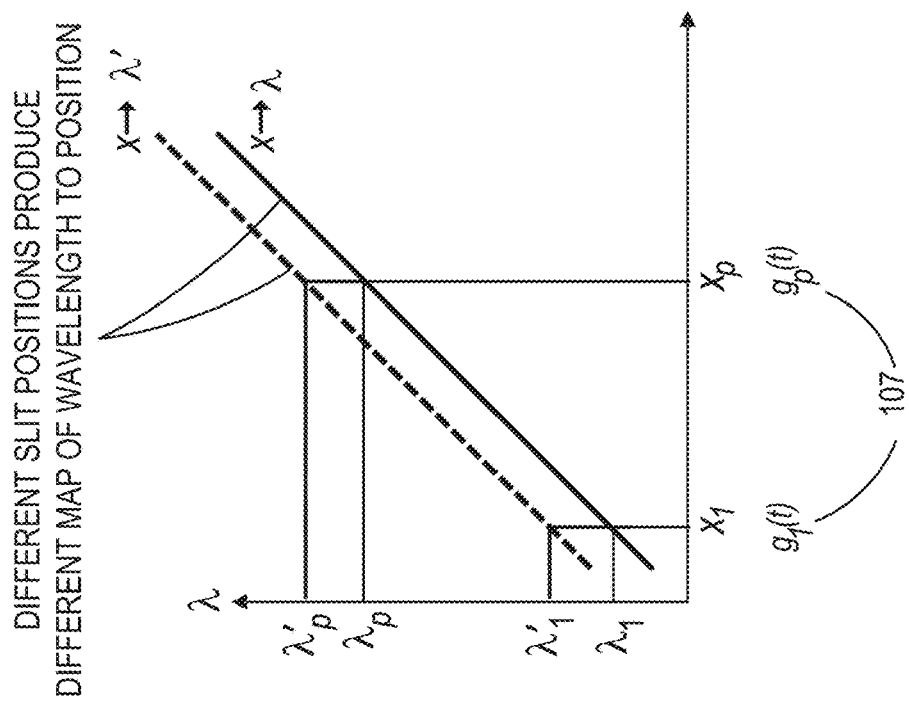
FIG. 20 shows an example of the shifting of wavelength-to-location mapping along the dispersive plane, such as described with respect to FIG. 19.

FIG. 20 shows a conceptual example of wavelength λ vs. location x along the x-axis, with the dashed line representing the wavelength-to-location mapping for light pumping the active slit 1602B and the solid line representing the wavelength-to-location mapping for light pumping the active slit 1602A. Wavelength shifts can allow modulation codes performed at particular x-axis locations to modulate different wavelength bins, by selective direction or scanning of a desired pumped region location or active slit 1602A, 1602B. Thus, by application of "shifts" in wavelength maps and measuring spectral response for each of the shifts, a much higher resolution spectrum can be obtained. This configuration and operation can be combined with the principle of Golay sequences, which can employ a set of digital shifts and modulation pattern ("Golay codes") that can work extremely efficiently and need only a single cross-correlation operation for signal-processing and code-reconstruction of the response signal. Regardless of whether Golay codes are employed, the present techniques can permit sampling different portions of the spectrum and then recreating a higher resolution spectrum, so long as the measurement does not change during the repetitive sampling. Even without scanning, it allows "tuning" the wavelength bins, such as to a desired set of locations along the x-axis, and can be combined with the wavelength calibration techniques described herein.

8. Spatial Coded Light Source (S-CLS) Example

The above description has emphasized techniques for making and using a spectrally-coded (wavelength-coded) light source (W-CLS). But an angular or other spatial coded light source (S-CLS) can additionally or alternatively be used to provide certain advantages. For example, a beam of light can be spread and projected such that different angular parts of the light beam cone can carry different codes.

FIG. 21A shows an example of an S-CLS 200. In this example, a light source 1900 can project a light beam cone including various angles $\theta_k$ through a multifunction modulator 804. The multifunction modulator 804 can differently spatially code different angularly projected regions Ok of the light cone, such as in either one or two dimensions. These different regions Ok of the light cone form angular bins, analogous to the spectral bins described herein with respect to spectroscopy. These different regions can be coded using different modulation code functions $g_k(t)$, such as to form the illuminating S-CLS 200 light that can be incident upon a target object or scene 117. A portion of the resulting S-CLS 200 coded light can be directed, at the transmit side, toward a reference detector 131. The reference detector 131 can measure an indication of the angular or spatial light distribution, and i information about such measurement can be provided to signal processing circuitry on the receive side of the system, in a similar manner to that explained above. The S-CLS 200 coded light itself may be spectrally broad, carrying wide range of spectral components, or it can be spectrally narrow, such as using an LED or laser generated light source. The multifunction modulator 804 can provide different modulation code functions $g_k(t)$ at different spatial location, in a manner similar to that of the multifunction modulator 105 used for spectral encoding (W-CLS), such as described previously. For example, the multifunction modulator 804 for the S-CLS configuration of FIG. 21A can employ one or more of the modulators shown and described with respect to one or more of FIG. 6A, 6B, 7A, or 7B. Light from the target object or scene 117, generated in response to the S-CLS illumination light 200, can be received at one or more detectors 821, 823, and transduced for decoding and other signal-processing by controller and signal processor circuitry, such as in a manner similar to that described previously.

FIG. 21B shows an example of a waveguide-based implementation of a multifunction modulator 804 for S-CLS. Broadband or narrowband light from the light source 1900 can be passed through a beam-splitter 803. FIG. 21B shows a 1× N beam-splitter 803, which produces a resulting N beams split from the light source 1900. Each of the N beams can undergo modulation by a different and unique modulation function $g_k(t)$, such as in a manner similar to that shown in FIG. 7A or 7B. The resulting modulated beams can be passed through a lens or other projection optics 1910 to form a S-CLS that can project light onto a target object or scene 117.

In general, much of the previous explanation regarding coding and reconstruction for W-CLS spectroscopy can be similarly applied to spatial coding and reconstruction using S-CLS. However, in S-CLS, the coded degrees of freedom are not wavelengths, but are instead spatial or angular dimension. Since the scattered light from the target object or scene 117 is proportional to local reflectance of the target object or scene 117 (which can be angle-dependent), each coded part of the S-CLS light beam intersects the target object or scene 117 at a specific location. This scattered light from the target object or scene 117 can be collected and transduced, such as by one or two or more photodetectors 821, 823 and decoded and otherwise signal-processed. Since the one or more photodetectors 821, 823 need only collect scattered photons, the collection optics associated with the photodetectors 821, 823 are not constrained by imaging the target object or scene 117. This can help permit collecting more light and can provide a numerical aperture that can be greater than other approaches involving imaging.

The one or more photodetectors 821, 823 used in the S-CLS configuration of FIG. 21A can be used or applied in a number of ways, some illustrative non-limiting examples of which are introduced and described here. In some examples, the outputs from various ones of multiple photodetectors 821, 823 can be combined, such as to help improve total collection of photons from the target object or scene 117. After S-CLS reconstruction, a particular modulation code maps to a particular location on the target object or scene 117, such as based on the illumination optics 1910. A mapping between the particular code and the location on the object can be independent of the placement of the photodetector 821, 823. It can depend only on the relationship between the S-CLS and the target object or scene 117. This is different than in a traditional approach to imaging in which the image formation depends on the object-receiver geometry. In one illustrative class of applications, angle-dependent reflectance for the entire target object or scene 117 can be measured by placing multiple detectors 821, 823 at multiple different angles with respect to the target object or scene 117.

The W-CLS approach, such as explained above, can offer a large light collection efficiency improvement. This can improve the signal-to-noise ratio (SNR), such as for diffuse light spectroscopy. There can be a similar advantage for S-CLS. Suppose the target object or scene 117 is uniformly illuminated with S-CLS light of intensity $I_0$. Then, the scattered light collected by the detector is given by:

$$P_{det} = I_0 \frac{a^2}{4(f\#)^2} \qquad \text{Eq. 13}$$

where a is the "pixel" or the detector area, and f # is the f-number of the lens or other light collection optics at a light input to the photodetector.

In an imaging sensor, such as line imager or a camera, light collection optics including a low f-number lens improves the light gathering. However, this comes at a cost of complex and bulkier optics. With some work, the size and weight of low f/#optics can be reduced. Furthermore, pixel size can be limited to be in 1-50 mm range (depending on the wavelength range to be imaged, e.g., from UV to LWIR). Otherwise, the imager chip becomes too large and extremely expensive. The particular photodetector or imaging photodetector array can optionally be selected based on a desired wavelength range to be used.

But with spatially coded illumination, S-CLS, there is no need to "pixelate" on the receive side. Therefore, using S-CLS, the photodetector and associated input light collection optics can be configured to collect as many photons as possible-without being subject to pixel or other imaging constraints. Using S-CLS, non-imaging optics with high light collection with equivalent f/#<1 are possible, such as using one or more photodetectors with corresponding solid lenses made from high refractive index material such as can be directly bonded to the photodetector sensor surface. The photodetector size itself can be large, such as in millimeter or centimeter scale, depending on the bandwidth needs of the system. Table 6 below gives a sense of enormous light collection improvement possible using S-CLS over an imaging approach.

TABLE 6

Comparison of S-CLS Coded illumination to Traditional Imaging

| Traditional Imaging | S-CLSCoded illumination | Signal advantage |
|---|---|---|
| Line imager with 10 um² area pixels in visible/NIR and f/2 optics (still quite expensive) | Detector with area of 10 mm² and non-imaging light collector, e.g., solid immersion lens with f/# ~0.5 | $\frac{10 \text{ mm}^2}{(10 \text{ }\mu\text{m})^2}\left(\frac{2^2}{0.5^2}\right) = 1.6 \times 10^6$ Or about a million times more light gathering power. |

This enormous light collection signal advantage of S-CLS makes it possible to use S-CLS even for applications in which the available illumination power is limited. Without loss of generality, some illustrative, non-limiting examples are described below.

Example 1: Plastic Sorting or Process Measurement Example

Plastic sorting is an important commercial and environmental priority, such as to reduce waste that ends up in a landfill. Similarly, in many cases of process control or quality control, a material moving on a conveyer belt needs to be identified or characterizes. Such identification or characterization can include observing its spectral signature.

Figure 22A:
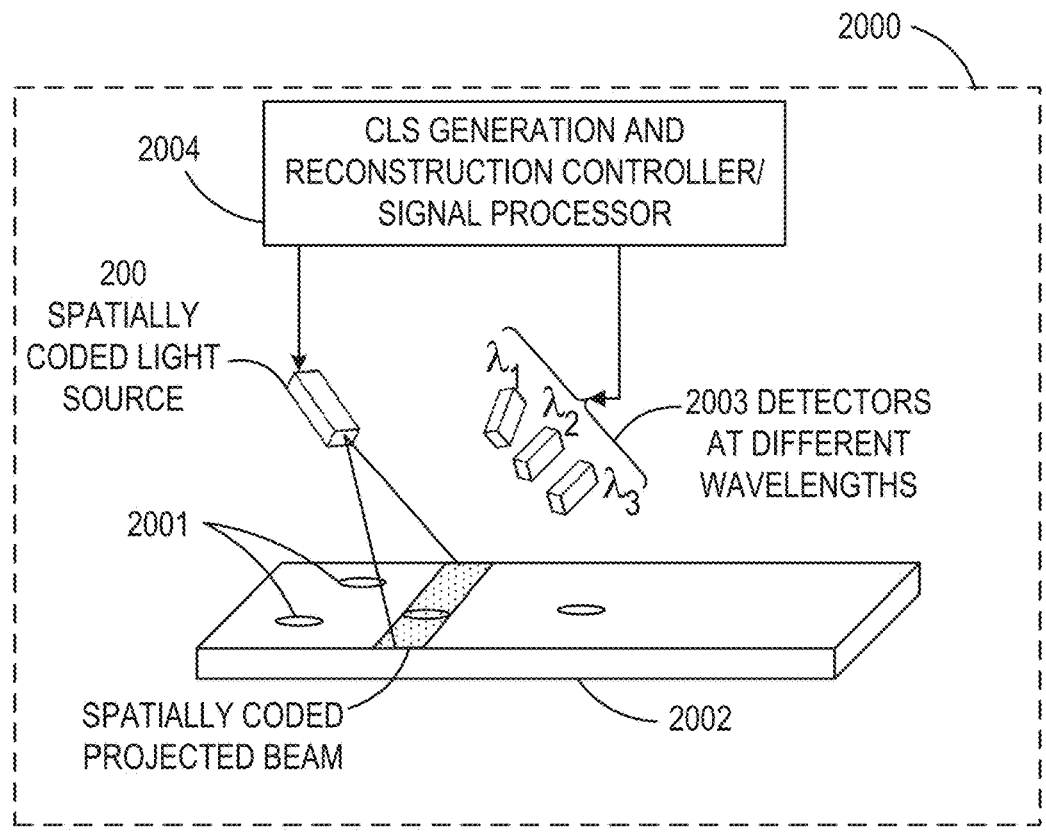
FIGS. 22A, 22B show examples in which the present techniques can be used, such as to implement a material identification or characterization system, such as for sorting or other applications.
Figure 22B:
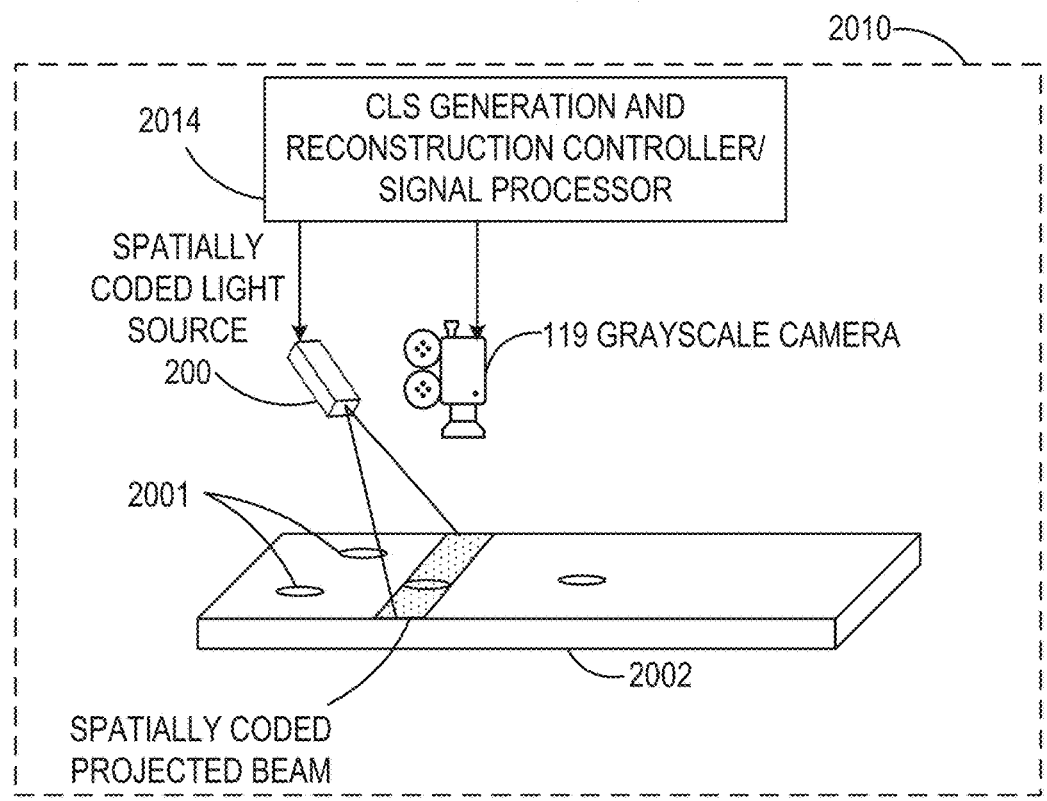

FIGS. 22A, 22B show examples in which the present techniques can be used, such as to implement a material identification or characterization system, such as for sorting or other applications.

FIG. 22A shows an example of a material identification, characterization, or sorting system 2000 that can spatially code the projected light. A broadband wavelength homogeneous light source LS can be spatially encoded, such as using coding functions $g_k(t)$ such as described herein, to generate a spatial coded light source S-CLS 200. The S-CLS 200 can project S-CLS illumination light onto target samples or objects 2001, such as can be carried upon a conveyer belt 2002. Multiple photodetectors 2003 can be arranged to receive response light from the target samples or objects 2001, such as can be individually configured to gather and transduce the response light at different light wavelengths. The resulting electrical signals can be communicated to controller or signal processor circuitry 2004, which can be used to perform the encoding and decoding of S-CLS light, and to perform signal-processing of the transduced and decoded S-CLS light response signals. A map of spectral response at each spatial location can be generated.

FIG. 22B shows an example of a material identification, characterization, or sorting system 2010 that can wavelength code the projected light. A broadband wavelength homogeneous light source LS can be spatially encoded, such as using coding functions $g_k(t)$ such as described herein, to generate a wavelength coded light source W-CLS 101. The W-CLS 101 can project W-CLS illumination light onto target samples or objects 2001, such as can be carried upon a conveyer belt 2002. A grayscale camera 119 (e.g., line imager or 2D imager) can be arranged to receive response light from the target samples or objects 1901, such as to identify the spectrum at each spatial location. The resulting electrical imaging signal can be communicated to controller or signal processor circuitry 2014, which can be used to perform the encoding and decoding of W-CLS light, and to perform signal-processing of the W-CLS response image signals. A map of spectral response at each spatial location can be generated.

Thus, in FIGS. 22A, 22B both the systems 2000, 2010 can respectively allow generating a map of spectral response at each spatial location. Depending on the wavelength region for analyzing a material of a particular sample 2001, or the needs of a particular process control problem, the S-CLS technique of FIG. 22A may be preferred over the W-CLS technique of FIG. 22B. For example, in the case of plastic sorting, much spectroscopic information can be readily available to identify or analyze different plastic types, such as using infrared spectroscopy at wavelengths between 1200-2000 nanometers. The gray scale camera 119 in the W-CLS configuration of FIG. 22B may be expensive, such as if using a focal plane array made from InGaAs. Thus, while the W-CLS implementation of FIG. 22B may provide higher spectral resolution that the S-CLS configuration of FIG. 22A, using a fast gray scale camera 119 for W-CLS analysis of objects on a fast moving conveyer belt may be costly. On the other hand, the S-CLS technique of FIG. 22A using a few discrete InGaAs photodetectors 2003 looking at the scattered light response to S-CLS illumination at a few well-chosen wavelengths can permit cost-effective material identification, classification, or sorting. The S-CLS approach of FIG. 22B can be extremely fast, with high light collection efficiency, and can be much less expensive than a hyperspectral imager. For a different problem involving sorting or measurement of process variables using light in a visible or near-infrared wavelength range, a silicon-based imager can be suitable, inexpensive, and highly sensitive, such that the W-CLS system 2010 of FIG. 22B may outperform the S-CLS system 2000 of FIG. 22A.

Example 2: THz Line Imager Example

The S-CLS technique is not limited to visible or IR region of the electromagnetic spectrum. Consider a millimeter wavelength system, for example, operating at 77 GHz. or 94 GHz, or at any other RF or millimeter wavelength band.

Figure 23:
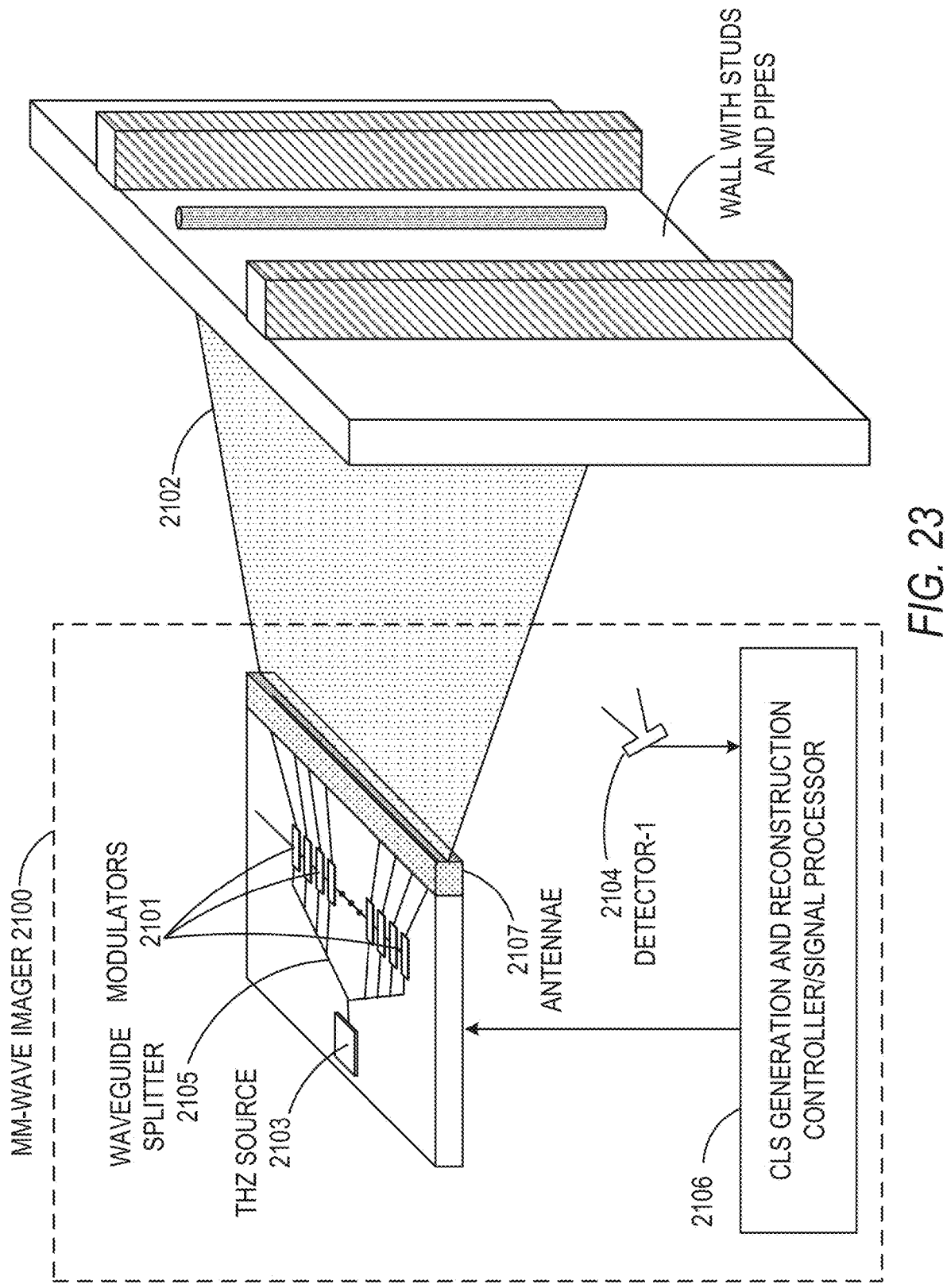
FIG. 23 shows an example of a system, similar to that shown in FIG. 21A, 21B, in which a millimeter-wavelength S-CLS can be produced, such as by direct modulation of multiple synchronized millimeter-wavelength light sources.

FIG. 23 shows an example of a system 2100, similar to that shown in FIG. 22A, 22B, in which a millimeter-wavelength S-CLS 2102 can be produced, such as by direct modulation of multiple synchronized millimeter-wavelength light sources. The encoded S-CLS 2102 can illuminate in different directions with different modulation codes. A receive-side response detector 2104 can include an antenna to receive reflected mm-waves, such as can be decoded and signal-processed by a controller or signal processor circuit 2106 to create an image of the target object or scene 117. Such millimeter-wave imaging can provide practical imaging behind a wall or other barrier. For example, where the millimeter-wavelength S-CLS 2102 is directed toward a typical house wall, the cavity behind the wall may contain metal or plastic pipes, wood or metal studs, etc. The millimeter-wave S-CLS 2102 reflectance measurement can show an image of these other objects behind the wall, since metals have a high reflectivity, and many wall materials are relatively transparent at these millimeter wavelengths. A frequency-swept mm-wave S-CLS 2102 can even be used for material identification, since different materials can have substantially different dielectric constants, in the THz region. Furthermore, THz S-CLS 2102 source can be amplitude modulated, such as in the MHz to GHz range. The previous discussion of measuring phase or time delays in diffuse light spectroscopy can be applied to the THz region techniques being described here. In the THz region, such phase or time-domain measurements can correspond to and provide an indication of a measurement of distance to the THz-reflecting object. The present techniques can be used to provide an amplitude modulated radar, but with the added advantage of generating an image of the target object as well as an ability to generate spectral reflectance. Thus, using the S-CLS 2102 in THz range, an image of objects behind a barrier, such as the wall, can be constructed. This THz image can be quite rich, with measurements at different THz frequencies (such as can be used to provide a THz hyperspectral imager) as well as to provide an indication of a distance to the target object.

In a practical implementation as an instrument, a human-visible red or green laser can be included in the system 2100 and its beam can be co-aligned to the human-invisible mm-wave beam. This can give user an indication of the mm-wave beam being directed at a target indicated by the human-visible red or green laser beam. Similarly, a visible light video or other camera can be included in the system 2100. The visible-light camera can be used by the system 2100 to take one or more pictures of the target scene, such as while the user scans the wall. Image processing can be performed by the controller or signal processor circuitry 2102, which can include or be coupled to a user interface that can include a display that can be configured to overlay a mm-wave image over a visible image including the instantaneous location of human-visible laser beam, which can be seen by the visible-light video camera.

These Examples 1 and 2 described above illustrate some non-limiting examples of ways in which the present S-CLS or W-CLS techniques, or both, can be applied. CLS based instrumentation can be applied in numerous ways to solve many practical problems involving spectral or spatial mapping of one or more objects.

In the example described with respect to FIG. 23, a system 2100 can include bank of mm-wave modulators 2101, which can be used to form an image and to measure distance, such as using the techniques described for high bandwidth W-CLS. The system 2100 can include (e.g., on a single integrated circuit (IC) chip) a "light" source (an electromagnetic radiation source). The electromagnetic radiation source can include a mm-wave source or a transmitter generating electromagnetic radiation in a frequency range from a few GHz to 100's of GHz. For example, the mm-wave source or transmitter can include a THz oscillator circuit 2103.

The system 2100 can include a waveguide splitter 2105, such as to receive electromagnetic radiation generated by the THz oscillator 2103 or other electromagnetic radiation source, and to divide the received source radiation into respective components for delivery to respective modulators 2101, e.g., in a bank of modulators 2101. The resulting modulated electromagnetic radiation can be delivered to specified locations of an antennae 2107. The antennae 2107 can generated coded THz radiation illumination 2102 for delivery to and illumination of a target object or scene. Thus, this is similar to the description of FIG. 21B. The modulators 2101 themselves can respectively include corresponding switches, such as to impose unique modulation codes $g_i(t)$.

On the receive side of the system 2100, a mm-wave detector 2104 can receive a response signal such as can be scattered or reflected from the target object or scene-which is shown in FIG. 23 as a wall with studs and pipes, as a practical example. A transduced electrical response signal from the detector 2104 can be received by and signal-processed by the signal processor circuitry 2106. The signal-processing can provide signal information about intensity corresponding to each of the modulation codes $g_i$, which is proportional to the corresponding location at a target object or scene toward which the radiation was targeted by the antennae 2107.

In a manner similar to that described previously for FD-DLS, the signal phase at each of the coded directions can be recovered by phase-recovery signal processing in the CLS generation and reconstruction controller/signal-processor 2106. In this case, phase delay corresponds to the time delay of the mm-wave. Hence, phase delay of the signal can be used to provide a "ranging" measurement of the distance to the object, while the intensity of the signal can provide imaging information. As explained with respect to FIG. 21B, the present techniques can be used in the visible or in the infra-red to construct a LIDAR imager. Various different coding schemes can be used to recover amplitude in time domain or amplitude-phase in frequency domain, such as described herein. For the case of a mm-wave imager, such as shown in FIG. 23, different source frequencies can be used to generate the radar image. In an example, this can include using a broadband source generator (e.g., such as the THz oscillator 2103) and one or more differently tuned detectors 2104, such as in a manner analogous that described earlier with respect to the example of FIG. 22A. In the case shown in FIG. 23, in which the target object or scene can include a visually-opaque wall facade backed with various studs, pipes, etc., such a system 2100 can not only provide image and distances to the wall and to the various objects located behind the wall, but can also be used to identify one or more materials used in their construction, such as by signal-processing and spectral analysis of their properties in the mm-wave region.

9. Polarization Coding Example

Observing a polarization sensitive image of an object can provide a sensitive method for finding defects, internal stress in materials, or surface scratches. For example, in dermatology, collagen fibers can provide a high polarization-dependent response, among other things. Polarization measurement is sensitive to material and structural birefringence. Material deformation, changes in the geometry of scattering particles, and changes in Fresnel reflections are all sensitive to polarization. Polarization-based imaging or measurements can be used for process control or measurement of materials. In general, the state of polarization of a target can be analyzed by observing the target object under different illumination light polarizations.

The CLS techniques described herein can be extended to include providing polarization information, such as to augment all wavelengths in the W-CLS techniques, or to augment all spatial locations in the S-CLS techniques. Additional polarization information can be provided along with the spectral or spatial measurements described herein. This can be accomplished by modulating the polarization of the light source at a frequency or at codes different than the frequency or code-space being used for modulating the spatial components in S-CLS or the spectral components in W-CLS. This can be illustrated when the codes correspond to the modulation frequency, but the analysis works equally well noise-like or other orthogonal or near-orthogonal modulation techniques are used.

FIG. 24 shows an example of a CLS system 2200 such as can include a linear polarized light source in a S-CLS or W-CLS system configuration. The system 2200 can include a rotating half-wave plate, such as which rotates the state of the linear polarization at frequency $f_{pol}$. Polarization modulation can be achieved in numerous ways. For example, a liquid crystal (LC) based electrically tunable wave plate or a quarter-wave plate can be included, followed by a rotating polarizer 2202. The polarizer 2202 can be placed before or after the multi-function modulator 105, 805 in the system 2200. Considering analysis using Fourier-like components, the multi-function modulator 105, 805 can generate sine or cosine components. The modulator 105, 805 can be arranged for modulation such that the individual modulation codes are separated by at $2*f_{pol}$. The rotating polarizer 2202 provides the polarization states and generates side-bands around each of the individual modulation codes, such as illustrated conceptually in FIG. 24. After the polarized CLS light has interacted with the target object or scene 117, the resulting response light can be received at one or more detectors 821 or cameras 119 included in the system 2200, such as described earlier, with different direction of polarization analyzers placed in front of them. As illustrated conceptually in FIG. 24, each of the frequencies $f_k$ from the coded modulation will develop sidebands at $f_k \pm f_{pol}$. Thus, by augmenting the reconstruction functions used in decoding and reconstruction to include these additional frequencies, a complete polarization-spectral or polarization-space mapping can be accomplished. This technique can be generalized to other time-varying functions and codes.

10. Examples of Interrelationships Between Different Coding Techniques

Multiple examples have been described to illustrate several advantages of coding the light source, such as using W-CLS or S-CLS, and measuring the degrees-of-freedom of the response light transduced by one or more detectors receiving the coded light. Furthermore, the coded illumination techniques can seamlessly with high frequency modulation techniques, such as explained herein. Such high frequency modulation techniques can be implemented as part of a multi-rate modulator 105, particularly if the modulator 105 it is based on integrated photonics. Such coding or high frequency modulation can also be performed by modulating the light source itself (e.g., switching electrical power to the light source at one or more desired modulation frequencies, or the like). The additional high frequency modulation can permit additional time delay or phase measurements to be performed, such as at a function of modulation frequency. Thus, such additional techniques can serve to measure distance, such as in the case of S-CLS, or to measure a spectral scattering or absorption characteristic, such as in the case of W-CLS. The polarization sensitive response can also be measured, such as by further modulating polarization of the light source, such as in a manner similar to the high-speed modulation of the light source, can such polarization response measurements can provide measurements of phase delay or distances. These techniques can be used together, or superposed, in the sense that each detector can measure the coded degrees of freedom.

The described examples and configurations of optical systems demonstrate how using coding on the source (transmit) side can help improve SNR, simplify optical design, and fundamentally improve measurements, such as in a way that allows measurements otherwise requiring expensive lab-grade equipment to be brought to the field via lower-cost instrumentation. In general, coding adds one extra measurement dimension, and high-speed source modulation adds two extra dimensions. This can be clearly seen in the first four rows in Table 7 below. To keep Table 7 simple, it can be assumed that high speed modulation for phase or time-delay measurement can be done for any of the systems, but is only shown for one detector. In each case, an extra degree of freedom can be added by including polarization modulation, which is also shown below in Table 7, for clarity. The shaded rows represent wavelength coding and unshaded rows represent spatial coding. This is summarized in Table 7 below.

TABLE 7

Dimensionality of Reconstructed Output

| Number of detectors | Dimension of the reconstructed output | | |
|---|---|---|---|
| | 1D | 2D | 3D |
| One detector | Spectroscopy $a(\lambda)$ Image of projection $a(x)$ | | |
| One detector + high speed modulation $f_{mod}$ | | Spectroscopy $(a(\lambda), \phi(\lambda))$ LIDAR/RADAR $a(x, z)$ or $a(x, f_{mod})$ | |
| 1D array of detectors | | Hyperspectral $a(x, \lambda)$ 2D image $a(x, y)$ | |
| n detectors; arbitrarily placed | | DLS, Multi-angle or multi-position spectroscopy such as BDRF; $a(\lambda, r_n)$ "color" measurements with each detector looking at different color $a(x; \lambda_n)$ | |
| 2D Array of detectors | | | Hyperspectral 2D array $a(x, y, \lambda)$ |

The techniques described herein are extensible. Advances in technology in photonic integrated circuits, focal-plane array, high-speed electronics can advantageously be used to provide an extremely rich data set helpful to understand many physical or biological systems. For example, CMOS based imagers can perform in-pixel demodulation at MHz rates to measure phase delay or time-of flight to each pixel. Such imagers can be referred to as TOF cameras. Such a camera, when used with the systems and techniques described herein, can be used to construct a 5D cube with full polarization description of the scene $a_{pol}(x, y, z, \lambda, pol)$. The pair $(x, y)$ or $(\theta_x, \theta_y)$ can come from using a focal plane array. The pair $(z, \lambda)$—distance and the spectral information—can be provided by W-CLS, such as described earlier. High frequency modulation and polarization can be measured sequentially or by modulation, such as described earlier, in which W-CLS was enhanced by polarization coding or by using polarization sensitive pixels.

11. Examples of Some Specific Applications

Example 3: Tissue Composition Analysis

Examples of applications and uses have been described in some detail, including explaining W-CLS based hyperspectral imaging or diffuse light spectroscopy. In particular, many biological parameters of significance can be targeted and extracted by such techniques. Also, such techniques can include one or more diagnostic or characterization algorithms that can be applied to such extracted information, such as can be used to convey alerts or other diagnostic information to a user, such as via a display or other user interface device. Examples of biological parameters that can be targeted, extracted, characterized, or diagnosed can include one or more of a skin disease such as psoriasis, blood and tissue composition, biological parameters such as oxygenation (at various places on the human body including, for example, in a brain of an infant or other subject), pH, glucose, temperature, hemoglobin concentration, and analysis of proteins or fats. The present techniques, including W-CLS, can permit leveraging information about spectroscopic determination of scattering and absorption parameters such as, for example, to help identify cancerous or other tissue abnormalities, such as melanoma. The present techniques can also be used in diffuse light spectroscopy of breast tissue or other human tissue analysis applications that can benefit from obtaining data from at multiple sites.

Other examples can include tissue analysis of plant tissue, for example, such as a leaf or a stem, which can provide information that can be useful in precision agriculture. For example, the present techniques can be applied to determine blight or other disease state of a plant sample, or to provide detailed characterization information that can be used to determine nutritional value or other more complex characteristic of the plant or other biological sample. Oils, grains, flour, fruits, or vegetables, among others, can be measured via spectroscopy analysis using the present techniques. Similarly, tissue analysis of meats or dairy products, e.g., from aquatic or land animals, can use the present techniques, such as to provide information and insight into meat quality, freshness, or other parameters, or even about the origin of the analyzed meat. The present techniques can be used to provide spectroscopic analysis or characterization information that can be used to determine or augment one or more measures of meat quality. Milk or milk derivatives such as cheese can be analyzed spectroscopically using the present techniques, such as to help determine protein content, fat content, or to identify pollutants or unwanted additives.

In such examples, using the present techniques, such as W-CLS, can provide multiple advantages or benefits. These can include extending spectroscopic range, providing high SNR for making fast and high-quality measurements. Analytical techniques needing laboratory-grade instrumentation can employ the present techniques, which can allow such analytical techniques to be ported to and performed in the field, with the convenience of not requiring dark calibration or white calibration, as explained herein. Many shortcomings or limitations of spectroscopy can be overcome using the present techniques, which can make possible and cost-effective the use of multiple detectors, of obtaining detailed or average data over a surface, or that can deploy hyperspectral imaging techniques that can be used with an inexpensive, portable, and widely available mobile phone camera, or can use any gray scale camera.

Scattering measurements (other than tissue) can include smoke or aerosol measurements, turbidity or water quality measurements, cytometry, surface texture or material composition measurements, any of which can be incorporated into other automated or semi-automated process control or quality control techniques, using the present techniques such to provide convenient one or multi-angle spectroscopy that can provide insight into materials and quality.

Absorption/transmittance measurements enabled by the present techniques can include, among other things, gas measurements such as explained with respect to FIGS. 14A, 14B. Any gas species or liquid measurements or surface reflectance measurements are amenable to the present techniques, such as using W-CLS.

Example 4: Oxygen Concentration Measurement

It can be challenging to measure oxygen concentration by absorption spectroscopy. As explained below, the present techniques, such as using W-CLS, can replace more expensive laser-based techniques. This example can be illustrative of the numerous ways in which the present techniques, such as including W-CLS, may be deployed.

Most light absorption measurement of gases or liquids in transmission depend on the Beer-Lambert law. For very weak absorbers, a long path length and a high degree of spectral stability are generally needed. Changes in the spectra change the absorption of the light, for the same given path length, and can thus lead to error in determining the concentration of a particular species of interest. Oxygen measurement at an optical wavelength of roughly 765 nanometers can experience the problem of substantial absorption of distances such as 100s of meters or many kilometers, and the absorption spectral lines are narrow for molecular gaseous oxygen. Thus, optical measurement of ambient or atmospheric oxygen has required precision spectroscopy using wavelength tunable laser sources.

Figure 25:
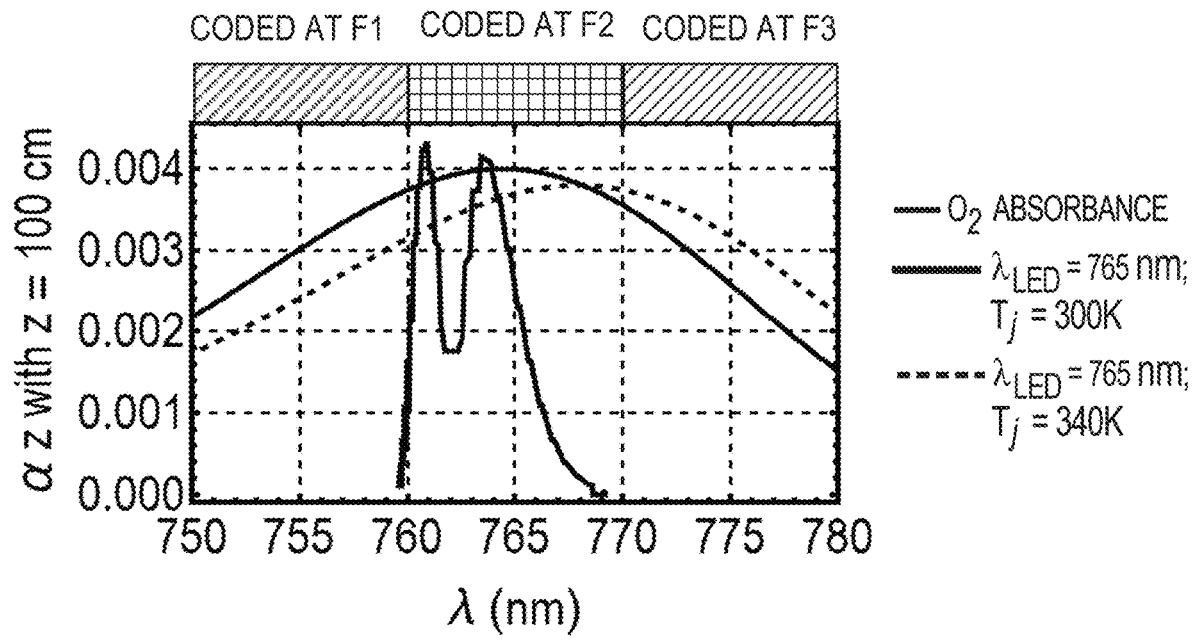
FIG. 25 includes a graph of absorption vs. wavelength for oxygen ($O_2$), and FIG. 25 also includes a table conceptually illustrating the impact of dust or dirty optics.

FIG. 25 includes a graph of absorption vs. wavelength for oxygen ($O_2$). FIG. 25 shows a relatively strong light absorption characteristic at wavelengths around 765 nanometers. This absorption characteristic can be used to measure the amount of oxygen in the atmosphere or other ambient environment, for example, such as in a furnace. Since these absorption lines are narrow and weak, e.g., compared to a profile of a LED's spectral output, such as shown in the same FIG. 25, measuring oxygen using light absorption and inexpensive LEDs is very challenging. Expensive and complicated techniques that may be employed may rely on swept-frequency diode lasers or high-resolution spectroscopy using broadband light.

The present techniques can employ an inexpensive LED light source, such as which can be coded such as by using W-CLS codes for three spectral regions (by way of non-limiting example) shown at frequencies $f_1$, $f_2$, and $f_3$ in FIG. 25. In the example of FIG. 25, only the central wavelength region (at or near $f_2$) is sensitive to the light absorption by oxygen. The two surrounding regions ($f_1$ and $f_3$) are affected by other factors, such as dust or dirty optics, etc., that affect all three bands $f_1$, $f_2$, and $f_3$ equally or similarly, as these frequency bands are close to each other. As shown in FIG. 25, $O_2$ light absorption is quite weak, and only 0.4% of the light is absorbed at a path length of 1 meter at the peak absorption wavelength. But as shown in the graph of FIG. 25, an LED spectrum tends to change, such as over temperature, injection current, time, and varying from manufacturing batch-to-batch.

The present techniques, such as using W-CLS and a transmit-side reference detector, can be used to help eliminate effects of variation in LED spectrum from the oxygen absorption measurement being performed by the main response detector on the receive side, after the illumination light has passed through a particular fixed length path through a gas containing oxygen. The present techniques, such as using W-CLS, can avoid a dark current offset effect. A differential spectroscopy approach using adjacent, non-absorbing channels such as at $f_1$ and $f_3$, the impact of dust and dirty optics can be substantially eliminated, such effects have similar impact on all three of wavelength bins $f_1$, $f_2$, and $f_3$.

FIG. 25 conceptually illustrates the impact of dust or dirty optics. As one can see from FIG. 25, any impact of dust or degraded optics or intervening smoke will affect all three wavelength bins (e.g., $f_1$, $f_2$, $f_3$) similarly. The changes in the bins (e.g., $f_1$, $f_3$) adjacent to the main absorbing bin(s) (e.g., $f_2$) become the proxy for what must have also happened in the absorbing bin (e.g., $f_2$) of interest. Thus, only differential (e.g., difference, ratio) changes in channel at $f_2$ over and above those expected from adjacent channels $f_1$, $f_3$ correspond to the true absorption by the targeted substance. Furthermore, since there is a reference measurement available, as described previously, changes in the source spectra, e.g., such as an LED light source, can be tracked and compensated for.

Oxygen absorption measurements can be subject to at least one other parameter: the stability of the W-CLS system itself, such as over time, over temperature, or both. For example, the particular spectral bin that is coded at a particular frequency itself can drift. As explained previously, in discussing wavelength calibration for W-CLS, a reference channel can be used. The reference channel can be provided with a stable thin film coating as a reference target or reference sample, which can be measured and used for calibration or as a feedback or other control input, such as to correct or stabilize other W-CLS measurements using other coded wavelengths. Thus, the present techniques can enable low-cost, efficient, and stable measurement of a weakly absorbing species, such as oxygen.

The present techniques, such as applied to differential spectroscopy measurement of oxygen or other weakly light-absorbing species, can employ the previously-described techniques of using an active slit or strip for providing the CLS source, such as described above with respect to FIGS. 16A-16E and 17A-17D, or direct input modulation of the electrical input signal to the LED or other light source, such as described above with respect to FIGS. 18A, 18B, and other techniques described elsewhere herein. As explained previously, an active slit light source in which different LEDs or phosphors can placed in the plane of the active slit, can contribute to different spectral bins, and a composite W-CLS can be formed by direct electrical input signal modulation of the different LEDs or phosphors. Such an approach is particularly suitable here, for differential spectroscopic or other measurement of a weakly-absorbed species, such as oxygen, since all the wavelengths for carrying out the measurement can be easily accessible from the same LED or from LEDs that are only slightly different in their central wavelengths. The techniques described here, focusing on an $O_2$ measurement example, can be extended to many other gases or solutes in liquids or gels or other materials that can be identified by their unique spectral signatures. FIG. 14B included a list of examples of some other commercially significant substances capable using similar techniques, including smoke, aerosols, or other particles, water, natural gas ($CH_4$), carbon dioxide, carbon monoxide, and corresponding light wavelengths that can be used.

Example 5: Long Range Smoke Alarm and Gas Detection

As previously mentioned with respect to FIGS. 14A, 14B, the present techniques can be applied for smoke, particulate matter, or environmental gas monitoring. In the example of FIGS. 14A, 14B, the detector can be located remote from the illuminator, or a retroreflector can be located in proximity to or remote from the illuminator and the detector. In many applications, such as smoke detection for buildings, factory floors, or the like, the distance span can range from 20-100 meters. Thus, movement of the building, obscuration of the light beam, or the like, can cause the system to generate an out-of-compliance alert or alarm, such as if the outgoing illumination beam misses the target detector or retroreflector.

Figure 26:
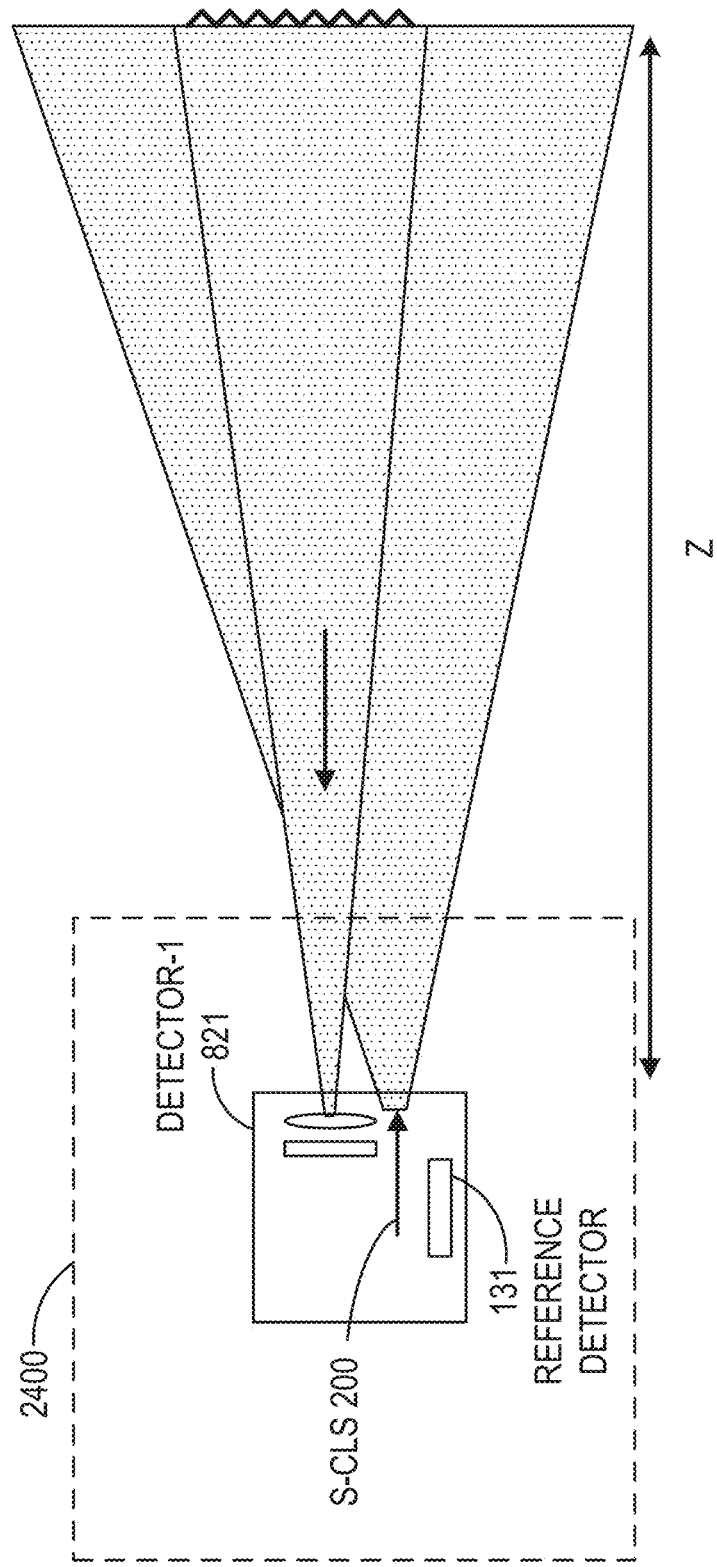
FIG. 26 shows an example in which a CLS system can be arranged in a convenient and robust geometry, such as to provide a divergent illumination beam, such as can be fanned out to provide an area that can span wider than a detector or reflector.

FIG. 26 shows an example in which a CLS system 2300 (such as S-CLS or W-CLS) can be arranged in a convenient geometry, such as can allow robust operation. For example, a CLS such as a S-CLS 200 can be arranged to provide a divergent illumination beam, such as can be fanned out to provide an area that can span that can be substantially wider than a retroreflective mirror, tape, or array. Such an arrangement can help accommodate possible movement of the retroreflector 2402 over time. A portion of the illumination light can be reflected back to a detector 821, such as can be located at or near the S-CLS 200. The amount of light reflected back to the detector 821 will depend on a ratio of the area of the retroreflector 2402 to an illumination area projected by the outgoing beam upon a plane of the retroreflector 2402.

In the example of FIG. 26, an S-CLS based system 2400 can optionally be used instead of the W-CLS based approach of FIG. 14B. The S-CLS 200 approach of FIG. 26 can provide certain advantages, such as in comparison to a point-detector system or an imaging based system approach. In the system 2400 of FIG. 26, the S-CLS illumination beam cone fans out and the retroreflected light beam can be measured by the detector 821. The reconstruction of one or more signals transduced by the detector 821 can provide an image of the retroreflector 2402. When the system 2400 is mounted in a building, as the building moves or sways, the receive-side signal processing can continue to track the image of retroreflector. In this way, any obscuration can be computed using only the pixels or codes corresponding to the image-tracked retroreflector 2402. This implementation can provide low computational complexity, low cost of electronic and other components, and can operate using a low-powered illumination light. Since the CLS technique rejects "DC", background ambient light conditions and variations can automatically be rejected. The wavelength of the S-CLS light source can be changed, such as to make measurements at more than one color, such as for aerosol identification. The system 2300 of FIG. 25 for measuring light-absorption of a specific gas using W-CLS can be combined with the S-CLS system 2400 of FIG. 26.

12. Examples of Other W-CLS Implementations and Applications

As explained previously, W-CLS can be enhanced in a number of ways, such as using an active slit or strip, such as can be combined with electrical input modulation of individual ones of multiple LED light sources contributing to the light being emitted via the active slit or strip. As explained, having multiple light sources occupying different vertical heights along the slit can advantageously help avoid using expensive and cumbersome order sorting filters. In general, gratings or other diffractive elements provide higher dispersion but, by their very nature, they generate higher diffraction orders, such that first order of wavelength $\lambda_2$ will overlap with $2^{nd}$ order of wavelength $\lambda_1$ whenever/$\lambda_2$=$2\lambda_1$. This applies to higher orders too. Thus, to use diffractive dispersive optics, typically some means needs to be provided to remove higher diffractive orders if the spectral range exceeds one octave. A variable optical thin film filter with spatially varying spectral transmission can be used as order sorting filter. In most spectrometry, the response light detector array is arranged in a rectilinear manner, and order sorting filters are needed. But with W-CLS 100 being used on the transmit side, there is much more optical freedom available in configuring the W-CLS.

Figure 27:
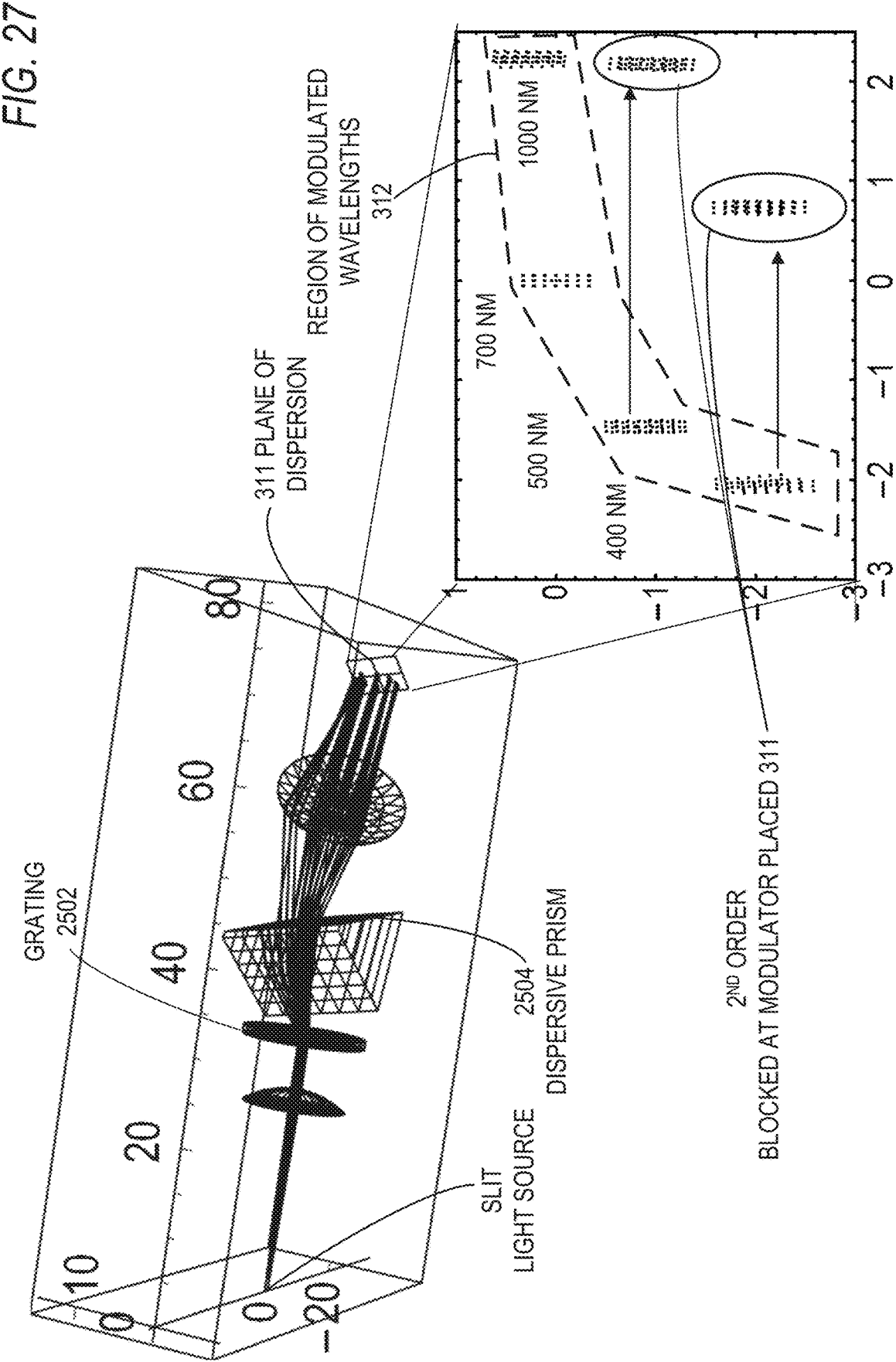
FIG. 27 shows an example of a configuration that can include both a grating and a dispersive prism.

FIG. 27 shows an example of a configuration 2500 that can include both a grating 2502 and a dispersive prism 2504. The grating 2502 can be arranged to help provide a fast dispersion along the dispersive axis, e.g., an x-axis. But the grating 2502 also generates higher order beams that overlap. Arranging a single prism 2504, such as shown in FIG. 27, can provide dispersion in a perpendicular direction to the x-axis, such that the colors are now spread along both of the orthogonal X and Y directions. But the prism 2504 does not suffer from a diffractive order sorting problem. The ray trace plot of FIG. 27 shows how some of the wavelengths can be spread in the plane of dispersion 311, such as which can serve as an input to a modulator. The region of overlapped orders will be separated vertically, with $2^{nd}$ order of 500 nanometers lying below (or top) of $1^{st}$ order of 1000 nanometers, and so on, such as shown in FIG. 27. Thus, a modulator, at the plane of dispersion 311, shaped to modulate wavelengths falling in the shaded region 312 will automatically eliminate or reduce higher diffractive orders of light incident upon the plane of dispersion 311. This can be accomplished by masking all but the region of interest 312. This is similar to the example shown in FIG. 17A-17D in the context of an active slit.

Example 6: Special Effects and Studio Recording

A W-CLS based hyperspectral imager can be used at visible light wavelengths to produce special effects or to help unburden video editors from the difficult problem of light and color balance adjustments. Using an extremely bright active-slit based or similar white light sources and using W-CLS coding in multiple spectral bins in the visible light portion of the electromagnetic spectrum, it becomes possible to illuminate a studio with 100s to 1000s of lux of wavelength-coded visible light. This can be enough illumination to create a 4K video with grayscale video camera at a high frame rate, such that, using the present W-CLS coding technique, a true reflectance of the target object or scene can be measured. It also makes the measurement independent of the properties of the camera's color filter array or its spatial arrangement on the imager such as a Bayer filter pattern and increases the sensitivity by almost 2× to 3× as there is no need for color filters. Thus, in a manner similar to that in which an audio engineer uses an audio equalizer to change the frequency spectrum of an audio signal for obtaining best or desired effects, using the present techniques and W-CLS coding of visible light, a video engineer can use hyperspectral data generated with W-CLS with perfect pixel registration, and can continue to use favorite lenses for creative video creation. Later in the video editing process, almost any lighting situation can be recreated, such as using digital processing from a W-CLS based hyperspectral imager generating a standard RGB video feed by appropriate weighted combination of hyperspectral channels.

This is best illustrated with an example, without any loss of generality. Consider the example of a challenging 60 frame per second (FPS) 4K video. The video can be recorded, for example, using codes for 10 visible light channels at wavelengths from 400 nanometers to 700 nanometers. By creating the video including near infra-red wavelengths or otherwise expanding the wavelength spectrum used for recording the video, a whole new class of special effects can be enabled for the movie. The coded spectral channels need not be equally spaced in wavelength or frequency, but may instead be chosen to satisfy some psycho-visual criteria, if desired. The present example can involve grayscale shooting using at least 1200 frames per second, which is realistic. A feature of W-CLS based hyperspectral imaging is that multiple cameras can be used to receive light from the target scene. Each of the cameras can be used to image a subset of coded wavelength regions-which can reduce the frame rate requirements for an individual camera (such as explained elsewhere herein). The images from the various cameras can be combined in a single seamless stream, since each of them are measuring pure reflectance of the scene.

Additionally, one or more invisible near infra-red channels can be concurrently recorded, and selectively used or ignored during video editing. A black-and-white camera will not need a color filter array on the pixel, and the actual optical throughput can be substantially improved with simplification of the optical and pixel design.

Example 7: W-CLS Based Optical Coherence Tomography (OCT)

Figure 28B:
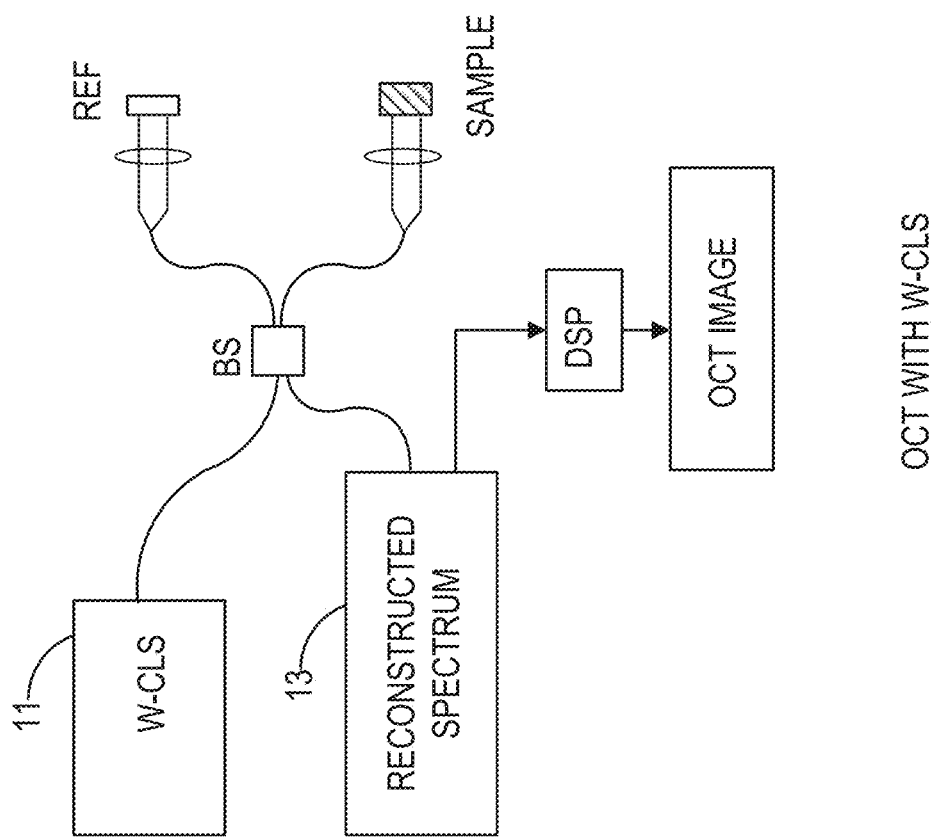
FIG. 28A, 28B, 28C show examples of various implementation of the present techniques in Optical Coherence Tomography (OCT).
Figure 28A:
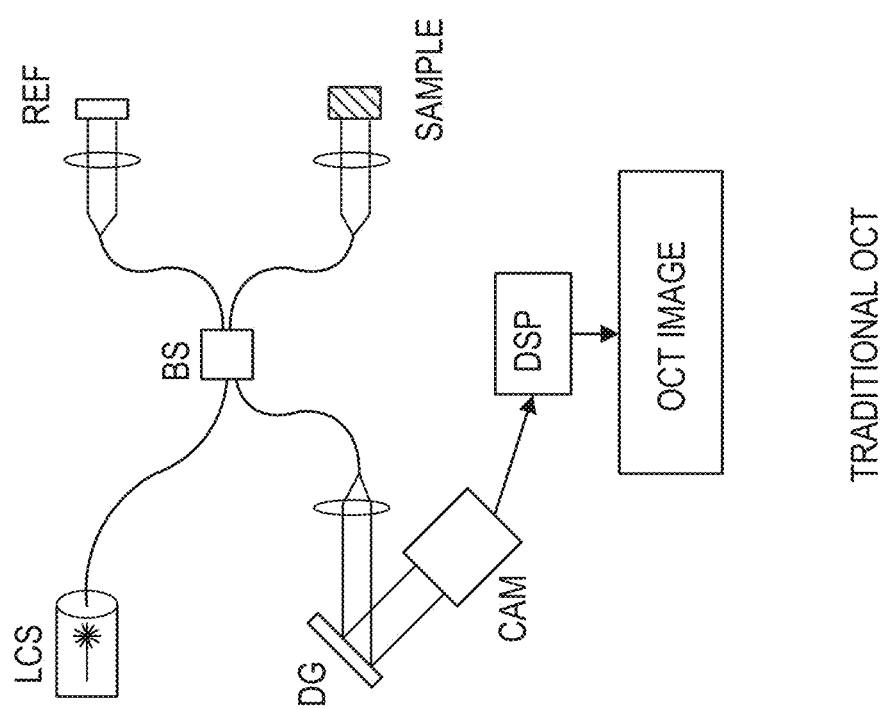

Optical Coherence Tomography (OCT) can include spectral domain OCT (SD-OCT) or Fourier Domain OCT (FD-OCT). In an approach, grating or dispersive optics is used after interfering reference arm and sample arm beams, such as shown in the example of FIG. 28A. FIG. 28B shows an approach in which the broadband, low coherence source of FIG. 28A is replaced with a W-CLS. In the approach in FIG. 28B, instead of using a spectrometer with a grating or dispersive optics after interferometry, a single detector can be used, without need for any such dispersive optics.

Thus, the approach of FIG. 28B can substantially increase the ability to collect light from the sample, such as previously explained. The number of spectral bins is controlled by the number of coded channels in the W-CLS. The approach of FIG. 28B can also help avoid the disadvantages of the CCD/CMOS photodetector array used in a spectrometer in a conventional SD-OCT, which cannot remove DC background signal, and which require pixel-to-pixel calibration. Most FD-OCT configurations use superluminescent LEDs ("SLEDs"). A PIC-based W-CLS, such as described herein with respect to FIGS. 7A, 7B can provide a spectral resolution of 100-1000 wavelengths. Furthermore, if an Arrayed Wavelength Grating (AWG) based spectral separator is used, then the modulation codes can correspond to equally spaced frequencies (rather than equally spaced wavelengths, as in the grating-based spectrometer used for FD-OCT). Thus, using the AWG approach, no interpolation from wavelength space to k-space or frequency space is needed for an OCT depth image.

The update rate or number of depth scans or A-scans (as sometimes referred to) per second of any FD-OCT system depends on number of spectra that can be read per second. In case of a W-CLS OCT system, the number of spectra that can be read per second will be limited by the modulation bandwidth of its modulator. A PIC based system can achieve modulation bandwidths in GHz range. For comparison, consider a very high-speed, FD-OCT system configured such as shown in FIG. 28A, operating at 100,000 A-scans per second, with roughly 200-500 wavelengths read by the spectrometer. Such an approach would use a readout bandwidth of ~ (number of A scans)*(number of pixels in spectrometer), which amounts to a raw readout rate of roughly 50-100 MHz. With GHz modulation rates of W-CLS, it is possible to reach a much higher read-out rate, speeding up a complete (x,y) scan, and reducing motion artifacts. The W-CLS approach can also collect more light, making it easier to reach higher speeds, since there will be almost zero losses for a W-CLS detector as compared to the optical efficiency of the spectrometer. Instead, in the W-CLS approach of FIG. 28B, there will be some similar losses on the transmit side, at which such power losses are of much lesser concern.

Further, multiple SLED based W-CLS sources can be combined, such as with each operating in different wavelength region, with the CLS light capable of being delivered via the same shared fiber-optic probe head to the same location. Different detectors operating in different wavelength regions can directly generate the OCT depth scan image across different spectral regions, providing extremely valuable information. Such a system can be quite compact, since a SLED based light source and PIC can be fit in a few $cm^2$ of board space.

Figure 28C:
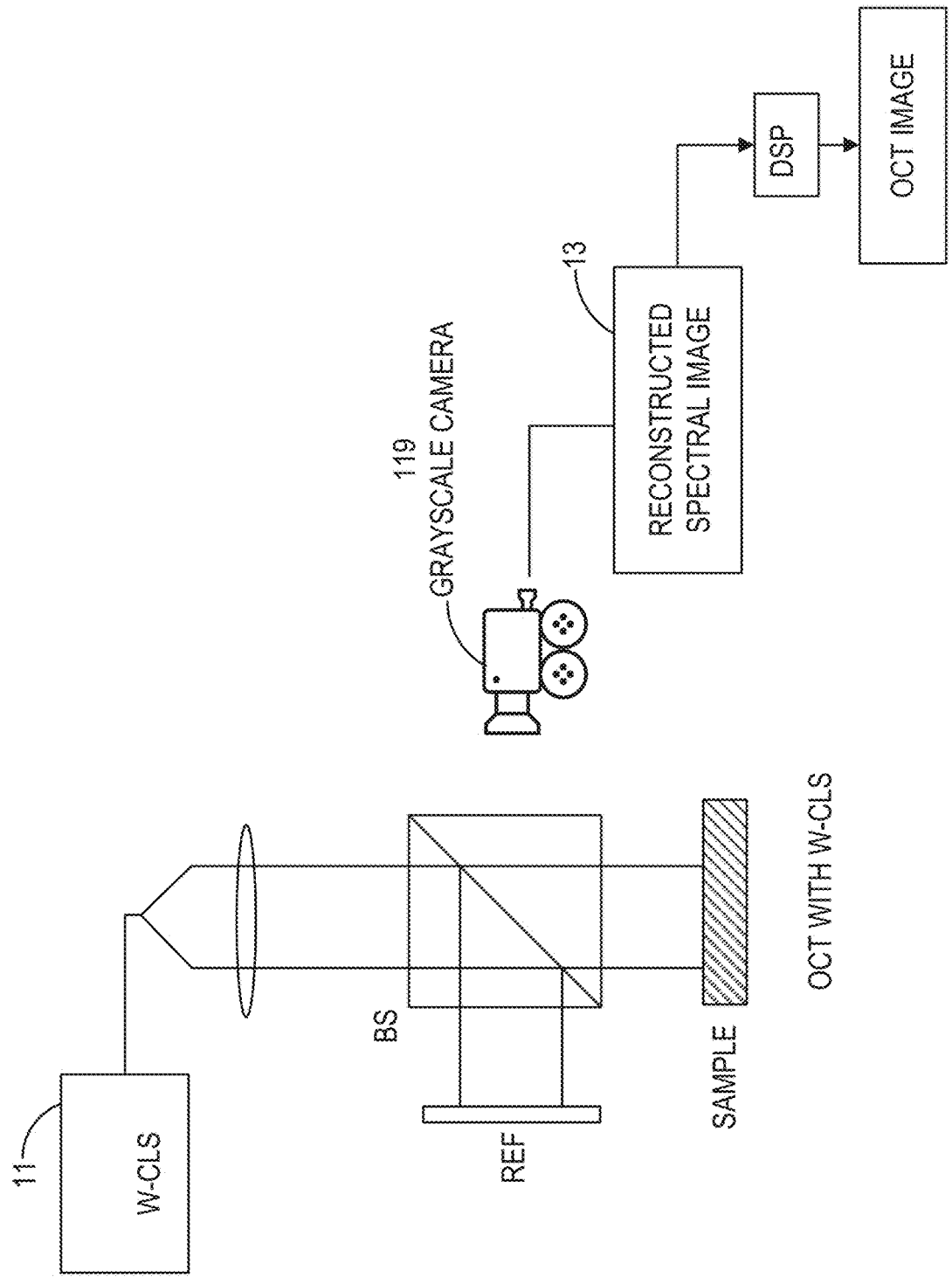
Figures 29A, 29B:
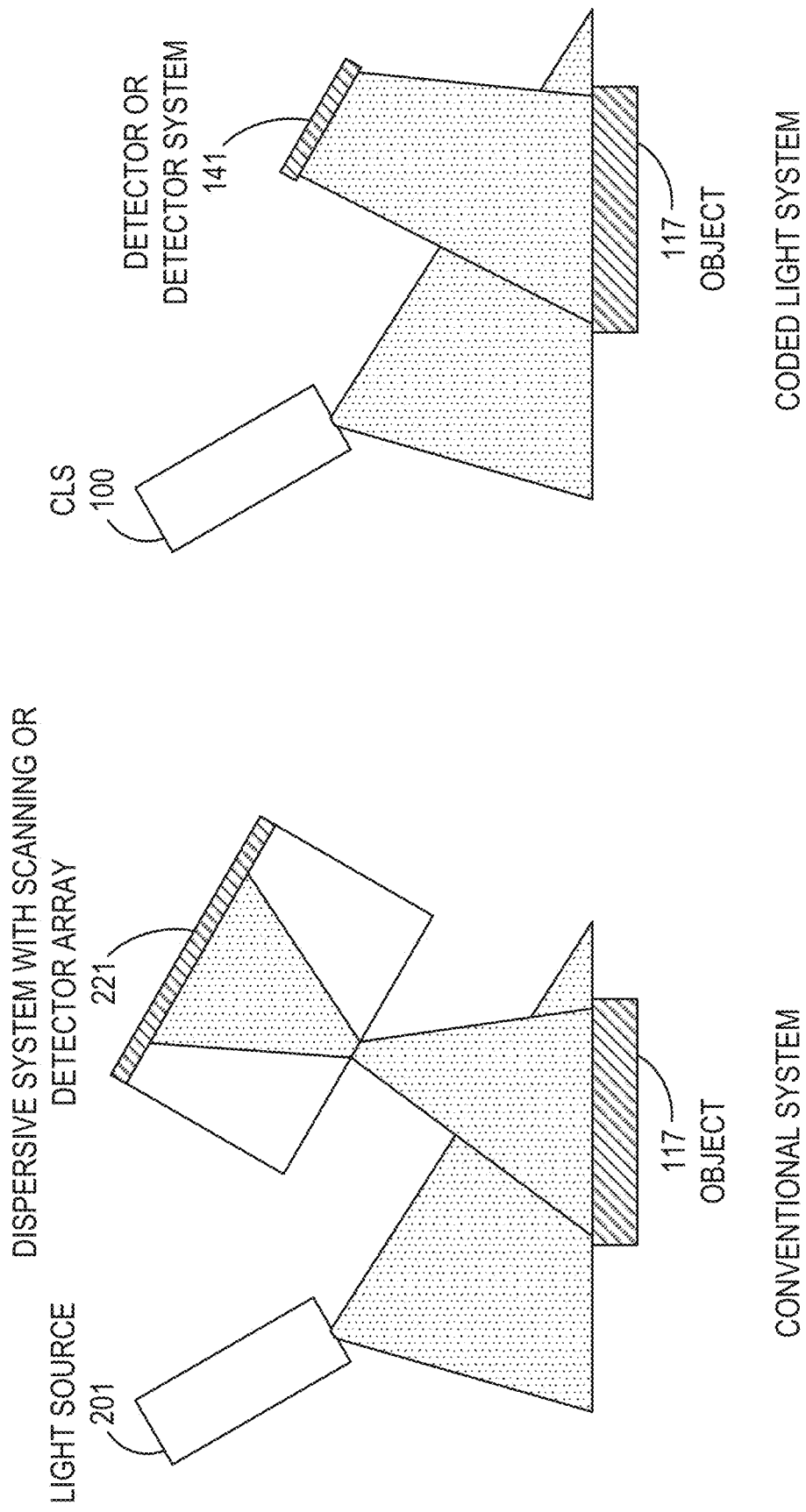
FIG. 29A, 29B show a comparison of a non-coded light approach to a coded-light approach.
Figure 30:
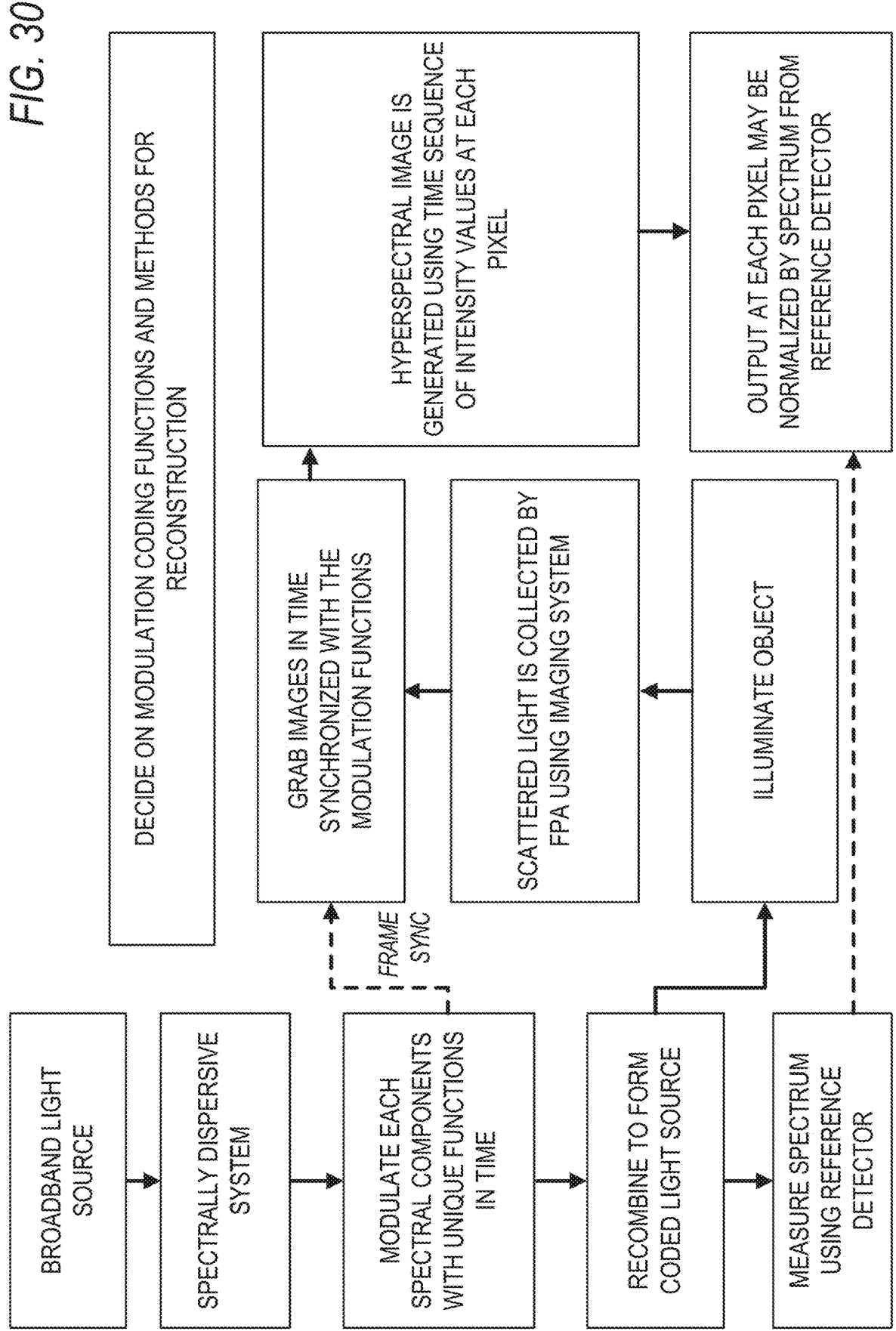
FIG. 30 shows an example of a method of using a coded light source for hyperspectral imaging.

But even with a slow mechanical modulator, such as where only a few thousand A scans are possible per second, this may still allow for a very wide wavelength range-since it can use many different light sources and provide higher spectral power. Thus, it may provide extremely useful information. The present techniques, such as described, can be scaled to an imaging system and can be configured like the W-CLS based hyperspectral imager described previously. This can enable performing a full-field OCT, such as shown in FIG. 28C.

13. Using Fluorescence, Raman, or Other Examples of Wavelength-Shifted Response for Imaging or Analyzing the Target Object or Scene The various techniques described herein, which can include modulation encoding an illumination beam of light using individual time-varying modulation functions corresponding to different spectral bins can additionally or alternatively be applied in the context of obtaining and using wavelength-shifted response information for imaging or analyzing the target object or scene, such as for providing fluorescence response spectroscopy, Raman spectroscopy, wavelength-shifted response imaging, or the like.

Fluorescence

The various techniques described herein, which can include modulation encoding an illumination beam of light using individual time-varying modulation functions corresponding to different spectral bins can additionally or alternatively be applied in the context of obtaining and using wavelength-shifted response information for imaging or analyzing the target object or scene. The coded illumination beam provided by the optical illuminator of the system 10 can include any group or groups of wavelengths. Such illumination wavelengths can be selected to help produce fluorescence by the particular material of the target object 117 when illuminated. An object is fluorescent when the incident illumination photon is absorbed by that object, and the incident photon energy converted partially into internal energy of the object and partially emitted from the object as "fluorescence response" light at a lower energy or frequency (or longer wavelength) of the emitted fluorescence response photon. The optical illumination "pump" frequency is a frequency at which a material component of the object fluoresces, and is a characteristic of that particular material component of the object. The fluorescence output or wavelength shifted emission spectrum from the object depends on the optical illumination pump wavelength incident upon the target object. A target object that is composed of a complex material, such as biological tissue or a heterogeneous mineral specimen, will exhibit a complex fluorescence response to different optical illumination pump wavelengths. For example, in many biological assays, a fluorescent molecule included or introduced in a biological sample object can act as a "probe" with identifiable characteristics that can be used to measure the presence of a target object molecule, such that the fluorescence is observed and measured only when the probe is bound to the target molecule. By using different fluorescent probes to attach to corresponding molecules in the target object, the presence of multiple target object molecules in the target object can be detected and an amount of such molecules present can be measured using the detected fluorescence response signal.

Figure 31:
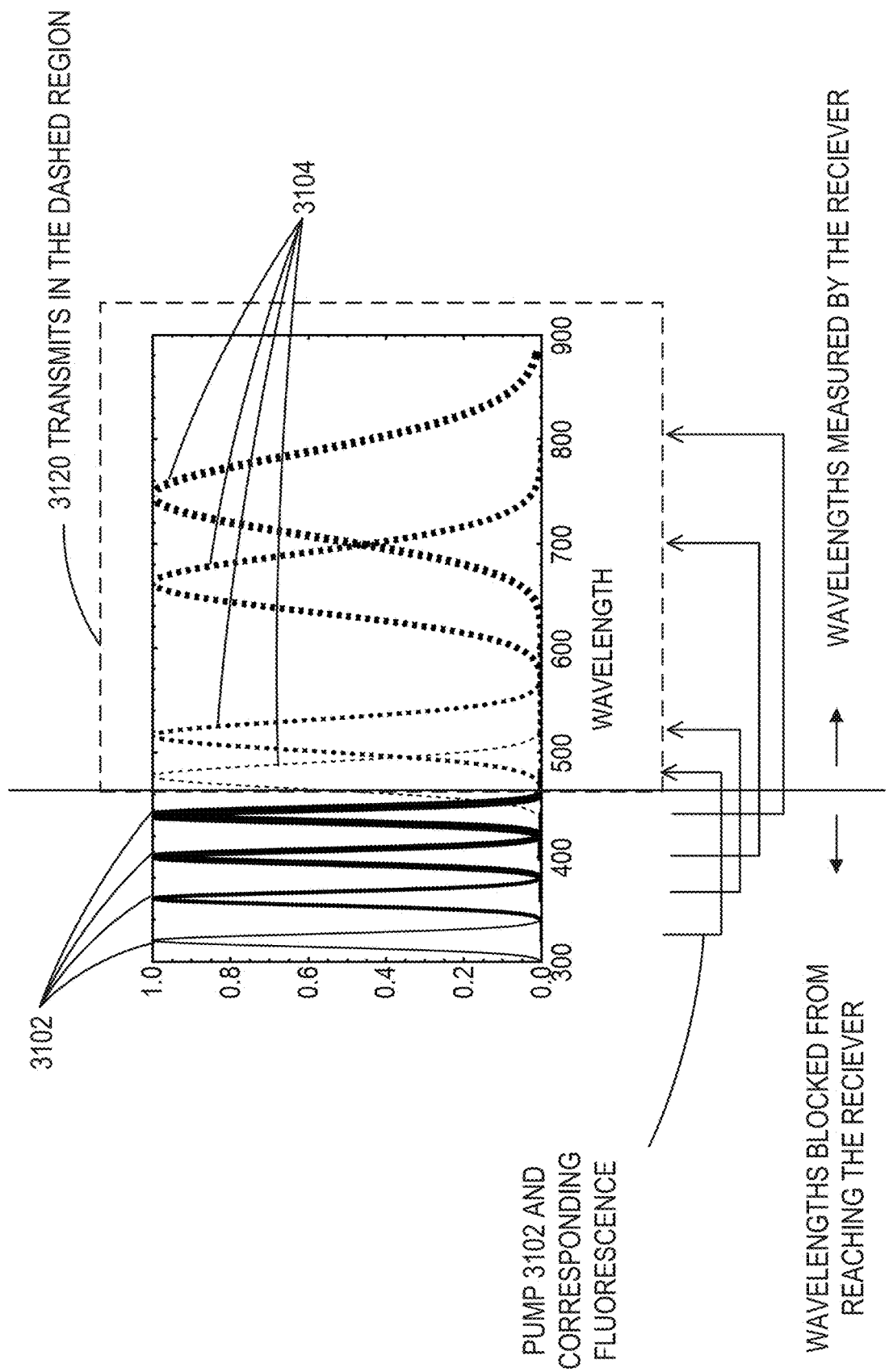
FIG. 31 is an illustrative conceptualized example of graph of normalized optical amplitude vs. wavelength, illustrating an example of emission response wavelengths from a target object or scene that can be wavelength-shifted from one or more specified pump spectral bins of wavelengths (also referred to as "pump wavelengths").

FIG. 31 is a conceptualized example of a graph of illumination (and wavelength-shifted response) light intensity vs. wavelength. FIG. 31 shows multiple optical illumination pump wavelengths 3102 (or spectral bins of wavelengths) that can be provided by an optical illuminator on the transmit side 11 of the system 10. While FIG. 31 shows four pump wavelength, one may use any number of pump wavelengths depending on the characteristics of the object. Each of the optical illumination pump wavelengths 3102 (or spectral bins) can be individually modulated using its own unique individual modulation code produced by the system 10, such as explained elsewhere herein. The W-CLS system 10 and techniques described herein can therefore be used to measure a wavelength-shifted light emission response signal from a target object 117 or sample, such as a fluorescence response. The target object 117 responds to by emitting fluorescence to each of the optical illumination pump wavelengths 3102 with the corresponding complex fluorescence response spectra 3104 that are correspondingly uniquely modulated according to the particular individual optical illumination pump wavelength 3102 that produced the particular individual response spectrum 3104. In FIG. 31, each response 3104 is shown as normalized for conceptual clarity but, in practice, some pump wavelengths 3102 may produce a strong corresponding fluorescence response spectrum 3104 and other pump wavelengths 3102 may produce a very weak corresponding fluorescence response spectrum 3104. Thus, these fluorescence response spectra 3104 characteristic responses to different optical illumination pump wavelengths 3102 can serve as fluorescent response spectrum or wavelength-shifted response spectrum. An optical blocking filter 3120 can be inserted in the optical pathway between the target object 117 or sample and the photodetector or FPA on the receive side 12 of the system 10 such as to block the wavelengths of the optical illumination pump light, but to allow the photodetector or FPA to receive longer, wavelength-shifted fluorescent response light from the target object 117 or sample or scene. The fluorescence response detected by the photodetector 119 or FPA can be read and decode by the signal processor/controller circuitry 13 of the receiver 12. When decoded, the decoded fluoresce response 3104 will now correspond to the fluorescence response 3104 in which all the fluorescence response light is measured corresponding to the optical illumination pump signal provided using its unique modulation code.

Improved SNR by Fluorescence Measured Using CLS

This present CLS techniques of wavelength-shifted fluorescence response measurement can be highly advantageous for rapid measurement or characterization of materials and fluorescent signatures. As an example, consider auto-fluorescence of biological cells. Depending on the chemical state of the cell, the auto-fluorescent spectrum can change, and this can be used to measure the state of the cell. This can be extremely useful such as, for example, for in-vitro fertilization or other applications in which it is not possible or is undesirable to use or add external, potentially toxic fluorescent probe molecules.

Typical fluorescence signals from most materials can be very weak, and thus very few photons are received from the target object or sample by the photodetector or the imager. In such cases, the ability to detect the wavelength-shifted fluorescence response signal is limited by the noise of the read-out electronics. This can be mitigated, such as by increasing the integration time to allow many more photons to be collected, by actively cooling and decreasing the temperature of the photodetector or imaging sensor to reduce thermal noise, and by increasing an intensity of the optical illumination pump light to the maximum extent possible without causing changes in the sample due to the increased illumination light intensity. However, according to the present CLS techniques for measuring fluorescence response, all of the wavelength shifted response light arrives at the photodetector or imaging sensor at the same time for all the spectral bins to be used for spectroscopic analysis or for hyperspectral or other colorimetric imaging. This means that the total number of photons received by the photodetector or other imaging sensor is many times larger using the present techniques. This increase in response light can be enough to overcome the receiver noise and make the measurement limited by the shot noise.

Furthermore, since the signal corresponding to the various spectral bins can be concurrently and continuously modulated and measured, some of the practical problems of dark currents, 1/f noise and drifts in the system that would otherwise occur due to longer integrations times of other techniques can be avoided. This, in turn, can allow reduction in optical illumination pump light intensity or lower integration time, or to far lower-cost detector systems not requiring active cooling. The CLS modulated fluorescent spectroscopy or measurement of wavelength shifted response light described herein, therefore, can help provide enormous practical advantages, which can apply throughout the various use-cases of the present techniques, but which can be particularly useful such as for spectroscopy of fluorescence and Raman signals, from a target object, scene, or sample, which are weak.

Fluorescence measurement can be combined with non-fluorescence measurements such as to permit concurrently characterizing the object by its reflectance or transmittance as well as by its fluorescence properties. As described in FIG. 15, high frequency coding of the pumped optical can provide fluorescence lifetime information that can further assist in characterizing the molecular and material composition or environment of the target object, sample, or scene.
Raman Raman spectroscopy is another example in which a component of the target material produces a wavelength-shifted response light. The physical mechanism for the Raman effect is different than fluorescence described above but CLS can be applied to provide Raman spectra of the material. The goal of Raman spectroscopy—a well-developed field—is to measure the spectrum of the wavelength-shifted response.

Figure 32:
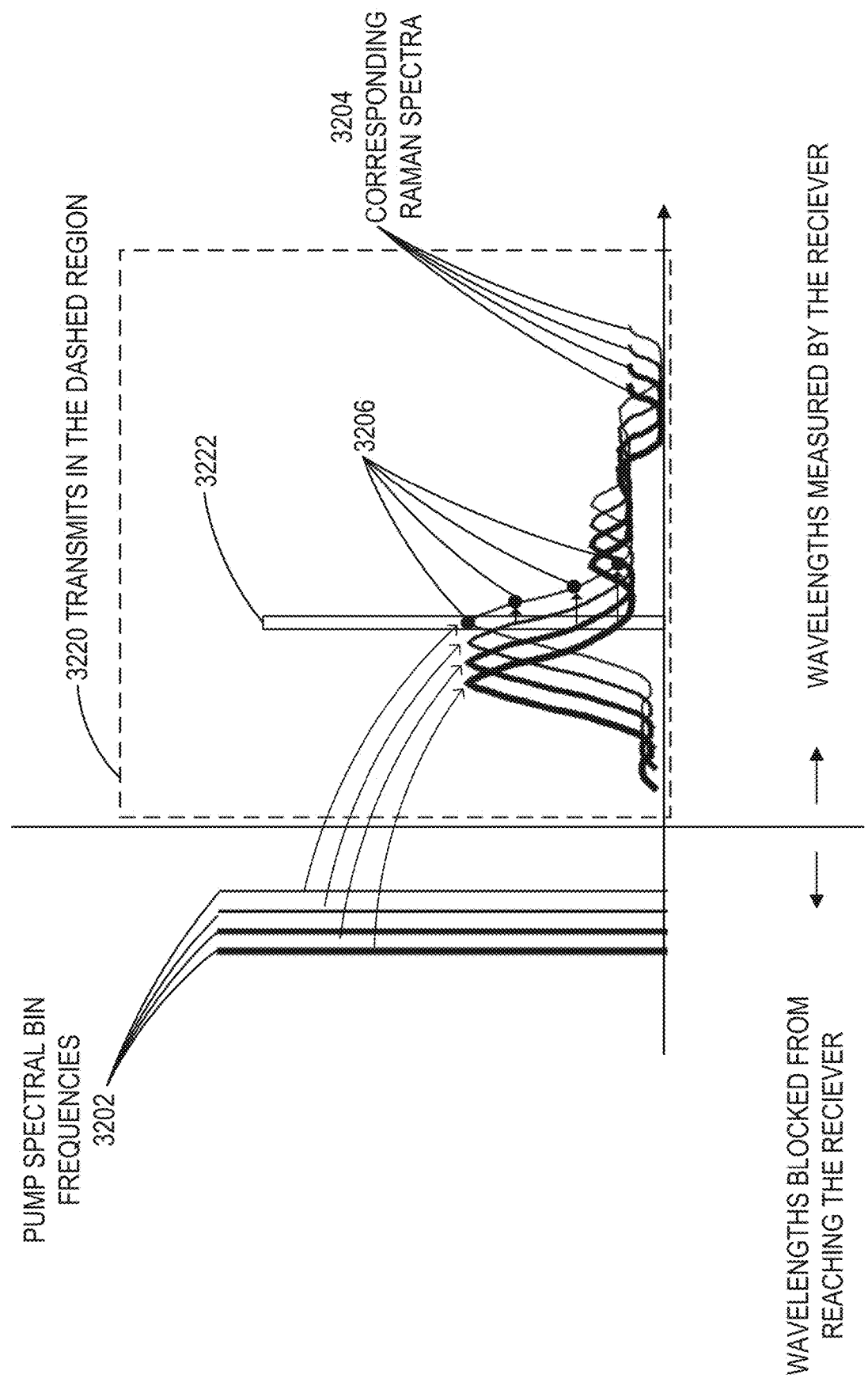
FIG. 32 is a conceptualized example of a graph of amplitude vs. wavelength showing Raman spectra and how the present techniques can be used with Raman spectroscopy techniques to provide enhanced spectroscopic analysis information.

FIG. 32 shows a conceptualized illustrative example of amplitude vs. frequency of wavelength-shifted Raman spectra 3204 (normalized for conceptual clarity) and corresponding optical illumination pump wavelengths 3202 from which such corresponding individual wavelength-shifted Raman spectra 3204 are elicited in response to. It is easier to think of Raman spectroscopy in terms of optical frequency, rather than optical wavelength, because for Raman the underlying phenomena is that of measurement of aspects of the energy levels of molecular components of the material of the target object 117 or sample or scene. Consider one of the optical illumination pump frequencies 3202—for example, the one represented by a solid line in FIG. 32. The material of the target object 117 produces a corresponding Raman spectrum 3204, which is also shown as a solid line in FIG. 32.

The position and shape of this Raman spectrum 3204 is a characteristic of one or more components of the material of the target object 117 and represents some of the internal vibrations between atoms and molecules within the target object. The wavelength-shifted Raman spectrum, when shifted to lower frequencies than the optical illumination pump frequency is referred to as Stokes, and when shifted to higher frequencies than the optical illumination pump frequency is called Anti-Stokes. The description herein applies to both Stokes as well as Anti-Stokes Raman spectra. The informative characteristic of the Raman spectra to be determined and measured is the amount by which the Raman spectrum is shifted with respect to the optical illumination pump frequency. Thus, changing the optical illumination pump frequency 3202 from that shown by a solid line in FIG. 32 to one denoted by dashed line in 3202, shifts the Stokes Raman response by the same amount to the corresponding dashed Raman spectrum 3204.

As in the CLS based fluorescence measurement techniques described herein, the optical illuminator on the transmit side 11 of the system 10 can be used to provide illumination of the target object 117 or sample using multiple optical illumination pump frequencies or wavelengths 3202, each with its own unique modulation code, and which can be concurrently delivered to the target object 117 or sample. This will result in a corresponding wavelength-shifted Stokes-Raman spectra response by the target object 117, each modulated in accordance with the unique modulation code that was used for its corresponding modulation encoding of its pump wavelength (or spectral bin) of the pumped optical illumination light.

Since the Raman response to all the pump wavelengths are the same except for the shift in frequency, in order to determine the Raman response, an additional optical filter 3222 is positioned in the optical pathway between the target object 117 and the photodetector 119 or imaging sensor receiving the wavelength-shifted Raman response from the target object 117. This additional optical filter 3222 can be configured to provide a specified light transmission profile, which can be a complex light transmission profile, if desired. For example, for the case shown in FIG. 32, the optical filter 3222 can be configured such that it only passes light having frequencies in its fixed passband (shown in FIG. 32 as a shaded region) corresponding to the optical filter 3222 positioned in the optical pathway between the target object 117 and the photodetector or imaging sensor receiving the wavelength-shifted Raman response from the target object 117. As can be readily seen from FIG. 32, the filtered decoded signals received by the photodetector or imaging sensor, reproduces the Raman spectrum as shown by 3206, which can be referred to as a "synthesized Raman spectrum." By using many pump optical illumination spectral bin frequencies, a portion of the Raman spectrum is synthesized. The resolution of the Raman spectrum will depend on the characteristics of pump spectral bins as well as the optical filter 3222. This follows from the property of the Raman effect previously explained, that is, that the Raman response wavelength/frequency need only be measured as the amount of shift from the corresponding pump wavelength/frequency. An optional blocking optical filter 3220 (e.g., having only the narrow fixed passband shown by the shaded region in FIG. 32 corresponding to the optical filter 3222) may be positioned in the optical pathway between the target object 117 and the photodetector or imaging sensor receiving the wavelength-shifted Raman response from the target object 117 such as to help reduce cross-talk from powerful concurrently deliverable modulation-encoded optical pump wavelengths, which can be helpful to measure the weak Raman signals. One or more such optical filters 3222 may themselves be constructed using thin-film filter technology or using a dispersive optics, for example.

Figure 33:
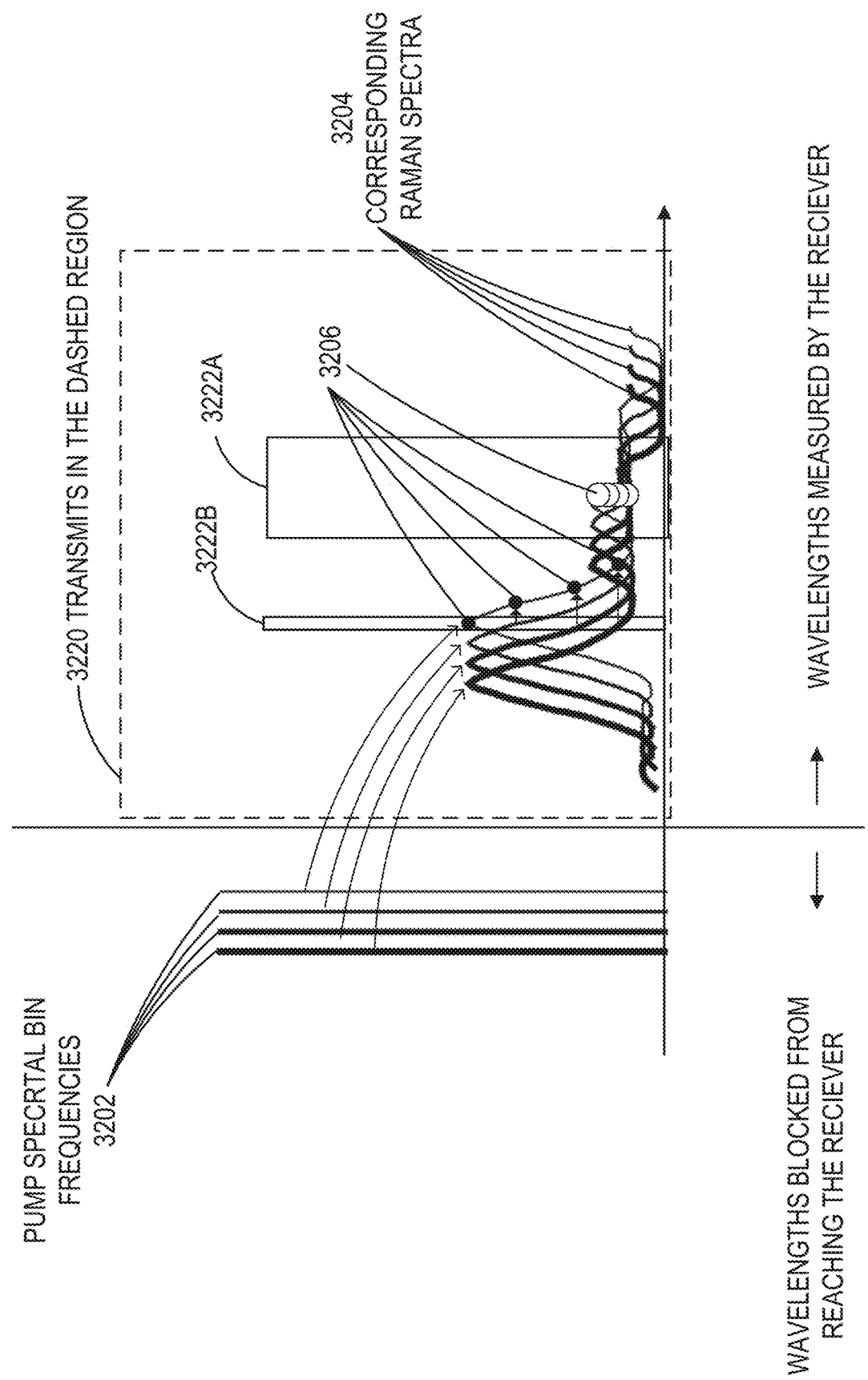
FIG. 33 shows a conceptualized example of a graph of amplitude vs. wavelength for a case in which multiple (differently modulation-encoded) pump wavelengths or spectral bins can be provided at a wavelength that is shorter than the blocking cutoff wavelength of an optical filter in an optical pathway between the target object or scene 117 (or other sample) and the photodetector or FPA on the receive side of the system such as to provide Raman spectra.

In FIG. 33, the optical filter 3322A is shown as a stop band filter (transmits in the two shaded gray regions) which narrowly blocks the Raman signal reaching the detector placed behind it. As illustrated in the example shown in FIG. 33, the entire portion of the Raman response under the particular the shaded area corresponding to the particular optical filter 3322A or 3322B is received by its corresponding photodetector, with a wider passband permitting the corresponding photodetector 119 or imaging sensor to collect many more Raman photons. The filtered decoded spectrum can directly serve to "fingerprint" a composition of the material of the target object 117 as it produces a mathematically transformed response to the underlying Raman spectrum that can serve directly as a proxy to the Raman spectrum. Furthermore, for a given filter shape 3322, it may be possible to recover the traditional Raman spectrum by employing further mathematical processing. Indeed, there are many possible constructions of optical filter shapes 3222 or 3322A and by appropriate choice of the filter, photon collection can be optimized while providing sufficient contrast in the filtered decoded synthetic Raman spectrum to allow rapid measurement of the material characteristics.

Furthermore, CLS based spectroscopy allows for multiple detectors or imaging systems to be positioned spatially to observe the scattered radiation from the object 117 as we have discussed for many applications earlier. Each system produces decoded spectrum. The same applies to wavelength shifted measurement of the fluorescence and Raman signals and can be used to increase SNR as well as accuracy in material identification.

Improved SNR by Raman Measured Using CLS

The wavelength-shifted Raman response measured by the CLS techniques described herein can help provide higher signal-to-noise ratio (SNR) in a shorter acquisition or measurement time, and can thus be advantageous over traditional Raman spectroscopy. The SNR advantages described herein with respect to fluorescence spectroscopy applies even more strongly to the case of Raman spectroscopy. In a traditional Raman spectrometer, the weak Raman response 3204 is further divided by the spectrometer into individual spectral bins and thus each particular detector corresponding to the particular spectral bin receives even fewer photons. In many cases of using a traditional Raman spectrometer, the photon levels in each bin are in the range of 1-100 of photons per second-even when using powerful optical illumination pump laser. This requires traditional Raman spectrometers to generally use cooled photodetectors and long integration times, which require highly stable opto-mechanics and electronics, further increasing the cost of such traditional Raman spectrometer systems. It also makes it difficult or even impossible to construct full Raman images of the target object 117, except by extremely slow scanning across the target object 117 and reconstructing the Raman spectrum point-by-point. By contrast, using the present CLS techniques, such as described herein, photons from multiple optical illumination pump wavelengths are all received by one or more photodetectors 119 or imaging sensors on the receive side 12 of the system at the same time, thus increasing the total photons detected far above the read-out noise. In case of the filter(s) 3322, it is expected that the photon levels may be raised by more than factor of ten to a regime in which a modest power CLS optical illumination source providing various modulation-encoded Raman optical illumination pump frequencies can generate enough response photons from the target object 117 delivered to the photodetector 119 or imaging sensor to allow use of uncooled photodetectors, lower power optical illumination light sources and even enabling generating a complete Raman image for the first time in a practical fashion. This has the potential to revolutionize our ability to measure and observe the world around us, such as for a wide variety of use-cases, such as ranging from label-free histopathology to measurement of analytes in complex media such as to assist with quality and process control.

The resulting wavelength-shifted emission response wavelengths 3104 can be used for imaging, spectroscopy, or other analysis, such as described elsewhere herein. Thus, modulation of spectral bins that provide pump wavelengths can permit the receiver 12 (e.g., photodetector 119 or imaging Focal Plane Array (FPA) receives wavelength-shifted emission wavelengths from the target object or scene 117 in response to the illumination beam provided by the optical illuminator of the transmit portion 11 of the system. These wavelength-shifted emission wavelengths 3104 can produce a modulated optical output from the target object or scene 117 corresponding to a particular pump spectral bin 3102. High frequency modulation can also provide fluorescence lifetime information for every pump spectral bin 3102, such as explained elsewhere herein, such as with respect to FIG. 15. Such high frequency modulation can be useful for spectroscopy, for imaging, or both. The imaging can use a Time-of-Flight (ToF) camera, such as described elsewhere herein, which can help provide fast demodulation.

The use of pump wavelengths or spectral bins 3102 to obtain spectroscopic or imaging information from wavelength-shifted emission response wavelengths or spectral bins 3104 can be particularly useful with electrical input modulation techniques of LEDs or other light sources (such as described elsewhere herein) to obtain modulated pump wavelengths or spectral bins 3104, because pumping to obtain a fluorescence emission response may be limited to a few well-chosen wavelengths for the expected material or material properties of a particular target object or scene 117 (e.g., less than 16 pump wavelengths, in an example). Moreover, for imaging a fluorescence or other similar emission response from a sample or target object or scene 117, the wavelength homogeneous illumination techniques described herein can be advantageous for measuring the resulting fluorescence image, since typical fluorescence response or Raman signals from a sample can be very weak. More particularly, wavelength homogeneous illumination can involve less receive-side signal processing to compensate for signals arriving from different locations or portions of the target object or scene. For weaker signals, such corrections can themselves introduce systematic bias or noise, so it would be better to help avoid such corrections, if possible.

14. Equalization and Dynamic Intensity Control Using Feedback

FIGS. 52A-52B are conceptualized schematic block diagrams illustrating an example of equalization and using feedback for dynamic spectral intensity control of the spectrum of the modulation-encoded CLS optical illumination light beam.

FIG. 52A shows an example of the CLS techniques described herein, the modulated optical illumination light beam from an optical illuminator at a transmit side 11 of a system 10 interacts with the target object, sample, or scene 117, and response light at a receiver side 12 of the system is detected by a photodetector 119 or FPA or other imaging sensor, and the resulting signal is read and decoded by signal processing circuitry 13, such as to form a response spectrum.

In the example of FIG. 52A, the target object 117 has high attenuation at some wavelengths or spectral bins and low attenuation at some other wavelengths or spectral bins, such as shown at the output spectral diagram 5201, which is obtained in response to a relatively flat optical illumination input spectrum 5202, which does not pre-emphasize any particular spectral bins over any other spectral bins. As shown in the output spectral diagram 5201, this may lead to too much signal in some spectral bins after demodulation and very little signal in some other spectral bins. This can result in saturation of the photodetector 119, such as by wavelengths in spectral regions having too much signal. In such cases, it can be helpful to reduce the light output in one or more particular spectral bins and increase the light output in one or more other spectral bins. This can be accomplished using the present CLS techniques (whether directly modulating light or by modulating LED or SLED or other light source electrical input signal by changing the drive current) such that the received, recovered, and demodulated output spectrum is more uniform.

FIG. 52B shows an example in which the optical illuminator in the transmit portion 11 of the system 10 can include spectral emphasis componentry 5204 that can increase light intensity in particular spectral bins relative to that of other spectral bins being modulation-encoded into the optical illumination beam for illuminating the target object 117. In the conceptual illustrative example of FIG. 52B, at 5206, an illustrative example of a pre-emphasized illumination spectrum is shown for use in modulation-encoding by the SLM or other multifunction modulator. The illustrative example of pre-emphasis shown at 5206 is shown in a manner intended to represent it as being suitable for use in compensating or equalizing the output spectrum 5201 shown in FIG. 52A as having high response from the sample in a mid-region of its spectrum, such that a decreased mid-region spectral intensity of optical illumination such as shown at 5206 in FIG. 52B is appropriate, and yields a more consistent amplitude output spectrum such as shown at 5208 of FIG. 52B. As shown in FIG. 52B, the resulting output spectrum at 5208, in response to using pre-emphasis for illumination such as shown at 5206, can be renormalized at 5212, such as by the signal processor circuitry 13, such as to yield the true output spectrum 5210 in FIG. 52B, such as for storage in a memory circuit, for further signal processing, or for display. Using pre-emphasis and renormalizing at 5212 to recover the true spectrum can be particularly useful in cases in which there is expected to be a large variation in the spectrum to be detected by the photodetector 119 and FPA or other imaging sensor, since doing so can help improve both the SNR and can help to inhibit or prevent saturation of the photodetector 119 or one or more pixels of the FPA or other imaging sensor.

For the case of an electrically drive CLS or one in which the SLM or other multifunction modulator 115 is electrically controlled to modulate encode various spectral wavelengths or spectral bins of the illumination beam, the output illumination spectrum can be dynamically adjusted by observing the resulting response spectrum from the target object 117 and using that feedback information to dynamically adjust the illumination intensity of one or more spectral bins on the transmit side 11 of the system. For a fixed SLM such as disk-based mask, the illumination spectrum can be shaped to provide a desired pre-emphasis, such as using or interchanging one or more gray-scale transmission masks, optical filters, or some other wavelength-dependent transmission componentry, which can be appropriately selected for the desired illumination pre-emphasis using the a-priori information about the actual or expected spectral response from the target object.

In addition or as an alternative to the pre-emphasis by spectral emphasizer componentry to pre-emphasize at least one spectral bin with respect to at least one other spectral bin, based on an actual measured or expected output spectrum from the target object or scene, before modulation encoding into the illumination light beam for illuminating the target object or scene, it is also possible to include spectral gain adjustment componentry on the receive side to adjust spectral gain in the signal processing circuitry 13 on the receiver and decoding 12 side of the system 10, such that a gain associated with at least one spectral bin is adjusted with respect to at least one other spectral bin.

Section B: High Spectral Purity LED Based Spectroscopy Examples

As mentioned in Section A, the different spectral bins can be modulation-encoded on the transmit side 11 of the system 10, such as by the optical illuminator including or being coupled to a multifunction optical modulator 105 that receives input light and optically modulates it, or by modulating an electrical control or power signal of an LED or other light source, and thereby modulation encoding the optical output in response to such electrical signal modulation. This Section B further explains examples of such electrical signal modulation of an LED or other light source, and explains particular applicability to examples for spectroscopic analysis of a biological target sample, such as for oxygen saturation (SPO2) measurement of blood oxygenation transdermally. Because in certain such applications, the skin or other intervening medium can act as an optical scattering medium, the optical illuminator output on the transmit portion 11 of the system 10 need not necessarily be wavelength homogeneous, such as described with respect to certain other examples in Section A. Among other things, this Section B explains techniques of using collimation and optical filters, such as to help better define spectral bins from respective LEDs, such as which can be electrically modulated to modulate corresponding optical outputs, such as for modulation encoding with different time varying modulation functions, as explained in Section A.

Figure 34B:
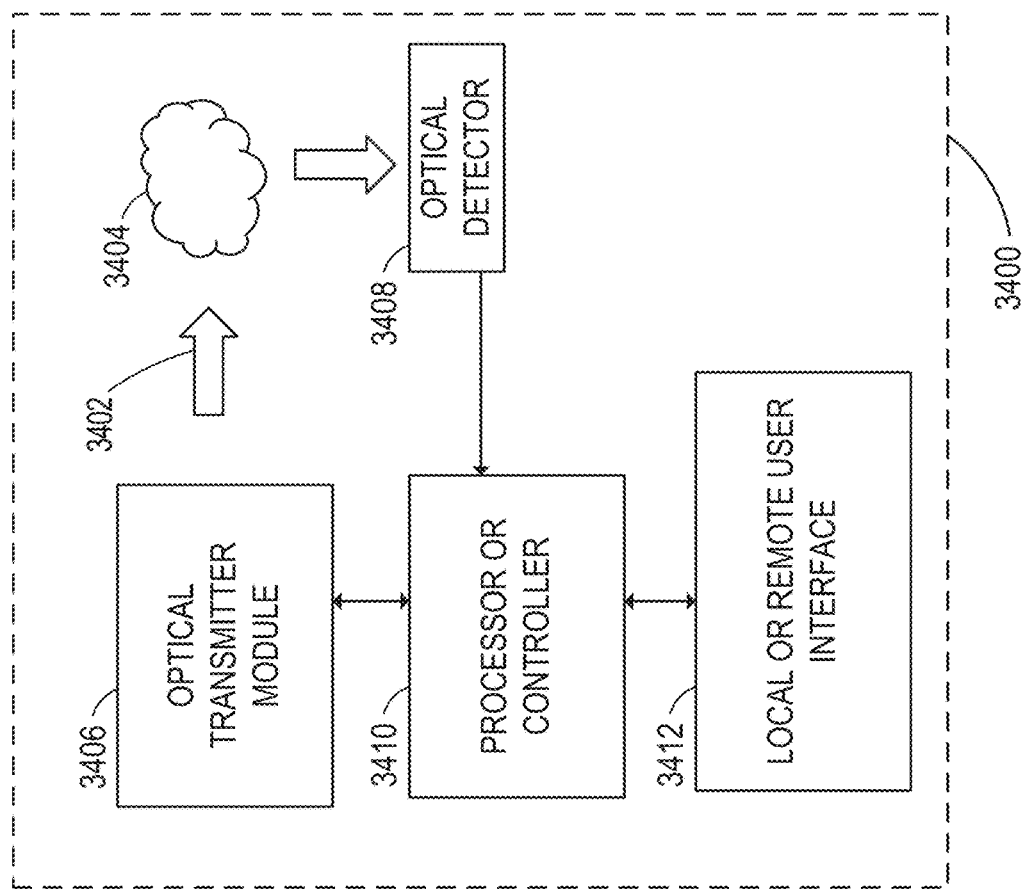
FIG. 34B is an illustrative schematic example of portions of an optical transmitter.
Figure 34A:
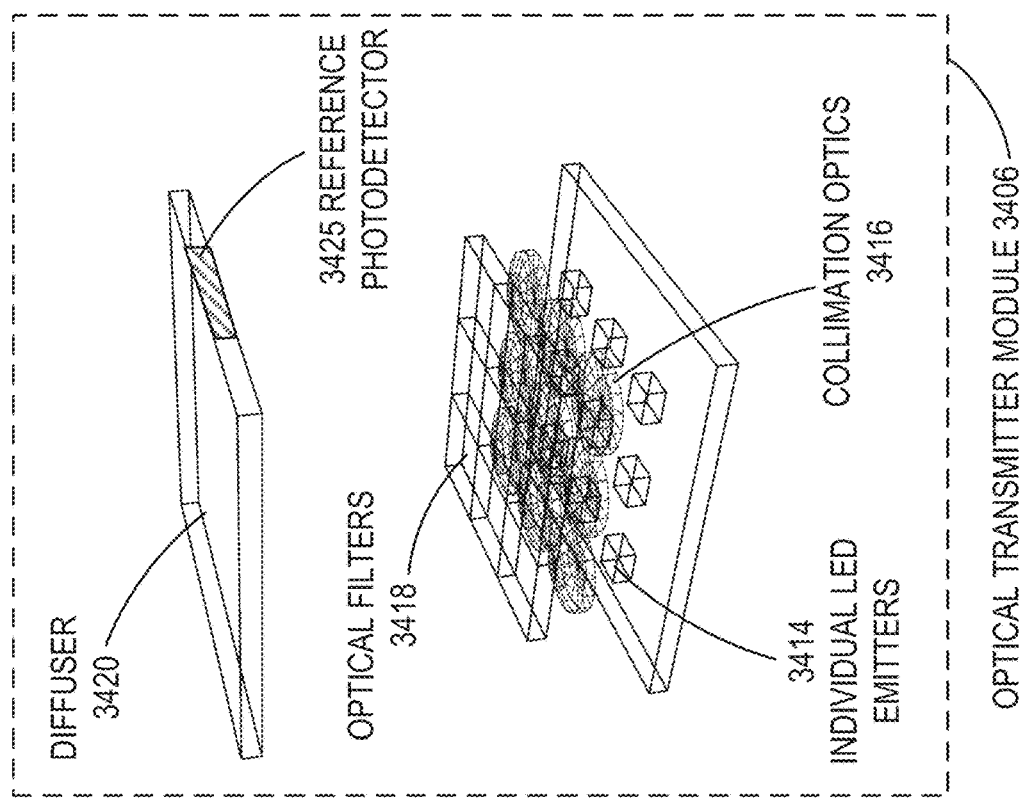
FIG. 34A is an illustrative block diagram that shows an example of portions of a system that can include a wearable or other device that can be used for multi-wavelength spectroscopic analysis of a biological or other target or object.

FIG. 34A is an illustrative block diagram that shows an example of portions of a system 3400 that can include a wearable or other device 3402 that can be used for multi-wavelength spectroscopic analysis of a biological or other target 3404 or object. For illustrative clarity, this Section B of this document will focus on a particular application-spectroscopic measurement and analysis of arterial blood oxygenation saturation. However, other applications will become clear from reading the present document.

In FIG. 34A, the device 3402 can include an optical illuminator, such as a multispectral optical transmitter 3406 module, an optical detector module 3408 such as which can include a photodetector, FPA, or other light transducer, and associated electronics such as can include signal processing or control or processor circuitry 3410, such as to control the generation and delivery of light by the optical transmitter 3406 or other optical illuminator and to control one or more of the detecting, processing, or analyzing of response light received from the object 3404 in response to illumination by the optical illuminator or other optical transmitter module 3406. The system 3400 or device 3402 can also include a local or remote user interface 3412, such as to accept user input or to display or otherwise communicate analysis results to the user or to another local or remote device, such as to a computer, mobile telephone, wireless network router, or the like.

FIG. 34B is an illustrative schematic example of portions of the optical illuminator or optical transmitter 3406. In the example of FIG. 34B, the optical transmitter 3406 can include multiple individual light-emitting diodes (LEDs) 3414. This plurality of individual LEDs 3414 can include at least two individual LEDs 3414 providing corresponding LED output illuminations having different individual selected, specified, or targeted illumination spectra. As an illustrative non-limiting example, a first one of the individual LEDs 3414 can be selected to emit light centered at a wavelength of 570 nanometers and a second one of the individual LEDs can be selected to emit light centered at a different wavelength, such as at a wavelength of 650 nanometers.

The optical transmitter 3406 can also include a plurality of optical collimators 3416. For example, this can include at least two individual optical collimators 3416 in respective optical pathways corresponding to respective individual LEDs 3414. FIG. 34B shows an illustrative non-limiting example in which there can be a one-to-one correspondence between the individual optical collimators 3416 and the individual LEDs 3414, such that each individual LED 3414 has an associated corresponding optical collimator 3416 in its optical emission pathway to collimate the light being emitted from that corresponding individual LED 3414.

The optical transmitter 3406 can also include one or more wavelength-selective optical filters 3418. For example, optical filters 3418 can be located in one or more of the respective optical pathways of the individual LEDs, such as downstream from individual corresponding collimators 3416 associated with the corresponding individual LEDs 3414. The optical filter 3418 can be configured to limit a corresponding spectral bandwidth of the respective LED output illuminations from the corresponding LED 3414, such as before or after collimation using a corresponding collimator 3416. FIG. 34B shows an illustrative example in which there can be a one-to-one correspondence between the individual optical filters 3416 and the individual LEDs 3414, such that each individual LED 3414 has an associated corresponding optical filter 3418 in its optical emission pathway to filter the light being emitted from that corresponding individual LED 3414, either before or after collimation by a corresponding collimator 3416.

In FIG. 34B, the LEDs 3414 can be arranged in a plane, such as to form a two-dimensional (2D) array of LEDs 3414. The processor or controller 3410 can issue control signals to control energizing the individual LEDs 3414, such as to permit individualized control of light emitted from the respective individual LEDs 3414. Downstream collimation optics, such as a 2D array of corresponding collimating lenses, parabolic or other collimating reflectors, or other collimators 3416, can be included in the respective optical emission pathways of the LEDs 3414. The collimated light from the LEDs 3414, as modified by the collimators 3416, can be directed to one or more optical filters 3418, such as a 2D array of corresponding optical filters that can respectively be located in the optical emission pathways of the individual corresponding LEDs 3414, such as downstream of the respective collimators 3416, such as shown in the example of FIG. 34B. In this manner, an individual LED 3414 can have its emission spectrum restricted to the transmission band of the corresponding optical filter 3418. Although the example of FIG. 34B shows a one-to-one correspondence between optical filters 3418 and LEDs 3414, this is not required. At certain wavelengths, it may be possible to provide an LED 3414 having a narrow enough emission spectrum that the corresponding downstream optical filter 3418 can be omitted for that particular individual LED 3414, while for other LEDs 3414 emitting light at other wavelengths, such a downstream optical filter 3418 may be useful to narrow the emission spectrum of a particular individual LED 3414.

For example, each of the LEDs 3414 can include broadband white LEDs 3414, and different ones of the corresponding optical filters 3418 can be configured to transmit different portions of the LED spectra such as to provide different colored light that can be output from the respective optical filters 3418, depending which particular LED 3414 is turned on. These filtered light sources can be directly presented for illumination of the target object 3404, such as for spectral measurement of response light from the target object 3404, or the filtered light can first be diffused by optional optical diffuser 3420 such as for more wavelength homogeneous illumination or projection toward the target object 3404.

An optional reference photodetector 3425 can be included, such as to provide a measurable indication of the outgoing light intensity (or an indication of a change or variability in such intensity) for each of the individual LEDs 3414. This reference photodetector 3425 can be optically coupled to the diffuser 3420, or otherwise located within the optical transmitter module 3406 such as to allow sampling of the output light downstream from each of the LEDs 3414. In this way, the arrangement in the example of FIG. 34B can provide an extremely compact light source optical transmitter module 3406 with different colored light being emitted with well-defined spectral characteristics and, optionally, an indication measured output light intensity from the photodetector 3425. This indication of measured output light intensity provided by the optional reference photodetector 3425 can be used to eliminate or compensate for output illumination light signal strength variability, such as over temperature, LED bias current, and from part-to-part, and can be determined prior to or without illuminating the target object 3404 or scene, such as to produce an electrical illumination variability indication signal that is independent of the target object 3404 or scene.

As shown in FIG. 34A, the response light from the target object 3404 under test from the illumination light from each of the individual LEDs 3414 (e.g., after one or both of collimation or filtering) can be measured at fixed spectral positions, such as can be determined by the optical filters 3418. If the optional reference photodetector 3425 is included, then the received response light from the target object 3404 can be normalized to a reference value, such as to provide a differential measurement. In an example, such a differential measurement can be obtained by the response light intensity being "divided" by the intensity output of the reference photodetector 3425 for each of the spectral components. This can help to provide a stable measurement of the spectral response from the target object 3404 to the illumination light from the individual LEDs 3414, but independent of variability in the output intensity of the individual LEDs 3414. The spectral response from the target object 3404 can include a measurement of a response parameter such as can include one or more of an absorption, a reflectance, a transmittance, a scattering, or a fluorescence, or the like, such as corresponding to the response detected by the optical detector 3408 from the light emitted by the individual LEDs 3414, after collimation, filtering, or both.

Furthermore, light emitted from corresponding ones of the individual LEDs 3414 can be modulated with time-domain signals, which can be used to separate measured signal response from the target object 3404. The LEDs 3414 can be sequentially energized, or can be provided with orthogonal coding in which multiple ones or even all of the LEDs 3414 can be concurrently energized together. An example of orthogonal code is a sinusoidal modulation with a different frequency for each individual LED 3414. Illustrative examples of illumination light coding are described in Deliwala U.S. Provisional Patent Application No. 63/200,241 entitled CODED LIGHT FOR TARGET IMAGING OR ANALYSIS, filed Feb. 24, 2021, which is incorporated herein by reference in its entirety, including for its description of illumination light coding, and which is bodily incorporated in Section A of this document.

In response to the coded or other illumination by the optical transmitter 3406, the optical signal response from the target object 3404 can be detected by one or more optical detectors 3408, and signal-processed by the processor or controller 3410, such as to analyze one or more spectral response characteristics of the light response signal from the target object 3404. One or more of these optical detectors 3408 may include a single photodetector or may include a pixel array detector or other camera such as which can permit detecting and measuring of the optical response across the target object 3404. The processor or controller 3410 electronics can include stored programmed instructions, such as to help analyze the optical signal response data. This can include making use of, for example, knowing when control signals were issued for energizing one or more or each of the individual LEDs 3414 (e.g., when the individual LEDs 3414 are energized sequentially) or by demodulating the optical response signal associated with individual ones of the LEDs 3414 (e.g., when two or more of the individual LEDs 3414 are energized concurrently) based on the coding associated with the individual LEDs 3414. Each of these techniques may have advantages or limitations, such that the use of a particular technique may depend upon the application, various applications of which are described or incorporated in this document.

FIGS. 35A, 35B, and 35C show illustrative examples of an arrangement of components and accompanying illustrative ray traces of an optical transmitter 3406 of a practical system 3400. The system 3400 can include an arrangement of a 2D array of LEDs 3414 (e.g., nine LEDs 3414 are shown in the perspective view of FIG. 35B and in the side view of FIG. 35A), an array of downstream corresponding lens (or other) collimators 3416 in the respective optical emission pathways of the corresponding LEDs 3414, and an array of downstream corresponding optical filters 3418 in the respective optical emission pathways of the corresponding LEDs 3414, either before or after collimation.

FIG. 35A also shows an array of corresponding optical baffles 3502 such as which can laterally surround each LED 3414. The baffles 3502 can provide a scaffolding or other mounting structure, such as for mounting the LEDs 3414, for mounting the collimating lenses or other collimators 3416, or for helping shield and inhibit or prevent stray light being emitted from an individual LED 3414 from entering the collimating lens 3416 of an adjacent LED 3414, which could otherwise create stray light rays and lots of unwanted light scatter. FIGS. 35A, 35B, and 35C can be extended to many more LEDs 3414 and wavelengths. The diagrams in FIGS. 35A, 35B, and 35C are shown to scale, in millimeters, such as can help to illustrate the compactness of the solution shown.

One or more of the optical filters 3418 can include, for example, a diffractive grating or other diffractive structure or a thin-film optical filter. The optical filter 3418 can be included to narrow the light emission bandwidth of one or more of the LEDs 3414. Such optical filtering can help to provide a well-defined light emission spectrum from a particular one of the individual LEDs 3414—even in the presence of a variable actual emission spectrum of light emitted from that particular LED 3414.

Figures 35D, 35E:
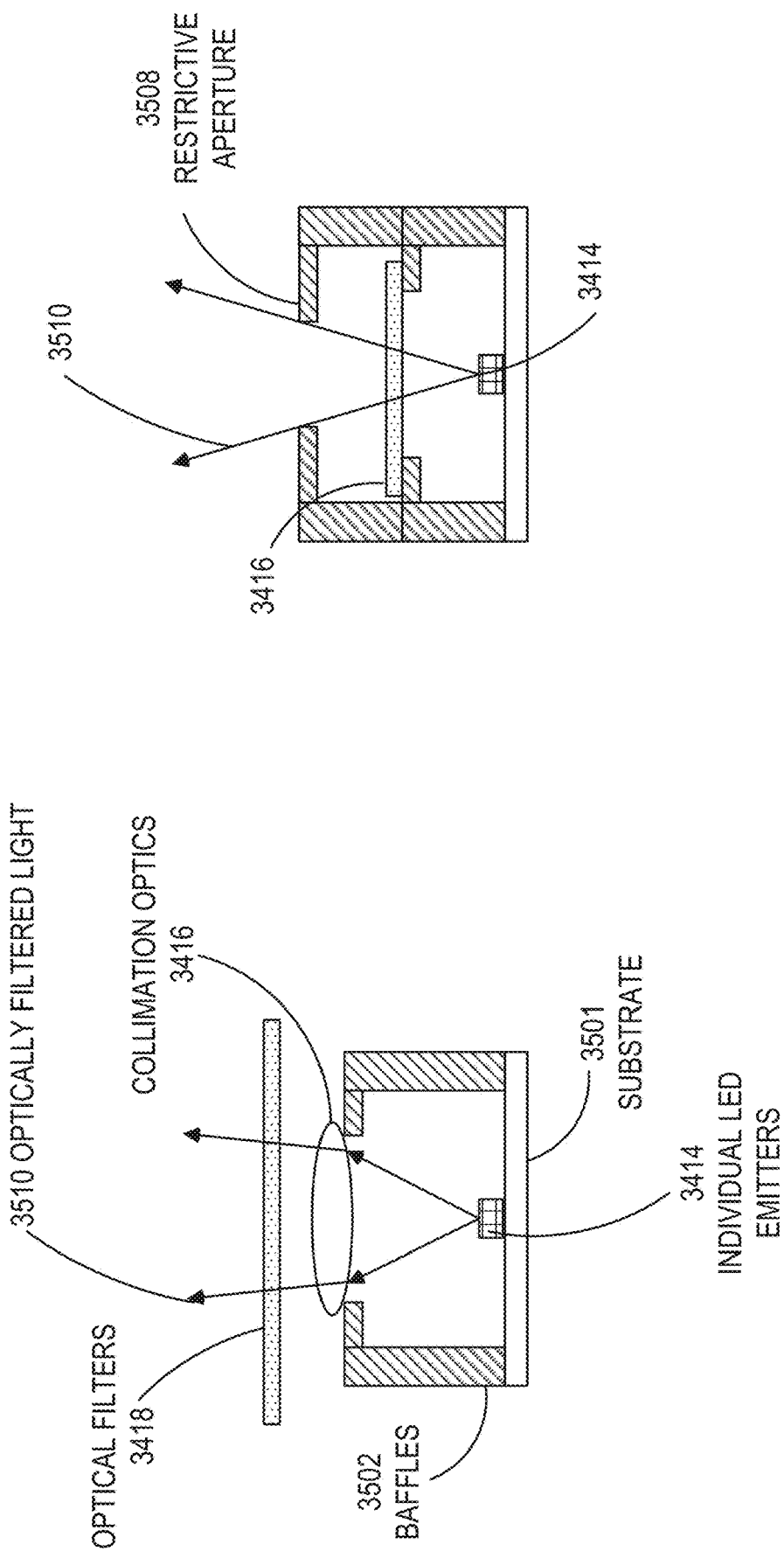
FIG. 35D shows an example of an optical emission pathway for one of the LEDs.
FIG. 35E shows an example of a cost-reduced optical pathway, such as compared to the example of FIG. 35D.
Figure 36:
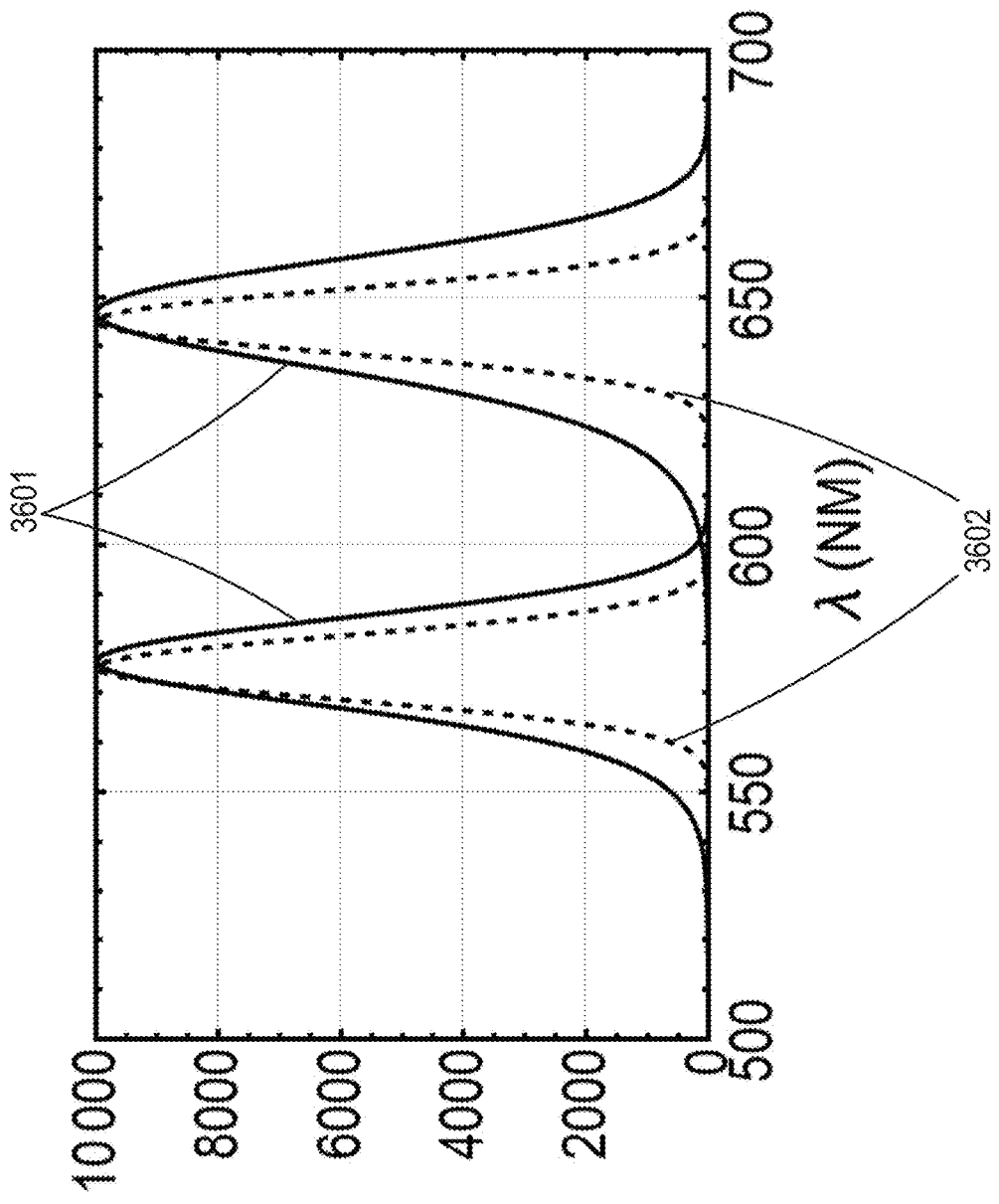
FIG. 36 illustrates an example of spectral bandwidth limiting or narrowing, such as by an optical filter or other illumination wavelength spectral distribution width limiter through which the optical emission spectrum of light emitted from an LED is routed or directed via.

FIG. 36 illustrates an example of spectral bandwidth narrowing by an optical filter 3418 of the optical emission spectrum of light emitted from an LED 3414. FIG. 36 shows light emission spectra 3601 from two different colored LEDs, and corresponding filtered light emission spectra 3602 after filtering by a corresponding optical filter in the downstream optical pathway from such respective individual LEDs 3414. For effective optical filtering by the optical filter 3418 to narrow the spectral bandwidth of the LED 3414 further, such as to a wavelength that is within a wavelength range of between 5 nanometers and 20 nanometers, light from the LED 3414 should be collimated by the collimator 3416. Such pre-filtering collimation can be helpful because spectral transmission or reflection of all types of optical filters 3418 will be sensitive to the incident angles of light upon the optical filter 3418. Collimation can help keep the incidence angles of the light being provided to the optical filter 3418 to an incidence angle that can be below 15 degrees to 20 degrees. This, in turn, can be helpful to providing such a sufficiently narrow optical filter spectral bandwidth, such as within a wavelength range of between 5 nanometers and 20 nanometers. In general, the narrower the optical bandwidth desired from the optical filter 3418, the narrower the range of incidence angles should be, such that better collimation becomes more desirable. Furthermore, to achieve high power efficiency, the collimators 3416 can collimate light from the LED 3414 using a collimating lens or a parabolic or other collimating reflector with a high numerical aperture (NA) before such collimated light is incident upon the optical filter 3418, such as shown in the FIGS. 35A, 35B, 35C or FIG. 37. The system 3400, such as shown in FIGS. 34A and 34B, provides an example that can help obtain the desired illumination spectrum, operation of the optical filters 3418, and the efficient collection of the light from the LEDs 3414.

FIG. 35C shows an example in which the optional optical diffuser 3420 can be included, and the resulting ray traces.

As explained above, it can be advantageous to collimate the light to lower the incidence angle of light being input to the optical filters 3418, and thereby increase the efficiency before optical filtering. This can be helpful even when using a diffractive structure, such as described elsewhere herein. Still, in some cases there may be sufficient LED emission illumination power available to permit avoiding including the collimating optics 3416, which can help to reduce the cost of making the device 3402.

FIG. 35D shows an example of an optical emission pathway for one of the LEDs 3414, such as described above, and FIG. 35E shows an example of a cost-reduced path, such as compared to the example of FIG. 35D.

In FIG. 35D, the optical pathway 3501 associated with an individual one of the LEDs 3414 is shown. The individual one of the LEDs 3414 can be mounted upon a printed circuit board (PCB), a package, or other substrate 3502. A corresponding opaque baffle 3504 can laterally surround the individual LED 3414. The baffle 3504 can constrain light emitted from the individual LED 3414 to be directed, such as via an aperture in the baffle 3504, to a respective collimator 3416. The light emitted from the individual LED 3414 can be collimated by the corresponding individual collimator 3416, such as to project collimated light and a more controlled (e.g., reduced range) of angle of incidence upon a respective optical filter 3418 corresponding to the individual LED 3414 and the individual collimator 3416. As explained, the optical filter 3418 can reduce or control the spectral bandwidth of light emitted by the individual LED 3414 and collimated by the individual collimator 3416. Such reduced or controlled spectral bandwidth light can be output from the optical filter 3418, such as for illuminating a target object 3404 for spectroscopic analysis of response light from the target object 34104. Optionally, such reduced or controlled spectral bandwidth illumination light can be modulated or encoded, such as using an individualized coding function, before illumination of the target object 3404, such as described or incorporated herein.

FIG. 35E shows an example of an optical pathway 3506 associated with an individual one of the LEDs. In the example of FIG. 2E, the collimation optics 3416 can optionally be omitted, such as to help save manufacturing costs. A restrictive aperture 3508 can be included in the optical pathway 3506, downstream of the optical filter 3418, such as by extending the baffle 3504 beyond the optical filter 3418. The restrictive aperture 3508 can extend inward from the extended portion of the baffle 3504. The restrictive aperture 3508 can be sized and shaped and located at a specified distance beyond the optical filter 3418, such as to provide an opening to permit only optically filtered light rays 3510 that subtend angles within a specified narrow cone to be emitted for downstream illumination beyond the baffle 3504. This, in effect, can restrict the filtered illumination light output to light rays that have been optically filtered in a specified manner such as to help provide a stable wavelength illumination light output in spite of wavelength variation of light emitted by the individual LED 3414. Thus, in the example of FIG. 35E, both optical filtering and adequate collimation can be achieved without requiring focusing collimation optics 3416, such as a lens or parabolic reflector. This can help reduce or manage the cost of making the device 3402.

Figure 37:
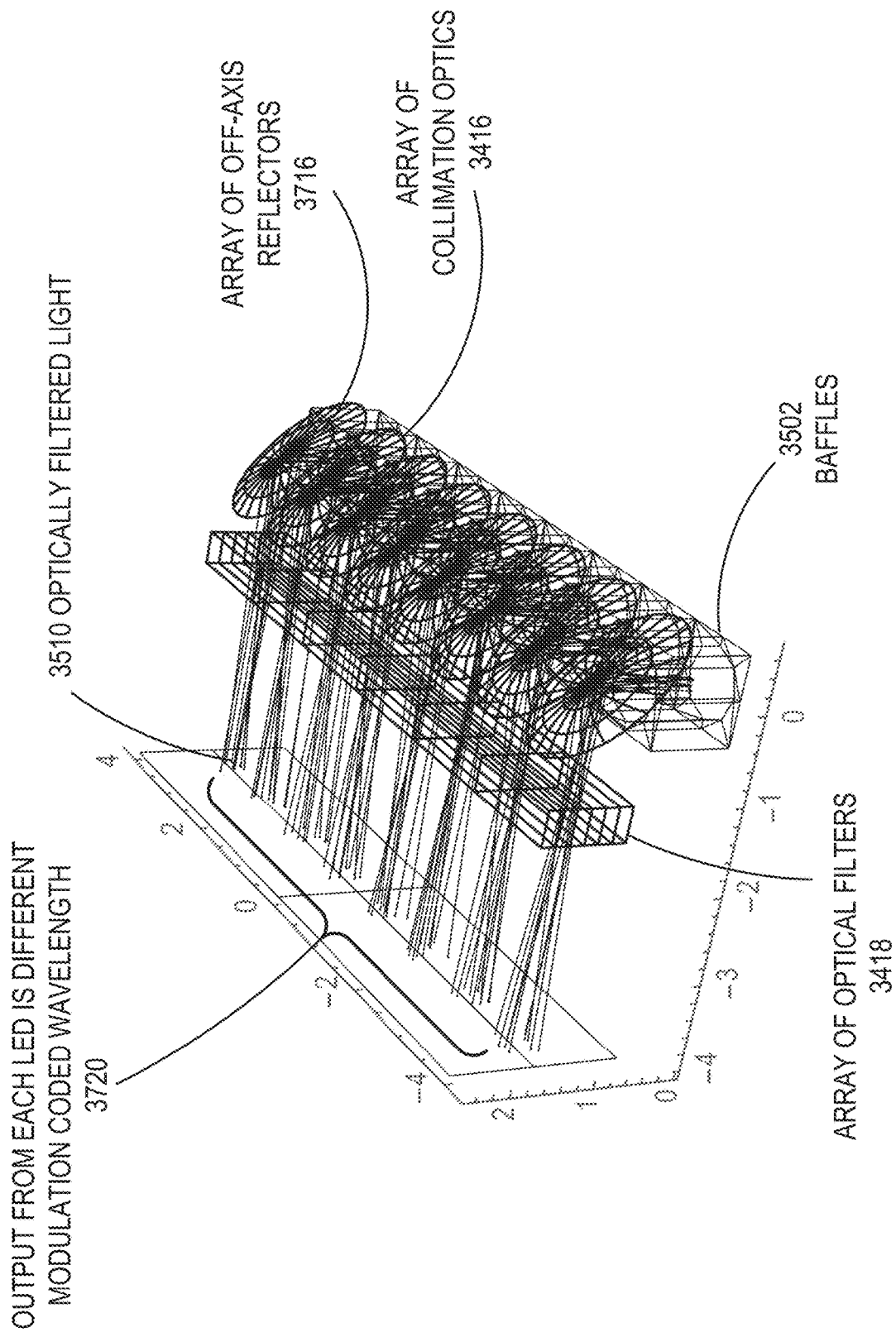
FIG. 37 shows an illustrative example of an optical transmitter of a practical system, such as which can leverage respective reflectors in the corresponding individual optical pathways.

FIG. 37 shows an illustrative example of an optical transmitter 3406 of a practical system 3400, such as which can leverage reflectors in the individual optical pathways. In the example of FIG. 37, a one-dimensional (1D) row of individual LEDs 3414 can be mounted to a PCB or other substrate 3502. Corresponding individual baffles 3504 can be provided, such as in a similar manner as described above, to constrain the light emitted by the individual LEDs 3414 in an individualized manner. The light rays emitted from the individual LEDs 3414 can be individually collimated by off-axis parabolic reflectors 3716. In such an off-axis arrangement, light emitted from an individual LED 3414 can be received as an input by the corresponding off-axis parabolic reflector 3716 and resulting reflected collimated output light can be provided at a 90 degree angle thereto. This can help provide a compact arrangement that can be useful, in certain applications. The reflectors 3716 can be made precisely, such as by metalizing an inner surface of a molded plastic to provide light reflectivity. The individual collimated reflected beams can be transmitted at a 90 degree angle from the input direction to respective optical filters 3418 in a row or other array of individual optical filters 3418. As explained above, the optical filters 3418 can help provide spectral selection and stability, and can optionally be omitted, such as if a stable narrowband LED 3414 can be cost-effectively manufactured and used in the device 3402. Such an arrangement of the optical transmitter 3406 can be quite thin, and the making of such reflectors 3716 can leverage the precision available in molded plastics.

Figure 38B:
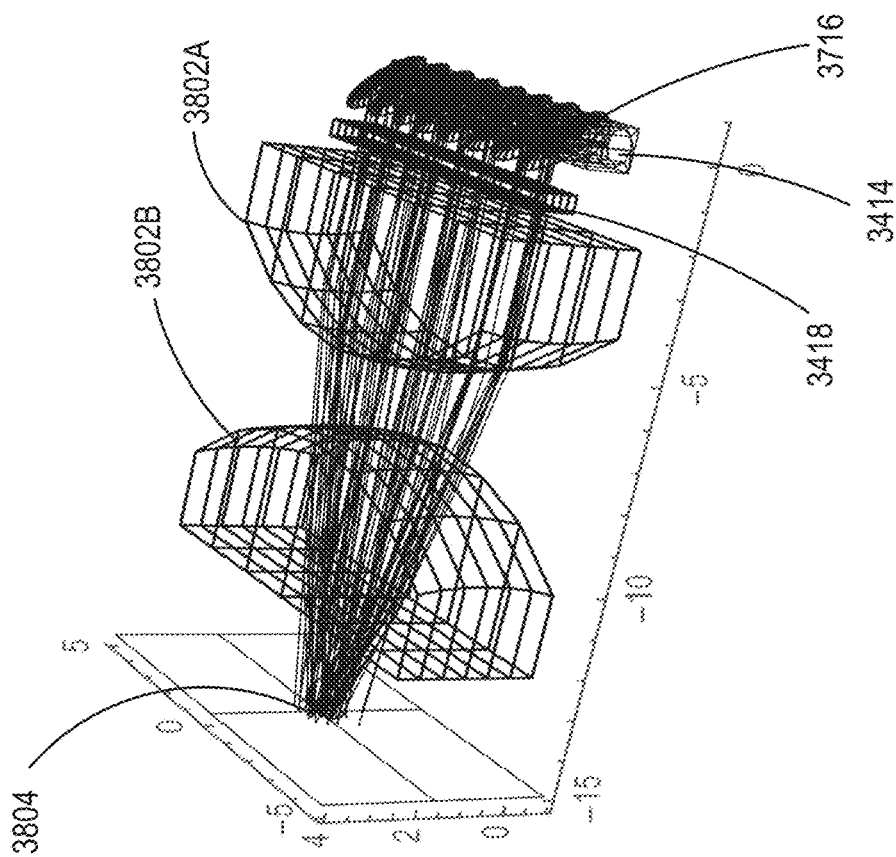
FIGS. 38A (top view) and 38B (perspective view) show further optional componentry that can be included with the arrangement shown in FIG. 37.
Figure 38A:
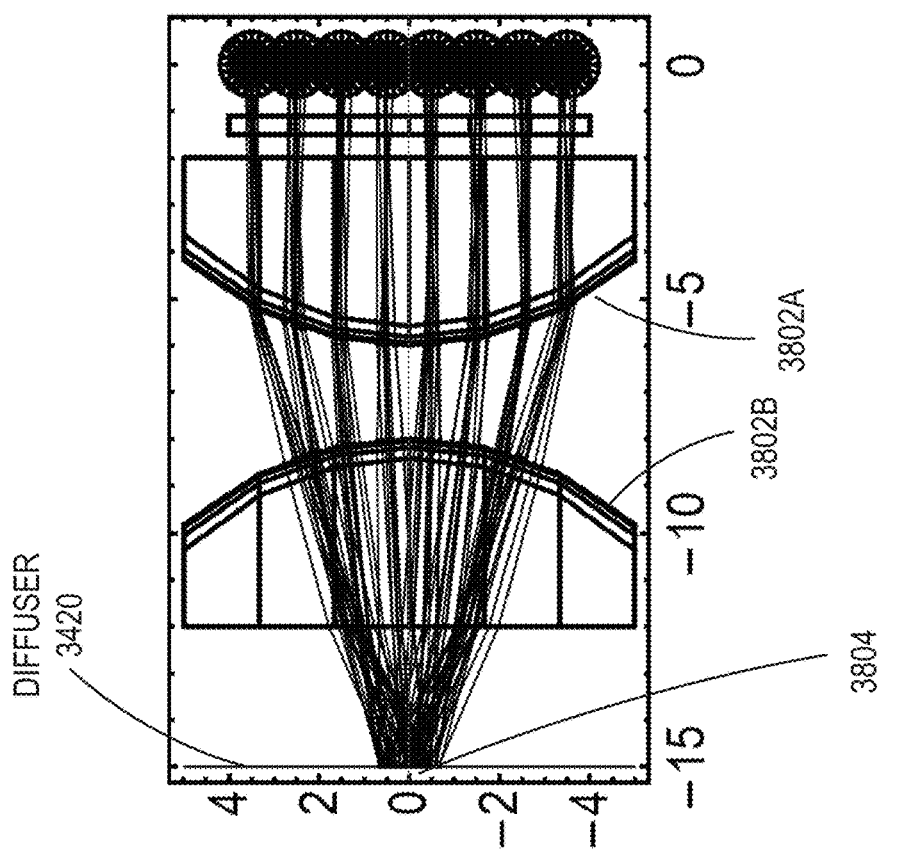

FIGS. 38A (top view) and 38B (perspective view) show further optional componentry that can be included with the arrangement shown in FIG. 37. In the further examples shown in FIGS. 38A, 38B, additional lenses 3802 can be included. For example, a pair of lenses L2 (3802A) and L1 (3802B) can serve to provide a shared exit location 3804 for illumination at which all the various spectral beams output by the individual optical filters 3418 can be combined and then diffused for subsequent illumination of a target object 3404. This may help improve the performance in some applications that can benefit from a highly homogeneous illumination light source for illuminating the target object 3404. For example, as explained herein, this can be helpful in spectrometric studying of complex tissue scattering and in improving measurement performance in an application that can benefit from all the spectral components being provided at the same exit location for illuminating the target object 3404.

Figure 39:
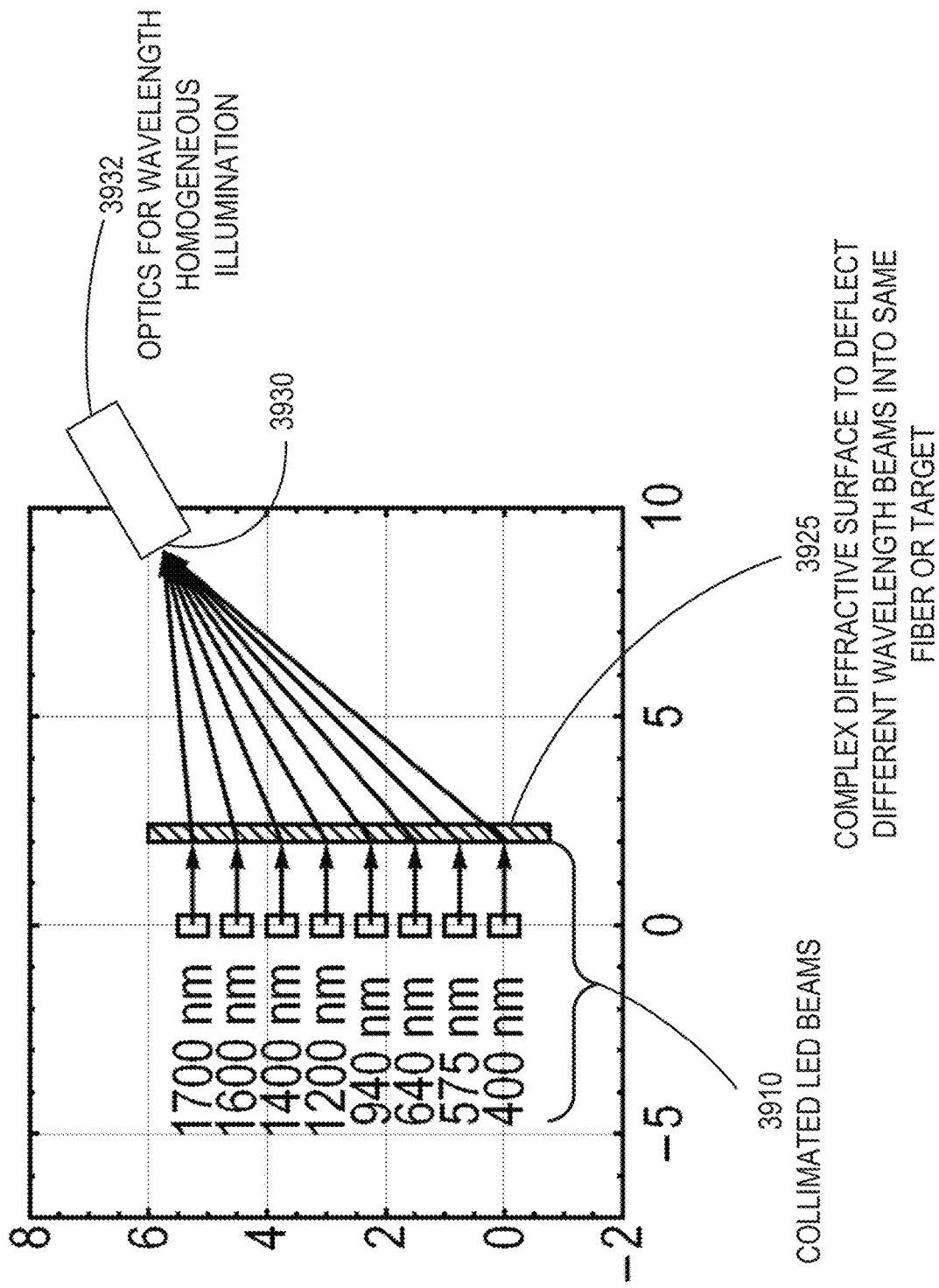
FIG. 39 is an example of an optical transmitter arrangement that can include diffractive componentry.

FIG. 39 is an example of an optical transmitter 3406 arrangement that can include diffractive componentry, such as to allow use of multiple individual LEDs 3414 respectively emitting light at different wavelengths that can span a wide wavelength range. The wavelengths shown in FIG. 39 are intended to serve as an illustrative example of a possible choice of wavelengths. The actual choice of wavelengths, as well as number of LEDs 3414, may depend on the particular application. In the example of FIG. 39, light emitted from individual LEDs 3414 can be individually collimated, such as by using an arrangement of corresponding individual lens or reflector collimation optics 3416, such as described elsewhere herein. The resulting collimated light can be provided to a variable grating or other diffractive element 3925 such as can be arranged to diffract each of the respective input light beams, received at respective input locations at respective different light wavelengths, towards a common shared location 3930 at which all of the different wavelengths of light can come together at a single spatial point or location 3930. An optical fiber bundle 3932, or homogenization optics such as a diffuser, can be placed with its input at 3930 to receive the light from the variable diffractive element 3925 and to provide a resulting homogenized beam of light such as for illuminating the target object 3404.

By placing a spatial filter close to the location 3930, one can provide spectral filtering functionality of the thin film or other optical filter 3418 of FIG. 34. In FIG. 39, the complex variable diffractive element 3925 can be configured to operate to collimate the light from the individual LED 3414 and redirect it to the location 3930. The variable grating diffractive element 3925 can be configured to receive light inputs generated from an array of LEDs 3414, with each individual LED 3414 emitting illumination light at a different wavelength The variable diffractive element 3925 can redirect light with an appropriate set of wavelengths from each LED 3414 toward the location 3930. Different wavelengths from the respective spectrums of each of the individual LEDs 3414 would generally reach the location 3930 with different spatial profiles, because of the dispersive nature of the surface of the diffractive element 3925. Thus, the spatial filter of the diffractive element 3925 can act as spectral filter for each of the LEDs 3414. Thus a single diffractive element 3925 can be configured to serve as both collimation optics 3416 and spectral optical filter 3418. In some cases, the position and the numerical aperture of an optical fiber placed at location 3930 can act as spatial filter and thus as spectral filter further simplifying the construction. The complex variable diffractive element 3925 may include sub-wavelength structures, or may be made using geometrical phase optics. It should be noted that the example of FIG. 39 can be extended as two dimensional (2D) array of diffractive elements 3925, such as to serve as the optical filter 3418 of FIGS. 34A, 34B and in various other examples, such as for wavelength filtering and spatially combining all of the various individual light beams to a common location 3930.

The various examples described herein, including the arrangement of FIG. 39 can be compact, can have well-defined light emission spectra, and the individual output optical spectrum of 5-20 nm (narrower than the intrinsic emission spectra of the corresponding individual LED 3414) can be stabilized, such as by adding diffractive or thin film optical filter structures. These examples can help enable high-volume manufacturing, can accommodate componentry placement errors such as in the mounting locations of the individual LEDs 3414, and can provide suitably manageable lens and optical filter implementations.

Figure 40A:
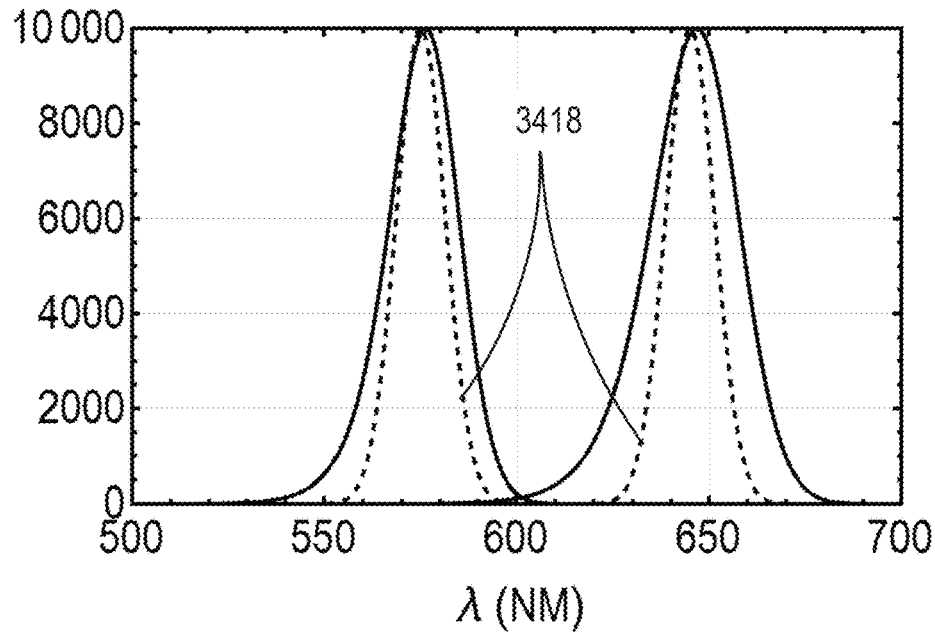
FIG. 40A shows a graph of light intensity vs. wavelength, such as illustrated for two LEDs.
Figure 40B:
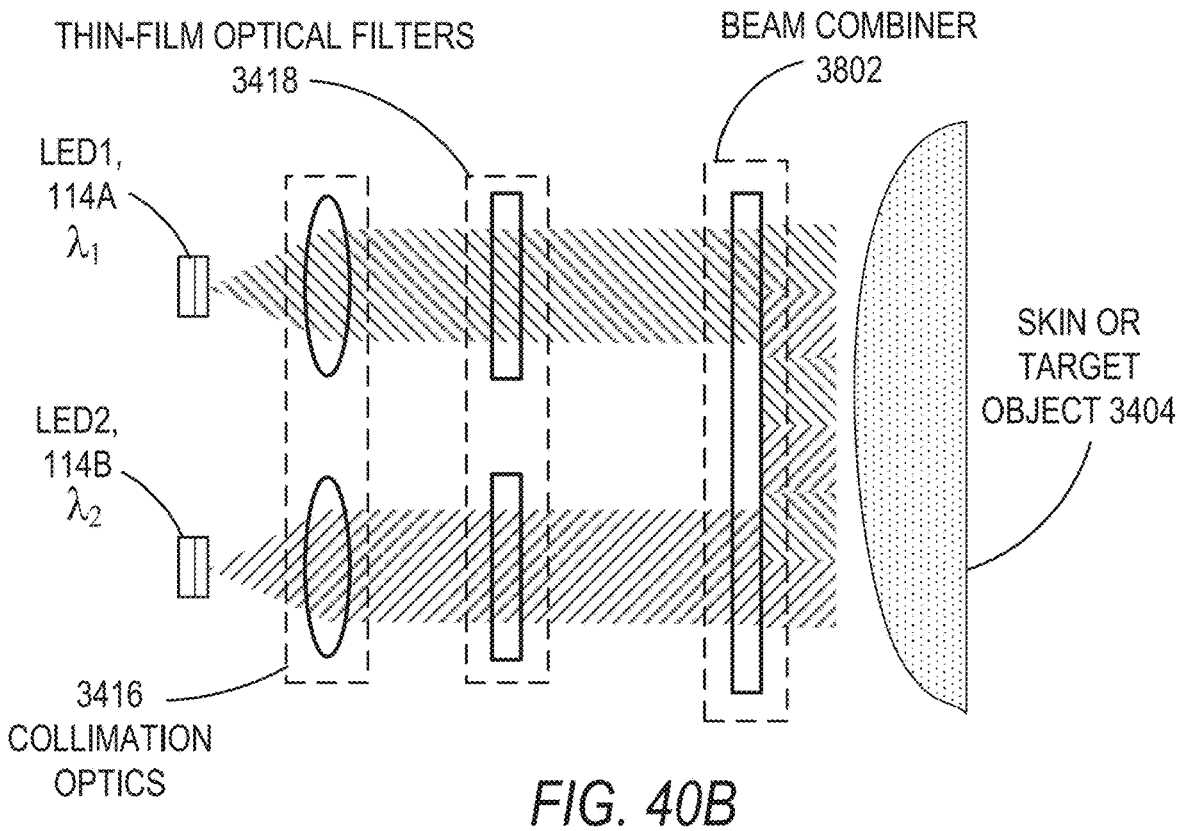
FIG. 40B shows a schematic example of portions of an optical transmitter module such as can include multiple LEDs.
Figure 40C:
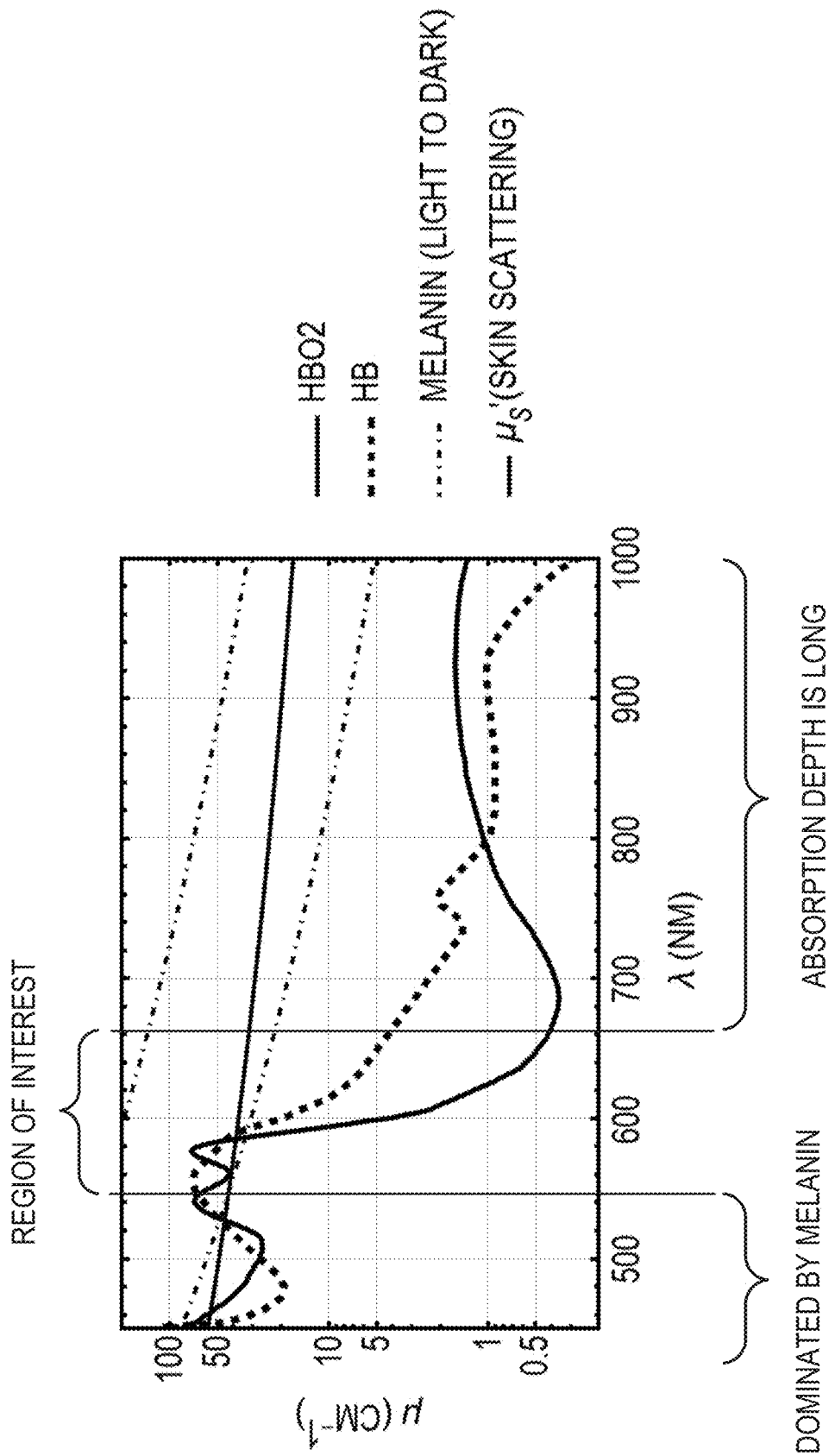
FIG. 40C is a computer-simulated example of a graph of light absorption μ (in cm-1) vs light wavelength λ (in nanometers).

FIGS. 40A, 40B, and 40C show an example of an optical construction and wavelength filtering operation of the optical transmitter module 3406. For clarity only two LEDs 3414 are shown, the optical transmitter module 3406 can be configured similarly to use more than two LEDs. FIG. 40B shows an example in which the light from each of the LEDs 3414 can be collimated, such as using collimation optics 3416, and directed at the optical filters 3418 that can provide the wavelength filtering surface (e.g., which can include a thin film filter, or a diffractive surface). This filtering operation is depicted for each of the LED spectra in FIG. 40A. After filtering, the filtered light can be projected onto a skin or diffuse scattering surface or other target object 3404 to be measured. FIG. 40C shows a specific use-case in which the sample is human tissue, and the application is to detect blood oxygenation. For each specific use case, a similar spectra can be obtained and can be analyzed to identify the spectrally relevant regions and filtering operation.

The examples of FIGS. 40A, 40B, and 40C can include using one or more of geometric phase optical elements, metasurface optical elements, or diffractive/sub-diffractive optical elements, such as to achieve one or both of (1) collimation or other focusing or (2) optical wavelength filtering. These two functions (e.g., focusing and optical wavelength filtering) need not require separate components to provide such functions. In an example, these two functions can be provided by shared componentry that can provide both such functions. For example, both focusing and optical wavelength filtering can be combined and provided using "flat optics." The flat optics can include multiple surfaces, such as to provide the combined functionality. In an example, the optical phase and amplitude shaping of light passed via the flat optic can be changed across the flat optic element, such as to select for different wavelengths across a broad swath of wavelengths.

FIG. 40A shows a graph of light intensity vs. wavelength, such as for two LEDs (e.g. such as at a first wavelength of about 575 nanometers, shown in yellow, and a second wavelength of around 640 nanometers, shown in red in FIG. 40A). Light from each such LED can be passed through an optical filter, such as to spectrally bandpass filter the light from each individual LED, such as by an optical filter having a Full Width at Half Maximum (FWHM) bandwidth of 15 nanometers. In this way, a corresponding downstream optical filter can be used to suppress variability in the light emission spectrum of an individual LED. Such variability in the light emission spectrum of an individual LED can be a function of one or more of: manufacturing batch of the LED, operating temperature of the LED, or bias current of the LED. Such variability in the light emission spectrum of an individual LED can be translated, by the optical filter, into effective filter efficiency of light output by the optical filter with respect to light input into the optical filter. Although it may be possible to use an LED having a narrow bandwidth light emission spectrum, such narrow bandwidth light emission spectrum LEDs can be less efficient and can exhibit greater manufacturing batch-to-batch variability, such as in its ratio of center wavelength to change in wavelength (e.g., 2%/ΔΔ) due to one or more factors such as mentioned above. Thus, FIG. 40A illustrates an example of spectral bandwidth limiting or narrowing, such as by an optical filter or other illumination wavelength spectral distribution width limiter through which the optical emission spectrum of light emitted from an LED is routed or directed via, such as explained above with respect to FIG. 36.

FIG. 40B shows a schematic example of portions of an optical transmitter module 106 such as can include multiple LEDs 3414, such as a first LED, LED 3414A, emitting light at a first wavelength, $\lambda_1$, and a second LED, LED2 114B, emitting light at a second wavelength, $\lambda_2$, which is different than the first wavelength, $\lambda_1$. Corresponding downstream lenses or other collimation optics 3416 can be included to provide collimation focusing of individual beams from the corresponding LEDs 3414, such as before optical filtering, such as can help improve the efficiency of such optical filtering. In FIG. 40B, further downstream, thin film optical filters 3418 can be provided, such as to help provide spectral stability in spite of any variations in LED emission spectrum variations. In FIG. 40B, still further downstream, a beam combiner 3802 can combine the various filtered beams into a consistent shared exit location for illuminating skin or other tissue or other target object 3404 and a common illumination incidence location, such as can help reduce any motion artifacts and can otherwise benefit response detection and analysis, such as explained elsewhere herein. A low profile (e.g., less than 4 millimeters in height) optical transmitter module 3406 can be provided, such as by using appropriate flat optics. This example is scalable to more LEDs or more colors, as desired. FIG. 40C is a computer-simulated example of a graph of light absorption μ (in cm$^{-1}$) vs light wavelength λ (in nanometers). Computer simulation data is shown for the absorption of oxygenated hemoglobin (hbO2), deoxygenated hemoglobin (hb), melanin (light to dark), and skin scattering ($\mu_s'$). FIG. 40C shows a region of interest (ROI) between light wavelengths of about 500 nanometers and about 660 nanometers—at light wavelengths below this ROI, light absorption is dominated by melanin, and at light wavelengths above this ROI, the light absorption depth is long. Within the ROI shown in FIG. 40C, blood oxygenation saturation can be determined, such as using a wrist-worn wearable monitor device, such as described elsewhere herein.

Examples of Modulation Techniques

For a small number (e.g., two or three) of LEDs 3414, it is possible to pulse the individual LEDs 3414 in sequence, and sequentially measure the response of the tissue or other target object 3404. Each individual LED 3414 makes a short but intense illumination pulse, the response to which can be captured from the target object 3404. But as the number of LEDs 3414 increases, this can become more and more problematic. This is because the duty cycle for each individual LED 3414 decreases as individual LEDs are added to the sequence and, therefore, the pulse amplitude will need to increase to maintain the same signal-to-noise ratio (SNR). This may become exceedingly difficult—the peak currents may become large and battery or other electrical limitations may become severe. For example, such large currents become difficult to generate in a battery-powered device such as smartwatch-type wearable monitor, or such large current draws may result in reduced battery life. For tissue measurement and other scattering media, there is large attenuation of the response light. This is similar to the case of weak signals in Raman or Fluorescence imaging. As explained earlier, combining all the wavelengths of interest by modulation, allows one to overcome limitations of detector and receiver noise and enables to reach target signal to noise ratio with lower signal power and, therefore, lower system power. Furthermore, optical filtering of the LED's source spectra also reduces the total light intensity available from each LED—while improving spectroscopic signature and reproducibility. The modulation technique described herein enables reaching required signal to noise ratio with necessary output response bandwidth and signal power levels.

In such a case, it may be advantageous to keep all of the LEDs 3414 working concurrently, such as at lower-level but continuous illumination. The response of the tissue or other target object 3404 can be separated for each of the different color LEDs 3414, such as by the use of orthogonal codes with which the individual LEDs 3414 can be modulated. Illustrative examples of such modulation encoding are described in Deliwala U.S. Provisional Patent Application No. 63/200,241 entitled CODED LIGHT FOR TARGET IMAGING OR ANALYSIS, filed Feb. 24, 2021, which is incorporated herein by reference in its entirety, including for its description of examples of modulation encoding and decoding techniques, and which is bodily incorporated in Section A of this document.

Application to SpO2 on the Wrist and Other Places on the Human Body

Measuring arterial blood oxygen saturation (SpO2) using pulse oximetry at locations other than through a subject's fingertip can be challenging. The fingertip is a physiologically preferred location due to the bone structure and light illumination and light response detection arrangement. Another physiologically preferred location is the pinna of a subject's ear. But both locations are inconvenient for ongoing, chronic, continuous measurement, such as during exercise or other activities of daily living. A smartwatch or other similar wearable device, such as can include one or more optical photoplethysmography (PPG) sensors, can be more suitable for ongoing, chronic, continuous measurement, but the wrist is a physiologically more challenging location from which to make SpO2 measurements by just adding Red and IR LEDs, such as used in fingertip pulse oximetry, to carry out SpO2 measurements on the wrist. Smart watches to measure blood oxygen using Red and IR LEDs perform very poorly compared to fingertip pulse oximetry sensors, and are extremely prone to errors due to motion artifact and person-to-person variation in calibration.

With the Covid-19 pandemic, the need for better approaches for continuous ongoing pulse oximetry for measuring SpO2 has become urgent, since the blood oxygen levels can help indicate the severity of the disease. A smartwatch or similar wearable device with accurate and reliable pulse oximetry measurement of SpO2 would be highly desirable and useful. A location such as the wrist is quite challenging—it presents several challenges to be overcome, and it is difficult to overcome all of these challenges together in a single solution. Examples of such challenges can include:

1. The sensor should fit within the smartwatch or a hearing-aid like wearable device and must be quite thin and small;
2. The sensor should be energy efficient as such wearable devices are powered with relatively small battery;
3. The sensor should be compatible with high volume manufacturing, which, for a smartwatch is already around 100 million units per year, and which, if accurate SpO2 and other blood analyte measurement technology is available, may easily reach billions of units per year; and
4. The sensor should work reliably and use principles and techniques that are compatible with tissue optics of the wrist.

These criteria, when taken together, make it exceedingly difficult to produce a suitable solution. But a specifically adapted version of the device shown in FIGS. 34A, 34B can be configured to satisfy all the above criteria together.

As an initial note, the wrist is a vastly different optical environment than the finger. For fingertip oximetry, illumination light from the Red and the IR LEDs must each travel around the central bone in the finger and reach the light detector, which is located on the other side of the finger from the illuminator. This arrangement at the fingertip ensures that the photon propagation paths for both the IR and Red photons are similar. Therefore, it can be assumed that illumination light at both of these illumination wavelengths has experienced a similar passage through the arteries in the finger. The ratio of the photon propagation distances $I_1/I_2$ is quite different for the Red and the IR illumination wavelengths, but the geometry of photon propagation in the finger makes these paths similar. This makes the two-color measurement extremely robust at a fingertip location, enabling successful and robust fingertip pulse oximetry.

These measurement techniques can be extended to using multiple colors for improved measurement of blood gases. A "ratio-of-ratio" (RoR) relationship can be used, such as can be expressed in the following equation, for two different wavelengths of illumination light, $\lambda_1$ and $\lambda_2$.

$$\frac{\left(\frac{AC}{DC}\right)_{\lambda_1}}{\left(\frac{AC}{DC}\right)_{\lambda_2}} =$$

$$RoR = \frac{\epsilon_{art}(\lambda_1)}{\epsilon_{art}(\lambda_2)}\left(\frac{l_1}{l_2}\right) = \frac{\epsilon_{deox}(\lambda_1) + SaO_2(\epsilon_{ox}(\lambda_1) - \epsilon_{deox}(\lambda_1))}{\epsilon_{deox}(\lambda_2) + SaO_2(\epsilon_{ox}(\lambda_2) - \epsilon_{deox}(\lambda_2))}\left(\frac{l_1}{l_2}\right)$$

Such a ratio-of-ratio (RoR) can be used to estimate the arterial oxygen levels. $\epsilon_{art}(\lambda)$ is the light absorption by the arterial blood at different wavelengths, $\lambda$. This, in turn, is related to the relative amount of light absorption by the oxygenated, E ox and deoxygenated, $\epsilon_{deox}$ hemoglobin in the arterial blood. In practice, a fit can be created between the measured RoR and the measured arterial oxygen, such as by inserting an arterial line or by using a calibrated pulse oximeter.

At a location on a subject's wrist, an oximetry sensor inside the smartwatch or similar wearable device necessitates a light response measurement in reflection on the same side of the wrist at which illumination is delivered-which is different than a fingertip arrangement in which illumination can be delivered on one side of the fingertip and tissue-transmitted response light can be detected at the other side of the fingertip. At the wrist location with same-side illumination and measurement, the illumination photon must scatter and "scatter backwards" to reach the light response detector, which can be placed next to the illumination light source. To further complicate matters, tendons and the bones of the wrist are quite close to the surface, and there is a considerable motion of these fibers that can cause random and erratic changes in the photon scattering (and thus in the received response signal) thereby reducing the effective signal-to-noise ratio. To make matters even more challenging, the same two wavelengths of Red and IR illumination light that work in fingertip pulse oximetry will no longer work as well at the wrist location, because these Red and IR wavelengths used for fingertip pulse oximetry have vastly different photon propagation distances, $l_1$ and $l_2$. This means that an assumption in the Ratio-of-Ratio measurement, as carried out for finger-based pulse oximetry, that $$\frac{l_1}{l_2} \sim 1$$

is violated, and there is no guarantee that the ratio will yield a useful answer. Also, this ratio can vary significantly over time for the same person and can also vary substantially from person-to-person due to placement of the smartwatch or other wearable and the complex anatomy of the wrist. These challenges cannot easily be addressed, even using approaches that can involve using a trained machine learning (ML) model to decipher the oxygen saturation at a wrist location. As described herein, using the present approach, wavelengths for which $$\frac{l_1}{l_2} \sim 1$$

can be selected. The present approach can also help ensure that the photon paths are short.

In practice, measurement of RoR can be carried out by measuring the ratio at each illumination light wavelength, such as by measuring AC and DC components of the PPG signal. For such an approach, the DC component should not be corrupted by direct stray reflections from other optics into the response light detector. For example, consider the case of a smartwatch placed on the wrist, such as shown in FIGS. 44A, 44B, and 44C. Uncollimated light from an individual LED 3414 can be quite difficult to keep away from the response light detector 3408 placed nearby-even with all the effort taken to isolate the illumination light from a particular LED 3414 from directly reaching the response light detector 3408, such as by using one or more baffles or barriers 4440. For example, if the skin is moved even by a few millimeters from the smartwatch surface at which illumination light emerges, some illumination light rays from a divergent LED will directly scatter from the surface of the skin (without passing through the underlying tissue) to reach the response light photodetector 3408. This will generate an error in the measurement of the ratio. But collimated illumination light from an LED 3414 will have far less impact on the ratio measurement as the skin moves away from the watch surface at which illumination light emerges. Providing collimated light allows response light photodetectors 3408 to be placed closer to the optical transmitter 3406, which can be advantageous in making a better matched measurement at multiple illumination light wavelengths.

Figure 41A:
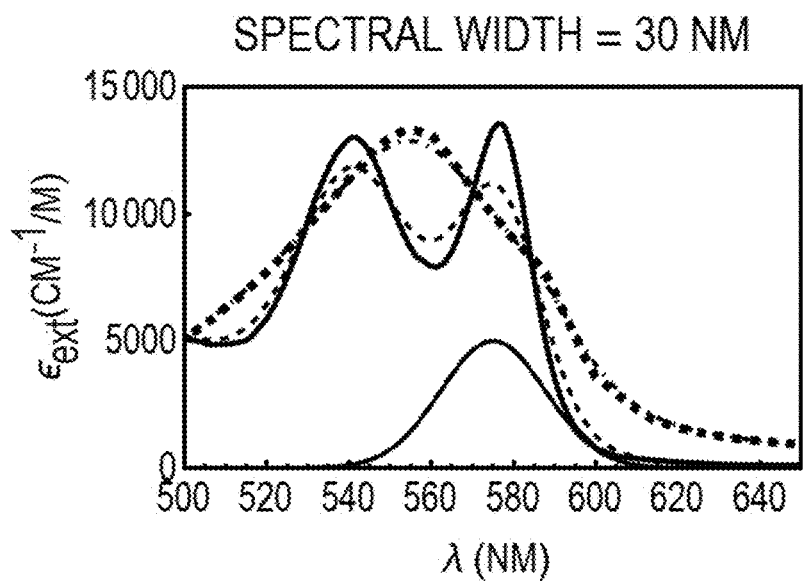
FIGS. 41A, 41B, and 41C are graphs of light absorption vs. light wavelength, showing the spectra of the blood and the effect of spectral averaging on the hemoglobin (Hb) spectra.
Figure 41B:
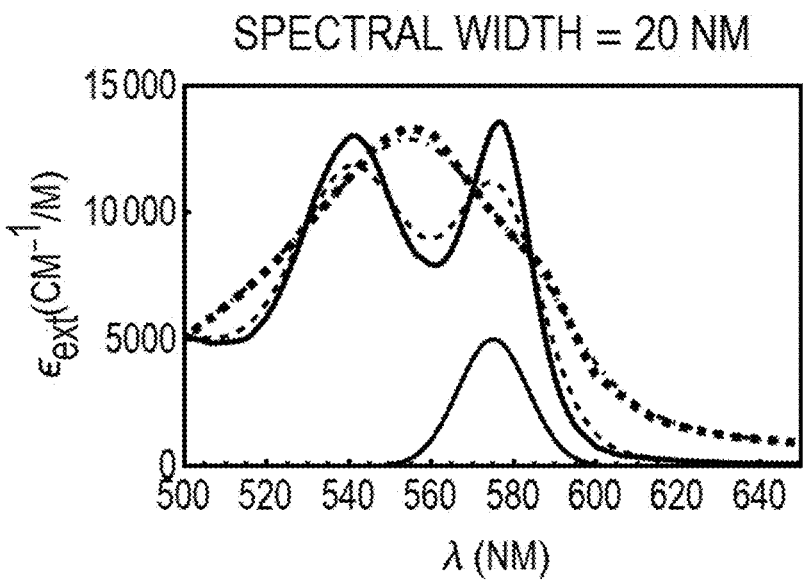
Figure 41C:
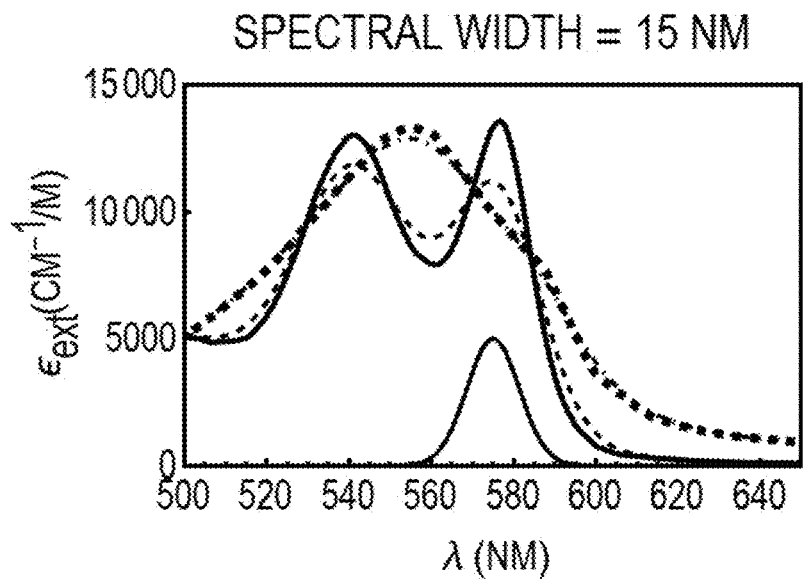

FIGS. 41A, 41B, and 41C are graphs of light absorption vs. light wavelength, showing the spectra of the blood and the effect of spectral averaging on the hemoglobin (Hb) spectra. The present approach can start with the fact the scattering paths of the two illumination light wavelengths should be as identical as possible. Also, the effective absorption lengths of the illumination light should be relatively short, so that photons do not travel too far into the wrist tissue and interact with tendons or other tissue structures that can be subject to movement and that can produce excess noise. A green (e.g., ~ 520 nanometer) colored LED can provide a short effective absorption depth. To determine which illumination wavelength pair is suitable for pulse oximetry on the wrist, several factors can be considered.

1. Using a bluer (or shorter) light wavelength can be advantageous as it has a short travel distance and hemoglobin (Hb) absorption is high—but so is absorption by melanin from dark skin. For very dark-skinned person, melanin would absorb most of the blue light and very little blue light will interact with the arterioles and arteries in the dermis, and even less response light would be available to be measured by the response light photodetector as such response light must make second (return) passage through the melanin layer. Thus, in an approach, we reject illumination wavelengths to the blue of ~ 520 nanometers.
2. The LED spectra are quite broad, e.g., having a spectral bandwidth that can be greater than 25-35 nanometers wide and, in some cases, wider still. But FIG. 41B shows that spectral averaging can make the shape of the oxygenated and deoxygenated Hb curves almost identical. This makes the Ratio-of-Ratio calculation extremely sensitive to noise, because both the species to be differentiated (oxygenated Hb and deoxygenated Hb) have similar spectral shapes. Thus, in an approach, the illumination light spectral bandwidth can be filtered or otherwise narrowed to somewhere less than 20 nanometers, and preferably, to around 15 nanometers in spectral bandwidth. Thus, FIGS. 41A, 41B, and 41C illustrates an example of spectral bandwidth limiting or narrowing, such as by an optical filter or other illumination wavelength spectral distribution width limiter through which the optical emission spectrum of light emitted from an LED is routed or directed via, such as explained above with respect to FIG. 36.
3. While there is a region that works well with broad LED spectra—the Red and the IR wavelengths used in fingertip pulse oximetry, such an approach is rejected as not being a good choice for reflection-based oximetry at a wrist location near tendons and bones, since similar scattering volumes are desired for the two illumination wavelengths selected.
4. A very narrow spectral width can be used, such as can be provided by lasers, such as to use the steep region shown in FIG. 40C between 600 and 650 nanometers. This will work. Detailed calculations that can account for batch-to-batch variability on the laser wavelengths and temperature dependence suggest that this may be quite impractical inside a smartwatch. The ratio-ofratio determination becomes sensitive to the actual laser wavelength, making it difficult to deploy in a consumer product.

Figure 42:
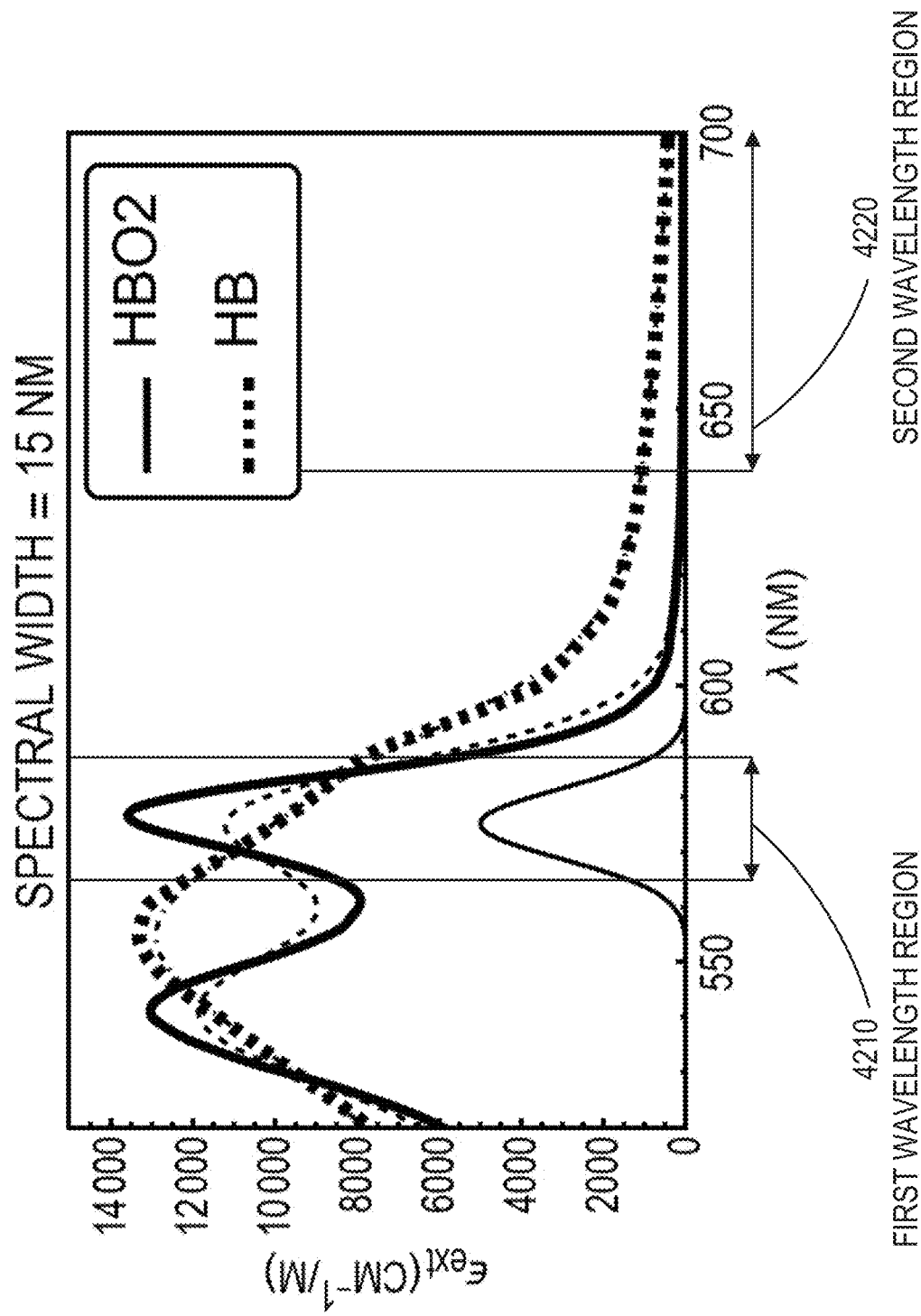
FIG. 42 is a light absorption vs. light wavelength graph that shows an example of two regions from which the two illumination wavelengths of the LEDs may be chosen.

FIG. 42 is a light absorption vs. light wavelength graph that shows an example of two regions from which the two illumination wavelengths of the LEDs 3414 may be chosen: a first wavelength region 4210 and a second wavelength region 4220. For the spectral width of illumination from each individual LED 3414 to be less than 20 nanometers, all the requirements can be met: substantial change in RoR vs $SPO_2$, low expected error with variation in the center wavelength caused by the manufacturing variability and the environment, and short illumination light absorption length in the target tissue. In FIG. 42, the first wavelength region 4210 is in the region between 550 to 590 nanometers (and more preferably between 560 and 580 nanometers). The second wavelength region 4220 is from 630 nanometers and longer, such as up to 950 nanometers, in an example. Computer simulations that include multiple sources of variability suggest that the second wavelength region 4220 being from 630 to 660 nanometers may be preferable. Other potential solutions include the first wavelength region 4210 being in the 510-530 nanometer range and the second wavelength region 4220 being in the 630 nanometers and longer range. In order to match the photon paths inside the tissue, the as second wavelength can be selected to be within the second wavelength range 4220 to be as near in wavelength to 630 nanometers as possible.

It is possible to eliminate certain steps and components in the construction of the optical transmitter 3406, such as to help reduce cost. For example, one may collimate illumination light emitted from the individual LEDs 3414 and not use any optical filters 3418, such as when the corresponding emission spectra of the individual LEDs 3414 themselves are sufficiently narrow. Such collimation without optical filtering will still provide improved matching of optical paths inside the tissue and robustness to measurement of ratio, such as described herein.

Figures 43A, 43B, 43C:
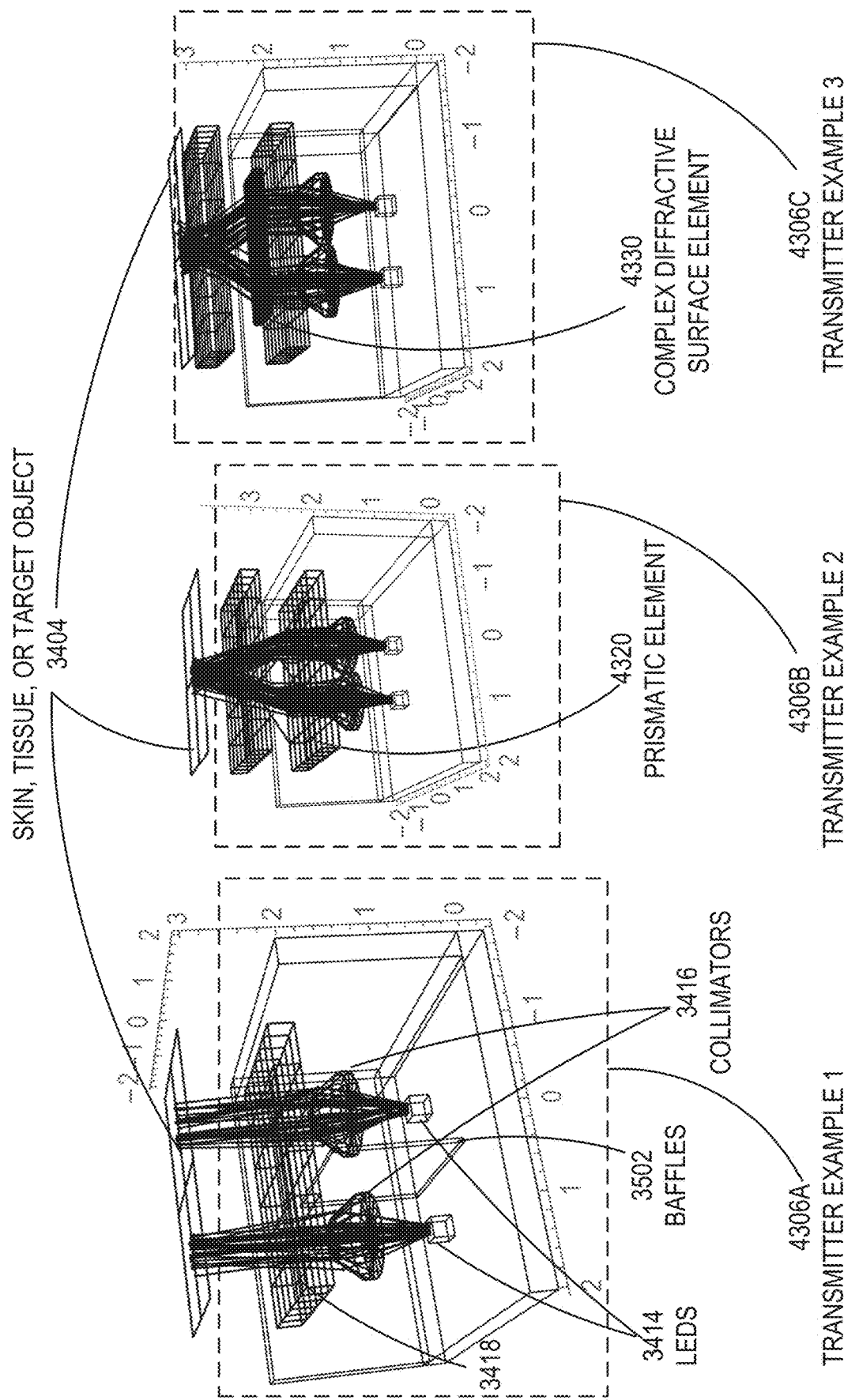
FIGS. 43A, 43B, and 43C show examples of three optical transmitter configurations for use in oximetry, such as in a wrist-worn wearable device.

FIGS. 43A, 43B, and 43C show examples of three optical transmitter 4306 configurations for use in oximetry, such as in a wrist-worn wearable device. FIG. 43A shows Example 1 of an optical transmitter 4306A that is similar to that described in FIGS. 35A, 35B, and 35C. FIG. 43B shows Example 2 of an optical transmitter 4306B that can include a prismatic surface 4320 such as to bend an output light beam to a common shared illumination exit location for illumination of a target object 3404 such as tissue for reflective-mode pulse oximetry such as using a wrist-worn wearable device. FIG. 43C shows Example 3 of an optical transmitter 4306C that can include a diffractive grating surface 4330 such as to bend an output light beam to a common shared illumination exit location for illumination of a target object 3404 such as tissue for reflective-mode pulse oximetry such as using a wrist-worn wearable device. The single point of entry at a common shared illumination exit provides that the photon paths for the two illumination light wavelengths experience as similar an environment as possible as they enter and scatter inside the complex physiological anatomy of the wrist or other tissue target object 3404.

FIGS. 44A, 44B, and 44C show various views of an example of a configuration in which an optical transmitter module 3406, 3306 can be included on the back of a smartwatch 4410 or similar wrist-worn or other wearable device such as an arm or chest strap or patch. The optical transmitter module 3406, 3306 may be accompanied on the back of the smartwatch 4410 by surrounding by response light detector photodiodes 3408, such as can be placed separately as part of the assembly of the smartwatch 4410 or the optical transmitter module 3406, 3306 itself may include response light detecting photodiodes 3418 and analog and digital processor or controller electronics 3410, such as an integrated module. The configuration of the optical transmitter 3406, 3306 may take any of the forms shown in FIG. 43A, 43B, or 43C, and may be extended to include other LEDs 3414 such as can respective provide other illumination light colors, which may or may not be optically filtered, such as explained elsewhere herein.

While these examples emphasize using two LEDs 3414 for measuring $SpO_2$ for clarity, more than two colors may be used and the module shown in FIGS. 44A-44C extended as needed. The problem of measuring $SpO_2$ on the chest or arm is similarly challenging, for some reasons that are similar to those involving the wrist, as well as for other reasons that are specific to the chest or arm. For example, at a chest location, a close proximity to the beating heart and the fact that arteries and veins are generally in close proximity to each other generates a pulsatile "cardiac stroke" component in both arteries and veins in the chest cavity. This makes determining $SpO_2$ quite difficult and the certain RoR algorithms may measure some weighted average of venous and arterial blood oxygen. One approach can be to combine data from LED light illuminated at wavelengths of 780/940 nanometers to determine and separate arterial and venous oxygenation. This is because the impact of the nearby beating heart on different arterioles and arteries as well as veins will be different due to its location with respect to the heart as well as the depth at which photons interact with the blood. These different wavelength-dependent effects, can be combined with anatomical insights at the application site, such as to provide blood oxygen levels from a device 3402 that can be located on the chest Examples of Measurement of Other Molecules The techniques described herein can be extended to spectroscopic measurement of other molecules or materials. For example, glucose may be monitored or measured similarly using a wearable device, such as by using infrared individual LEDs 3414 that can provide illumination at different illumination light colors that can span the absorption wavelength spectrum of glucose, such as in the 1500 nanometers to 2500 nanometers region. In another example, blood alcohol may be monitored or measured using individual LEDs 3414 that can provide illumination light wavelengths sensitive to the alcohol wavelength spectrum, such as in the wavelength region around 1200 nanometers. In an example, multiple individual LEDs 3414 can be placed in an optical transmitter module 3406, 3306, some of which can be used for oximetry to monitor or measure $SpO_2$, some of which can be used for blood alcohol spectroscopic measurement or monitoring, and some of which can be used for glucose measurement or monitoring, for example. This can include, for example, LEDs 3414 and/or corresponding optional optical filters 3418 that can be configured for measurement of $SpO_2$, a few wavelengths around 1200 nm for blood alcohol, and a few more between 1500 and 1900 nm for blood glucose. A sub-group of particular ones of the individual LEDs 3414 can be sequentially or concurrently energized and used for a particular analyte measurement, as appropriate. Thus, not all the measurements for each of the target chemical compounds need to be carried out concurrently.

In some cases, the processor or controller 3410 may include instructions such as to use a pulse locking technique, such as described herein in the RoR discussion, such as to measured arterial blood oxygenation components. In some cases, various ones of multiple individual response light photodetectors 3408 can be arranged at different distances from the LEDs 3414 of the optical transmitter 3406, 4306, such as to measure one or more changes in the absorption or scattering coefficients, or both, at various illumination light wavelengths of corresponding ones of the LEDs 3414. Individual LEDs 3414 with corresponding optional downstream optical filters 3418 can be used, such as shown in and described with respect to FIGS. 34A, 34B and elsewhere herein.

Example of Placement on the Body or as a Stand-Alone Device

Although the description in this document has focused on an application for use as a wearable that can be located on a wrist of the subject, the present techniques can be applied to many other areas of a subject's body, or to spectroscopic analysis of other target objects 3404 that need not be biological or related to a human or animal body. For example, the present techniques can be used on a subject's fingertip, such as for multi-analyte measurement at a fingertip location. In example, all or portions of the present device 3402 can be built into another component or an article of manufacture, such as being built into an arm band, a chest strap, or a bone-fracture cast or component thereof, such as for measurement of one or more indications of wound healing. For example, compartment syndrome can occur when blood flow within a casted limb is significantly impeded or even stops. This can be due to internal pressure that is applied by the cast onto the casted limb. The effects of compartment syndrome may result in a need to surgically remove the affected limb. A good estimate of the blood oxygen levels of limb tissue encompassed within the cast-whether the cast is located on a leg, an arm, or any other part of the body, can help avoid such consequences. The entire device 3402 can be built into a cast or brace, and can include a battery and an RF or other wireless communication module via which blood oxygen measurements can be communicated to a caregiver or other user or to a monitoring device.

In another example, all or portions of the present device 3402 can be built into another component, such as in a stand-alone device, such as a health-pod, a smart speaker, a personal computer, or the like, such as which can include a fixture or other interface to help a subject position a fingertip or other appropriate body part for spectroscopic measurement and analysis such as described herein.

Multispectral Illumination for Spectroscopy

As discussed herein, and as can be supported by or combined with the subject matter incorporated herein from Deliwala U.S. Provisional Patent Application No. 63/200, 241 entitled CODED LIGHT FOR TARGET IMAGING OR ANALYSIS, filed Feb. 24, 2021, the techniques (e.g., systems, devices, or methods) described or incorporated herein can be used to provide stable multi-spectral light source. Such a light source can be coupled to an optical fiber or fiber bundle, such as for delivery to an endoscope input, a microscope input, or otherwise such as for use as a light source for spectroscopy. The LEDs 3414 can provide illumination wavelengths that can span from 200 nanometers to 10,000 nanometers, such as can depend on the application needs. Illustrative examples of other applications can include colorimetry for analyte measurement, spectroscopy of specific molecules such as in industrial process control or gas and aerosol measurement, such as described in Deliwala U.S. Provisional Patent Application No. 63/200,241 entitled CODED LIGHT FOR TARGET IMAGING OR ANALYSIS, filed Feb. 24, 2021, which is incorporated herein by reference, including for its examples of such other applications, and which is bodily incorporated in Section A of this document. Multiple identical (or different) optical transmitter modules 3406 can optionally be combined, such as to help produce more intense illumination, if desired.

Other Light Sources

While the description in this document has focused on using LEDs, super luminescent light emitting devices (SLEDs) can additionally or alternatively be used. Some or all of the LEDs 3414 in the array shown in FIG. 34B can be substituted with other componentry, such as a vertical-cavity surface emitting laser (VCSEL), which will avoid the need for collimation and filtering. In general, VCSELs may not be currently available at all the wavelengths desired for molecular spectroscopy.

Other Comments

As described herein and in Deliwala U.S. Provisional Patent Application No. 63/200,241 entitled CODED LIGHT FOR TARGET IMAGING OR ANALYSIS, filed Feb. 24, 2021, multiple response light receiver photodiodes or other photodetectors can be placed at different distances from the collimated spectrally filtered light source, and can be used to estimate absorption and scattering coefficients of a sample or target object 3404. By having multiple wavelengths of illuminating light delivered to the sample or target object 3404 so as to start from the same location, and with substantially similar angular spread, a substantial source of error in the estimation of these parameters can be reduced. Such estimates of absorption and scattering coefficients can be combined with signal-processing, such as to measure one or more changes in the material structure and properties. For example, a few illumination wavelengths can be used to measure at two different distances (e.g., such as shown in and described in Section A of this document with respect to FIG. 12A).

Figure 45:
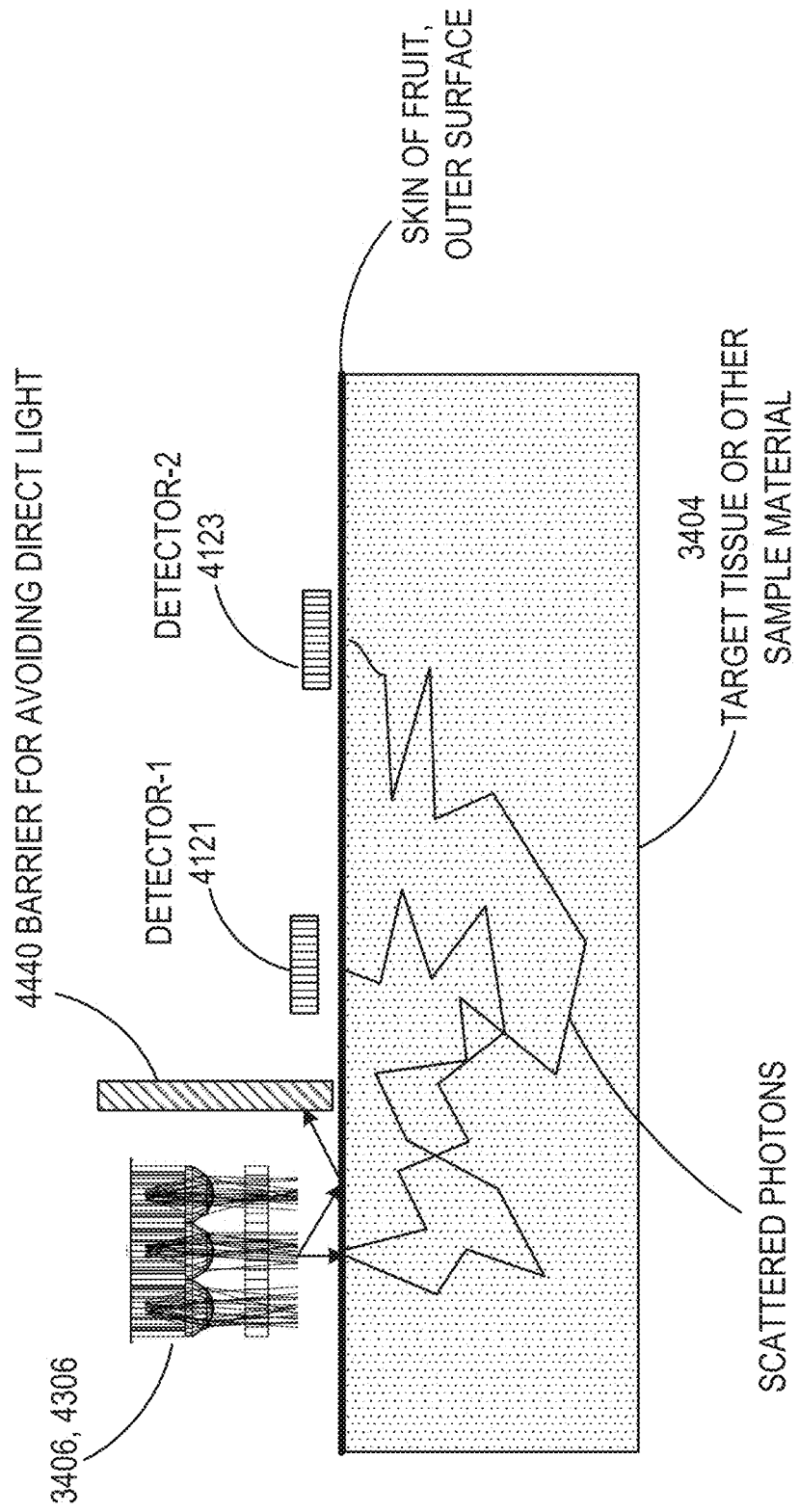
FIG. 45 shows a similar example, such as a configuration for performing spectrometric analysis on a target object such as can include a fruit having an outer skin.

FIG. 45 shows a similar example, such as a configuration for performing spectrometric analysis on a target object 3404 such as can include a fruit having an outer skin. By having locating a first response light photodetector 4121 at a first measurement site, and locating a second response light photodetector 4123 at a differently located second measurement site, and by including an optical transmitter 306 providing more or less collimated input light (which can be optionally modulated, such as using W-CLS, such as described herein in Section A and in Deliwala U.S. Provisional Patent Application No. 63/200,241 entitled CODED LIGHT FOR TARGET IMAGING OR ANALYSIS, filed Feb. 24, 2021 into the sample, one can "remove" the effect of the common skin, which is often more light absorbing, and can determine one or more parameters of the underlying fruit pulp. This can allow measuring dryness of the fruit or its cellular rigidity. Similar techniques can be applied to measurement of human dermis or epidermis.

Figure 46:
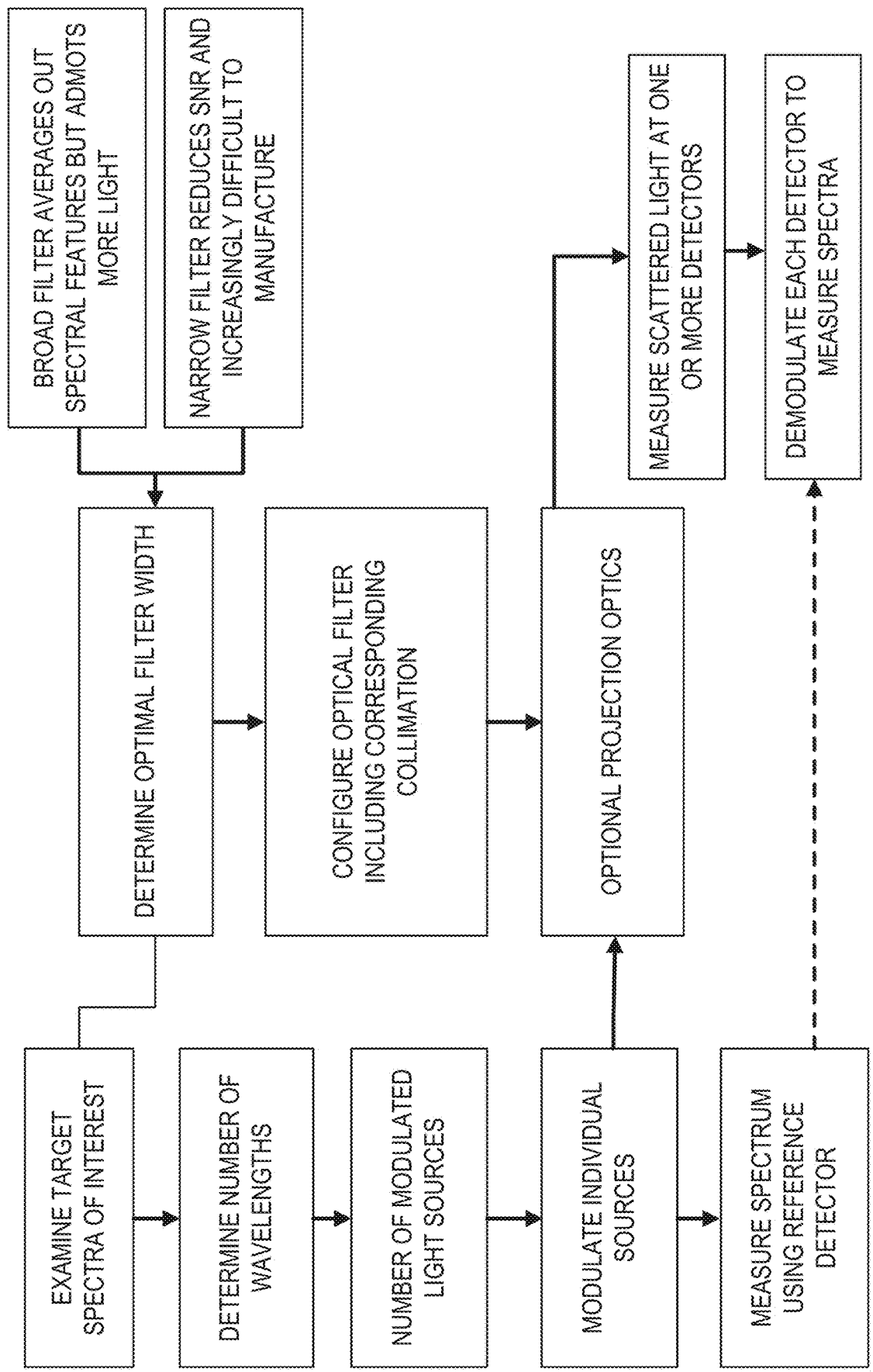
FIG. 46 shows an example of portions of a decision tree for a methodology for selecting various components of the system, such as can include selecting particular optical filters.

FIG. 46 shows an example of portions of a decision tree for a methodology for selecting or configuring various components of the system 3400, such as including selecting particular optical filters 3418. The number of illumination light wavelengths to be used and the optical filter passband width can each depend on the target spectra of the target object 3404 and the optical wavelength emission spectral width of the LED 3414 light source. For the case of blood oxygenation saturation (SpO$_2$) such as using a wrist-worn device such as described herein, making the optical filter passband width too wide (or having no optical filter at all) loses the ability to detect the blood oxygenation at the selected illumination light wavelengths. Making the optical filter passband width too narrow can reduce the amount of illumination light available for making a good measurement. These and similar considerations may need to be balanced on a case-by-case basis. But the present approach allows operability by appropriately configuring the system 3400 and permits different optical filter passband functions, each of which can be selected to make the detection of the changes in the target spectrum discernible to achieve the desired measurement.

In another example, the present approach can be used for in-vivo use glucose sensing. In such an example, a number of different light wavelengths can be selected at particular wavelengths to be spread between 1500 nanometers to 2400 nanometers, such as may be used to measure glucose. Such a glucose measurement application may benefit from each measurement at each wavelength being carried out with SNR exceeding, e.g., 60 dB at a 50 Hz illumination repetition rate. These parameters may change for a particular system 3400 and may depend on the part of the body at which the measurement is intended to be carried out. But these parameters, taken together, will directly determine number of measurement light wavelengths, the optical filter bandwidth, as well as the actual selection of the particular wavelengths to be used.

Figure 47:
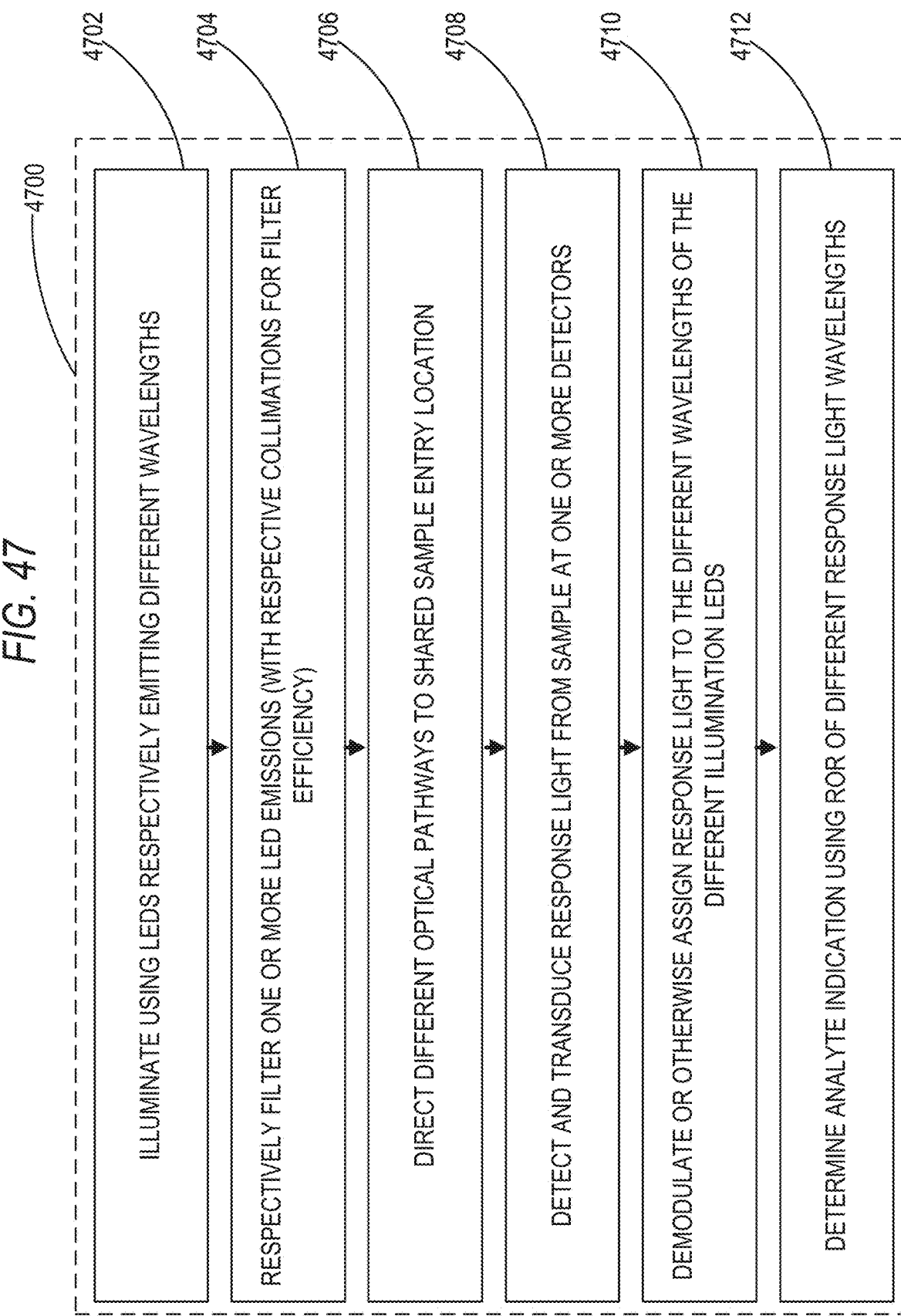
FIG. 47 shows an example of portions of a method of LED-based spectroscopic analysis, such as of a tissue sample or other target object.

FIG. 47 shows an example of portions of a method 4700 of LED-based spectroscopic analysis, such as of a tissue sample or other target object 3404 using a system 3400 or device 3402.

At 4702, illumination can be produced by individual ones of multiple LEDs 3414 in an optical transmitter module 3406 emitting different light wavelengths, sequentially or concurrently. If concurrent, orthogonal coding can optionally be used to modulate or encode the individual light emission wavelengths in the respective optical pathways of the individual LEDs.

At 4704, one or more or all of the LED light emissions from the individual LEDs can be filtered, e.g., narrowed, such as in a respective optical pathway of the individual LED. This can help reduce spectral variations in the LED light emissions and can help enable spectroscopic analysis of otherwise challenging target analyte or target location. Pre-collimating the LED emission light, using collimation optics 3416 in the individual optical pathway, can improve the filtering efficiency of the corresponding optical filter 3418.

At 4706, the different optical pathways from the different individual LEDs at different illumination wavelengths can be directed toward a shared or common target sample entry location. This can include using one or more of: a baffle, an aperture, a complex variable diffractive or sub-diffractive grating, a metasurface optical element, a geometric phase optical element, an optical fiber or optical fiber bundle, or other component, such as described herein. Optionally, wavelength homogenization can be provided, such as using a light diffuser. Coding/modulation can optionally be provided, such as with concurrent illumination using multiple LEDs, such as described or incorporated herein.

At 4708, response light from the sample, obtained in response to the illumination of the target, can be detected and transduced, such as using one or more photodetectors, which can be placed at desired locations with respect to the target and with respect to the common/shared entry point of the illumination light.

At 4710, if the illumination light was modulated or encoded, the response light can be decoded to yield an individual response corresponding to the individual illumination wavelengths. If the individual different wavelengths of light were sequentially issued by activating the corresponding individual LEDs 3414, then the corresponding responses can be assigned to such illumination wavelengths accordingly for analysis.

At 4712, concentration or other indication of a target analyte (e.g., oxygen in hemoglobin, glucose, alcohol, or other analyte) can be determined using the RoR of different response light wavelengths. Notably, such RoR analysis may not otherwise be possible without the filtering of one or more LED illumination light wavelengths, as described herein. As shown in the computer-model data of FIGS. 41B, 41C, and 41C, only as the illumination spectral bandwidth is narrowed (e.g., such as from 30 nanometers in FIG. 41A, to 20 nanometers in FIG. 41B or to 15 nanometers in FIG. 41C), does the spectral response (dashed lines) begin to represent the spectral characteristic of the corresponding target analyte (oxygenated blood vs. deoxygenated blood, in this example).

Thus, the present techniques (e.g., such as including optical wavelength filtering, such as with pre-filtering collimation) can help provide spectrally well-defined illumination light from each of the potentially broadband light sources, such as can include individual LEDs or SLEDs. The present techniques can also help provide a well-defined projection beam into a sample, which can significantly reduce unwanted scatter, which, in turn, can help to ensure that the illumination photons reach the nearby photodetectors such as to be detectable as response light. The present techniques can include coding or modulation of illumination light, such as using orthogonal encoding functions, such as described or incorporated herein, which can help allow concurrent illumination. Concurrent coded illumination can help improve the SNR, which may otherwise suffer as the number of different wavelengths is increased and a sequential illumination scheme is used.

In case of SpO$_2$, the response signal can be measured at sufficiently high measurement repetition rate, such as at 50 Hz, so as to recognize and compensate for any pulsatile component in the response signal, such as superimposed by the cardiac stroke of a beating heart. The Ratio of Ratio (RoR) described herein can be calculated, from which an oxygen level determination can be made. When there are many more different illumination light wavelengths, then a more sophisticated fitting can be used to fit the spectrum of the analyte concentration. This can be performed for the AC/DC ratio at each wavelength, for the "DC" spectrum, or both. The changes in the "DC" spectrum across different photodetectors at different locations can provide a direct measure of absorption and scattering coefficients from the tissue sample or other target object, and can be used to monitor chemical and structural changes over time. The AC/DC spectrum (or the ratio spectrum) can be useful in that it can allow measuring changes in the arterial blood (or anything that pulses with the heart) and can allow tracking of one or more analytes in the blood.

The above-described measurements can be applied to one or more other analytes, such as glucose or alcohol. Because the spectra of these molecules can be affected by small changes in the amount of the target analyte present, such molecules can benefit from a detection technique having providing high SNR. But good measurements can also benefit from high spectral certainty. Thus, the present techniques can be used to provide an appropriate illumination spectral width (corresponding to illumination at a particular illumination wavelength) to retain the spectral features of the analyte, such as to help produce high contrast to help reduce measurement error of measurements that can be made at multiple illumination wavelengths. Such an approach can be helpful to measure changes in the analyte in the presence of background spectral influences and shifts. The present techniques can help enable in-vivo measurement in humans as well as measurement of other molecules in other samples or target objects, such as plant or other media.

Section C: Coded Light for Target Imaging or Analysis Examples

This Section C presents examples of using the coded light techniques described herein for target imaging or analysis, for example, such as for machine vision of a moving target or object, such as a semiconductor wafer or other moving object (e.g., on a conveyor belt) to be inspected.

Briefly, as an illustrative example, described in this Section C, coded light illumination by an optical illuminator on a transmit portion 11 of a system can be used with a focal plane array (FPA) light imager serving as an imaging photodetector 119 on the receive 12 portion of the system 10 receiving response light from a moving target object 117, such as for machine vision inspection of integrated circuit (ICs) or semiconductor wafers or other parts to be inspected on a moving stage or belt. The illumination light can be encoded with orthogonal functions, such as a Red-Green-Blue (RGB) illumination sequence, or a sequence of combinations of spectrally contiguous or non-contiguous colors. This approach can provide advantages over certain other machine vision moving target inspection approaches, such as a dichroic combiner or a 3 CCD imaging system using dichroic splitting at a camera as opposed to modulation encoding light at the illumination side.

As an illustrative example, moving target objects can be inspected using machine vision, which can include using an optical imaging color inspection system. This can include inspecting one or more integrated circuit (IC) die on one or more semiconductor wafers that have been placed on a moving stage or belt passing by the semiconductor wafer inspection system.

One possible approach to such a color inspection system is to include a camera having three charge-coupled device (CCD) sensors for respectively analyzing red, green, and blue (RGB) components of light from a passing moving target object such as a semiconductor IC or wafer. In this approach, dichroic splitting of light into the RGB components is performed on the receive side, that is, at the camera imaging using an optical signal received from the passing moving target object. This approach can be prone to issues from vibration of the CCD sensors, alignment of the CCD sensors, or both. CCD sensor matching or calibration may be needed to obtain a desired performance level using this approach, such as similarly explained above with respect to "Example 6: Special effects and studio recording."

Therefore, the present inventor has recognized, among other things, that there is a need in the art to provide a three-or-more color imaging system, such as which can meet or exceed the performance of a 3 CCD sensor color imaging system, and such as which can be less prone to sensor vibration and alignment, without requiring sensor matching, and with less burdensome calibration. It can also be desirable to maintain an update rate, of updating of the resulting color image, exceeding 100 Hz. As explained herein, an approach can be provided to use an optical illuminator to provide modulation-encoded light ("coded light"), such as to illuminate moving target objects, such as parts to be inspected. Such coded light illumination for machine vision color imaging can include using a repeatedly strobed short pulse light flash (e.g., using a flashed Xenon lamp or the like), such as to "freeze" motion, for imaging purposes, such as for producing a three or more color image of a moving target object (such as a semiconductor IC or wafer). The coded light can be received by one or more cameras on a receive side of the system, such as at a focal plane array (FPA) imaging photodetector, and transduced into an electrical signal that can be decoded, such as can include using information about the modulation encoding by the optical illuminator on the transmit side to provide one or more advantages over machine vision imaging that does not employ coded light illumination of the target object. It can also be desirable to permit the present techniques to also use and leverage (or be compatible with) certain imaging infrastructure in imaging systems. It can also be desirable to permit the present techniques to provide an ability or flexibility to define arbitrary spectral regions (e.g., other than RGB regions) such as for application-specific inspection of one or more still or moving target objects.

Figure 48:
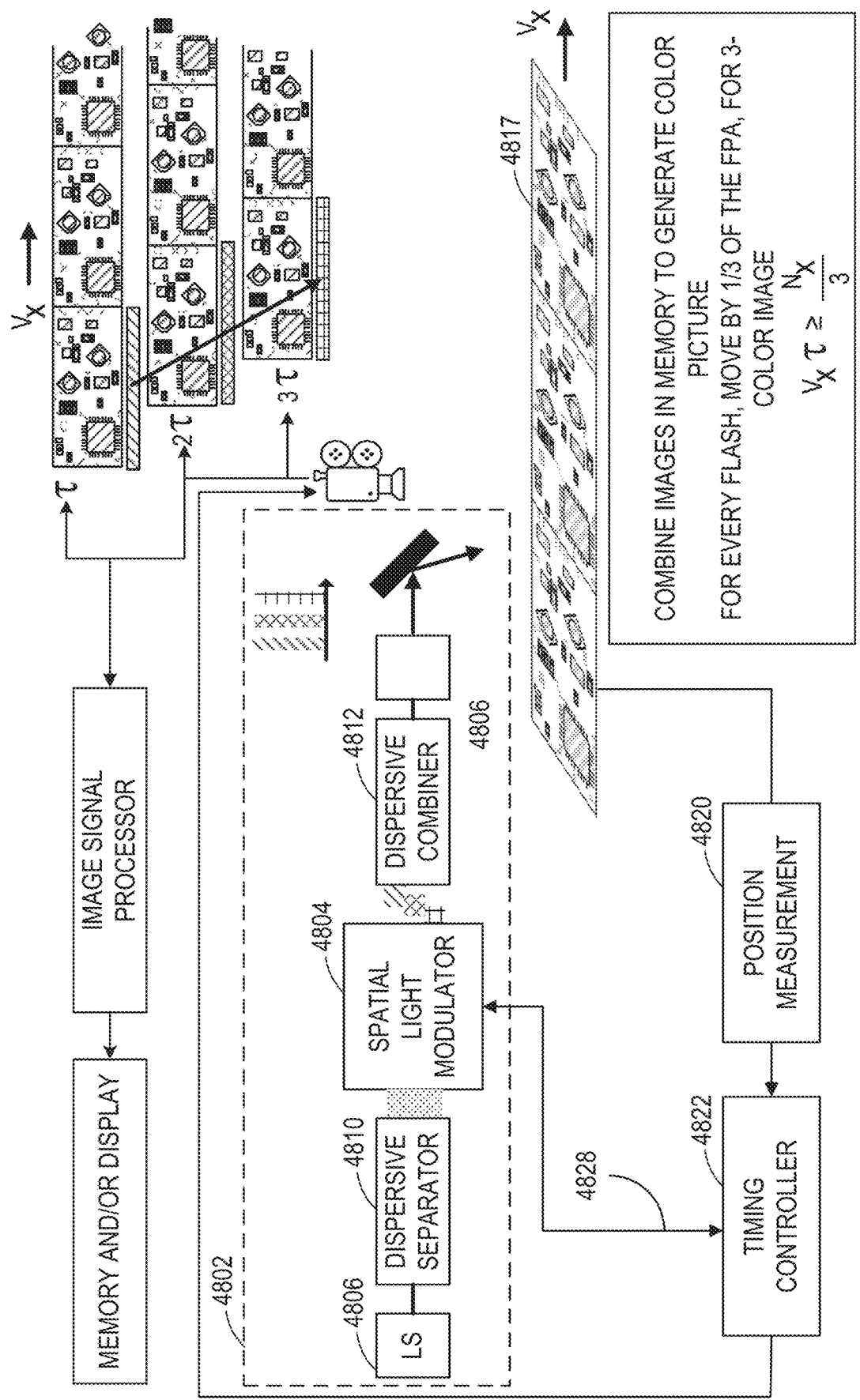
FIG. 48 shows an example of portions of a system that can employ a coded light approach for machine vision of a moving target object.

FIG. 48 shows and describes an example of portions of a system 4800 that can employ a coded light approach for machine vision of a moving target 4817, such as a semiconductor IC or wafer (or other part) to be inspected, such as can be placed on a moving stage or belt. In the example shown in FIG. 48, an optical illuminator 4802 can include or can be coupled to an optical modulator, such as a spatial light modulator (SLM) 4804. The optical illuminator 4802 can include a flashed or otherwise strobed or pulsed Light Source (LS) 4806. For example, the Light Source 4806 can include a Xenon flash light source, a broadband pulsed laser, an LED pumped phosphor, or a shuttered continuous light source 4806. Thus, the light source 4806 can be configured to operate to limit an output light pulse duration, which, in turn, limits the exposure time of a focal plane array (FPA) light imager, such as can be included in a camera 4808 that can be included on a receive side of the system 4800, such as shown in FIG. 48. The flashed light source 4806 can output light via an optical pathway to a downstream prism or other dispersive separator 4810. The dispersive separator 4810 can disperse the received light from the flashed light source 4806 into spatially spread apart different spectral components. These different spectral components from the dispersive separator 4810 can be provided via an optical pathway to a downstream spatial light modulator (SLM) 4804. The SLM 4804 can modulate individual spectral bins of the received different spectral components differently, such as to perform modulation encoding of the different individual spectral bins or components according to different (e.g., orthogonal, identifiable, or unique) time-varying modulation functions. The modulated light output from the SLM 4804 can be provided to a dispersive combiner 4812, such as when it is desired to re-combine the different spectral bins or components into a wavelength homogeneous output from the dispersive combiner 4812 or to allow directing desired modulated wavelengths for illuminating corresponding desired locations on the moving target object. Thus, in certain applications the dispersive combiner 4812 may be substituted for by a non-dispersive combiner, such as shown in and described above in Section A with respect to FIG. 5C and also in the incorporated U.S. Provisional Patent Application Ser. No. 63/200,241 entitled CODED LIGHT FOR TARGET IMAGING OR ANALYSIS, or for combining illumination light output into a randomized optical fiber bundle or other optical illumination beam output, for example. A goal can be to generate coded light output from the dispersive combiner 4812 (or other non-dispersive combiner) that can be consistent with and advantageous for good spectral imaging. As shown, one or more of refractive optics 4814 or reflective optics 4816 can be used to direct the modulated light provided by the dispersive combiner 4812 (or other non-dispersive combiner) toward the moving target object 4817, such as can include a semiconductor IC or wafer (or other part) to be inspected, such as on a moving stage or belt moving in a direction, which can be defined as an x-direction, such as with a velocity vx, such as shown in FIG. 48. The present approach to visualization or inspection is not limited to wafer inspection. The principles described with respect to the present approach can also be applied to material identification and sorting, for example, such as shown in and described above in Section A with respect to FIG. 22B and also included in the incorporated U.S. Provisional Patent Application Ser. No. 63/200,241 entitled CODED LIGHT FOR TARGET IMAGING OR ANALYSIS, such as of target objects on a moving belt or cells or other target objects in a moving medium or otherwise moving in some manner.

As shown in FIG. 48, a camera 4808 can include a one-dimensional (1D) or two-dimensional (2D) focal plane array (FPA) imager, such as including an array of imaging pixels. FIG. 48 illustrates a use case in which M=3 modulation functions (e.g., RGB) can be provided by the SLM 4804 for modulation encoding that can optionally be used. With a smaller M such as M=3, a new class of modulation functions work well in an efficient fashion. These are described later in FIG. 51 and explained herein. A coded illumination beam is provided by 480 for illuminating the moving target 4817 to be inspected. The moving target object 4817 (or the moving stage or belt upon which the target object 4817 is placed) can include visual or other position measurement indicia, which can be read by the position measurement reading componentry 4820 shown. Such position information, by itself or additionally or alternatively using velocity information generated therefrom, can be provided to a timing controller circuitry 4822. Using such position or velocity information, the timing controller circuitry 4822 can provide one or more control signals to the light source 4802, such as to control flashing or pulsing of the flashed light source 4802. For example, such flashing timing control can optionally be used to help provide pixel synchronization or alignment of the focal plane array imaging pixels in the FPA in the camera 4808, such as described herein. For example, the timing controller 4822 can control generating a flash of light such that pixel-level alignment can be maintained for some integer translation of pixels for consecutive flashes, such as explained herein. The modulation coded light machine vision system 4800 such as shown in FIG. 48 can be configured such that consecutive wavelength groups (consecutive "spectral bins") can be presented to the moving target object 4817 at the desired precise time, such as explained herein. Although the example shown in FIG. 48 focuses on a moving target object 4817 that can be located on a moving stage or belt, the techniques illustrated and described can also be used without such moving stage or belt—for example, such as where the inspection device or system 4800 itself is moved with respect to a stationary target object 4817, e.g., in a "pushbroom" or similar manner such that the target object 4817 is still "moving" with respect to (e.g., relative to) the inspection device or system 4800.

The focal plane array (FPA) imager in the camera 4808 includes an array of pixels having enough pixels in a direction of motion of the target moving object (e.g., the x-direction in the example of FIG. 48) to capture images from N flashes of sequentially modulated illumination pulses, albeit offset from each other by τ=1/N, where N≥M. Encoded information from the different modulation functions can be decoded or reconstructed by the image signal processor circuitry 4824, such as using timing information received from the timing controller 4822, such as for storing or displaying the image in a memory/display 4826. The decoded or reconstructed information can combine information from same or like locations on the moving target object 4817 with each other, as explained herein, such as by applying an appropriate offset in memory circuitry associated with information readout from the focal plane array (FPA) imager in the camera 4808 to generate a color picture of a particular portion of the target moving object 4817, such as illustrated in FIG. 48 for the case of N=M=3.

In the illustrative, non-limiting example of FIG. 48, in which N=M=3, the motion of the belt or stage can be such that it moves across 1/N (e.g., ⅓) of the Focal Plane Array (FPA) in the camera 4808 for every flash for an N=M=3 color image. For N=M=3, the flash rate, the number of pixels $N_x$ in the direction of motion (x-direction), and the velocity $v_x$ of the moving stage are related, such that $v_x \tau \leq (N_x/3)$.

More generally, assume for example that we want to create a N-channel spectral image of an object on a moving stage or belt (e.g., target moving object 4817). The stage or belt moves at a velocity $v_x$, as seen by the FPA imaging array of pixels of the camera 4808. Furthermore, assume that the FPA imaging array used in the camera 4808 has $N_x$ pixels in the x-direction of the motion of the stage or belt. This means that a completely new image will show up in the field of view (FOV) of the camera 4808 with no overlap in time $$T = \frac{N_x p}{v_x},$$

where p is the width or the size of the pixel in the FPA of the camera 4808.

A goal can be to get M exposures of the coded light source from the optical illuminator 4802, each exposure containing a unique combination of wavelengths (or spectral bin), made within time T. These M exposures can be used to reconstruct a spectral image of M channels as described above in Section A and as included in the incorporated U.S. Provisional Patent Application Ser. No. 63/200,241 entitled CODED LIGHT FOR TARGET IMAGING OR ANALYSIS, filed Feb. 24, 2021. But the target object 4817 is moving and hence the image reconstruction can only happen if each point on the target object 4817 that corresponds to different pixel locations on an FPA imaging array in the camera 4808 due to motion of the target object 4817 has been exposed to all M exposures. This means that all M exposure must occur in time T and each exposure will be spaced in time by $$\tau \leq \frac{T}{M}.$$

In this way, the reconstruction of the combined image of the same region of the moving target object 4817 can be performed by identifying the same points or locations on the target object 4817—which are translated from each other by $$n_x = \frac{v_x \tau}{p}$$

pixels in the image. This "realignment" can be done in the memory 4826 such as during image pre-processing for display or analysis. For example, a continuous reconstruction can be performed for every point on the target object 4817 in a rolling fashion since the coded light source of the optical illuminator 4802 can be operated to produce periodically repeating codes.

Furthermore, it can be advantageous to have each flashed exposure occur at the integer multiple of pixels in the FPA of the camera 4808. This can involve coordinating the flash of light (and/or electronic/mechanical shutter of the camera 4808) at the precise time when the moving belt or stage has translated the moving target object 4817 by $n_x$ pixels. This makes "realignment" easier to perform in the memory 4826. This can be managed by the timing controller 4822 that receives input from the SLM 4804 or optical illuminator 4802 or sends timing control signal information to the SLM 4804 or to the optical illuminator 4802 so that the SL 4804 or the optical illuminator 4802 is in the appropriate state and then generates a flash of modulation-encoded light or triggers a shutter of other exposure of the camera 4808 at the time suitable for pixel-level alignment.

Additionally, but not necessarily, a moving target object 4817 can optionally be "frozen" at a level of blur of b pixels with the exposure time (either limited by the flash duration of the optical illuminator 4802 or by shutter opening of the camera 4808) is given by $$\tau_{exp} \leq \frac{bp}{v_x}.$$

In the illustrative example of FIG. 48, the diagram shows the timing controller 4822 capable of either (or both) "receiving" input at node/bus 4828 from spatial light modulator 4804 to signal its state, or "sending" the signal to the spatial light modulator 4804 or other component of the optical illuminator 4802 to prepare the correct state of the coded light source, such as depending on the type of modulator used by the optical illuminator 4802. The timing controller 4822 also directs the flashing of the light source 4806 (as shown in example of the diagram of FIG. 48) but alternatively could be configured for triggering the exposure on the FPA of the camera 4808, or both.

In FIG. 48, the diagram and explanations are made for an illustrative example in which N=3 and M=3 and in which the modulation codes can correspond to one or more circulant matrices (e.g., a matrix in which each of the wavelength groups (or spectral bins) corresponds to a column of the circulant matrix and in which the rows of the circulant matrix form a time sequence for modulation). But as the discussion above shows, the present techniques, including any use of a circulant matrix or other modulation functions, are generalizable to different pairs of values of N and M. Imaging of a stationary object can be made using any of the techniques described herein, or any of the techniques described above in Section A and also in the incorporated U.S. Provisional Patent Application Ser. No. 63/200,241 entitled CODED LIGHT FOR TARGET IMAGING OR ANALYSIS, filed Feb. 24, 2021. Other than circulant matrices, other illustrative examples of different modulation functions that can be used for modulation encoding, such as by the optical illuminator 4802, can include one or more other orthogonal modulation functions such as, for example, components of a Fourier series, Hadamard series, or one or more other orthogonal functions.

In an example, the focal plane array light imager of the camera 4808 can include one or more optical filters associated with corresponding pixels of the focal plane array light imager (e.g., such as an RGB camera 4808). The one or more optical filters can be arranged, for example, in an optical pathway between the target object 4817 and the camera 4808, such that different pixels of the focal plane array light imager of the camera 4808 receive a response to different portions of the modulation-coded different wavelength light components of the illuminating beam provided by the optical illuminator 4802.

In an example, the optical illuminator 4802 can include an optical modulator (such as or in addition to SLM 4804), which can be configured to provide an additional higher frequency modulation, and the image signal processing circuitry 4824 can be configured to use the response signal from the focal plane array (FPA) imager of the camera 4808 to also decode such higher frequency modulation. For example, such additional higher frequency modulation information can be used to measure a time delay or a phase delay of one or more of the (lower-frequency modulation) wavelength (or spectral bin) components using the decoded information about the higher frequency modulation.

Figures 49A, 49B, 49C:
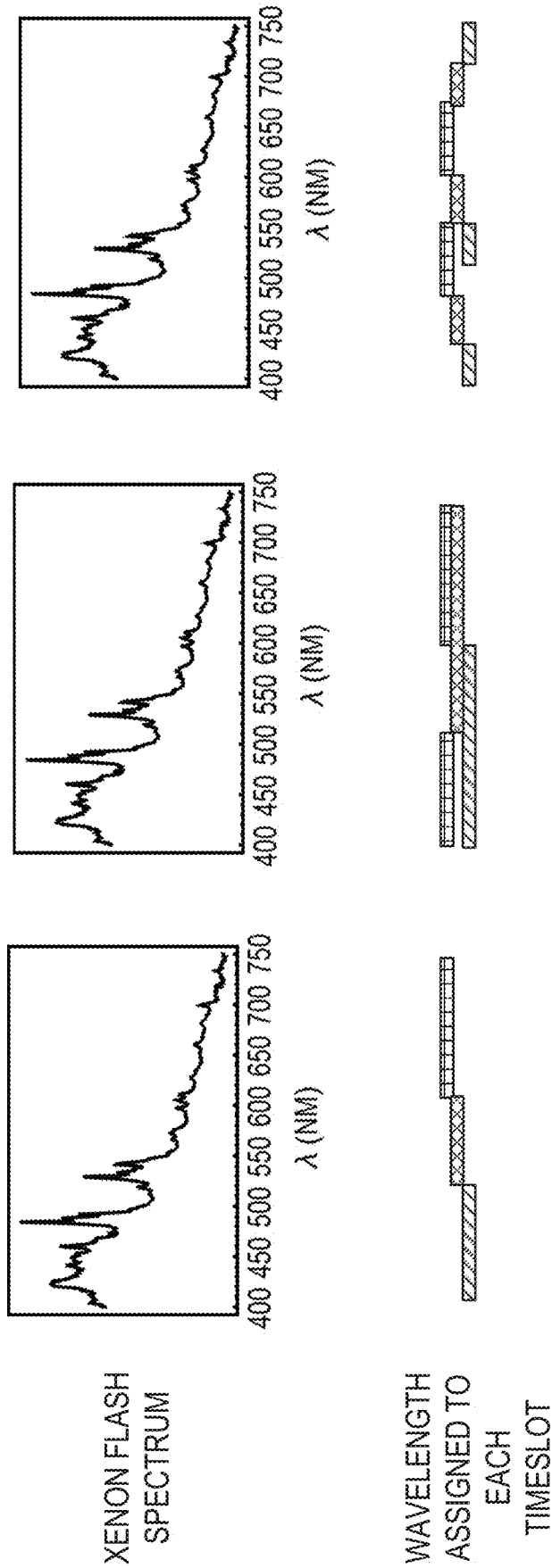
FIGS. 49A, 49B, and 49C describe illustrative conceptual examples of flexible spectral measurements, including RGB (FIG. 49A), combinations of RGB (e.g., such as BG, GR, and RB.

FIGS. 49A, 49B, and 49C describe illustrative conceptual examples of flexible spectral measurements, including RGB (see FIG. 49A), combinations of RGB (e.g., such as BG, GR, and RB, see FIG. 49B) and arbitrary wavelength components (see FIG. 49C) that can be spectrally contiguous or non-contiguous.

In each of FIGS. 49A, 49B, and 49C, the top portion of the diagram illustrates a spectral diagram of light intensity vs. wavelength for a particular example of the Light Source 4806 (e.g., a Xenon flash light source). In each of FIGS. 49A, 49B, and 49C, the middle and bottom portions of the diagram show assigning of temporal sequencing of time slots to various wavelength components (spectral bins) of the Xenon flash light source 4806.

In FIG. 49A, a temporal sequence of orthogonal modulation functions of illuminating light upon the moving target object 4817 shows issuances of a pulse of Red illumination light (R) followed by a pulse of Green illumination light (G) followed by a pulse of Blue illumination light (B).

In FIG. 49B, a temporal sequence of orthogonal modulation functions of illuminating light upon the moving target object 4817 shows issuances of a pulse of Blue and Green illumination light (BG) followed by a pulse of Green and Red illumination light (GR) followed by a pulse of Red and Blue illumination light (RB). However, the temporal sequence need not issue spectrally-adjacent consecutive pulses.

In FIG. 49C, a temporal sequence of orthogonal modulation functions of illuminating light upon the moving target object 4817 shows issuances of a pulse of a first set of wavelengths of illumination light (C1) followed by a pulse of a second set of wavelengths of illumination light (C2) followed by a pulse of a third set of wavelengths of illumination light (C3)—within a particular set of wavelengths, non-contiguous wavelengths can be included, and between temporally adjacent pulses of sets of wavelengths, non-contiguous sets of wavelengths can be included, such as shown in this example.

FIG. 50 is a diagram comparing various versions of the techniques described with respect to FIGS. 49A, 49B, and 49C to help explain some potential benefits of substituting combined spectral channels (e.g., such as shown in FIGS. 49B and 49C) in place of the simple RGB channels shown in FIG. 49A. More particularly, instead of modulation coding illumination in a simple sequence such as RGB, there may be a benefit to instead code combinations such as BR, RG, and GB, since, as shown conceptually in FIG. 50, doing so can increase the illumination light on the moving target object 4817, and hence, the response light from the moving target object 4817 on the focal plane array (FPA) imager of the camera 4808 by a calculated factor of almost 2, thereby enabling providing a signal-to-noise ratio (SNR) comparable to that of a non-dispersive system. Other wavelength combinations can be used for coding the illumination light, e.g., such as shown in FIG. 49C for example, such as to match to a specific spectral reflectance of the moving target object 4817. This can help improve discrimination of features in the resulting image detected by the focal plane array imager of the camera 4808, and can be done with a straightforward change in the coding scheme of the system 4800, such as explained above with respect to FIG. 49C.

To recap, there can be some advantages of using the present techniques in a machine vision application such as for imaging a moving target object 4817 such as an IC or semiconductor wafer or other part to be inspected on a moving stage or belt. The approach shown and described with respect to FIGS. 48, 49A-C, and 50 can help enable high signal-to-noise ratio (SNR) measurement, such as for using a monochrome camera 4808. The disclosed techniques can help provide excellent alignment of the spectral or color response of each location on the moving target object 4817. These techniques can be used to help the optical illuminator 4802 provide high spectral purity illumination light to the target object 4817. The arrangement and methods shown and described are compatible with a moving target object (e.g., moving with respect to the inspection device or system 4800). The present techniques can help enable using and improving existing camera equipment, imaging optics, and motion measurement. The present techniques can help provide a flexible architecture, such as can help permit a choice of camera, imaging optics, or both. The present techniques can be extended to near infrared (NIR) wavelengths, to 4-color combinations, or to more numerous or more complex color combinations, such as can be useful for thin film or other measurements. The present techniques can be extended to short wave infrared (SWIR) wavelengths. The present techniques can be extended to many more colors, or can even be extended all the way to hyperspectral imaging of a moving target object 4817, or of a stationary target object 117, such as shown and described above in Section A and also in the incorporated U.S. Provisional Patent Application Ser. No. 63/200,241 entitled CODED LIGHT FOR TARGET IMAGING OR ANALYSIS. Optical simulation performed on a computer indicates that about 10% to 25% of the light from a Xenon flash lamp Light Source 4806 can be modulation-encoded such as for imaging in color.

Table 8 provides the present inventor's views (conceptualized, not based on real data) regarding a comparative analysis of (1) the present coded light approach to color imaging for inspecting ICs, semiconductor wafers, or other parts, with comparison against (2) a dichroic combiner approach; (3) a color filter wheel or tunable filter approach; and (4) a 3 CCD detector system approach. The present approach can use a dispersive coded illumination system approach, as explained herein. The dichroic combiner approach uses dichroic filters to combine light from three or more light sources into a common path for illuminating a target object. The color filter wheel or tunable filter approach can use a moving color filter wheel that can be placed in front of a camera such as to employ large area filters for imaging different colors in the color filter wheel or other tunable filter. The 3-CCD system involves dichroic splitting at the camera (e.g., the opposite of the dichroic combiner approach) to perform simultaneous measurement by three cameras, using illumination from one illumination light source. Various attributes of the various approaches are explained in Table 8, including implementation, measurement method, spatial uniformity, spectral uniformity, calibration, light efficiency, imager acceptance angle, optical complexity, defects, reproducibility, and flexibility.

TABLE 8

Conceptualized (not real data) Comparative Analysis of Expected Attributes

| Attribute | Coded Light (Present Approach) | Dichroic Combiner Approach | Color Filter Wheel/Tunable Filter | 3-CCD System |
|---|---|---|---|---|
| Implementation | Dispersive and coded system | Three or more light sources are combined by dichroic filters into a common path | A moving color filter wheel placed in front of the camera; Large Area filters | Dichroic splitting at the camera, Opposite of Dichroic combiner |
| Measurement method | Sequential presentation and computational recovery One Imager, One Light source | Each light source is pulsed in sequence One imager, three light sources | Sequential presentation of each filter. Rotating wheel or tunable filter (slow) One Imager, One light source | Simultaneous measurement by three cameras Three imagers, one light source |

TABLE 8-continued

Conceptualized (not real data) Comparative Analysis of Expected Attributes

| Attribute | Coded Light (Present Approach) | Dichroic Combiner Approach | Color Filter Wheel/Tunable Filter | 3-CCD System |
|---|---|---|---|---|
| Spatial uniformity | High as combination is created at the source | High as combination is created at the source; | Small tilts or changes in thickness of filters cause pixel registration errors | Vibration or relative motion between cameras is a difficult mechanical challenge |
| Spectral Uniformity | Excellent because simple dispersive system is used | Higher than color wheel since the light at the source can be homogenized | Difficult to maintain uniformity across large area. Filters have high variability from batch to batch | Depends on the quality of the dichroic separator |
| Calibration | Dispersive systems have high repeatability | Required on each dichroic filter assembly, each of the three light sources, and periodically over time | Each filter batch must be calibrated for spatially dependent spectral transmission | Each dichroic separator must be calibrated Additional pixel alignment map between three cameras |
| Light efficiency; Imager acceptance angle | One light source through a dispersive system Use any lens system | Most losses due to dichroic combination Use any lens system | Depends on acceptance angle and filter quality May use higher f/# optics | Depends on the acceptance angle and quality of filter May require higher f/# optics |
| Optical complexity | Low | Medium. Three sources must be aligned to maintain output collimation and dichroic filter performance | Medium. Custom lens and microscope design in front of FPA | High. Complex assembly to maintain three cameras in focus through a long optical train |
| Defects | Low. Uses extremely mature, simple optical elements | Low | Low. Uniform filters can be expensive over large area | Complicated. Fixed pattern noise, vibration, vignetting, color splitter are intertwined |
| Reproducibility | Built-in wavelength and intensity calibration. No filters. Simplified imaging optics. | Solved by calibration | Solved by calibration | Solved by calibration |

TABLE 8-continued

Conceptualized (not real data) Comparative Analysis of Expected Attributes

| Attribute | Coded Light (Present Approach) | Dichroic Combiner Approach | Color Filter Wheel/Tunable Filter | 3-CCD System |
|---|---|---|---|---|
| Flexibility | Extend to UV, IR, more channels or complex spectral combinations | Hard to scale to more than three because dichroic combiners become unwieldy | Add more filters to the filter wheel. Overlapping and complex filters. | Hard to scale to more than three because dichroic combiners become unwieldy |

Figure 51A:
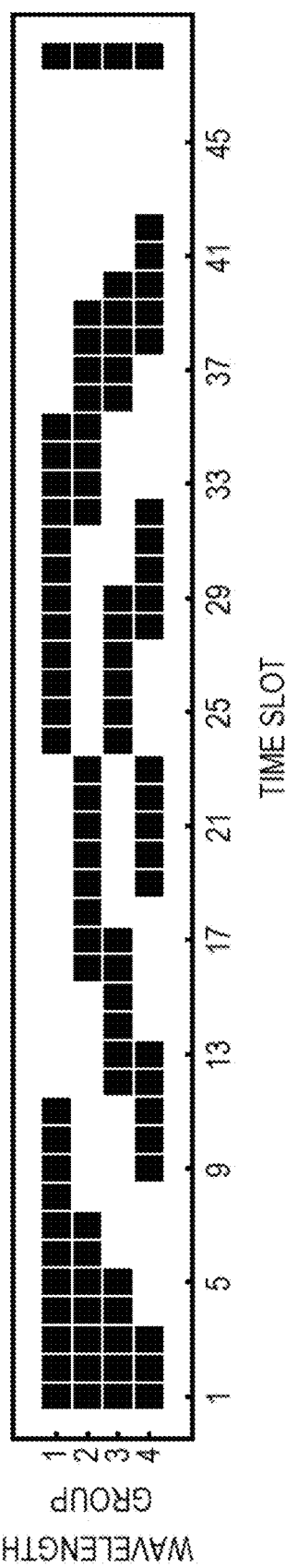
FIGS. 51A, 51B, and 51C collectively provide an illustrative example of certain modulation functions that can be applied to wavelength groups or spectral bins, such as can be used sequentially and/or concurrently illuminating a moving or stationary target object.
Figure 51C:
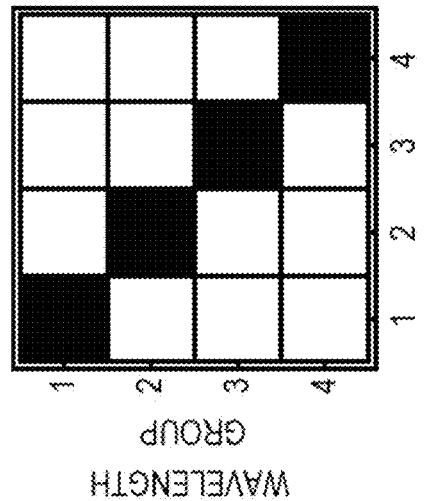
Figure 51B:
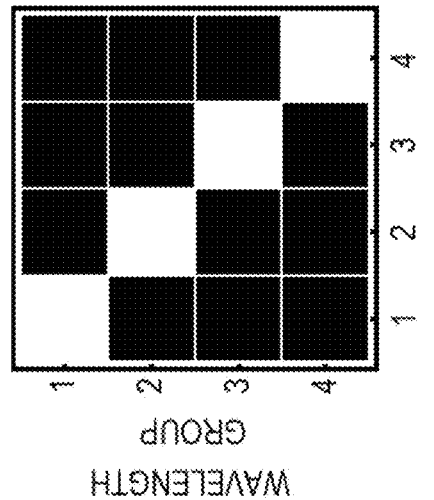

FIGS. 51A, 51B, and 51C collectively provide an illustrative example of certain modulation functions that can be applied to wavelength groups or spectral bins, such as can be used sequentially and/or concurrently illuminating a moving or stationary target object 4817.

Consider the following two (amongst many possibilities) cases of modulation functions that can modulate different wavelength components (spectral bins) from a multi-wavelength light source 4806. The illustrative cases can include: (1) an orthogonal coding derived from cosine functions as basis set (see FIG. 51A) and (2) orthogonal coding derived from a straightforward example of a circulant matrix (see FIGS. 51B, 51C).

FIG. 51A shows a case of using cosine basis functions and using 48 timeslots by way of example. Here, we take an example showing only 4 wavelength groups to illustrate the pattern shown in FIG. 51A. The pattern repeats in time. The black and white regions shown correspond to the light being blocked (black) or transmitted (white) by the modulator 4804 such as of the optical illuminator 4802. As described above in Section A and also in U.S. Provisional Patent Application Ser. No. 63/200,241 entitled CODED LIGHT FOR TARGET IMAGING OR ANALYSIS, the spatial modulator 4804 can include use of a spinning circular disc, such as which can include an alignment "clock" or timing or position indicator printed along a side of the disc, such as for use to coordinate illumination modulation with focal plane array imager detection and sampling of the light response signal by the camera 4808 from the target moving object 4817. The circular disc is one example of an SLM 4804. Modulation patterns may also be presented using Micro-ElectroMechanical Machines (MEMs) or using another spatial modulator 4804. The pattern shown in FIG. 51A is merely representative of many patterns that can be selected for modulating illumination of light, with the modulation encoded light being incident upon a stationary or moving target object or scene 4817, 117.

FIGS. 51B, 51C shows examples of controller circuitry using a straightforward circulant illumination generating matrix for coordinating encoding illumination for designated timeslots using one wavelength group (spectral bin) at a time (FIG. 51B, with illumination indicated by light boxes in corresponding time slots, and light blocking indicated by dark boxes in corresponding time slots) or multiple wavelength groups (spectral bins) concurrently (FIG. 51C, with illumination indicated by light boxes in corresponding time slots, and light blocking indicated by dark boxes in corresponding time slots). Similarly, decoding can be coordinated by using an inverse of the illumination coding generating matrix.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device for imaging or analyzing a target object or scene, using different spectral bin light components, an individual one of the different spectral bin light components comprising an individual wavelength or wavelength distribution, the device comprising:
   an optical illuminator, arranged to provide at least two individually modulated different spectral bin light components modulation encoded, using respective different non-binary light output time-varying modulation functions, and combined into an illumination light beam for illuminating the target object or scene to be imaged or analyzed, the illumination light beam concurrently providing non-binary orthogonal modulation encoded at least two individually modulated different spectral bin light components to the target object or scene;
   a target light transducer, arranged to receive response light from the target object or scene in response to the illumination light beam illuminating the target object or scene, and to transduce the response light into an electrical response signal;
   signal processing circuitry, coupled to the target light transducer to receive the electrical response signal and, using information about the respective different time-varying modulation functions, decoding the electrical response signal to recover information about a respective response parameter of the modulation encoded different spectral bin light components to provide a spectral bin response output affected by the target object or scene; and
   wherein the optical illuminator is configured to modulate a corresponding electrical input signal of one or more corresponding light-emitting diode (LED) or other light sources arranged to provide at least two individually modulated different spectral bin light components that are modulation encoded, using the respective different time-varying modulation functions, and combined into a wavelength homogeneous illumination light beam projected from a shared single exit location for illuminating the target object or scene to be imaged or analyzed, the illumination light beam concurrently providing the modulation encoded at least two individually modulated different spectral bin light components to the target object or scene, wherein at the shared single exit location the wavelength homogeneous illumination light beam is such that different wavelength light components cannot be separated by spatial or angular division of the wavelength homogeneous illumination light beam.

2. The device of claim 1, wherein the shared single exit location includes a shared aperture, wherein the shared aperture is configured to receive and to restrict a wavelength range of each of the at least two individually modulated different spectral bin light components without requiring individually separately restricting the wavelength range of each of the at least two individually modulated different spectral bin light components.

3. The device of claim 1, wherein the target light transducer includes a Focal Plane Array (FPA) transducer to receive the response light from the target object or scene in response to the illumination light beam concurrently providing the non-binary orthogonal modulation encoded at least two individually modulated different spectral bin light components to the target object or scene, wherein the FPA is configured to produce from the response light an electrical spatially-resolved imaging signal; and
   wherein the signal processing circuitry is coupled to the FPA to receive the electrical spatially-resolved imaging signal to recover spatially resolved information about a respective response parameter of the modulation encoded different spectral bin light components to provide a spectral bin response output affected by the target object or scene.

4. The device of claim 1, wherein:
   the optical illuminator, is configured to provide, at corresponding specified target pump wavelengths of the target object or scene, the at least two individually modulated different spectral bin light components modulation encoded, using the respective different time-varying modulation functions, and combined into the illumination light beam for illuminating the target object or scene to be imaged or analyzed, the illumination light beam concurrently providing the modulation encoded at least two individually modulated different spectral bin light components to the target object or scene;
   the target light transducer is arranged to receive wavelength-shifted emission response light from the target object or scene, at corresponding wavelength-shifted emission response wavelengths of the target object or scene responsive to the corresponding specified target pump wavelengths of the target object or scene, in response to the illumination light beam illuminating the target object or scene, and to produce the electrical response signal thereto, wherein the wavelength-shifted emission response light includes a wavelength-shifted emission response to the corresponding specified target pump wavelengths; and the signal processing circuitry is configured to use information about the respective different time-varying modulation functions, decoding the electrical response signal to recover information about the respective response parameter of the modulation encoded different spectral bin light components to provide the wavelength-shifted emission spectral bin response affected by the target object or scene.

5. The device of claim 4, wherein the wavelength-shifted emission spectral bin response includes at least one of a fluorescence response or a Raman response to the corresponding target pump wavelengths, and further comprising an optical blocking filter located between the target object or scene and the light transducer, wherein the optical blocking filter is configured to attenuate or block the specified target pump wavelengths from reaching the light transducer.

6. The device of claim 1, wherein:
the spectral bin response output affected by the target object or scene is in response to the illumination light beam interacting with a material of the target object or scene to produce at least one of an absorption spectral bin response, a reflectance spectral bin response, a transmittance spectral bin response, a scattering spectral bin response, a Raman wavelength shifted spectral bin response, or a fluorescence wavelength shifted spectral bin response; and
the response parameter includes at least one of an amplitude parameter, a phase parameter, a polarization parameter, or a complex amplitude parameter.

7. The device of claim 1, wherein:
the optical illuminator is configured to provide an electrical, optical, frame clock or other pattern, radiofrequency (RF) or other electromagnetic or other timing reference signal in addition to the illumination beam; and
wherein the signal processing circuitry is configured to use information from the timing reference signal and information about the respective different time-varying modulation functions to recover information about the parameter of the modulation encoded different spectral bin components to provide the spectral bin response output affected by the target object or scene.

8. The device of claim 1, comprising:
a light source measurement transducer, coupled to receive a portion of light provided to form the illumination light beam, the portion of light being independent of illumination of the target object or scene to produce an electrical illumination variability indication signal that is independent of the target object or scene; and
wherein the signal processing circuitry is configured to use information from the electrical illumination variability indication signal and information from the electrical response signal from the target object or scene to provide the spectral bin response output affected by the target object or scene.

9. The device of claim 1, wherein the spectral bins include one or more spectral bins selected and non-binary modulation-encoded to characterize blood oxygenation or other physiological parameter or other secondary parameter.

10. The device of claim 1, wherein at least one of:
the optical illuminator includes spectral emphasizer componentry to pre-emphasize at least one spectral bin with respect to at least one other spectral bin, based on an actual measured or expected output spectrum from the target object or scene, before modulation encoding into the illumination light beam for illuminating the target object or scene; or the signal processing circuitry includes spectral gain adjustment componentry to adjust a spectral gain based on an actual measured or expected output spectrum from the target object or scene.

11. The device of claim 1, comprising, in an optical pathway upstream from the target, at least one of: a diffractive or sub-diffractive optical element, a geometrical phase optical element, or a metasurface optical element.

12. The device of claim 1, comprising:
controller circuitry to encode LED output illuminations with orthogonal modulation coding functions; and
wherein the signal processing circuitry is configured to decode the response electrical signal to determine individual spectral response indications to respective individual LED output illuminations.

13. The device of claim 1, comprising:
the signal processing circuitry configured to process the response electrical signal to determine individual spectral response indications to respective individual LED output illuminations; and
wherein the light transducer includes individual photodiodes at different distances from an illumination exit region to estimate absorption and scattering indications at the respective wavelengths of the individual LED output illuminations.

14. A method of using a device for imaging or analyzing a target object or scene, using different spectral bin light components, an individual one of the different spectral bin light components comprising an individual wavelength or wavelength distribution, the method comprising:
illuminating the target object or scene using different spectral bin light components modulation encoded, using respective different non-binary light output time-varying modulation functions, and combined into a wavelength homogeneous illumination light beam projected from a shared single exit location for illuminating the target object or scene to be imaged or analyzed, the illumination light beam concurrently providing the modulation encoded at least two individually modulated different spectral bin light components to the target object or scene, wherein at the shared single exit location the wavelength homogeneous illumination light beam is such that different wavelength light components cannot be separated by spatial or angular division of the wavelength homogeneous illumination light beam;
transducing response light from the target object or scene, in response to the illumination light beam illuminating the target object or scene, to produce an electrical response signal in response thereto;
using information about the respective different time-varying modulation functions, decoding the response signal to recover information about a respective response parameter of the modulation encoded different spectral bin light components to provide a spectral bin response output affected by the target object or scene;
providing, using one or more LED or other light sources, corresponding LED output illuminations having different individual targeted illumination spectra, having respective corresponding illumination wavelength spectral distribution widths, corresponding to the different spectral bin light components; and
limiting a corresponding illumination wavelength spectral distribution width of the corresponding LED output illuminations for respectively providing the different spectral bin light components.

15. The method of claim 14, wherein limiting a corresponding illumination wavelength spectral distribution width of the corresponding LED output illuminations for respectively providing the different spectral bin light components comprises:
passing illumination light originating from the one or more LED or other light sources and modulation encoded into at least two individually modulated different spectral bin light components through a shared aperture that restricts a wavelength range of each of the at least two individually modulated different spectral bin light components without requiring individually separately restricting the wavelength range of each of the at least two individually modulated different spectral bin light components.

16. The method of claim 14, comprising:
providing the at least two individually modulated different spectral bin light components including visible Red, Green, and Blue spectral bin light components modulation encoded, using respective different time-varying modulation functions, and combined into an illumination light beam for illuminating the target object or scene to be imaged or analyzed, the illumination light beam concurrently providing the modulation encoded visible Red, Green, and Blue individually modulated different spectral bin light components to the target object or scene;
producing from the response light an electrical spatially-resolved imaging signal including visible Red, Green, and Blue spectral bin light component channels;
using the electrical spatially-resolved imaging signal including visible Red, Green, and Blue spectral bin light component channels to recover spatially resolved information about a respective response parameter of the modulation encoded different spectral bin light components to provide a spectral bin response output affected by the target object or scene to provide an RGB image of the target object or scene for display; and
wherein at least one of:
the spectral bins respectively include three corresponding spectrally contiguous or disjoint wavelength distributions; or
three spectral bin responses are mapped as outputs to a RGB display including encoded spectral bins that are decoded or directly correspond to visible RGB spectral distributions.

17. The method of claim 14, comprising at least one of:
pre-emphasizing at least one spectral bin with respect to at least one other spectral bin, based on an actual measured or expected output spectrum from the target object or scene, before modulation encoding into the illumination light beam for illuminating the target object or scene; or
adjust a spectral gain based on an actual measured or expected output spectrum from the target object or scene.

18. A device for multi-wavelength spectroscopic analysis of a biological or other target, the device comprising:
an optical illuminator, including an optical transmitter module, comprising:
a plurality of light-emitting diodes (LEDs), including at least two individual LEDs providing corresponding LED output illuminations having different individual targeted illumination spectra;
a plurality of optical collimators, including at least two individual optical collimators in respective optical pathways corresponding to respective individual LEDs;
one or more wavelength-selective optical filters, in one or more of the respective optical pathways to limit a corresponding spectral bandwidth of the respective LED output illuminations before or after collimation;
wherein the optical illuminator is arranged to provide at least two individually modulated different spectral bin light components modulation encoded, using a plurality of respective different non-binary light output time-varying orthogonal modulation functions, and combined into an illumination light beam for illuminating the target to be imaged or analyzed, the illumination light beam concurrently providing the modulation encoded at least two individually modulated different spectral bin light components to the target; and
at least one diffuser in the one or more respective optical pathways to perform post-modulation wavelength homogenization without requiring an optical fiber, to provide a wavelength homogeneous illumination light beam that is projected from a shared single exit location for illuminating the target, the wavelength homogeneous illumination light beam having, at the shared single exit location for illuminating the target, a wavelength-homogeneous distribution of modulation-coded different wavelength light components across different emanating angles of illumination, such that at the shared single exit location the wavelength homogeneous illumination light beam is such that different wavelength light components cannot be separated by spatial or angular division of the wavelength-homogeneous light beam.

19. The device of claim 18, comprising, in the respective optical pathways upstream from the target, at least one of: a diffractive or sub-diffractive optical element, a geometrical phase optical element, or a metasurface optical element.

20. The device of claim 18, comprising:
controller circuitry to encode the LED output illuminations with orthogonal modulation coding functions;
a light detector to detect a response light signal from the target, and to produce a resulting response electrical light signal based thereon; and
signal processing circuitry to decode the response electrical signal to determine individual spectral response indications to respective individual LED output illuminations.

21. The device of claim 18, comprising:
a light detector to detect a response light signal from the target, and to produce a resulting response electrical light signal based thereon;
signal processing circuitry to process the response electrical signal to determine individual spectral response indications to respective individual LED output illuminations; and
wherein the light detector includes individual photodiodes at different distances from an illumination exit region to estimate absorption and scattering indications at the respective wavelengths of the individual LED output illuminations.

22. The device of claim 18, comprising:
a light detector to detect a response light signal from the target, and to produce a resulting response electrical light signal based thereon;
signal processing circuitry to process the response electrical signal to determine individual spectral response indications to respective individual LED output illuminations;
wherein at least one of the LED output illuminations is limited to a first spectral region that includes wavelengths of between 510 nanometers and 580 nanometers, and wherein at least one of the LED output illuminations includes a second spectral region that includes wavelengths of between 630 nanometers and 950 nanometers; and wherein the signal processing circuitry determines an indication of blood or tissue oxygenation of the target based at least in part on a first indication of light from the first spectral region and a second indication of light from the second spectral region.

23. The device of claim 18, comprising:
a light detector to detect a response light signal from the target, and to produce a resulting response electrical light signal based thereon;
signal processing circuitry to process the response electrical signal to determine individual spectral response indications to respective individual LED output illuminations to measure at least one of light absorbance, light transmittance, or light scattering.

24. The device of claim 18, comprising:
a light detector to detect a response light signal from the target, and to produce a resulting response electrical light signal based thereon;
signal processing circuitry to process the response electrical signal to determine individual spectral response indications to respective individual LED output illuminations to measure indications of multiple analytes of the target.

25. The device of claim 18, wherein the optical transmitter module, comprises:
at least first and second LED-sourced light outputs, including at least one of the respective LED output illuminations having an illumination wavelength spectral distribution width of less than nanometers in wavelength; and
at least one light detector, arranged on a same side of the biological target as the optical transmitter, to detect a back-scattering light response from the biologic target in response to illumination directed toward the biological target and to produce a resulting back-scattering electrical response signal; and
signal-processing circuitry, coupled to the at least one light detector to receive the back-scattering electrical response signal and to determine therefrom an indication of oxygen saturation or other physiological parameter of the biological target.

26. The device of claim 18, wherein:
the optical illuminator is configured to provide an electrical, optical, frame clock or other pattern, radiofrequency (RF) or other electromagnetic or other timing reference signal in addition to the illumination beam; and
comprising signal processing circuitry configured to use information from the timing reference signal and information about the respective different time-varying modulation functions to recover information about a parameter of the modulation encoded different spectral bin components to provide a spectral bin response output affected by the target.

27. The device of claim 18, wherein at least one of:
the optical illuminator includes spectral emphasizer componentry to pre-emphasize at least one spectral bin with respect to at least one other spectral bin, based on an actual measured or expected output spectrum from the target, before modulation encoding into the illumination light beam for illuminating the target; or comprising signal processing circuitry that includes spectral gain adjustment componentry to adjust a spectral gain based on an actual measured or expected output spectrum from the target.

28. A device for multi-wavelength spectroscopic analysis of a biological or other target, the device comprising:
an optical illuminator, including an optical transmitter module, comprising:
a plurality of light-emitting diodes (LEDs), including at least two individual LEDs providing corresponding LED output illuminations having different individual targeted illumination spectra;
one or more wavelength-selective optical filters, in one or more of respective optical pathways to limit a corresponding spectral bandwidth of the respective LED output illuminations;
wherein the optical illuminator is arranged to provide at least two individually modulated different spectral bin light components modulation encoded, using respective different non-binary light output time-varying modulation functions, and combined into an illumination light beam for illuminating the target to be imaged or analyzed, the illumination light beam concurrently providing the modulation encoded at least two individually modulated different spectral bin light components to the target;
wherein the optical illuminator includes at least one diffuser in the one or more respective optical pathways to perform post-modulation wavelength homogenization to provide a wavelength homogeneous illumination light beam projected from a shared single exit location for illuminating the target, wherein at the shared single exit location the wavelength homogeneous illumination light beam is such that different wavelength light components cannot be separated by spatial or angular division of the wavelength homogeneous illumination light beam.

29. The device of claim 28, comprising optics arranged for combining light from the respective optical pathways to a shared exit location for delivery to a shared entry location of a sample being tested as the target.

30. The device of claim 27, comprising:
diffraction optics for diffracting light in the respective optical pathways toward a shared exit location for delivery to a target to provide both collimating and the optical filtering in the respective optical pathways;
wherein the LED output illuminations are encoded with respective orthogonal modulation coding functions.

31. A device for imaging or analyzing a target object or scene, using different spectral bin light components, an individual one of the different spectral bin light components comprising an individual wavelength or wavelength distribution, the device comprising:
an optical illuminator, arranged to provide at least two individually modulated different spectral bin light components modulation encoded, using respective different non-binary light output time-varying modulation functions, and combined into an illumination light beam for illuminating the target object or scene to be imaged or analyzed, the illumination light beam concurrently providing the modulation encoded at least two individually modulated different spectral bin light components to the target object or scene;
a target light transducer, arranged to receive response light from the target object or scene in response to the illumination light beam illuminating the target object or scene, and to transduce the response light into an electrical response signal;

signal processing circuitry, coupled to the target light transducer to receive the electrical response signal and, using information about the respective different time-varying modulation functions, decoding the electrical response signal to recover information about a respective response parameter of the modulation encoded different spectral bin light components to provide a spectral bin response output affected by the target object or scene; and wherein the optical illuminator is configured to modulate a corresponding electrical input signal of one or more corresponding light-emitting diode (LED) or other light sources arranged to provide at least two individually modulated different spectral bin light components that are modulation encoded, using the respective different time-varying modulation functions, and combined into a wavelength homogeneous illumination light beam projected from a shared single exit location for illuminating the target object or scene to be imaged or analyzed, the illumination light beam concurrently providing the modulation encoded at least two individually modulated different spectral bin light components to the target object or scene; and wherein:

the optical illuminator, is configured to provide, at corresponding specified target pump wavelengths of the target object or scene, the at least two individually modulated different spectral bin light components modulation encoded, using the respective different time-varying modulation functions, and combined into the illumination light beam for illuminating the target object or scene to be imaged or analyzed, the illumination light beam concurrently providing the modulation encoded at least two individually modulated different spectral bin light components to the target object or scene;

the target light transducer is arranged to receive wavelength-shifted emission response light from the target object or scene, at corresponding wavelength-shifted emission response wavelengths of the target object or scene responsive to the corresponding specified target pump wavelengths of the target object or scene, in response to the illumination light beam illuminating the target object or scene, and to produce the electrical response signal thereto, wherein the wavelength-shifted emission response light includes a wavelength-shifted emission response to the corresponding specified target pump wavelengths; and the signal processing circuitry is configured to use information about the respective different time-varying modulation functions, decoding the electrical response signal to recover information about the respective response parameter of the modulation encoded different spectral bin light components to provide the wavelength-shifted emission spectral bin response affected by the target object or scene.

32. The device of claim 31, wherein the wavelength-shifted emission spectral bin response includes at least one of a fluorescence response or a Raman response to the corresponding target pump wavelengths, and further comprising an optical blocking filter located between the target object or scene and the light transducer, wherein the optical blocking filter is configured to attenuate or block the specified target pump wavelengths from reaching the light transducer.

33. A device for imaging or analyzing a target object or scene, using different spectral bin light components, an individual one of the different spectral bin light components comprising an individual wavelength or wavelength distribution, the device comprising:

an optical illuminator, arranged to provide at least two individually modulated different spectral bin light components modulation encoded, using respective different non-binary light output time-varying modulation functions, and combined into an illumination light beam for illuminating the target object or scene to be imaged or analyzed, the illumination light beam concurrently providing the modulation encoded at least two individually modulated different spectral bin light components to the target object or scene;

a target light transducer, arranged to receive response light from the target object or scene in response to the illumination light beam illuminating the target object or scene, and to transduce the response light into an electrical response signal;

signal processing circuitry, coupled to the target light transducer to receive the electrical response signal and, using information about the respective different time-varying modulation functions, decoding the electrical response signal to recover information about a respective response parameter of the modulation encoded different spectral bin light components to provide a spectral bin response output affected by the target object or scene; and wherein the optical illuminator is configured to modulate a corresponding electrical input signal of one or more corresponding light-emitting diode (LED) or other light sources arranged to provide at least two individually modulated different spectral bin light components that are modulation encoded, using the respective different time-varying modulation functions, and combined into a wavelength homogeneous illumination light beam projected from a shared single exit location for illuminating the target object or scene to be imaged or analyzed, the illumination light beam concurrently providing the modulation encoded at least two individually modulated different spectral bin light components to the target object or scene; and wherein at least one of:

the optical illuminator includes spectral emphasizer componentry to pre-emphasize at least one spectral bin with respect to at least one other spectral bin, based on an actual measured or expected output spectrum from the target object or scene, before modulation encoding into the illumination light beam for illuminating the target object or scene; or the signal processing circuitry includes spectral gain adjustment componentry to adjust a spectral gain based on an actual measured or expected output spectrum from the target object or scene.

34. A device for multi-wavelength spectroscopic analysis of a biological or other target, the device comprising:

an optical illuminator, including an optical transmitter module, comprising:

a plurality of light-emitting diodes (LEDs), including at least two individual LEDs providing corresponding LED output illuminations having different individual targeted illumination spectra;

a plurality of optical collimators, including at least two individual optical collimators in respective optical pathways corresponding to respective individual LEDS;

one or more wavelength-selective optical filters, in one or more of the respective optical pathways to limit a corresponding spectral bandwidth of the respective LED output illuminations before or after collimation; and wherein the optical illuminator is arranged to provide at least two individually modulated different spectral bin light components modulation encoded, using respective different non-binary light output time-varying modulation functions, and combined into an illumination light beam for illuminating the target to be imaged or analyzed, the illumination light beam concurrently providing the modulation encoded at least two individually modulated different spectral bin light components to the target;

at least one diffuser in the one or more respective optical pathways to perform post-modulation wavelength homogenization without requiring an optical fiber, to provide a wavelength homogeneous illumination light beam having a wavelength-homogeneous distribution of modulation-coded different wavelength light components across different emanating angles of illumination, such that there is a spectral variation of less than 50% across the different emanating angles of illumination across an illumination Field Of View (FOV) that is projected from a shared single exit location for illuminating the target; and wherein at least one of:

the optical illuminator includes spectral emphasizer componentry to pre-emphasize at least one spectral bin with respect to at least one other spectral bin, based on an actual measured or expected output spectrum from the target, before modulation encoding into the illumination light beam for illuminating the target; or signal processing circuitry that includes spectral gain adjustment componentry to adjust a spectral gain based on an actual measured or expected output spectrum from the target.

* * * * *

UNITED STATES PATENT AND TRADEMARK OFFICE
CERTIFICATE OF CORRECTION

| | | |
|---|---|---|
| PATENT NO. | : 12,165,372 B2 | Page 1 of 1 |
| APPLICATION NO. | : 18/045701 | |
| DATED | : December 10, 2024 | |
| INVENTOR(S) | : Shrenik Deliwala | |

It is certified that error appears in the above-identified patent and that said Letters Patent is hereby corrected as shown below:

On the Title Page

In item (57) "Abstract", in Column 2, Line 9, delete "SpO2," and insert --$SpO_2$,-- therefor In the Claims In Column 119, Line 35, in Claim 25, after "than", insert --25--

In Column 120, Line 44, in Claim 30, delete "27," and insert --28,-- therefor

In Column 123, Line 4, in Claim 34, delete "LEDS;" and insert --LEDs;-- therefor Signed and Sealed this
Twenty-eighth Day of October, 2025

John A. Squires
*Director of the United States Patent and Trademark Office*